(12) United States Patent
Gloanec et al.

(10) Patent No.: US 10,138,260 B2
(45) Date of Patent: Nov. 27, 2018

(54) COMPOUNDS OF PHOSPHINANES AND AZAPHOSPHINANES, A PROCESS FOR THEIR PREPARATION AND PHARMACEUTICAL COMPOSITIONS CONTAINING THEM

(71) Applicant: LES LABORATOIRES SERVIER, Suresnes (FR)

(72) Inventors: Philippe Gloanec, Marly le Roi (FR); Arnaud-Pierre Schaffner, Marly le Roi (FR); Patricia Sansilvestri-Morel, Antony (FR); Alain Rupin, Savonnieres (FR); Philippe Mennecier, Conflans Sainte Honorine (FR); Marie-Odile Vallez, Montreuil (FR)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 15/548,533

(22) PCT Filed: Jan. 13, 2017

(86) PCT No.: PCT/FR2017/050075
§ 371 (c)(1),
(2) Date: Aug. 3, 2017

(87) PCT Pub. No.: WO2017/121969
PCT Pub. Date: Jul. 20, 2017

(65) Prior Publication Data
US 2018/0016288 A1 Jan. 18, 2018

(30) Foreign Application Priority Data
Jan. 14, 2016 (FR) .................................... 16 70004

(51) Int. Cl.
| | |
|---|---|
| A61K 31/66 | (2006.01) |
| C07F 9/6568 | (2006.01) |
| C07F 9/6584 | (2006.01) |
| A61K 9/00 | (2006.01) |
| A61K 31/675 | (2006.01) |
| A61K 45/06 | (2006.01) |

(52) U.S. Cl.
CPC .......... *C07F 9/6568* (2013.01); *A61K 9/0019* (2013.01); *A61K 31/66* (2013.01); *A61K 31/675* (2013.01); *A61K 45/06* (2013.01); *C07F 9/6584* (2013.01); *C07F 9/65846* (2013.01)

(58) Field of Classification Search
CPC .... A61K 9/0019; A61K 31/66; A61K 31/675; A61K 45/06; C07F 9/6568; C07F 9/6584; C07F 9/65846
See application file for complete search history.

(56) References Cited

U.S. PATENT DOCUMENTS

2005/0234021 A1 10/2005 Petasis

OTHER PUBLICATIONS

Z. Wang et al., 19 Drug Discovery Today, 145-150 (2014).*
U.K. Marelli et al., 3 Frontiers in Oncology, 1-12 (2013).*
Y-X Wang et al., Thrombosis and Haemostasis, 54-61 (2007).*
P.J. Declerck et al., 3 Hämostaseologie, 165-173 (2011).*
A. Burns et al., 23 Drugs Aging, 887-896 (2006).*
D. Neary et al., 4 The Lancet Neurology, 771-780 (2005).*
A.D. Korezyn et al., 248 Journal of the Neurological Sciences, 3-8 (2006).*
G.C. Roman et al., 226 Journal of the Neurological Sciences, 81-87 (2004).*

(Continued)

*Primary Examiner* — Alexander R Pagano
(74) *Attorney, Agent, or Firm* — Hueschen and Sage

(57) ABSTRACT

Compounds of formula (I)

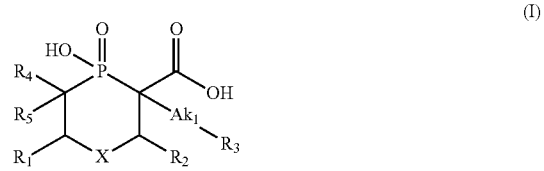

wherein:
$Ak_1$ represents an alkyl chain,
X represents —$(CH_2)_m$—, —CH(R)—, —N(R)—, —$CH_2$—N(R)—, —N(R)—$CH_2$— or —$CH_2$—N(R)—$CH_2$—,
m and R are as defined in the description,
$R_1$ and $R_2$ each represent H when X represents —$(CH_2)_m$—, —CH(R)—, —N(R)—, —$CH_2$—N(R)— or —N(R)—$CH_2$—,
or together form a bond when X represents —$CH_2$—N(R)—$CH_2$—,
$R_3$ represents $NH_2$, Cy-$NH_2$, Cy-$Ak_3$-$NH_2$ or piperidin-4-yl,
Cy and $Ak_3$ are as defined in the description,
$R_4$ and $R_5$, which may be identical or different, each represent H or F,
their optical isomers, and addition salts thereof with a pharmaceutically acceptable acid.
Medicinal products containing the same which are useful in treating conditions requiring a TAFIa inhibitor.

19 Claims, No Drawings

(56) References Cited

OTHER PUBLICATIONS

T. Ueta et al., 116 Ophthalmology, 362 (2009).*
N. Herrmann et al., 161 American Journal of Psychiatry, 1113 (2004).*
K. Kehoe et al., 40 Neurochemical Research, 81-88 (2015).*
International Search Report for PCT/FR2017/050075 dated Mar. 9, 2017.

* cited by examiner

COMPOUNDS OF PHOSPHINANES AND AZAPHOSPHINANES, A PROCESS FOR THEIR PREPARATION AND PHARMACEUTICAL COMPOSITIONS CONTAINING THEM

The present invention relates to new compounds of phosphinanes and azaphosphinanes, to a process for their preparation, and to pharmaceutical compositions containing them.

The compounds of the invention are TAFIa (activated thrombin-activatable fibrinolysis inhibitor) inhibitors.

TAFI (also called plasma procarboxypeptidase B, procarboxypeptidase R or procarboxypeptidase U) is a plasma glycoprotein of 60 kDa produced by the liver, which circulates in the form of a zymogen. During blood coagulation and fibrinolysis, thrombin and plasmin cleave the pro-segment of TAFI in the region of the Arg92-Ala93 bond and convert it into an active enzyme, TAFIa, the half-life of which is from 8 to 15 minutes at 37° C. Cleavage of the pro-segment by thrombin is accelerated by thrombomodulin, a cofactor which is present in plasma and at the surface of vascular endothelial cells (Bouma B N and Meijers J C, *Thrombin-activatable fibrinolysis inhibitor,* 2003, Journal of Thrombosis and Haemostasis, 1: 1566-1574). TAFIa regulates fibrinolysis negatively by cleaving the C-terminal lysine residues of the fibrin fibres which appear during the partial degradation of fibrin by the first traces of plasmin. These C-terminal lysine residues on the partially degraded fibrin behave like ligands of the circulating plasma plasminogen and of the tissue plasminogen activator (tPA) generated by the endothelial cells during thrombotic ischaemia. They thus permit localisation of the conversion of plasminogen to plasmin by the tPA without interference either with the circulating plasmin inhibitor α2-antiplasmin or with the circulating tissue plasminogen activator inhibitor (PAI-1). Cleavage of the C-terminal lysine sites by TAFIa therefore reduces the rate at which plasmin is generated. Endogenous fibrinolysis is then inhibited and lysis of arterial and venous fibrinous thromboses as well as therapeutic thrombolysis undertaken in patients in the acute post-thrombotic ischaemic phase are likewise diminished. TAFIa inhibitors therefore have the potential to increase endogenous and therapeutic fibrinolysis and to behave like antithrombotic and profibrinolytic agents without the risk of major haemorrhage, since they do not interfere either with platelet activation or with coagulation during blood haemostasis.

The property of inhibiting TAFIa therefore makes it possible to envisage using the compounds of the invention in the treatment and prevention of thrombotic events in at-risk patients.

Their use will be valuable in the treatment, prevention and secondary prevention of vascular complications, more especially cardiovascular, pulmonary and cerebrovascular complications, associated with atherothrombotic diseases, with atherosclerosis, with diabetes, with hyperlipidaemia, with hypertension, with chronic venous diseases, with obesity-related metabolic syndrome or with cancer.

The compounds according to the invention are especially useful for the treatment, prevention and secondary prevention of myocardial infarction, angina pectoris, cerebrovascular accidents, aortic aneurysms, arteritis of the lower limbs, fibrotic diseases, venous thromboses and pulmonary embolism.

Vascular risk factors and vascular diseases such as hypertension, obesity, diabetes, cardiac diseases, cerebrovascular diseases and hyperlipidaemia, and therefore atherosclerosis, play a role in the genesis of dementias such as Alzheimer's disease and vascular dementia (Qiu C., De Ronchi D. and Fratiglioni L., *The epidemiology of the dementias: an update,* 2007, Current Opinion in Psychiatry, 20:380-385). The compounds of the invention will therefore also be of use for the treatment and/or prevention of dementias such as Alzheimer's disease and vascular dementia.

TAFIa lowers endogenous fibrinolytic potential. As TAFIa inhibitors, the compounds of the present invention are therefore of use to accompany acute treatment by injectable fibrinolytics, such as recombinant tPA (for example alteplase, tenecteplase, reteplase, desmoteplase), recombinant uPA or streptokinase, which are used in emergencies (for example myocardial infarction, cerebrovascular accident).

The compounds of the present invention reinforce the activity of these injectable fibrinolytics and therefore lead to the use thereof with fewer haemorrhagic and neurotoxic risks (reduction of the dose thereof and therefore reduction of the side-effects thereof).

The present invention relates more especially to compounds of formula (I):

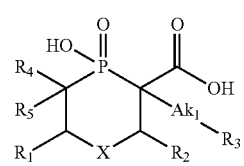

wherein:
Ak$_1$ represents a $C_1$-$C_6$-alkyl chain,
X represents —(CH$_2$)$_m$—, —CH(R)—, —N(R)—, —CH$_2$—N(R)—, —N(R)—CH$_2$— or —CH$_2$—N(R)—CH$_2$—,
  m represents 0 or an integer from 1 to 4,
  R represents a hydrogen atom or a group selected from $C_1$-$C_6$-alkyl, -Ak$_2$-Ar$_1$, -Ak$_2$-Ar$_1$—Ar$_2$ and -Ak$_2$-Ar$_1$—O—Ar$_2$, -Ak$_2$-cycloalkyl or -Ak$_2$-OH,
  Ak$_2$ represents a linear or branched $C_1$-$C_6$-alkyl chain,
  Ar$_1$ and Ar$_2$, which may be identical or different, each represent an aryl or heteroaryl group,
R$_1$ and R$_2$ each represent a hydrogen atom when X represents —(CH$_2$)$_m$—, —CH(R)—, —N(R)—, —CH$_2$—N(R)— or —N(R)—CH$_2$—,
or together form a bond when X represents —CH$_2$—N(R)—CH$_2$—,
R$_3$ represents NH$_2$, Cy-NH$_2$, Cy-Ak$_3$-NH$_2$ or piperidin-4-yl,
  Cy represents a group selected from cycloalkyl, aryl and heteroaryl,
  Ak$_3$ represents a $C_1$-$C_3$-alkyl chain,
R$_4$ and R$_5$, which may be identical or different, each represent a hydrogen atom or a fluorine atom,
their optical isomers and addition salts thereof with a pharmaceutically acceptable acid.

Aryl group is understood as meaning phenyl, naphthyl or biphenyl optionally substituted by one or more identical or different groups selected from halogen, hydroxy, amino, linear or branched ($C_1$-$C_6$)-alkyl optionally substituted by one or more halogen atoms, methylsulphonyl, methylthio, carboxy, linear or branched ($C_1$-$C_6$)-alkoxy optionally substituted by one or more halogen atoms, linear or branched ($C_1$-$C_6$)-aminoalkyl, the amino group of the aminoalkyl group being optionally substituted by one or two linear or branched ($C_1$-$C_6$)-alkyl groups.

Heteroaryl group is understood as meaning a monocyclic aromatic group or a bicyclic aromatic or partially aromatic group having from 5 to 12 ring members and containing one, two or three hetero atoms selected from oxygen, nitrogen and sulphur, it being understood that the heteroaryl may be optionally substituted by one or more identical or different groups selected from halogen, hydroxy, amino, oxo, linear or branched ($C_1$-$C_6$)-alkyl optionally substituted by one or more halogen atoms, linear or branched ($C_1$-$C_6$)-alkoxy optionally substituted by one or more halogen atoms, linear or branched ($C_1$-$C_6$)-aminoalkyl, the amino group of the aminoalkyl group being optionally substituted by one or two linear or branched ($C_1$-$C_6$)-alkyl groups.

Among the heteroaryl groups there may be mentioned, without implying any limitation, the groups pyridyl, thienyl, furyl, imidazolyl, pyrimidinyl, pyrazolyl, pyrrolyl, oxazolyl, isoxazolyl, thiazolyl, isothiazolyl, pyrazinyl, pyridazinyl, benzofuryl, benzothienyl, benzimidazolyl, imidazopyridinyl, isoquinolinyl, dihydrobenzofuryl, dihydrobenzoxazolyl, dihydroindolyl, dihydroindazolyl, benzodioxolyl.

Cycloalkyl group is understood as meaning a monocyclic, saturated hydrocarbon group having from 5 to 7 ring members, it being understood that the ring may be optionally substituted by one or more identical or different groups selected from halogen, linear or branched ($C_1$-$C_6$)-alkyl. Among the cycloalkyl groups there may be mentioned, without implying any limitation, the groups cyclopentyl, cyclohexyl, cycloheptyl.

Optical isomers are understood as being the diastereoisomers and the enantiomers.

The compounds of formula (I) have at least one asymmetric centre:

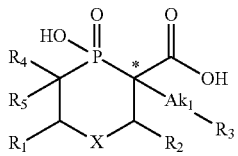

(I)

When the configuration of a compound of formula (I) having a single asymmetric centre is not specified, the compound is obtained in the form of a mixture of the two enantiomers.

When the configuration of a compound of formula (I) having two asymmetric centres is not specified, the compound is obtained in the form of a mixture of diastereoisomers.

Among the pharmaceutically acceptable acids there may be mentioned, without implying any limitation, hydrochloric, hydrobromic, sulphuric, phosphoric, acetic, trifluoroacetic, lactic, pyruvic, malonic, succinic, glutaric, fumaric, tartaric, maleic, citric, ascorbic, oxalic, methanesulphonic, benzenesulphonic, p-toluenesulphonic, camphoric acid.

One aspect of the present invention relates to the compounds of formula (I) wherein $Ak_1$ represents —$(CH_2)_4$—.

Another aspect of the present invention relates to the compounds of formula (I) wherein X represents —N(R)—.

Another aspect of the present invention relates to the compounds of formula (I) wherein X represents —N(R)—, —$CH_2$—N(R)—, —N(R)—$CH_2$— or —$CH_2$—N(R)—$CH_2$—, and R represents a group selected from -$Ak_2$-$Ar_1$, -$Ak_2$-$Ar_1$—$Ar_2$ and -$Ak_2$-$Ar_1$—O—$Ar_2$.

Another aspect of the present invention relates to the compounds of formula (I) wherein X represents —N(R)—, —$CH_2$—N(R)—, —N(R)—$CH_2$— or —$CH_2$—N(R)—$CH_2$—, R represents a group selected from -$Ak_2$-$Ar_1$, -$Ak_2$-$Ar_1$—$Ar_2$ and -$Ak_2$-$Ar_1$—O—$Ar_2$, and $Ak_2$ represents —$CH_2$—.

Another aspect of the present invention relates to the compounds of formula (I) wherein $R_1$ and $R_2$ each represent a hydrogen atom.

Another aspect of the present invention relates to the compounds of formula (I) wherein $R_3$ represents $NH_2$.

Another aspect of the present invention relates to the compounds of formula (I) wherein $R_4$ and $R_5$ each represent a hydrogen atom.

Another aspect of the present invention relates to the compounds of formula (I) wherein $R_1$, $R_2$, $R_4$ and $R_5$ each represent a hydrogen atom, $R_3$ represents $NH_2$, X represents —N(R)—, —$CH_2$—N(R)—, —N(R)—$CH_2$— or —$CH_2$—N(R)—$CH_2$—, and R represents a group selected from -$Ak_2$-$Ar_1$, -$Ak_2$-$Ar_1$—$Ar_2$ and -$Ak_2$-$Ar_1$—O—$Ar_2$.

Another aspect of the present invention relates to the compounds of formula (Ia), a particular case of the compounds of formula (I):

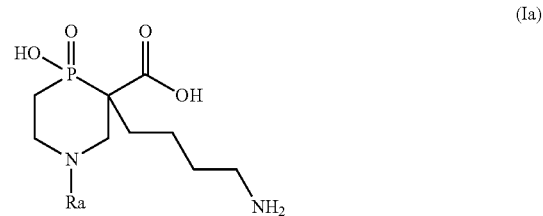

(Ia)

wherein Ra represents a group selected from —$CH_2$—$Ar_1$ and —$CH_2$—$Ar_1$—$Ar_2$, wherein $Ar_1$ and $Ar_2$ are as defined for formula (I).

The present invention relates also to a process for the preparation of the compounds of formula (I) starting from the compound of formula (II):

(II)

wherein X, $R_1$, $R_2$, $R_4$ and $R_5$ are as defined for formula (I), Y represents a linear or branched $C_1$-$C_4$-alkoxy group or a dialkylamino group in which the alkyl groups are $C_1$-$C_4$, linear or branched, which is reacted with $CO(OG)_2$, wherein G represents a protecting group of the acid function, such as alkyl or benzyl, preferably tert-butyl or benzyl, in the presence of a base, to yield the compound of formula (III):

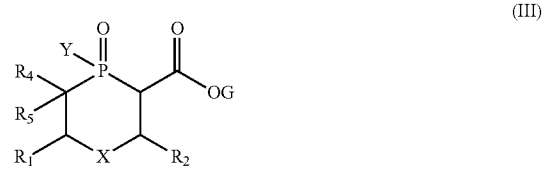

(III)

wherein X, Y, $R_1$, $R_2$ and G are as defined hereinbefore, which is reacted, in the presence of a base, with the compound Br-$Ak_1$-$R'_3$, wherein $Ak_1$ is as defined for formula (I), and $R'_3$ represents $N(Boc)_2$, Cy-$N(Boc)_2$, Cy-$Ak_3$-$N(Boc)_2$ or N-Boc-piperidin-4-yl, to yield the compound of formula (IV):

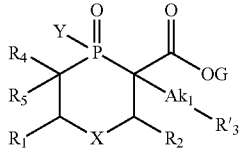
(IV)

wherein X, Y, $R_1$, $R_2$, G, $Ak_1$ and $R'_3$ are as defined hereinbefore, the amino, carboxy and phosphinic functions of which are deprotected to yield the compound of formula (I) or an addition salt thereof with a pharmaceutically acceptable acid.

The compound of formula (IV) has at least two asymmetric centres:

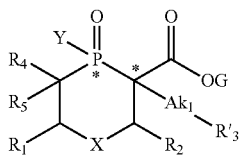
(IV)

The diastereoisomers of the compound of formula (IV) can be separated by means of a chiral column, allowing the optically pure compounds of formula (I) to be obtained by the process described above.

The nomenclature (3aR*, 4S*, 6aS*) used for the octahydrophospholo[3,4-c]pyrrole compounds indicates a relative configuration. It means that the compound is in the form of a mixture of the compounds of absolute configurations (3aR,4S,6aS) and (3aS,4R,6aR).

The present invention relates also to a process for the preparation of the compounds of formula (Ia), a particular case of the compounds of formula (I), starting from the compound of formula (IVa), a particular case of the compounds of formula (IV):

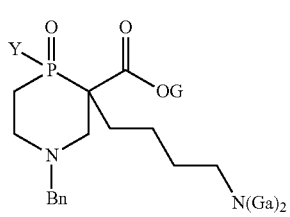
(IVa)

wherein Y and G are as defined for formula (II), and Ga represents a protecting group of the amino function, such as Boc, which is debenzylated to yield the compound of formula (V):

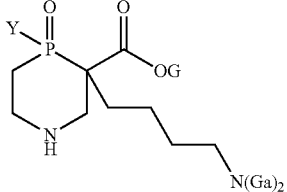
(V)

wherein Y, G and Ga are as defined hereinbefore,
which is subjected to a reductive amination reaction with the aldehyde of formula $R_6$—CHO, wherein $R_6$ represents —$Ar_1$ or —$Ar_1$—$Ar_2$, wherein $Ar_1$ and $Ar_2$ are as defined for formula (I), to yield the compound of formula (VI):

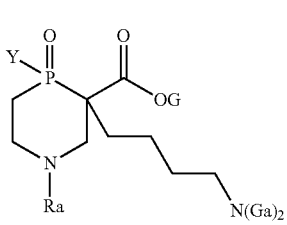
(VI)

wherein Y, G, Ga and Ra are as defined hereinbefore,
the amino, carboxy and phosphinic functions of which are deprotected to yield the compound of formula (Ia) or an addition salt thereof with a pharmaceutically acceptable acid.

The compound of formula (IVa) has two asymmetric centres:

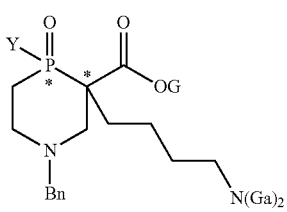
(VIa)

The diastereoisomers of the compound of formula (IVa) can easily be separated by means of a chiral column, allowing the optically pure compounds of formula (Ia) to be obtained by the process described above.

The compounds of the invention are TAFIa inhibitors.

As such, they can be used in the prevention or treatment of thrombotic events in at-risk patients. Their use will be valuable in the treatment and prevention of vascular complications, more especially cardiovascular, pulmonary and cerebrovascular complications, associated with atherothrombotic diseases, with atherosclerosis, with diabetes, with hyperlipidaemia, with hypertension, with chronic venous diseases, with obesity-related metabolic syndrome or with cancer.

The compounds according to the invention are especially useful for the treatment, prevention and secondary prevention of myocardial infarction, angina pectoris, cerebrovascular accidents of any origin (especially atherothrombotic, cardioembolic or caused by atrial fibrillation), aortic aneurysms or arteritis of the lower limbs, venous thromboses (especially in catheterised cancer patients) and pulmonary embolism.

Vascular risk factors and vascular diseases such as hypertension, obesity, diabetes, cardiac diseases, cerebrovascular diseases and hyperlipidaemia, and therefore atherosclerosis, play a role in the genesis of dementias such as Alzheimer's disease and vascular dementia (Qiu C., De Ronchi D. and Fratiglioni L., *The epidemiology of the dementias: an update*, 2007, Current Opinion in Psychiatry, 20:380-385). The compounds of the invention will therefore also be of use for the treatment and/or prevention of dementias such as Alzheimer's disease and vascular dementia.

TAFIa lowers endogenous fibrinolytic potential. As TAFIa inhibitors, the compounds of the present invention are therefore of use to accompany acute treatment by injectable fibrinolytics, such as recombinant tPA (for example alteplase, tenecteplase, reteplase, desmoteplase), recombinant uPA or streptokinase, which are used in emergencies (for example myocardial infarction, cerebrovascular accident).

The compounds of the present invention reinforce the activity of these injectable fibrinolytics and therefore lead to the use thereof with fewer haemorrhagic and neurotoxic risks (reduction of the dose thereof and therefore reduction of the side-effects thereof).

The present invention relates also to pharmaceutical compositions comprising a compound of formula (I) in combination with one or more inert, non-toxic, pharmaceutically acceptable excipients or carriers.

The useful dosage varies according to the age and weight of the patient, the administration route, the nature and severity of the disorder and any associated treatments, and ranges from 0.5 mg to 1000 mg per day in one or more administrations.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, gelatin capsules, capsules, suppositories, creams, ointments, dermal gels, injectable or drinkable preparations, aerosols, and eye or nasal drops.

According to one aspect of the present invention, the pharmaceutical composition is an injectable preparation for intravenous administration.

According to another aspect of the present invention, the pharmaceutical composition is a tablet for oral administration.

In addition to the compound of formula (I), the tablets according to the invention comprise one or more excipients or carriers, such as diluents, lubricants, binders, disintegrators, absorbents, colourants and sweeteners.

There may be mentioned as examples of excipients or carriers:
  for the diluents: lactose, dextrose, sucrose, mannitol, sorbitol, cellulose, glycerol,
  for the lubricants: silica, talc, stearic acid and its magnesium and calcium salts, polyethylene glycol,
  for the binders: aluminium and magnesium silicate, starch, gelatin, tragacanth, methylcellulose, sodium carboxymethylcellulose and polyvinylpyrrolidone,
  for the disintegrators: agar, alginic acid and its sodium salt, effervescent mixtures.

The percentage of active ingredient of formula (I) in the tablet is preferably between 5% and 50% by weight.

According to one aspect of the present invention, the compound of formula (I) according to the present invention is administered in association with a fibrinolytic, more especially an injectable fibrinolytic, such as recombinant tPA (for example alteplase, tenecteplase, reteplase or desmoteplase), recombinant uPA or streptokinase, or with an anticoagulant, such as, for example, warfarin, dabigatran etexilate, rivaroxaban.

The administration in association may be in the form of a simultaneous or successive co-administration of two separate pharmaceutical compositions each containing one of the active ingredients (free association), or in the form of the administration of a fixed association of the two active ingredients in the same pharmaceutical composition.

According to one aspect of the present invention, the compound of formula (I) is administered in the form of an injectable preparation, in free association with an injectable preparation of alteplase.

According to another aspect of the present invention, the compound of formula (I) is administered in the form of an injectable preparation, in free association with an injectable preparation of tenecteplase.

The examples which follow illustrate the present invention. The structures of the compounds described in the examples have been determined by the conventional spectrophotometric techniques (infra-red, nuclear magnetic resonance, mass spectrometry).

ABBREVIATIONS

AcOEt: ethyl acetate
AIBN: azobisisobutyronitrile
DCM: dichloromethane
DEA: diethylamine
DIBAlH: diisobutylaluminium hydride
DMAP: dimethylaminopyridine
DMF: dimethylformamide
DMSO or dmso: dimethyl sulphoxide
OD: optical density
EDTA: ethylenediaminetetraacetic acid
eq: molar equivalent
HMPA: hexamethylphosphoramide
HPLC: high performance liquid chromatography
IR: infra-red
LDA: lithium diisopropylamide
LiHMDS: lithium hexamethyldisilazane or lithium bis(trimethylsilyl)amide
MTBE: methyl tert-butyl ether
RP: rotatory power
NMR: nuclear magnetic resonance
TAFIa: activated thrombin-activatable fibrinolysis inhibitor
TEA: triethylamine
TFA: trifluoroacetic acid
THF: tetrahydrofuran
TMS: trimethylsilyl
tPA: tissue plasminogen activator
uPa: urokinase plasminogen activator or urokinase
Xantphos: 4,5-bis(diphenylphosphino)-9,9-dimethylxanthene Procedure for Synthesis of the Side Chains—Procedures I, J, K (Intermediates 204 to 212)

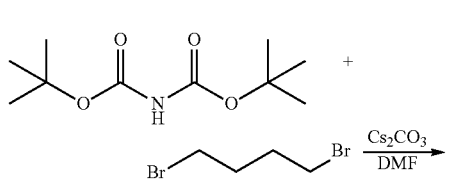

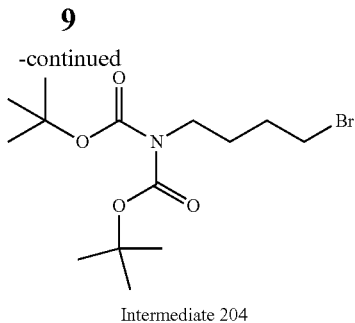

Intermediate 204

Procedure I:

Caesium carbonate (60 g, 184 mmol, 2 eq) is added in portions to a solution of di-tert-butyl iminodicarboxylate (20 g, 92 mmol) in 1 L of DMF under an argon atmosphere and at ambient temperature. Vigorous stirring is maintained for 1 hour, before 1,4-dibromobutane (99.2 g, 459 mmol, 5 eq) is added. After 24 hours at ambient temperature, the reaction mixture is filtered over Celite and concentrated under reduced pressure. The residue obtained is purified by flash chromatography on silica gel using as eluant a heptane/AcOEt gradient (100% to 90:10). Intermediate 204 (26.1 g, 74.1 mmol) is obtained in the form of an colourless oil with a yield of 81%.

Intermediate 204

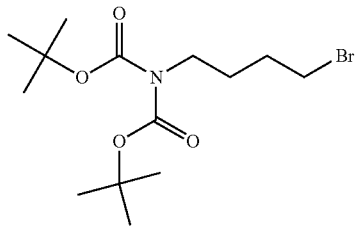 [SMILES: CC(C)(C)OC(=O)N(CCCCBr)C(=O)OC(C)(C)C]

$^1$H NMR: (CDCl$_3$, 400 MHz) δ 3.60 (t, 2H), 3.42 (t, 2H), 1.87 (quint., 2H), 1.73 (quint., 2H), 1.51 (s, 18H).
IR: 1790-1744-1693 cm$^{-1}$ (C═O), 1125 cm$^{-1}$ (C—O).

Intermediate 205

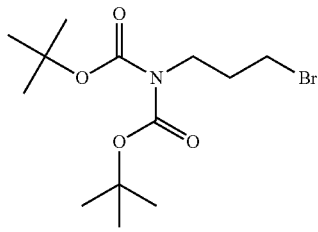 [SMILES: CC(C)(C)OC(=O)N(CCCBr)C(=O)OC(C)(C)C]

Intermediate 205 is obtained starting from 1,3-dibromopropane in accordance with procedure I described hereinbefore.

Product isolated in the form of a colourless oil (24.7 g, 73.0 mmol) with a yield of 79%.

$^1$H NMR: (CDCl$_3$, 400 MHz) δ 3.6 (m, 2H), 3.5 (t, 2H), 2.05 (quint., 2H), 1.51 (s, 18H).
IR: 1791-1744-1693 cm$^{-1}$ (C═O), 1125 cm$^{-1}$ (C—O).

Intermediate 206

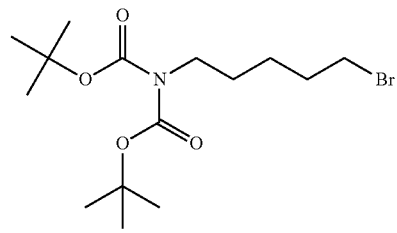 [SMILES: CC(C)(C)OC(=O)N(CCCCCBr)C(=O)OC(C)(C)C]

Intermediate 206 is obtained starting from 1,5-dibromopentane in accordance with procedure I described hereinbefore.

Product obtained in the form of a colourless oil (27.9 g, 76.2 mmol) with a yield of 83%.

$^1$H NMR: (CDCl$_3$, 400 MHz) δ 3.60 (t, 2H), 3.40 (t, 2H), 1.90 (m, 2H), 1.60 (m, 2H), 1.45 (m, 2H), 1.50 (s, 18H) ppm.
IR: 1740, 1693 (C═O), 1787 cm$^{-1}$ (C═O weak).

Intermediate 207

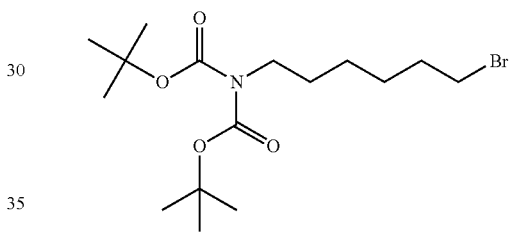

Intermediate 207 is obtained starting from 1,6-dibromohexane in accordance with procedure I described hereinbefore.

$^1$H NMR: (CDCl$_3$, 400 MHz) δ 3.58 (t, 2H), 3.40 (t, 2H), 1.89 (m, 2H), 1.65-1.25 (m, 6H), 1.45 (m, 6H), 1.51 (s, 18H) ppm.

Procedure J

Intermediate 208

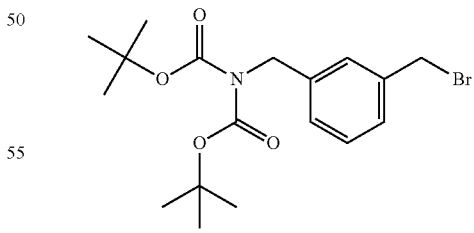

tert-Butyl iminodicarboxylate (2.47 g, 11.37 mmol, 1 eq) is added, in portions, to a 60% NaH suspension (0.682 g, 17 mmol, 1.5 eq) in a mixture of THF (25 mL) and DMF (3 mL) under argon and at ambient temperature. The reaction mixture is stirred at ambient temperature for 15 minutes and then warmed at 45° C. for 45 minutes. This suspension is then added to a solution of 1,3-dibromomethylbenzene (3 g, 11.37 mmol, 1 eq) in THF (100 mL). Stirring is continued at ambient temperature for 16 hours. The mixture is hydrolysed dropwise with a 10% NH$_4$Cl solution (100 mL). The organic phase is extracted with AcOEt (2×50 mL), washed with a saturated NaCl solution (50 mL) and dried over MgSO$_4$. The solvent is evaporated off under reduced pressure and the crude product is purified by flash chromatography on silica gel using as eluant a heptane/DCM gradient (50:50 to 100%). Intermediate 208 (2.07 g, 5.17 mmol) is obtained in the form of a colourless oil with a yield of 45%.

$^1$H NMR: (DMSO-d$_6$, 400 MHz) δ 7.33 (d, 2H), 7.3 (sl, 1H), δ 3.15 (t, 1H), 4.70/4.68 (2s, 4H), 1.40 (s, 18H).

IR: 1790-1747-1699 cm$^{-1}$ (C═O), 1224-1143-1110 cm$^{-1}$ (C—O—C), 854-781-699 cm$^{-1}$ (CH—Ar).

MS: m/z 422 [M+Na].

Intermediate 209

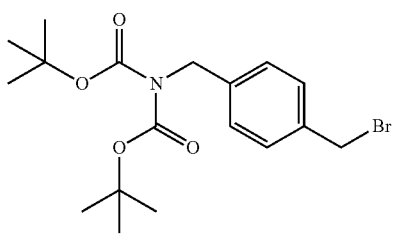 [SMILES: CC(C)(C)OC(=O)N(Cc1ccc(CBr)cc1)C(=O)OC(C)(C)C]

Intermediate 209 is obtained starting from 1,4-dibromomethylbenzene in accordance with procedure J described hereinbefore.

A white solid (2.02 g, 5.05 mmol) is obtained with a yield of 44%.

$^1$H NMR: (DMSO-d$_6$, 400 MHz) δ 7.40 (d, 2H), 7.20 (d, 2H), 4.69 (2s, 4H), 1.39 (s, 18H).

IR: 1767-1693 cm$^{-1}$ (C═O).

MS: m/z 343 [M-C$_4$H$_8$].

Procedure K

Intermediate 210

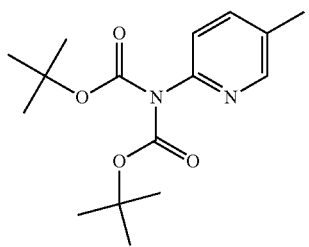 [SMILES: Cc1ccc(N(C(=O)OC(C)(C)C)C(=O)OC(C)(C)C)nc1]

Diisopropylethylamine (59.34 g, 462 mmol, 2 eq) is added dropwise to a solution of 2-amino-5-methylpyridine (25 g, 230 mmol) in DCM (450 mL) at 0° C. under an argon atmosphere. A solution of (Boc)$_2$O (125.5 g, 575 mmol, 2.5 eq) is then added dropwise, followed by N,N-dimethylaminopyridine (28.1 g, 230 mmol, 1 eq). The reaction mixture is stirred for 15 hours at ambient temperature. The aqueous phase is extracted with AcOEt (2×400 mL). The organic phases are combined and washed with a 10% NH$_4$Cl solution (400 mL), with a saturated NaCl solution (400 mL), with a 10% NaHCO$_3$ solution (400 mL) and finally with a saturated NaCl solution (400 mL). The organic phase is dried over MgSO$_4$ and the solvent is evaporated off under reduced pressure. The residue obtained in purified by flash chromatography on silica gel using as eluant a heptane/AcOEt gradient (90:10 to 75:25). Intermediate 210 (32.78 g, 106.3 mmol) is obtained in the form of a colourless oil with a yield of 46%.

$^1$H NMR: (400 MHz, CDCl3) δ ppm 8.3 (s, 1H), 7.75 (dd, 1H), 7.1 (d, 1H), 2.3 (s, 3H), 1.45 (s, 18H)

IR: 1742-1707 cm$^{-1}$ (C═O).

Intermediate 211

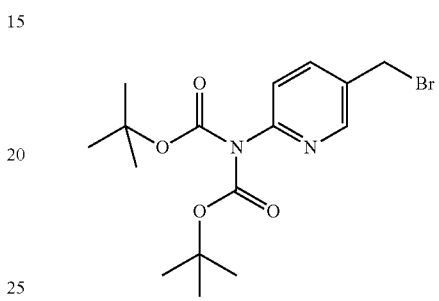

AIBN (0.164 g, 1 mmol) is added to a solution of intermediate 210 (3.08 g, 10 mmol) and N-bromosuccinimide (1.87 g, 10.5 mmol, 1.05 eq) in CCl$_4$ (50 mL). The reaction mixture is heated at reflux for 20 hours. Once at ambient temperature, the insoluble components are filtered off and the filtrate is concentrated under reduced pressure. The residue is purified by flash chromatography on silica gel using as eluant a DCM/AcOEt gradient (from 99:1 to 95:5). Intermediate 211 (2.15 g, 5.56 mmol) is obtained in the form of a white solid with a yield of 56%.

$^1$H NMR: (400 MHz, CDCl3) δ ppm 8.55 (d, 1H), 7.75 (dd, 1H), 7.3 (d, 1H), 4.45 (s, 2H), 1.45 (s, 18H)

IR: 1753-1743-1710 cm$^{-1}$ (C═O).

Intermediate 212

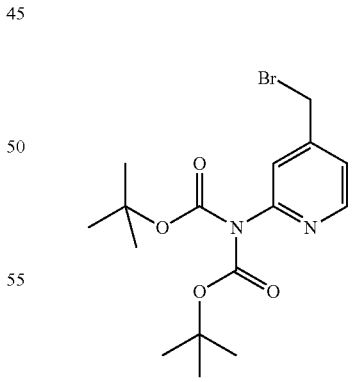

Intermediate 212 is obtained starting from 2-amino-4-methylpyridine in accordance with procedure K described hereinbefore.

$^1$H NMR: (400 MHz, CDCl3) δ ppm 8.48 (d, 1H), 7.3 (d, 1H), 7.22 (d, 1H), 4.4 (s, 2H), 1.45 (s, 18H)

IR: 1788-1755-1724 cm$^{-1}$ (C═O).

Procedure A—Synthesis of Examples 1 to 19

Step A1

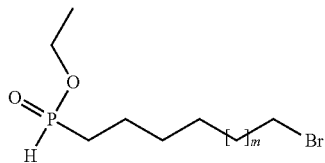

m = 0 to 4

Tetraethyl orthosilicate (25 mL, 112 mmol, 1.0 eq) is added to a solution of hypophosphorous acid (7.42 g, 112 mmol, 1.0 eq) in acetonitrile (160 mL) under argon and at ambient temperature. The reaction mixture is heated at reflux for 2 hours 30 minutes and then cooled to ambient temperature. Bromoalkene $CH_2$=CH—$(CH_2)_{m+2}$—Br (0.5 eq), $Pd_2dba_3$ (0.769 g, 0.84 mmol) and Xantphos (0.356 g, 0.62 mmol) are then added and the reaction mixture is heated at reflux for 18 hours. The solution is then filtered over filter paper at ambient temperature and concentrated under reduced pressure. The crude product is purified by flash chromatography on a silica column using a heptane/AcOEt gradient as eluant. The compound of step A1 is obtained in the form of an oil.

Step A2

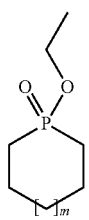

m = 0 to 4

A solution of 1.06M LiHMDS/THF (220 mL, 1.0 eq) is added dropwise to a solution, degassed with argon for 30 minutes, of the compound of step A1 (233 mmol, 1 eq) in THF (870 mL) at −78° C. After the addition, the reaction mixture is stirred at ambient temperature for 2 hours 30 minutes. The reaction is then quenched at 0° C. by addition of a saturated aqueous NaCl solution (870 mL). After extraction with ethyl acetate (3×800 mL), the organic phases are combined, washed with a saturated NaCl solution and dried over $MgSO_4$, before being concentrated under reduced pressure. The crude product is then purified by flash chromatography on a silica column using as eluant a DCM/EtOH mixture 95:5. The compound of step A2 is obtained in the form of an oil.

Step A3

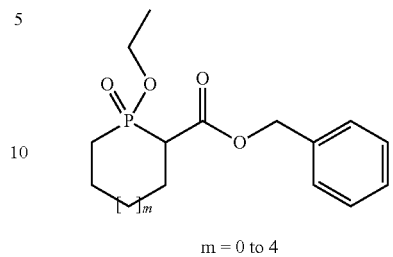

m = 0 to 4

LDA (6.4 mL, 12.8 mmol, 1.5 eq) is added to a solution of the compound of step A2 (8.5 mmol, 1 eq) in THF (20 mL) at −70° C. and under a stream of argon. Stirring is maintained for 20 minutes. A solution of dibenzyl carbonate (2.88 g, 11.9 mmol, 1.4 eq) in THF (11 mL) is then added dropwise. The mixture is stirred for 45 minutes, and then a second addition of LDA (6.4 mL, 12.8 mmol, 1.5 eq) is carried out. The solution is stirred for 2 hours at −70° C. A 10% $NH_4Cl$ solution (60 mL) is then added dropwise, the temperature of the reaction mixture being maintained at −70° C. AcOEt (20 mL) is then added and the reaction mixture is gradually brought to ambient temperature. The reaction mixture is then extracted with AcOEt (2×80 mL). The organic phases are combined and dried over $MgSO_4$, filtered and concentrated under reduced pressure. The crude product is purified by flash chromatography on a silica column using as eluant a DCM/EtOH gradient. The compound of step A3 is obtained in the form of an oil.

Step A4

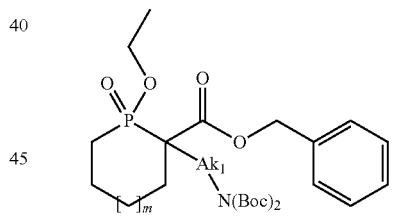

m, $Ak_1$ as defined for formula (I)

A solution of intermediate 204 to 212 (7.65 mmol, 1.1 eq.) in 8 ml of DMSO and then, dropwise, a solution of the compound of step A3 (6.96 mmol, 1 eq) in 5 mL of DMSO are added in succession to a 60% NaH suspension (0.448 g, 11.14 mmol) in 5 mL of DMSO at 10° C. and under argon. When the addition is complete, the reaction mixture is brought to ambient temperature and stirred for 3 hours. The treatment is carried out at 0° C. by adding 10% $NH_4Cl$ (100 mL) and then AcOEt (100 mL). After decantation, the aqueous phase is re-extracted with AcOEt (2×80 mL). The organic phases are combined, washed with a saturated NaCl solution (2×80 mL), dried over $MgSO_4$, filtered and concentrated under reduced pressure. The crude product is purified by flash chromatography on a silica column using as eluant a DCM/EtOH gradient. The compound of step A4, a mixture of diastereoisomers, is obtained in the form of a colourless oil.

Step A5

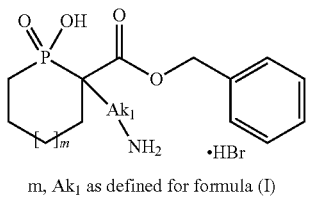

m, Ak₁ as defined for formula (I)

Bromotrimethylsilane (0.721 mL, 5.47 mmol, 8 eq) is added dropwise to a solution of the compound of step A4 (0.683 mmol, 1.0 eq) in DCM (30 mL) at 0° C. and under argon. The mixture is stirred for 20 hours at ambient temperature. Evaporation under reduced pressure is carried out, and then the mixture is evaporated to dryness using a vane-type pump for 30 minutes. The mixture is taken up in MeOH (30 mL), stirred for 30 minutes and then evaporated under pressure and to dryness using a vane-type pump for 30 minutes. The mixture is taken up in MeOH again, stirred and evaporated. This operation is carried out a third time. The compound of step A5 is obtained in the form of the hydrobromide salt and is used directly in the following hydrogenation reaction.

Step A6—Examples 1 to 19

10% Pd/C (10 mol %) is added to a solution of the compound of step A5 in MeOH (15 mL). The mixture is stirred for 18 hours under an $H_2$ atmosphere at ambient temperature. The catalyst is filtered off over a Whatman frit. The filtrate is evaporated to dryness. 12 eq of TFA are added to the crude product. The product is purified by flash chromatography on a reverse-phase RP18 column using an $H_2O$/MeCN/TFA gradient as eluant. After lyophilisation, the expected product (Examples 1 to 19), TFA salt, is obtained in the form of a white hygroscopic solid.

EXAMPLE 1: 2-(3-AMINOPROPYL)-1-HYDROXY-1-OXO-1-PHOSPHOLANE-2-CARBOXYLIC ACID, TRIFLUOROACETATE

Example 1 is obtained starting from intermediate 205 in accordance with procedure A described hereinbefore.
$^1$H NMR: (300 MHz, dmso-d6) δ ppm 12-11 (sl, 1H), 8.3-7.3 (sl, 3H), 2.8 (q, 2H), 2.25 (m, 1H), 1.9 (m, 1H), 1.8-1.4 (m, 8H)
ESI/FIA/HR and MS/MS: ESI+/−: infusion: [M+H]+=222.1
Elemental analysis: C=35.39 (35.83); H=5.44 (5.11); N=4.60 (4.18)

EXAMPLE 2: 2-(4-AMINOBUTYL)-1-HYDROXY-1-OXO-1-PHOSPHOLANE-2-CARBOXYLIC ACID, TRIFLUOROACETATE

Example 2 is obtained starting from intermediate 204 in accordance with procedure A described hereinbefore.
$^1$H NMR: (400 MHz, dmso-d6) δ ppm 12.5 (sl, 1H), 7.75 (sl, 3H), 2.8 (q, 2H), 2.21-1.6 (m, 2H), 1.9-1.35 (m, 2H), 1.8-1.5 (m, 6H), 1.6-1.2 (m, 2H)
ESI/FIA/HR and MS/MS: [M+H]+=236.1041 (236.1051)
Elemental analysis: C=38.94 (37.83); H=5.81 (5.48); N=4.50 (4.01)

EXAMPLE 3: 2-[(6-AMINOPYRIDIN-3-YL)METHYL]-1-HYDROXY-1-OXO-1-PHOSPHOLANE-2-CARBOXYLIC ACID, TRIFLUOROACETATE

Example 3 is obtained starting from intermediate 211 in accordance with procedure A described hereinbefore.
$^1$H NMR: (400 MHz, dmso-d6) δ ppm 13 (sl, 2H), 7.9 (sl, 3H), 7.7 (m, 2H), 6.85 (d, 1H), 3.2 (m, 1H), 2.7 (m, 1H), 2.05 (m, 1H), 1.85-1.5 (m, 5H)
ESI/FIA/HR and MS/MS: [M+H]+=271.0842 (271.0847)
Elemental analysis: C=41.20 (40.64); H=4.52 (4.20); N=8.06 (7.29)

EXAMPLE 4: 2-(5-AMINOPENTYL)-1-HYDROXY-1-OXO-1-PHOSPHOLANE-2-CARBOXYLIC ACID, TRIFLUOROACETATE

Example 4 is obtained starting from intermediate 206 in accordance with procedure A described hereinbefore.
$^1$H NMR: (300 MHz, dmso-d6) δ ppm 12.5 (sl, 1H), 2.78 (m, 2H), 1.8 to 1.4 (m, 4H), 7.68 (sl, 3H), 2.22/1.65 (m, 2H), 1.98/1.3 (m, 2H), 1.52 (t, 2H), 1.4 to 1 (m, 4H)
ESI/FIA/HR and MS/MS: [M+H]+=250.1209 (250.1208)
Elemental analysis: C=39.69 (39.68); H=5.91 (5.83); N=4.37 (3.86)

EXAMPLE 5: 2-(3-AMINOPROPYL)-1-HYDROXY-1-OXO-1-PHOSPHINANE-2-CARBOXYLIC ACID, TRIFLUOROACETATE

Example 5 is obtained starting from intermediate 205 in accordance with procedure A described hereinbefore.
$^1$H NMR: (400 MHz, dmso-d6) δ ppm 13.0 (sl, 1H), 7.73 (sl, 3H), 2.77 (m, 2H), 1.93-1.66-1.44 (3*(m, 2+10H)
ESI/FIA/HR and MS/MS: [M+H]+=236.1051 (236.1051)
Elemental analysis: C=38.07 (37.83); H=5.85 (5.48); N=4.11 (4.01)

EXAMPLE 6: 2-(5-AMINOPENTYL)-1-HYDROXY-1-OXO-1-PHOSPHINANE-2-CARBOXYLIC ACID, TRIFLUOROACETATE

Example 6 is obtained starting from intermediate 206 in accordance with procedure A described hereinbefore.
$^1$H NMR: (300 MHz, dmso-d6) δ ppm 7.65 (sl, 3H), 2.75 (m, 2H), 1.9 (m, 2H), 1.0-1.85 (m, 14H)
ESI/FIA/HR and MS/MS: ESI+/−: infusion: [M+H]+=264.1
Elemental analysis: C=40.84 (41.39); H=5.66 (6.14); N=3.76 (3.71)

EXAMPLE 7: 2-(4-AMINOBUTYL)-1-HYDROXY-1-OXO-1-PHOSPHINANE-2-CARBOXYLIC ACID, TRIFLUOROACETATE

Example 7 is obtained starting from intermediate 204 in accordance with procedure A described hereinbefore.
$^1$H NMR: (300 MHz, dmso-d6) δ ppm 7.68 (sl, 3H), 2.78 (m, 2H), 2.02 to 1.16 (m, 14H)
ESI/FIA/HR and MS/MS: ESI+/−: infusion: [M+H]+=250.1

EXAMPLE 8: 2-(4-AMINOBUTYL)-1-HYDROXY-1-OXO-1-PHOSPHEPANE-2-CARBOXYLIC ACID, TRIFLUOROACETATE

Example 8 is obtained starting from intermediate 204 in accordance with procedure A described hereinbefore.
$^1$H NMR: (400 MHz, dmso-d6) δ ppm 13 to 11.5 (sl, 1H), 7.75 (sl, 3H), 2.8 (m, 2H), 2.1 to 1.85 (m, 2H), 1.85 to 1.2 (m, 14H)
ESI/FIA/HR and MS/MS: ESI+/−: infusion: [M+H]+=264.1

EXAMPLE 9: 2-[[4-(AMINOMETHYL)PHENYL]METHYL]-1-HYDROXY-1-OXO-1-PHOSPHOLANE-2-CARBOXYLIC ACID, TRIFLUOROACETATE

Example 9 is obtained starting from intermediate 209 in accordance with procedure A described hereinbefore.
$^1$H NMR: (400 MHz, dmso-d6) δ ppm 13 to 12 (sl, 1H), 7.39 (d, 2H), 2.1 to 1.5 (m, 6H), 7.22 (d, 2H), 8.3 (sl, 3H), 3.98 (m, 2H), 3.39/2.75 (2dd, 2H)
ESI/FIA/HR and MS/MS: [M+H]+=284.1048 (284.1051)
Elemental analysis: C=48.29 (48.84); H=5.45 (5.99); N=4.64 (4.38)

EXAMPLE 10: 2-(5-AMINOPENTYL)-1-HYDROXY-1-OXO-1-PHOSPHEPANE-2-CARBOXYLIC ACID, TRIFLUOROACETATE

Example 10 is obtained starting from intermediate 206 in accordance with procedure A described hereinbefore.
$^1$H NMR: (400 MHz, dmso-d6) δ ppm 12 (sl, 1H), 7.68 (sl, 3H), 2.76 (m, 2H), 2.12 to 1.9 (m, 2H), 1.87 to 1.11 (m, 16H)
ESI/FIA/HR and MS/MS: [M+H]+=278.1518 (278.1521)
Elemental analysis: C=41.99 (42.97); H=6.38 (6.44); N=3.53 (3.58)

EXAMPLE 11: 1-HYDROXY-1-OXO-2-(2-PIPERIDIN-4-YLETHYL)-1-PHOSPHINANE-2-CARBOXYLIC ACID, TRIFLUOROACETATE

Example 11 is obtained starting from N-Boc-4-bromoethylpiperidine in accordance with procedure A described hereinbefore.
$^1$H NMR: (400 MHz, dmso-d6) δ ppm 12 (sl, 1H), 8.49-8.2 (2*(m, 2H), 3.24 (dl, 2H), 2.82 (m, 2H), 1.94-1.65-1.45-1.2 (4*(m, 12H), 1.79 (tl, 2H), 1.39 (m, 1H), 1.2 (m, 2H)
ESI/FIA/HR and MS/MS: [M+H]+=290.1526 (290.1521)
Elemental analysis: C=44.65 (44.67); H=5.93 (6.25); N=3.41 (3.47)

EXAMPLE 12: 2-[[3-(AMINOMETHYL)PHENYL]METHYL]-1-HYDROXY-1-OXO-1-PHOSPHINANE-2-CARBOXYLIC ACID, TRIFLUOROACETATE

Example 12 is obtained starting from intermediate 208 in accordance with procedure A described hereinbefore.
$^1$H NMR: (400 MHz, dmso-d6) δ ppm 8.19 (sl, 3H), 7.3 (m, 2H), 7.22 (s, 1H), 7.14 (d, 1H), 3.99 (m, 2H), 3.32/2.97 (2dd, 2H), 1.9 to 1.4 (m, 8H)
ESI/FIA/HR and MS/MS: [M+H]+=298.12 (298.120821)
Elemental analysis: C=47.00 (46.72); H=4.82 (5.15); N=3.39 (3.41)

EXAMPLE 13: 2-(6-AMINOHEXYL)-1-HYDROXY-1-OXO-1-PHOSPHINANE-2-CARBOXYLIC ACID, TRIFLUOROACETATE

Example 13 is obtained starting from intermediate 207 in accordance with procedure A described hereinbefore.
$^1$H NMR: (400 MHz, dmso-d6) δ ppm 7.65 (sl, 3H), 2.77 (m, 2H), 1.93 (m, 2H), 1.8 to 1.14 (m, 16H)
ESI/FIA/HR and MS/MS: [M+H]+=278.1522 (278.15212)
Elemental analysis: C=42.69 (42.97); H=6.26 (6.44); N=3.79 (3.58)

EXAMPLE 14: 2-(4-AMINOBUTYL)-1-HYDROXY-1-OXO-1-PHOSPHOCANE-2-CARBOXYLIC ACID, TRIFLUOROACETATE

Example 14 is obtained starting from intermediate 204 in accordance with procedure A described hereinbefore.
$^1$H NMR: (400 MHz, dmso-d6) δ ppm 7.72 (sl, 3H), 2.8 (m, 2H), 2.11 to 1.32 (m, 18H)
ESI/FIA/HR and MS/MS: [M+H]+=278.1522 (278.1521)
Elemental analysis: C=43.34 (42.97); H=6.35 (6.44); N=2.91 (3.58)

EXAMPLE 15: 2-[(2-AMINOPYRIDIN-4-YL)METHYL]-1-HYDROXY-1-OXO-1-PHOSPHINANE-2-CARBOXYLIC ACID, TRIFLUOROACETATE

Example 15 is obtained starting from intermediate 212 in accordance with procedure A described hereinbefore.
$^1$H NMR: (400 MHz, dmso-d6) δ ppm 13.5 to 12 (sl, 1H), 7.8 (d, 1H), 7.87 (sl, 3H), 6.75 (s, 1H), 6.6 (d, 1H), 3.25/3 (m, 2H), 2 to 1.35 (m, 8H)
ESI/FIA/HR and MS/MS: [M+H]+=285.1012 (285.1004)

EXAMPLE 16: 2-[2-(TRANS-4-AMINOCYCLOHEXYL)ETHYL]-1-HYDROXY-1-OXO-1-PHOSPHINANE-2-CARBOXYLIC ACID, TRIFLUOROACETATE

Example 16 is obtained starting from tert-butyl [trans-4-(2-bromoethyl)cyclohexyl]-carbamate, in accordance with procedure A described hereinbefore.
$^1$H NMR: (300/400/500 MHz, dmso-d6) δ ppm 7.9 (sl, 3H), 2.9 (m, 1H), 2.01 (m, 2H), 1.91-1.74 (2m, 4H), 1.64 (m, 2H), 1.53 (m, 2H), 1.39 (m, 2H), 1.29-0.95 (m, 4H), 1.11 (m, 4H), 1.09 (m, 1H)
$^{13}$C NMR: (300/400/500 MHz, dmso-d6) δ ppm 49.8, 36.8, 31.6, 30.8, 30.5, 30.5, 30.5, 23.6, 22.9
ESI/FIA/HR and MS/MS: [M+H]+=304.1648 (304.1677)

EXAMPLE 17: 2-[2-(CIS-4-AMINOCYCLOHEXYL)ETHYL]-1-HYDROXY-1-OXO-1-PHOSPHINANE-2-CARBOXYLIC ACID, TRIFLUOROACETATE

Example 17 is obtained starting from tert-butyl [cis-4-(2-bromoethyl)cyclohexyl]carbamate, in accordance with procedure A described hereinbefore.
$^1$H NMR: (400/500 MHz, dmso-d6) δ ppm 7.9 (sl, 3H), 3.15 (m, 1H), 1.96-1.62 (2m, 2H), 1.94-1.73 (2m, 2H), 1.71-1.65 (2m, 2H), 1.68-1.65 (2m, 2H), 1.56-1.39 (m, 4H), 1.49-1.36 (2m, 2H), 1.38 (m, 1H), 1.23-1.16 (2m, 2H)

$^{13}$C NMR: (400/500 MHz MHz, dmso-d6) δ ppm 173.3, 51, 47.9, 34, 31, 28.7, 27.9, 26.5, 26.5, 23.4, 21.6

$^{13}$C NMR: (400/500 MHz, dmso-d6) δ ppm 173.3, 51, 47.9, 34, 31, 28.7, 27.9, 26.5, 26.5, 23.4, 21.6

ESI/FIA/HR and MS/MS: [M+H]+=304.1671 (304.1677)

Elemental analysis: C=45.47 (46.05); H=6.68 (6.52); N=3.58 (3.36)

EXAMPLE 18: 2-(5-AMINOPENTYL)-1-HYDROXY-1-OXO-1-PHOSPHOCANE-2-CARBOXYLIC ACID, TRIFLUOROACETATE

Example 18 is obtained starting from intermediate 206 in accordance with procedure A described hereinbefore.

$^1$H NMR: (400 MHz, dmso-d6) δ ppm 12.0-11.0 (sl, 1H), 7.7 (m, 3H), 2.8 (m, 2H), 2.05 (m, 2H), 1.9-1.3 (m, 18H)

ESI/FIA/HR and MS/MS: [M+H]+=292.1656 (292.1677)

Elemental analysis: C=44.17 (44.45); H=6.69 (6.71); N=3.42 (3.46)

EXAMPLE 19: 2-(5-AMINOPENTYL)-1-HYDROXY-1-OXO-1-PHOSPHONANE-2-CARBOXYLIC ACID, TRIFLUOROACETATE

Example 19 is obtained starting from intermediate 206 in accordance with procedure A described hereinbefore.

$^1$H NMR: (400 MHz, dmso-d6) δ ppm 12.4-11 (sl, 1H), 7.7 (sl, 3H), 2.75 (t, 2H), 2.3 (m, 1H), 2.05 (m, 1H), 1.9-1.2 (m, 20H)

ESI/FIA/HR and MS/MS: [M+H]+=306.1834 (306.1834)

Elemental analysis: C=45.54 (45.82); H=6.98 (6.97); N=3.26 (3.34)

Procedure B—Synthesis of the Phosphinanes

Step B1 (Intermediate 6)

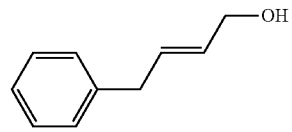

Ethyl (triphenylphosphorylidene)acetate (100 g, 287 mmol, 1.2 eq) is added in portions to a solution of phenylacetaldehyde (28.74 g, 239 mmol) in DCM (380 mL) and at ambient temperature. The reaction mixture is stirred for 20 hours at ambient temperature and then the mixture is concentrated in vacuo. The residue is taken up in heptane (400 mL), stirred for 1 hour, and then the insoluble component is filtered off. The heptane is evaporated off in vacuo and the residue obtained is purified by flash chromatography on silica gel using as eluant a heptane/DCM mixture (60:40). Intermediate 6 (27.25 g, 143 mmol) is obtained in the form of a colourless oil with a yield of 60%.

$^1$H NMR: (400 MHz, CDCl3) δ ppm 7.3 (t, 2H), 7.25 (t, 1H), 7.2 (d, 2H), 7.1 (dt, 1H), 5.8 (d, 1H), 4.2 (quad, 2H), 3.5 (d, 2H), 1.3 (t, 3H)

IR (cm$^{-1}$): 1716, 1653

Step B2 (Intermediate 7)

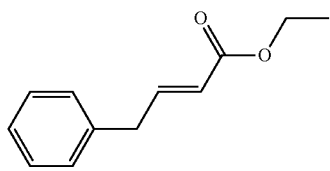

A solution of 1M DIBAlH in THF (355 mL, 355 mmol) is added to a solution of intermediate 6 (28.35 g, 149 mmol) in DCM (375 mL) at ambient temperature and under an argon atmosphere. After 45 minutes at 0° C., the reaction mixture is stirred for 16 hours at ambient temperature. The reaction mixture is then cooled to 0° C. and treated with 3N HCl (300 mL). The mixture is extracted with DCM (350 mL), and the organic phase is washed with H$_2$O (2×100 mL), dried over Na$_2$SO$_4$ and then evaporated in vacuo. The residue obtained is purified by flash chromatography on silica gel using as eluant a heptane/AcOEt mixture (75:25). Intermediate 7 (16.05 g, 108 mmol) is obtained in the form of a colourless oil with a yield of 72%.

$^1$H NMR: (400 MHz, CDCl3) δ ppm 7.1-7.4 (m, 5H), 5.65-5.9 (2m, 2H), 4.1 (d, 2H), 3.35 (d, 2H), 1.5 (m, 1H)

IR (cm$^{-1}$): 3600-3200, 1716, 1650

Step B3 (Intermediate 8)

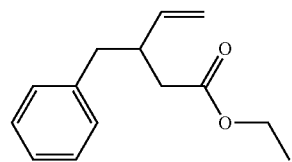 [SMILES: C=CC(CC(=O)OCC)Cc1ccccc1]

A mixture of intermediate 7 (3.7 g, 25 mmol) with triethyl orthoacetate (16.2 g, 100 mmol, 4 eq) and propionic acid (5 drops) is stirred for 1 hour 20 minutes in a microwave (250 W) at 140° C. The mixture is taken up in Et$_2$O (300 mL) and H$_2$O (100 mL). The organic phase is then washed with H$_2$O (100 mL), dried over MgSO$_4$ and then concentrated in vacuo. The residue obtained is purified by flash chromatography on silica gel using as eluant a heptane/AcOEt mixture (80:20). Intermediate 8 (4.53 g, 20.7 mmol) is obtained in the form of an oil with a yield of 83%.

$^1$H NMR: (400 MHz, CDCl3) δ ppm 7.15-7.3 (m, 5H), 5.7 (m, 1H), 5 (m, 2H), 4.1 (q, 2H), 2.85 (m, 1H), 2.7 (m, 2H), 2.25-2.4 (m, 2H), 1.25 (t, 3H)

IR (cm$^{-1}$): 1732, 699-747

Step B4 (Intermediate 9)

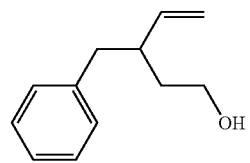

LiAlH$_4$ (6.12 g, 161 mmol, 2 eq) is added in portions to a solution of intermediate 8 (17.58 g, 80.5 mmol) in THF (275 mL) at 0° C. and under argon. The reaction mixture is stirred at ambient temperature for 16 hours. Excess LiAlH$_4$ is hydrolysed by addition of H$_2$O (4.2 mL) and then with a 20% NaOH solution (3.4 mL) and H$_2$O (15.4 mL). The precipitate is filtered off and the filtrate is evaporated in vacuo. The residue obtained is purified by flash chromatography on silica gel using as eluant a heptane/AcOEt mixture (70:30). Intermediate 9 (8.09 g, 45.9 mmol) is obtained in the form of a colourless oil with a yield of 57%.

Step B5 (Intermediate 10)

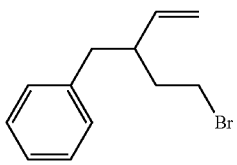

Triphenylphosphine (24.07 g, 91.8 mmol, 2 eq) is added in portions to a solution of intermediate 9 (8.09 g, 45.9 mmol) and CBr$_4$ (30.4 g, 91.8 mmol) at ambient temperature in Et$_2$O (325 mL). The mixture is stirred for 16 hours. The reaction mixture is filtered and the filtrate is evaporated in vacuo. The residue is taken up in heptane (250 mL), stirred for 30 minutes and then filtered. The filtrate is evaporated in vacuo. The residue obtained is purified by flash chromatography on silica gel using heptane as eluant. Intermediate 10 (8.64 g, 36 mmol) is obtained in the form of a colourless oil with a yield of 78%.

$^1$H NMR: (400 MHz, CDCl$_3$) δ ppm 7.28 (t, 2H), 7.18 (t, 1H), 7.13 (d, 2H), 5.53 (ddd, 1H), 5.02 (d, 1H), 5 (d, 1H), 3.42 (m, 1H), 3.3 (m, 1H), 2.65 (d, 2H), 2.53 (m, 1H), 1.95 (m, 1H), 1.8 (m, 1H)

IR (cm$^{-1}$): 916, 739-698

Step B6 (Intermediate 11)

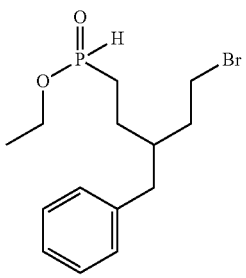 [SMILES: CCO[PH](=O)CCC(CCBr)Cc1ccccc1]

Tetraethyl orthosilicate (3.48 g, 16.7 mmol, 1 eq) is added to a solution of hypophosphorous acid (1.1 g, 16.7 mmol) in acetonitrile (25 mL) under argon and at ambient temperature. The reaction mixture is heated at reflux for 2 hours 30 minutes and then cooled to ambient temperature. The reaction mixture is degassed with argon and then there are added in succession intermediate 10 (2 g, 8.36 mmol) in solution in MeCN (5 mL), Xantphos (0.048 g, 0.0836 mmol) and then Pd$_2$dba$_3$ (0.038 g, 0.0418 mmol). The mixture is heated at reflux for 16 hours. After evaporation in vacuo, the residue obtained is purified by flash chromatography on silica gel using AcOEt as eluant. Intermediate 11 (1.61 g, 4.85 mmol) is obtained in the form of an oil with a yield of 58%.

$^1$H NMR: (400 MHz, dmso-d6) δ ppm centred at 6.95 (d, 1H), 7.3 (t, 2H), 7.2 (m, 3H), 4 (m, 2H), 3.55 (m, 2H), 2.59 (d, 2H), 1.9 (m, 1H), 1.78 (m, 4H), 1.45 (m, 2H), 1.21 (t, 3H)

IR (cm$^{-1}$): 2343

Step B7 (Intermediate 12)

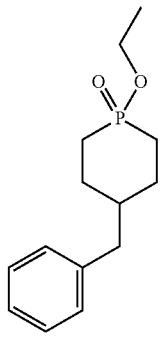 [SMILES: CCOP1(=O)CCC(Cc2ccccc2)CC1]

A solution of 1.06 M LiHMDS in THF (4.53 mL, 4.8 mmol, 1 eq) is added dropwise at −78° C. to a solution of intermediate 11 (1.6 g, 4.8 mmol) in 50 mL THF and under an argon atmosphere. The reaction mixture is stirred for 30 minutes at −78° C. and then for 4 hours 30 minutes at ambient temperature, before being treated with a saturated NaCl solution (50 mL). After addition of AcOEt (150 mL), the organic phase is dried over MgSO$_4$ and then evaporated in vacuo. The residue obtained is purified by flash chromatography on silica gel using a DCM/EtOH mixture (95:5) as eluant. Intermediate 12 (0.889 g, 3.52 mmol) is obtained in the form of a colourless oil with a yield of 73%.

$^1$H NMR: (400 MHz, CDCl3) δ ppm 7.3 (t, 2H), 7.2 (t, 1H), 7.12 (d, 2H), 4.08 (m, 2H), 2.6/2.51 (2d, 2H), 2.1-1.8 (m, 4H), 1.8-1.55 (m, 3H), 1.5-1.3 (m+t, 5H)

IR (cm$^{-1}$): 3433

Step B8 (Intermediate 13)

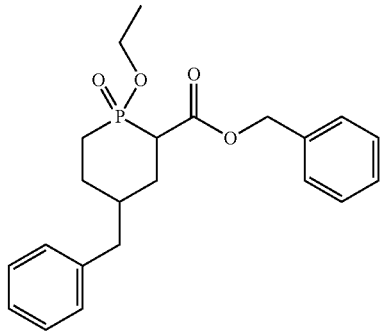 [SMILES: CCOP1(=O)CCC(Cc2ccccc2)CC1C(=O)OCc1ccccc1]

A solution of 2M LDA in THF (2.6 mL, 5.2 mmol, 1.5 eq) is added to a solution of intermediate 12 (0.875 g, 3.47 mmol) in THF (10 mL) at −78° C. and under argon. After 40 minutes, a solution of dibenzyl carbonate (1.18 g, 4.85 mmol) in THF (5 mL) is added dropwise. The reaction mixture is stirred for 1 hour, and then a further 1.5 eq of 2M LDA in THF (2.6 mL, 5.2 mmol) is added. After 4 hours at −78° C., the reaction mixture is hydrolysed while cold with a 10% aqueous NH₄Cl solution (9 mL). AcOEt (18 mL) and a 10% aqueous NH₄Cl solution (18 mL) are then added. After returning to ambient temperature, the reaction mixture is extracted with AcOEt (2×50 mL). The organic phase is dried over MgSO₄ and then concentrated in vacuo. The residue obtained is purified by flash chromatography on silica gel using a DCM/EtOH mixture (97.5:2.5) as eluant. Intermediate 13 (0.996 g, 2.58 mmol) is obtained in the form of an oil with a yield of 74%.

$^1$H NMR: (400 MHz, CDCl3) δ ppm 7.4-7 (m, 10H), 5.18 (s, 2H), 4.15-3.9 (m, 2H), 3.2-2.8 (1 dd, 1H), 2.58 (d, 2H), 2.3-1.4 (m, 7H), 1.25 (t, 3H)

IR (cm$^{-1}$): 1726

Step B9 (Intermediate 14)

A solution of intermediate 206 (1.11 g, 3.03 mmol, 1.3 eq) in DMSO (5 mL) and a solution of intermediate 13 (0.9 g, 2.33 mmol) in DMSO (4 mL) are added dropwise, in succession, to a suspension of sodium hydride (0.150 g, 3.75 mmol, 1.6 eq) in DMSO (5 mL). After stirring for 4 hours at ambient temperature, the reaction mixture is added at 0° C. to a mixture (1:1) of a 10% NH₄Cl solution (100 mL) and AcOEt (100 mL). The aqueous phase is re-extracted with AcOEt (2×50 mL). The organic phases are combined, dried over MgSO₄ and then concentrated in vacuo. Intermediate 14 so obtained is used directly without being purified further.

Step B10 (Intermediates 15 and 16)

TMSBr (3.68 mL, 28 mmol, 12 eq) is added to a solution of intermediate 14 (1.56 g, 2.33 mmol) in DCM (125 mL) at ambient temperature and under argon. The reaction mixture is stirred for 16 hours at ambient temperature, before being concentrated in vacuo. The oil obtained is taken up in MeOH (60 mL), stirred for 30 minutes and concentrated in vacuo. The same operation is repeated twice. The residue obtained is purified by reverse-phase chromatography using as eluant an H₂O/MeCN/TFA gradient. Intermediates 15 (0.423 g, 0.95 mmol) and then 16 (0.155 g, 0.35 mmol) (in the order of elution) are obtained in the form of white solids after lyophilisation with yields of 41% and 15%, respectively. The absolute configuration of intermediates 15 and 16 has not been verified.

Intermediate 15: Benzyl 2-(5-aminopentyl)-4-benzyl-1-hydroxy-1-oxo-1-phosphinane-2-carboxylate, trifluoroacetate—dia 1 racemic $^1$H NMR: (400 MHz, dmso-d6) δ ppm 12 (m, 1H), 7.75 (m, 3H), 7.35-7.05 (m, 10H), 5.18/5 (2d, 2H), 2.6 (m, 3H), 2.4 (dd, 1H), 2.1 (m, 1H), 1.9-1.5 (m, 8H), 1.4 (m, 2H), 1.15 (m, 2H), 0.8/0.52 (2m, 2H)

$^{19}$F NMR: (400 MHz, dmso-d6) δ ppm −74

IR (cm$^{-1}$): 3300-2500, 1716, 1678

Intermediate 16: Benzyl 2-(5-aminopentyl)-4-benzyl-1-hydroxy-1-oxo-1-phosphinane-2-carboxylate, trifluoroacetate—dia 2 racemic $^1$H NMR (400 MHz, dmso-d6) δ ppm 7.4 (m, 5H), 7.25 (t, 2H), 7.18 (t, 1H), 7 (d, 2H), centred at 5.11 (AB, 2H), 7.65 (m, 3H), 2.71 (m, 2H), 2.4 (d, 2H), 1.95-1.1 (m, 15H)

$^{19}$F NMR: (400 MHz, dmso-d6) δ ppm −74

IR (cm$^{-1}$): 3300-2500, 1774, 1716, 1676

EXAMPLE 20: 2-(5-AMINOPENTYL)-4-BENZYL-1-HYDROXY-1-OXO-1-PHOSPHINANE-2-CARBOXYLIC ACID, DIA 1 RACEMIC

Intermediate 15 (0.413 g, 0.74 mmol) in solution in 60 mL of a H₂O/MeOH mixture (3:1) is stirred at ambient temperature under an H₂ atmosphere, in the presence of 10% Pd/C (41 mg), for 4 hours. The reaction mixture is filtered and then concentrated in vacuo. The residue obtained is purified by reverse-phase chromatography using as eluant an H₂O/MeCN gradient. Example 20 (0.209 g, 0.591 mmol) is obtained in the form of a white solid after lyophilisation with a yield of 80%.

$^1$H NMR: (500 MHz, D2O) δ ppm 7.3 (t, 2H), 7.24 (d, 2H), 7.19 (t, 1H), 2.59/2.37 (m, 2H), 2.41 (t, 2H), 1.91/1.55 (m, 2H), 1.77/1.6 (m, 2H), 1.77/1.35 (m, 2H), 1.64/1.38 (m, 2H), 1.63 (m, 1H), 1.24 (m, 2H), 1.16/1.1 (m, 2H), 0.7 (m, 2H)

$^{13}$C NMR: (500 MHz, D2O) δ ppm 129.2, 128.2, 125.7, 42.5, 40, 35.5, 35.4, 31.3, 31.1, 30.2, 26, 25.9, 22.8

IR (cm$^{-1}$): 3300-2100, 1691, 1631, 1605

Elemental analysis: C=60.65 (61.18); H=7.58 (7.99); N=3.91 (3.96)

ESI/FIA/HR and MS/MS: [M+H]+=354.1831 (354.1834)

EXAMPLE 21: 2-(5-AMINOPENTYL)-4-BENZYL-1-HYDROXY-1-OXO-1-PHOSPHINANE-2-CARBOXYLIC ACID, DIA 2 RACEMIC

Intermediate 16 (0.148 g, 0.265 mmol) in solution in 20 mL of an H₂O/MeOH mixture (3:1) is stirred at ambient temperature under an H₂ atmosphere, in the presence of 10% Pd/C (15 mg), for 2 hours 30 minutes. The reaction mixture is filtered and then concentrated in vacuo. The residue obtained is purified by reverse-phase chromatography using as eluant an H₂O/MeCN gradient. Example 21 (0.053 g, 0.15 mmol) is obtained in the form of a white solid after lyophilisation with a yield of 56%.

$^1$H NMR: (500 MHz, D2O) δ ppm 7.29 (t, 2H), 7.2 (d, 2H), 7.2 (t, 1H), 2.57 (t, 2H), 2.45 (m, 2H), 1.84 (m, 1H), 1.81/1.33 (m)+(m, 1+1H), 1.78/1.29 (m)+(m, 1+1H), 1.69/1.31 (m)+(m, 1+1H), 1.68/1.27 (m)+(m, 1+1H), 1.41/1.19 (m)+(m, 1+1H), 1.38 (m, 2H), 1.2 (m, 2H)

$^{13}$C NMR: (500 MHz, D₂O) δ ppm 129.3, 128.2, 125.7, 43, 42.4, 40, 35.9, 34.6, 30.4, 29.4, 27, 26.7, 25

IR (cm$^{-1}$): 3250-1800, 1694+1661, 1618

Elemental analysis: C=61.18 (61.18); H=7.90 (7.99); N=3.96 (3.96)

ESI/FIA/HR and MS/MS: [M+H]+=354.1837 (354.1834)

In the same manner, Examples 22 and 23 are obtained in accordance with procedure B described hereinbefore by replacing intermediate 206 by intermediate 204.

EXAMPLE 22: 2-(4-AMINOBUTYL)-4-BENZYL-1-HYDROXY-1-OXO-1-PHOSPHINANE-2-CARBOXYLIC ACID, DIA 1 RACEMIC $^1$H NMR: (400 MHz, dmso-d6) δ ppm 7.7 (sl, 3H), 7.3 (dd, 2H), 7.2 (dd+t, 3H), 2.7 (m, 2H), 2.55-2.4 (m, 2H), 1.95 (m, 1H), 1.8-13 (m, 10H), 1.1-0.85 (m, 2H)

ESI/FIA/HR and MS/MS: [M+H]+=340.1677 (340.1677)

Elemental analysis: C=51.00 (50.33); H=5.90 (6.00); N=3.22 (3.09)

EXAMPLE 23: 2-(4-AMINOBUTYL)-4-BENZYL-1-HYDROXY-1-OXO-1-PHOSPHINANE-2-CARBOXYLIC ACID, DIA 2 RACEMIC $^1$H NMR: (300 MHz, dmso-d6) δ ppm 15.8 (m, 2H), 7.95 (m, 2H), 7.25 (t, 2H), 7.18 (t, 1H), 7.1 (d, 2H), 2.75 (m, 2H), 2.6-2.35 (m, 2H), 2.15 (m, 1H), 1.75-1 (m, 12H)

ESI/FIA/HR and MS/MS: [M+H]+=340.1683 (340.1677)

Elemental analysis: C=60.20 (60.17); H=7.34 (7.72); N=3.96 (4.13)

Synthesis of the Azaphosphinanes

Intermediate 17

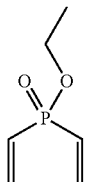

Intermediate 17 was synthesised using a procedure described in the literature by V. Gouverneur et al., *J. Org. Chem.* 2005, 70, 10803.

A 1M solution in THF of vinyl magnesium bromide (170 mL, 170 mmol, 2 eq) is added to a solution of ethyl dichlorophosphinate (10 mL, 84.26 mmol) in 100 mL of THF at −78° C. and under argon. Stirring is maintained for 1 hour at −78° C. EtOH (30 mL) is then added dropwise and the reaction mixture is returned to ambient temperature. The reaction mixture is then concentrated under reduced pressure and the residue obtained is purified by flash chromatography on silica gel using a DCM/EtOH mixture (96:4) as eluant. Intermediate 17 (6.37 g, 43.6 mmol) is obtained in the form of a colourless oil with a yield of 52%.

$^1$H NMR: (400 MHz, DMSO-d$_6$) δ 6.1-6.4 (m, 6H), δ 3.90 (q, 2H), δ 1.25 (t, 3H).

IR (cm$^{-1}$): 3500 (OH(H$_2$O)), 1609 (C=C), 1210 (P=O), 1032 and 935 cm$^{-1}$ (P—O).

GC: t$_r$ 5.83 min.

Intermediate 18

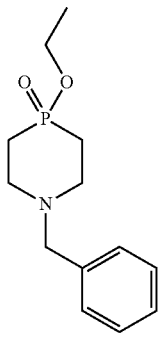 [SMILES: CCOP1(=O)CCN(Cc2ccccc2)CC1]

N-benzylamine (4.79 mL, 43.6 mmol, 1 eq.) is added in a single batch to a solution of intermediate 17 (6.37 g, 43.6 mmol) in an autoclave and under argon. The reaction mixture is heated to 100° C., stirred for 16 hours and concentrated under reduced pressure. The residue is taken up in AcOEt (100 mL), and the organic phase is washed with a saturated NaCl solution (3×100 mL) and dried over MgSO$_4$. The solvent is evaporated off and the residue obtained is purified by flash chromatography on silica gel using a DCM/EtOH mixture (95:5) as eluant. Intermediate 18 (8.68 g, 34.3 mmol) is obtained in the form of a yellowish oil with a yield of 79%.

$^1$H NMR: (CDCl$_3$, 400 MHz) δ 7.31 (m, 5H), 4.08 (m, 2H), 3.60 (s, 2H), 2.98 (m, 2H), 2.64 (m, 2H), 1.97 (m, 2H), 1.85 (m, 2H), 1.35 (t, 3H).

GC: t$_r$ 12.29 min.

Intermediate 19

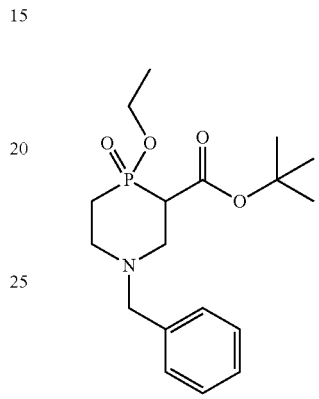

A solution of 2M LDA (75.6 mL, 37.8 mmol, 1.5 eq) in THF is added to a solution of intermediate 18 (6.38 g, 25.19 mmol) in THF (30 mL) at −70° C. and under argon. After 15 minutes at −70° C., a solution of Boc$_2$O (7.68 g, 35.3 mmol, 1.4 eq) in 30 mL of THF is then added dropwise. Stirring is maintained for 90 minutes and 1.5 eq of LDA (75.6 mL, 37.8 mmol) are then added dropwise. When the addition is complete, the reaction mixture is maintained at −70° C. for 90 minutes. A saturated NH$_4$Cl solution (30 mL) as well as AcOEt (60 mL) are added and the reaction mixture is slowly returned to ambient temperature. The product is then extracted with AcOEt (2×150 mL). The organic phases are combined, washed with a saturated NaCl solution (2×150 mL), dried over MgSO$_4$ and concentrated under reduced pressure. The residue obtained is purified by flash chromatography on silica gel using a DCM/THF gradient (95:5 to 40:60) as eluant. Intermediate 19 (6.73 g, 19.04 mmol) is obtained in the form of a yellowish oil with a yield of 76%.

$^1$H NMR: (CDCl$_3$, 400 MHz) δ 7.35 to 7.2 (m, 5H), δ 4.3 to 4.05 (m, 2H), δ 3.60 (dd, 2H), δ 3.3 to 2.5 (m, 5H), δ 2.1 to 1.8 (m, 2H), δ 1.50 (s, 9H), δ 1.35 (t, 3H).

IR (cm$^{-1}$): 3500 (OH), 1721 (C=O), 1150 (P=O), 1032 and 935 (P—O).

MS: m/z 355 [M+1].

Procedure C: Procedure for alkylation of intermediate 19

60% NaH (8 mmol, 1.6 eq) at 10° C. is added in portions to a solution of intermediate 204 to 212 (5 mmol, 1 eq) in DMSO (10 mL) under argon. Intermediate 19 (5 mmol) in solution in DMSO (5 mL) is then added to the suspension and the mixture is stirred for 4 hours at ambient temperature. The reaction mixture is then hydrolysed with an aqueous NH$_4$Cl solution (50 mL) and extracted with AcOEt (2×100 mL). The organic phase is washed with H$_2$O (2×100 mL), dried over MgSO$_4$ and concentrated in vacuo. The residue obtained is purified by flash chromatography on silica gel using as eluant a DCM/AcOEt gradient (90:10 to 50:50). Intermediate 20a-f is obtained in the form of a mixture of 4 diastereoisomers.

Procedure D: Deprotection of the Amino and Phosphinic Functions

TMSBr (7.92 mL, 60 mmol, 12 eq) is added dropwise to a solution of intermediate 20a-f (5 mmol) in DCM (40 mL) under argon and at ambient temperature. The mixture is stirred for 16 hours at ambient temperature and then concentrated in vacuo. The residue is taken up in MeOH (40 mL) and stirred for 20 minutes at ambient temperature, before being evaporated to dryness. The evaporate is dissolved in DCM (20 mL), and trifluoroacetic acid (44.6 mL, 60 mmol, 12 eq) is added. The reaction mixture is stirred for 10 hours at ambient temperature and then concentrated in vacuo. The residue obtained is purified by reverse-phase chromatography using as eluant an H$_2$O/MeCN gradient. The final product (Examples 24 to 30) (zwitterion or TFA salt), a mixture of 2 enantiomers, is obtained in the form of a white solid after lyophilisation.

Intermediate 20a: tert-Butyl 3-{3-[bis(tert-butoxycarbonyl)amino]propyl}-1-benzyl-4-ethoxy-4-oxo-1,4-azaphosphinane-3-carboxylate Intermediate 20a is obtained starting from intermediates 19 and 205 in accordance with procedure C described hereinbefore.

$^1$H NMR: (400 MHz, dmso-d6) δ ppm 7.35-7.2 (m, 5H), 4 (m, 2H), 3.8 (m, 2H), centred at 3.52 (AB, 2H), 3-2.25 (m, 4H), 2-1.8 (m, 4H), 1.45/1.35 (2s, 27H), 1.2 (t, 3H), 1.2 (m, 2H)

EXAMPLE 24: 3-(3-AMINOPROPYL)-1-BENZYL-4-HYDROXY-4-OXO-1,4-AZAPHOSPHINANE-3-CARBOXYLIC ACID

Example 24 is obtained starting from intermediate 20a in accordance with procedure D described hereinbefore.

$^1$H NMR: (400 MHz, D2O) δ ppm 7.5 (m, 5H), centred at 4.35 (AB, 2H), 3.75/3.35 (2m, 2H), 3.5/3.15 (2dd, 2H), 2.92 (t, 2H), 2.3/1.8 (2m, 2H), 1.95 (m, 1H), 1.6-1.4 (m, 3H)

ESI/FIA/HR and MS/MS: [M+H]+=327.1478 (327.1473)

Elemental analysis: C=55.38 (55.21); H=6.85 (7.10); N=8.41 (8.58)

Intermediate 20b: tert-Butyl 3-{4[bis(tert-butoxycarbonyl)amino]butyl}-1-benzyl-4-ethoxy-4-oxo-1,4-azaphosphinane-3-carboxylate Intermediate 20b is obtained starting from intermediates 19 and 204 in accordance with procedure C described hereinbefore.

$^1$H NMR: (DMSO-d$_6$, 400 MHz) δ 7.30 (m, 5H), 3.97 (m, 2H), 3.63-3.43 (dd, 2H), 3.36 (m, 2H), 2.93-2.33 (m, 2H), 2.79 to 2.47 (m, 2H), 1.93 (m, 2H), 1.93 (m, 2H), 1.43 (m, 2H), 1.42 (s, 18H), 1.36 (s, 9H), 1.21 (t, 3H), 0.83 (m, 2H). IR (cm$^{-1}$): 1744, 1711 cm$^{-1}$ (C=O), 1276 cm$^{-1}$ (P=O).

EXAMPLE 25: 3-(4-AMINOBUTYL)-1-BENZYL-4-HYDROXY-4-OXO-1,4-AZAPHOSPHINANE-3-CARBOXYLIC ACID

Example 25 is obtained in accordance with procedure D described hereinbefore starting from intermediate 20b.

$^1$H NMR: (400 MHz, dmso-d6) δ ppm 8.2 (sl, 3H), 7.3 (m, 5H), 3.7/3.5 (2*(d, 1+1H), 3.05/2.4 (2*(m, 1+1H), 2.75/2.55 (2*(m, 1+1H), 2.7 (m, 2H), 1.8 (m, 1H), 1.6-1.1 (m, 7H)

ESI/FIA/HR and MS/MS: [M+H]+=341.1628 (341.1630)

Elemental analysis: C=55.99 (56.46); H=7.14 (7.40); N=8.13 (8.23)

Intermediate 20c: tert-Butyl 3-{5-bis(tert-butoxycarbonyl)amino]pentyl}-1-benzyl-4-ethoxy-4-oxo-1,4-azaphosphinane-3-carboxylate Intermediate 20c is obtained starting from intermediates 19 and 206 in accordance with procedure C described hereinbefore.

$^1$H NMR: (400 MHz, dmso-d6) δ ppm 7.32-7.2 (m, 5H), 3.99 (m, 2H), 3.8 (m, 2H), centred at 3.5 (AB, 2H), 3-2.3 (m, 4H), 2-1.8 (m, 4H), 1.45/1.35 (2s, 27H), 1.35/1.15 (2m, 4H), 1.2 (t, 3H), 0.75 (m, 2H)

EXAMPLE 26: 3-(5-AMINOPENTYL)-1-BENZYL-4-HYDROXY-4-OXO-1,4-AZAPHOSPHINANE-3-CARBOXYLIC ACID

Example 26 is obtained starting from intermediate 20c in accordance with procedure D described hereinbefore.

$^1$H NMR: (400 MHz, D2O) δ ppm 7.5 (m, 5H), centred at 4.32 (AB, 2H), 3.7/3.35 (2m, 2H), 3.5/3.1 (2dd, 2H), 2.9 (t, 2H), 2.2/1.78 (2m, 2H), 1.95/1.45 (2m, 2H), 1.6 (m, 2H), 1.3 (m, 2H), 1.1 (m, 2H)

ESI/FIA/HR and MS/MS: [M+H]+=355.1792 (355.1786)

Elemental analysis: C=58.04 (57.62); H=7.37 (7.68); N=7.95 (7.90)

Intermediate 20d: tert-Butyl 1-benzyl-3-({6-[bis-tert-butoxycarbonyl)amino]pyridin-3-yl}methyl)-4-ethoxy-4-oxo-1,4-azaphosphinane-3-carboxylate Intermediate 20d is obtained starting from intermediates 19 and 211 in accordance with procedure C described hereinbefore.

$^1$H NMR: (400 MHz, dmso-d6) δ ppm 8.18 (s, 1H), 7.4-7.25 (m, 6H), 7.18 (d, 1H), 4 (m, 2H), 3.8 (m, 2H), 3.58/3.5 (2d, 2H), 3-2.6 (m, 4H), 2.25/2.1 (2m, 2H), 1.4 (s, 27H), 1.2 (t, 3H)

EXAMPLE 27: 3-[(6-AMINOPYRIDIN-3-YL)METHYL]-1-BENZYL-4-HYDROXY-4-OXO-1,4-AZAPHOSPHINANE-3-CARBOXYLIC ACID

Example 27 is obtained starting from intermediate 20d in accordance with procedure D described hereinbefore.

$^1$H NMR: (400 MHz, D2O) δ ppm 7.51 (dd, 1H), 7.42 (d, 1H), 7.4-7.25 (m, 5H), 6.75 (d, 1H), centred at 4.25 (AB, 2H), 3.78 (m, 1H), 3.4 (dd+m, 2H), 2.95 (dd, 1H), 2.7 (dd, 1H), 2.6 (dd, 1H), 2.28/1.85 (2m, 2H)

ESI/FIA/HR and MS/MS: [M+H]+=376.1418 (376.1426)

Elemental analysis: C=57.18 (57.60); H=5.82 (5.91); N=11.25 (11.19)

EXAMPLE 28: 3-[(2-AMINOPYRIDIN-4-YL)METHYL]-1-BENZYL-4-HYDROXY-4-OXO-1,4-AZAPHOSPHINANE-3-CARBOXYLIC ACID

Example 28 is obtained starting from intermediates 19 and 212 in accordance with procedures C and D described hereinbefore without intermediate purification.

$^1$H NMR: (400 MHz, D2O) δ ppm 7.6 (dl, 1H), 7.4 (m, 5H), 6.55 (m, 2H), 4.6/4 (dd, 2H), 3.9-3.4 (m, 2H), 3.6/2.75 (dd, 2H), 3/2.7 (dd, 2H), 2.3/1.9 (m, 2H)
ESI/FIA/HR and MS/MS: [M+H]+=376.1428 (376.1426)
Elemental analysis: C=56.70 (57.60); H=5.45 (5.91); N=10.87 (11.19)

Intermediate 20e: tert-Butyl 1-benzyl-3-(3-{[bis-(tert-butoxycarbonyl)amino]methyl}-benzyl)-4-ethoxy-4-oxo-1,4-azaphosphinane-3-carboxylate Intermediate 20e is obtained starting from intermediates 19 and 208 in accordance with procedure C described hereinbefore.
$^1$H NMR: (400 MHz, dmso-d6) δ ppm 7.4-7.3 (m, 5H), 7.15 (t, 1H), 7.1 (sl, 1H), 7.05/6.95 (d, 2H), 4.6 (s, 2H), 4 (m, 2H), 3.7/3.45 (dd, 2H), 3.35 (m, 2H), 2.9/2.15 (m, 2H), 2.7/2.55 (dd, 2H), 2.05 (m, 2H), 1.4 (s, 27H), 1.2 (t, 3H)

EXAMPLE 29: 3-[[3-(AMINOMETHYL)PHENYL]METHYL]-1-BENZYL-4-HYDROXY-4-OXO-1,4-AZAPHOSPHINANE-3-CARBOXYLIC ACID

Example 29 is obtained starting from intermediate 20e in accordance with procedure D described hereinbefore.
$^1$H NMR: (400 MHz, D2O) δ ppm 7.3 (m, 5H), 7.3-7.05 (m, 4H), 4.4/3.95 (dd, 2H), 4 (dd, 2H), 3.8-3.3 (m, 2H), 3.55/2.75 (dd, 2H), 3/2.7 (dd, 2H), 2.2/1.8 (m, 2H)
ESI/FIA/HR and MS/MS: [M+H]+=389.1623 (389.1630)
Elemental analysis: C=61.37 (61.85); H=6.30 (6.49); N=7.05 (7.21)

Intermediate 20f: tert-Butyl 1-benzyl-3-(4-{[bis(tert-butoxycarbonyl)amino]methyl)}-benzyl)-4-ethoxy-4-oxo-1,4-azaphosphinane-3-carboxylate Intermediate 20f is obtained starting from intermediates 19 and 209 in accordance with procedure C described hereinbefore.
$^1$H NMR: (400 MHz, dmso-d6) δ ppm 7.35 (m, 5H), 6.99 (d, 2H), 6.91 (d, 2H), 4.6 (s, 2H), 3.98 (m, 2H), 3.5 (s, 2H), 3.27 (m, 2H), 2.95/2.22 (2*m, 2H), 2.75/2.49 (2*m, 2H), 2.05 (m, 2H), 1.35 (2*s, 27H), 1.18 (t, 3H)
$^{13}$C NMR: (400 MHz, dmso-d6) δ ppm 152, 138, 137, 135, 130, 128, 126, 82, 62, 60, 55.5, 50.5, 48.5, 34, 28, 24.5, 16

EXAMPLE 30: 3-[[4-(AMINOMETHYL)PHENYL]METHYL]-1-BENZYL-4-HYDROXY-4-OXO-1,4-AZAPHOSPHINANE-3-CARBOXYLIC ACID

Example 30 is obtained starting from intermediate 20f in accordance with procedure D described hereinbefore.
$^1$H NMR: (400 MHz, D2O) δ ppm 7.2 (m, 5H), 7.1/7 (dd, 4H), 4.3/3.9 (dd, 2H), 4 (m, 2H), 3.7-3.25 (m, 2H), 3.45/2.65 (dd, 2H), 2.9/2.65 (dd, 2H), 2.15/1.75 (m, 2H)
ESI/FIA/HR and MS/MS: [M+H]+=389.1623 (389.1630)
Elemental analysis: C=61.41 (61.85); H=6.36 (6.49); N=7.40 (7.21)

Intermediate 20b: tert-Butyl 3-{4[bis(tert-butoxycarbonyl)amino]butyl}-1-benzyl-4-ethoxy-4-oxo-1,4-azaphosphinane-3-carboxylate DMSO (30 mL) and 60% NaH (8.48 g, 212 mmol, 1.5 eq) are introduced in succession, under an argon atmosphere, into a 1 L three-necked flask equipped with mechanical stirring. The flask is maintained at ambient temperature by means of a water bath. A solution of intermediate 204 (54.6 g, 155 mmol, 1.1 eq) in DMSO (25 mL) is then added dropwise over a period of 5 minutes. A solution of intermediate 19 (50 g, 141.5 mmol) in DMSO (120 mL) is then added dropwise, the temperature being maintained below 20° C. When the addition is complete, 100 mL of anhydrous THF are then added in order that stirring can be maintained. After 3 hours, the reaction mixture is cooled by means of an ice-water bath and hydrolysed by addition of 500 mL of a saturated NH4Cl solution. The mixture is then extracted with AcOEt (3×300 mL). The organic phases are then combined, washed with a saturated NaCl solution (2×300 mL) and dried over MgSO4, before being concentrated under reduced pressure. The yellowish residue (92.5 g) so obtained is then purified by chromatography on silica gel using a $CH_2Cl_2$/AcOEt/MeOH mixture as eluant. The expected product (69.3 g, 110.9 mmol), a mixture of 4 diastereoisomers, is obtained in the form of a white solid with a yield of 78%.
Procedure E: Procedure for Debenzylation by Hydrogenolysis Intermediate 21: tert-Butyl 3-{4-[bis(tert-butoxycarbonyl)amino]butyl}-4-ethoxy-4-oxo-1,4-azaphosphinane-3-carboxylate Intermediate 20b (73.6 g, 117.8 mmol), ethanol (1 L), Pd/C (7.36 g, 10% by mass) and 37% HCl (7.85 mL, 0.8 eq) are introduced in succession into a 2 L flask at ambient temperature and under a stream of argon. The argon is then replaced by a hydrogen atmosphere. The reaction is monitored by LC/MS. After 4 hours, the reaction is complete and the catalyst is filtered off over glass fibre. The filtrate is evaporated to dryness in order to obtain a yellow oil, which is taken up in AcOEt (400 mL) and in a 10% $NaHCO_3$ solution (400 mL). After decantation, the aqueous phase is extracted with AcOEt (3×100 mL). The organic phases are combined and then washed with a saturated NaCl solution (400 mL), dried over MgSO4 and concentrated to yield the expected intermediate 21 in the form of a white solid (57.6 g, 107.7 mmol) with a yield of 91%.
$^1$H NMR: (DMSO-$d_6$, 400 MHz) δ 4.05 to 3.85 (m, 2H), 3.45 (m, 2H), 3.1 to 2.6 (m, 4H), 2.3-1.7 (m, 4H), 1.45 (s, 18H), 1.40 (s, 9H), 1.20 (t, 3H), 1.5-0.9 (m, 4H).
IR (cm$^{-1}$): 3100-3500 cm$^{-1}$ (OH), 3314 cm$^{-1}$ (NH), 1712-1693 cm$^{-1}$ (C=O).
Procedure L: Procedure for Synthesis of the Aldehydes $Ar_2$—$Ar_1$—CHO by a Suzuki Coupling
The Non-Commercial Aldehydes were Prepared in Accordance with the Procedure Described Below:
Ethanol (500 mL), boronic acid $Ar_2$—$B(OH)_2$ (92.7 mmol, 1.2 eq) and bromoarylaldehyde or bromoheteroarylaldehyde Br—$Ar_1$—CHO (77.3 mmol) are introduced in succession into a 1 L flask under argon and at ambient temperature. The solution is degassed with argon for 15 minutes. Pd(PPh$_3$)$_4$ (1.78 g, 1.55 mmol) and Na$_2$CO$_3$ (92.7 mL of a 2M solution in H$_2$O, 185 mmol, 2.4 eq) are then introduced in a single portion. After the addition, the reaction mixture is heated at reflux for 5 hours. The mixture is then evaporated to dryness. The residue is taken up in DCM (1 L) and H$_2$O (200 mL). After decantation, the aqueous phase is extracted with DCM (200 mL). The organic phases are combined and then washed with a saturated NaCl solution (400 mL), dried over MgSO4 and concentrated under reduced pressure. The residue is then purified by flash chromatography on silica gel. The expected product is obtained with yields of from 59 to 94%.

Intermediate 213

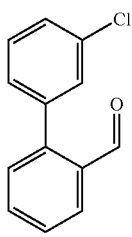

¹H NMR: (400 MHz, dmso-d6) δ ppm 9.89 (s, 1H), 7.94 (dd, 1H), 7.77 (td, 1H), 7.63 (tl, 1H), 7.54 (dl, 1H), 7.54/7.4 (2m, 4H)

Intermediate 214

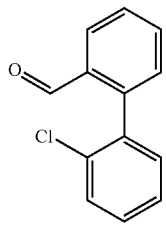 [SMILES: O=Cc1ccccc1-c1ccccc1Cl]

¹H NMR: (400/500 MHz, dmso-d6) δ ppm 9.72 (s, 1H), 7.96 (d, 1H), 7.79 (t, 1H), 7.65 (t, 1H), 7.6 (t, 1H), 7.48 (m, 3H), 7.4 (d, 1H)

Intermediate 215

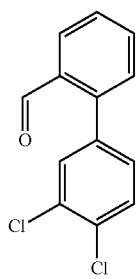 [SMILES: O=Cc1ccccc1-c1ccc(Cl)c(Cl)c1]

¹H NMR: (400/500 MHz, dmso-d6) δ ppm 9.91 (s, 1H), 7.95 (d, 1H), 7.78 (m, 1H), 7.78 (m, 1H), 7.74 (d, 1H), 7.64 (t, 1H), 7.53 (d, 1H), 7.44 (dd, 1H)
DEI (70 eV): [M]+.=250

Intermediate 216

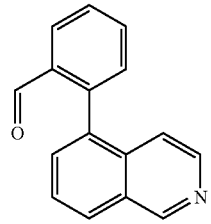 [SMILES: O=Cc1ccccc1-c1cccc2cnccc12]

¹H NMR: (400 MHz, dmso-d6) δ ppm 9.59 (s, 1H), 9.43 (s, 1H), 8.46 (d, 1H), 8.26 (d, 1H), 8.06 (d, 1H), 7.85 (t, 1H), 7.81 (t, 1H), 7.77 (d, 1H), 7.74 (t, 1H), 7.51 (d, 1H), 7.24 (d, 1H)

Intermediate 217

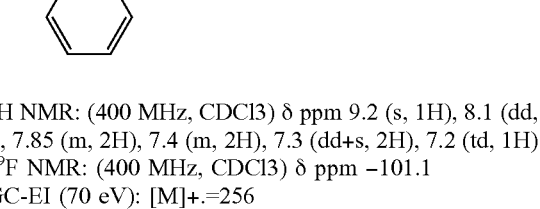

¹H NMR: (400 MHz, CDCl3) δ ppm 9.2 (s, 1H), 8.1 (dd, 1H), 7.85 (m, 2H), 7.4 (m, 2H), 7.3 (dd+s, 2H), 7.2 (td, 1H)
¹⁹F NMR: (400 MHz, CDCl3) δ ppm −101.1
GC-EI (70 eV): [M]+.=256

Intermediate 218

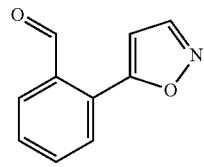 [SMILES: O=Cc1ccccc1-c1ccno1]

¹H NMR: (400 MHz, dmso-d6) δ ppm 9.25 (s, 1H), 8.8 (d, 1H), 8 (m, 1H), 7.85 (m, 1H), 7.85/7.75 (2m, 2H), 7.05 (d, 1H)

Intermediate 219

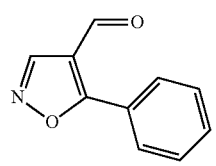 [SMILES: O=Cc1cnoc1-c1ccccc1]

¹H NMR: (400 MHz, dmso-d6) δ ppm 10.05 (s, 1H), 9.2 (s, 1H), 8.05 (m, 2H), 7.7 (m, 3H)

Intermediate 220

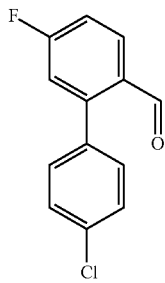

¹H NMR: (400 MHz, dmso-d6) δ ppm 9.81 (s, 1H), 8.02 (dd, 1H), 7.58/7.52 (2d, 4H), 7.46 (td, 1H), 7.4 (dd, 1H)

GC-EI (70 eV): [M]+.=234

Intermediate 221

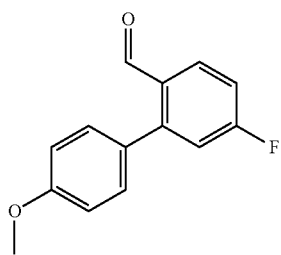 [SMILES: COc1ccc(-c2cc(F)ccc2C=O)cc1]

¹H NMR: (400 MHz, dmso-d6) δ ppm 9.82 (s, 1H), 7.97 (dd, 1H), 7.42 (d, 2H), 7.38 (td, 1H), 7.35 (dd, 1H), 7.09 (d, 2H), 3.83 (s, 3H)

Intermediate 222

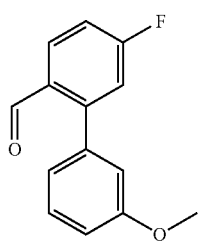 [SMILES: COc1cccc(-c2cc(F)ccc2C=O)c1]

¹H NMR: (400 MHz, dmso-d6) δ ppm 9.82 (s, 1H), 7.99 (dd, 1H), 7.42 (m, 3H), 7.08/7.01 (2dl, 2H), 7.06 (sl, 1H), 3.82 (s, 3H)

Intermediate 223

¹H NMR: (400 MHz, dmso-d6) δ ppm 9.9 (s, 1H), 7.92 (dd, 1H), 7.78 (td, 1H), 7.69 (dd, 1H), 7.65 (dd, 1H), 7.38 (d, 1H), 7.07 (d, 1H), 3.68 (s, 3H)

Intermediate 224

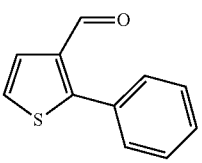 [SMILES: O=Cc1ccsc1-c1ccccc1]

¹H NMR: (400 MHz, dmso-d6) δ ppm 9.8 (sl, 1H), 7.68 (dd, 1H), 7.62 (m, 2H), 7.54 (m, 3H), 7.5 (d, 1H)

GC-EI (70 eV): [M]+.=188

Intermediate 225

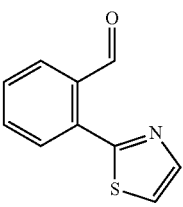 [SMILES: O=Cc1ccccc1-c1nccs1]

¹H NMR: (400 MHz, dmso-d6) δ ppm 10.35 (s, 1H), 8.07 (d, 1H), 7.99 (d, 1H), 7.88 (m, 2H), 7.79/7.67 (2*t, 2H)

Intermediate 226

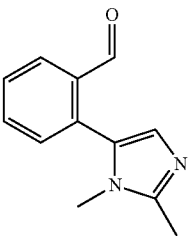

¹H NMR: (400 MHz, dmso-d6) δ ppm 9.9 (s, 1H), 7.95 (d, 1H), 7.8 (m, 1H), 7.65 (m, 1H), 7.5 (d, 1H), 6.85 (s, 1H), 3.4 (s, 3H), 2.4 (s, 3H)

Intermediate 227

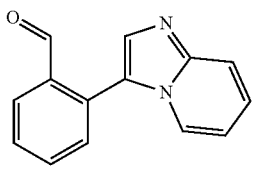 [SMILES: O=Cc1ccccc1-c1cnc2ccccn12]

¹H NMR: (400 MHz, dmso-d6) δ ppm 9.85 (s, 1H), 8.15 (m, 1H), 8.06 (m, 1H), 7.85 (m, 1H), 7.74 (s, 1H), 7.7 (m, 1H), 7.7 (m, 1H), 7.7 (m, 1H), 7.35 (m, 1H), 6.95 (m, 1H)

Intermediate 228

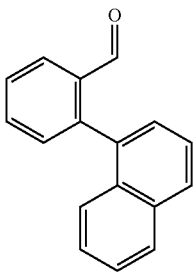 [SMILES: O=Cc1ccccc1-c1cccc2ccccc12]

¹H NMR: (400/500 MHz, dmso-d6) δ ppm 9.53 (s, 1H), 8.08 (d, 1H), 8.08 (d, 1H), 8.02 (dd, 1H), 7.83 (td, 1H), 7.71 (tt, 1H), 7.63 (dd, 1H), 7.57 (td, 1H), 7.51 (d, 1H), 7.49 (d, 1H), 7.49 (td, 1H), 7.38 (dt, 1H)

¹³C NMR: (400/500 MHz, dmso-d6) δ ppm 192, 143.5, 135.5, 135, 134, 133, 132, 128.5, 128.5, 128, 128, 127, 127, 126.5, 125.5, 125

Intermediate 229

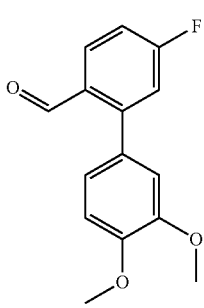 [SMILES: COc1ccc(-c2cc(F)ccc2C=O)cc1OC]

¹H NMR: (400 MHz, CDCl3) δ ppm 9.9 (s, 1H), 8.05 (dd, 1H), 7.15 (m, 2H), 7 (d, 1H), 6.9 (m, 2H), 3.95 (2 s, 6H)

DEI (70 eV): [M]+.=260

Intermediate 230

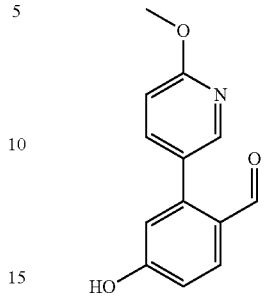

¹H NMR: (400 MHz, dmso-d6) δ ppm 10.8 (sl, 1H), 9.7 (s, 1H), 8.2 (d, 1H), 7.83 (d, 1H), 7.79 (dd, 1H), 6.95 (dd, 1H), 6.91 (d, 1H), 6.77 (d, 1H), 3.9 (s, 3H)

Intermediate 231

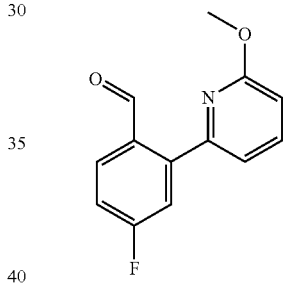

¹H NMR: (400 MHz, CDCl3) δ ppm 10.2 (s, 1H), 8 (dd, 1H), 7.75 (t, 1H), 7.4 (dd, 1H), 7.2 (m, 2H), 6.8 (d, 1H), 3.95 (s, 3H)

GC-EI (70 eV): [M]+.=231

Intermediate 232

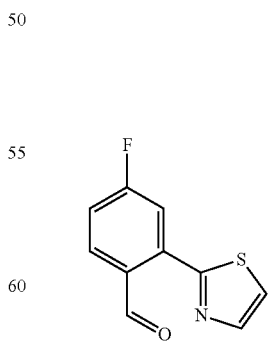

¹H NMR: (400 MHz, CDCl3) δ ppm 10.5 (m, 1H), 8.1 (dd, 1H), 8 (m, 1H), 7.5 (d, 1H), 7.4 (dd, 1H), 7.25 (td, 1H)

GC-EI (70 eV): [M]+.=207

Intermediate 233

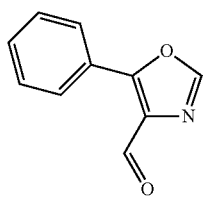 [SMILES: O=Cc1ncoc1-c1ccccc1]

¹H NMR: (400 MHz, dmso-d6) δ ppm 10 (s, 1H), 8.65 (s, 1H), 8.06 (m, 2H), 7.6 (m, 3H)

Intermediate 234

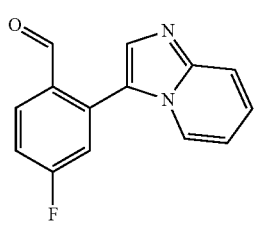 [SMILES: O=Cc1ccc(F)cc1-c1cnc2ccccn12]

¹H NMR: (400 MHz, CDCl3) δ ppm 9.8 (s, 1H), 8.2 (dd, 1H), 8 (d, 1H), 7.8 (d, 1H), 7.75 (s, 1H), 7.3 (m, 3H), 6.95 (t, 1H)
GC-EI (70 eV): [M]+.=240

Intermediate 235

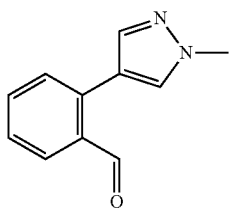

¹H NMR: (400 MHz, dmso-d6) δ ppm 10.15 (d, 1H), 8.05 (s, 1H), 7.86 (dd, 1H), 7.7 (d, 1H), 7.68 (td, 1H), 7.53 (dd, 1H), 7.46 (td, 1H), 3.91 (s, 3H)

Intermediate 236

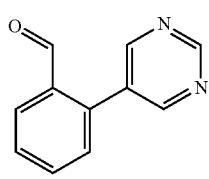 [SMILES: O=Cc1ccccc1-c1cncnc1]

¹H NMR: (400 MHz, dmso-d6) δ ppm 10 (s, 1H), 9.25 (s, 1H), 8.91 (s, 2H), 8.05 (dd, 1H), 7.83 (td, 1H), 7.73 (td, 1H), 7.58 (dd, 1H)

Intermediate 237

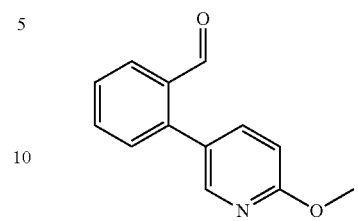

¹H NMR: (300 MHz, dmso-d6) δ ppm 9.9 (s, 1H), 8.25 (s, 1H), 7.95 (d, 1H), 7.85 (dd, 1H), 7.75/7.6 (2*m, 2H), 7.55 (d, 1H), 6.95 (d, 1H), 3.9 (s, 3H)

Intermediate 238

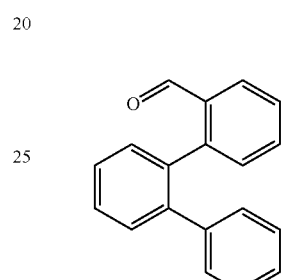

¹H NMR: (400/500 MHz, dmso-d6) δ ppm 9.64 (s, 1H), 7.68 (d, 1H), 7.63 (t, 1H), 7.57 (t, 1H), 7.51 (t, 1H), 7.47 (d, 1H), 7.45 (t, 1H), 7.42 (d, 1H), 7.34 (d, 1H), 7.17/7.03 (2*m, 5H)

Intermediate 239

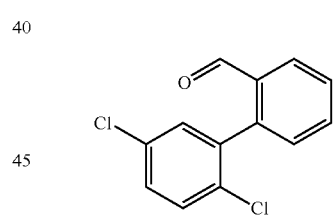

¹H NMR: (400 MHz, dmso-d6) δ ppm 9.8 (s, 1H), 8 (d, 1H), 7.8 (t, 1H), 7.69 (t, 1H), 7.6 (d, 1H), 7.55 (m, 2H), 7.4 (d, 1H)
GC-EI (70 eV): [M]+.=250

Intermediate 240

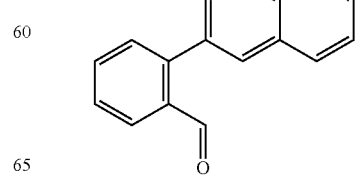

¹H NMR: (400/500 MHz, dmso-d6) δ ppm 9.95 (s, 1H), 8.07 (d, 1H), 8.02 (m, 2H), 7.99 (d, 1H), 7.98 (dd, 1H), 7.8 (td, 1H), 7.64 (d, 1H), 7.62 (td, 1H), 7.62 (m, 1H), 7.6 (m, 2H)

¹³C NMR: (400/500 MHz, dmso-d6) δ ppm 192, 134, 131.5, 129, 128, 128, 128, 128, 127.5, 127

Intermediate 241

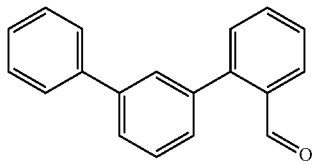 [SMILES: O=Cc1ccccc1-c1cccc(-c2ccccc2)c1]

¹H NMR: (400/500 MHz, dmso-d6) δ ppm 9.98 (s, 1H), 7.95 (dd, 1H), 7.78 (m, 1H), 7.78 (m, 1H), 7.75 (d, 2H), 7.72 (t, 1H), 7.63 (d, 1H), 7.62 (t, 1H), 7.61 (t, 1H), 7.49 (t, 2H), 7.44 (dt, 1H), 7.4 (t, 1H)

¹³C NMR: (400/500 MHz, dmso-d6) δ ppm 192, 145.5, 140, 134, 133.5, 131, 129, 129, 128, 128, 128, 127.5, 127, 127, 127

Intermediate 242

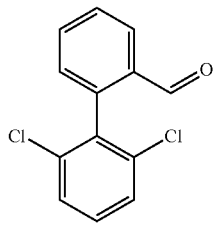 [SMILES: O=Cc1ccccc1-c1c(Cl)cccc1Cl]

¹H NMR: (400 MHz, dmso-d6) δ ppm 9.77 (s, 1H), 8.05 (dd, 1H), 7.82 (td, 1H), 7.7 (td, 1H), 7.6 (d, 2H), 7.5 (t, 1H), 7.35 (dd, 1H)

Intermediate 243

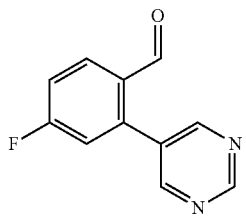 [SMILES: O=Cc1ccc(F)cc1-c1cncnc1]

¹H NMR: (400 MHz, dmso-d6) δ ppm 9.9 (s, 1H), 9.25 (s, 1H), 8.95 (s, 2H), 8.15 (dd, 1H), 7.55 (m, 2H)

¹⁹F NMR: (400 MHz, dmso-d6) δ ppm −102.8

Intermediate 244

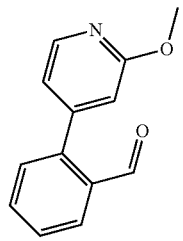 [SMILES: COc1cc(-c2ccccc2C=O)ccn1]

¹H NMR: (400 MHz, CDCl3) δ ppm 10 (s, 1H), 8.25 (dd, 1H), 8.05 (dd, 1H), 7.7 (td, 1H), 7.55 (td, 1H), 7.4 (dd, 1H), 6.9 (dd, 1H), 6.75 (dd, 1H), 4 (s, 3H)

Intermediate 245

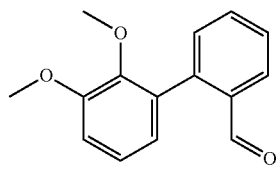 [SMILES: COc1cccc(-c2ccccc2C=O)c1OC]

¹H NMR: (400 MHz, dmso-d6) δ ppm 9.7 (s, 1H), 7.9 (dd, 1H), 7.75 (td, 1H), 7.58 (t, 1H), 7.43 (d, 1H), 7.25-7.15 (m, 2H), 6.91 (dd, 1H), 3.87 (s, 3H), 3.38 (s, 3H)

Intermediate 246

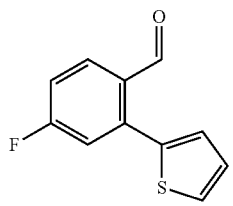 [SMILES: O=Cc1ccc(F)cc1-c1cccs1]

¹H NMR: (300/400/500 MHz, dmso-d6) δ ppm 10.03 (s, 1H), 7.98 (dd, 1H), 7.83 (dd, 1H), 7.46 (dd, 1H), 7.43 (td, 1H), 7.36 (dd, 1H), 7.25 (dd, 1H)

¹³C NMR: (300/400/500 MHz, dmso-d6) δ ppm 190.2, 165, 140.3, 137.3, 131.2, 130.7, 130.6, 129, 128.4, 117.8, 115.9

¹⁹F NMR: (300/400/500 MHz, dmso-d6) δ ppm −103

Intermediate 247

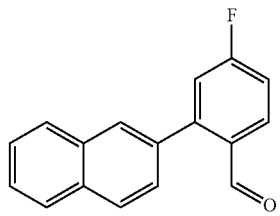 [SMILES: O=Cc1ccc(F)cc1-c1ccc2ccccc2c1]

¹H NMR: (300/400/500 MHz, dmso-d6) δ ppm 9.9 (s, 1H), 8.06 (s, 1H), 8.05 (d, 1H), 8.04-8.02 (m, 3H), 7.64 (dd, 1H), 7.61 (td, 2H), 7.51-7.47 (m, 2H)

¹³C NMR: (300/400/500 MHz, dmso-d6) δ ppm 190.4, 165, 148.3, 131.2, 130.6, 129.5-128.2, 128.2, 127.7, 127.1, 117.9/115.5

¹⁹F NMR: (300/400/500 MHz, dmso-d6) δ ppm −103.2

Intermediate 248

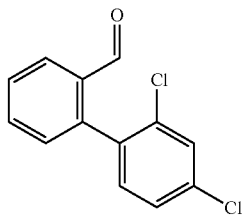 [SMILES: O=Cc1ccccc1-c1ccc(Cl)cc1Cl]

¹H NMR: (400 MHz, CDCl3) δ ppm 9.88 (s, 1H), 8.1 (dd, 1H), 7.74 (s, 1H), 7.29 (td, 1H), 7.14 (s, 1H), 7.1 (dd, 1H), 3.56 (s, 3H)

Intermediate 249

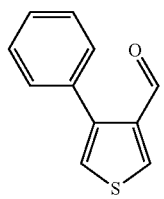 [SMILES: O=Cc1cscc1-c1ccccc1]

¹H NMR: (400 MHz, dmso-d6) δ ppm 9.84 (s, 1H), 8.27 (d, 1H), 8.04 (dd, 1H), 7.5 (td, 1H), 7.43 (dd, 1H), 7.1 (dd, 1H), 6.96 (s, 1H), 3.91 (s, 3H)

¹⁹F NMR: (400 MHz, CDCl3) δ ppm −101.2

Intermediate 250

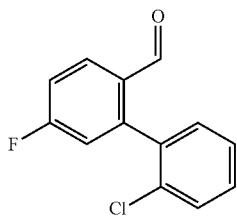 [SMILES: O=Cc1ccc(F)cc1-c1ccccc1Cl]

¹H NMR: (400 MHz, dmso-d6) δ ppm 10.1 (s, 1H), 8.12 (d, 1H), 7.93 (d, 1H), 7.78 (dd, 1H), 7.39 (dd, 1H), 7.3 (td, 1H), 3.91 (s, 3H)

Intermediate 251

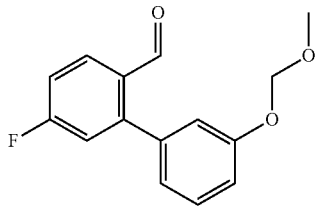 [SMILES: COCOc1cccc(-c2cc(F)ccc2C=O)c1]

¹H NMR: (400 MHz, dmso-d6) δ ppm 9.76 (s, 1H), 7.98 (dd, 1H), 7.79 (td, 1H), 7.77 (d, 1H), 7.68 (td, 1H), 7.56 (dd, 1H), 7.47 (d, 1H), 7.39 (dd, 1H)

Intermediate 252

¹H NMR: (400 MHz, dmso-d6) δ ppm 9.84 (s, 1H), 8.59 (d, 1H), 7.69 (d, 1H), 7.5-7.3 (m, 5H)

Intermediate 253

¹H NMR: (400 MHz, dmso-d6) δ ppm 9.64 (s, 1H), 8.04 (dd, 1H), 7.62 (d, 1H), 7.5 (m, 1H), 7.5 (m, 3H), 7.32 (dd, 1H)

Intermediate 254

¹H NMR: (400 MHz, dmso-d6) δ ppm 9.8 (s, 1H), 8 (dd, 1H), 7.45 (m, 3H), 7.15 (m, 2H), 7.1 (dd, 1H), 5.25 (s, 2H), 3.4 (s, 3H)

Intermediate 255

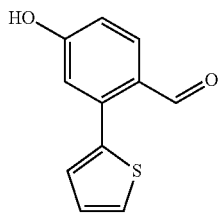

¹H NMR: (400 MHz, dmso-d6) δ ppm, 10.75 (s, 1H), 9.95 (s, 1H), 7.85 (d, 1H), 7.75 (d, 1H), 7.25 (d, 1H), 7.2 (d, 1H), 6.95 (dd, 1H), 6.9 (s, 1H)

GC-EI (70 eV): [M]+.=204

Intermediate 256

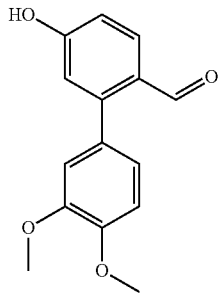

¹H NMR: (400 MHz, dmso-d6) δ ppm 10.6 (s, 1H), 9.7 (s, 1H), 7.8 (d, 1H), 7.05 (d, 1H), 7 (s, 1H), 6.9 (m, 2H), 6.8 (s, 1H), 3.8 (2s, 6H)

Intermediate 257

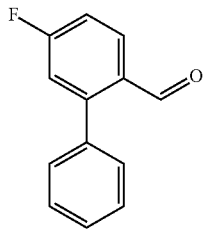 [SMILES: O=Cc1ccc(F)cc1-c1ccccc1]

¹H NMR: (300 MHz, CDCl3) δ ppm 9.9 (s, 1H), 8.09 (dd, 1H), 7.5/7.4 (unresolved peak, 5H), 7.21 (dd, 1H), 7.15 (dd, 1H)

¹⁹F NMR: (300 MHz, CDCl3) δ ppm −103.7

Intermediate 258

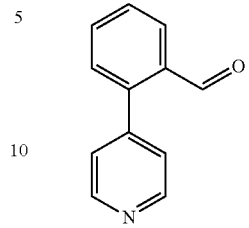

¹H NMR: (400 MHz, CDCl3) δ ppm 10 (s, 1H), 8.73 (d, 2H), 8.08 (dd, 1H), 7.71 (dt, 1H), 7.61 (dt, 1H), 7.42 (dd, 1H), 7.35 (d, 2H)

Intermediate 259

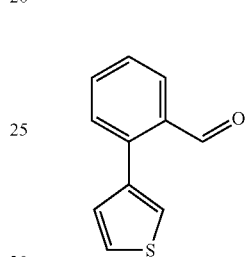

¹H NMR: (400 MHz, CDCl3) δ ppm 10.1 (d, 1H), 8 (dd, 1H), 7.62 (dt, 1H), 7.48 (2*m, 2H), 7.46 (dd, 1H), 7.3 (dd, 1H), 7.2 (dd, 1H)

Intermediate 260

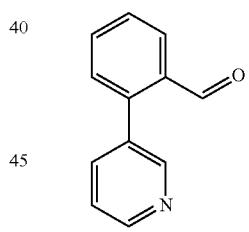

¹H NMR: (400 MHz, CDCl3) δ ppm 9.99 (s, 1H), 8.71 (dd, 1H), 8.67 (d, 1H), 8.07 (dl, 1H), 7.75 (dt, 1H), 7.7 (tl, 1H), 7.59 (tl, 1H), 7.44 (dd, 1H), 7.43 (dl, 1H)

Intermediate 261

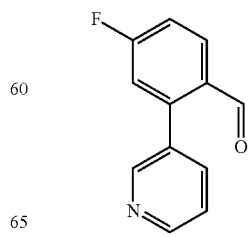

¹H NMR: (300 MHz, CDCl3) δ ppm 9.9 (d, 1H), 8.74 (dd, 1H), 8.69 (dd, 1H), 8.12 (dd, 1H), 7.74 (ddd, 1H), 7.47 (ddd, 1H), 7.28 (m, 1H), 7.15 (dd, 1H)
¹⁹F NMR: (300 MHz, CDCl3) δ ppm −102.6

Intermediate 262

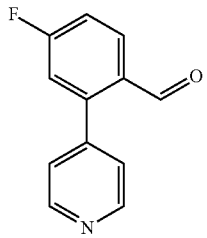 [SMILES: O=Cc1ccc(F)cc1-c1ccncc1]

¹H NMR: (400 MHz, CDCl3) δ ppm 9.89 (s, 1H), 8.75 (d, 2H), 8.11 (dd, 1H), 7.33 (d, 2H), 7.27 (td, 1H), 7.12 (dd, 1H)

Intermediate 263

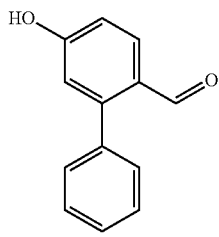

¹H NMR: (400 MHz, CDCl3) δ ppm 9.82 (s, 1H), 8.01 (d, 1H), 7.45 (m, 3H), 7.38 (m, 2H), 6.94 (dd, 1H), 6.85 (df, 1H), 5.72 (sl, 1H)

Intermediate 264

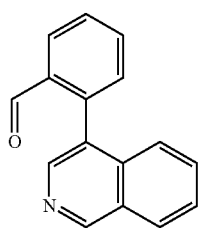 [SMILES: O=Cc1ccccc1-c1cncc2ccccc12]

¹H NMR: (400 MHz, CDCl3) δ ppm 9.68 (s, 1H), 9.35 (s, 1H), 8.5 (s, 1H), 8.15 (dd, 1H), 8.1 (m, 1H), 7.75 (dt, 1H), 7.67 (2*m, 2H), 7.65 (dt, 1H), 7.51 (m, 1H), 7.47 (dd, 1H)
GC-EI (70 eV): [M]+.=233.1

Intermediate 265

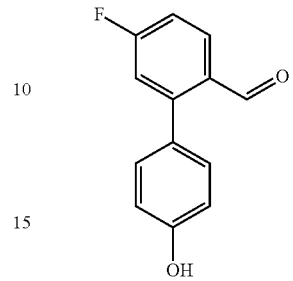

¹H NMR: (300 MHz, CDCl3) δ ppm 9.9 (sl, 1H), 8.03 (dd, 1H), 7.24 (d, 2H), 7.12 (td, 1H), 7.1 (dd, 1H), 6.95 (d, 2H), 5.3 (s, 1H)
¹⁹F NMR: (300 MHz, CDCl3) δ ppm −102.4

Intermediate 266

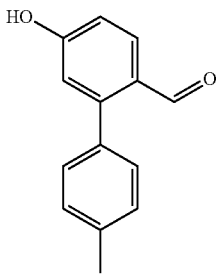

¹H NMR: (400 MHz, dmso-d6) δ ppm 10.65 (s, 1H), 9.65 (s, 1H), 7.8 (d, 1H), 7.3 (s, 4H), 6.9 (dd, 1H), 6.75 (s, 1H), 2.35 (d, 3H)

Intermediate 267

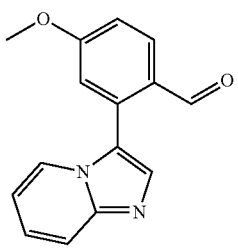 [SMILES: COc1ccc(C=O)c(-c2cnc3ccccn23)c1]

¹H NMR: (400 MHz, dmso-d6) δ ppm 9.8 (s, 1H), 8.2 (d, 1H), 8.05 (d, 1H), 7.75 (s, 1H), 7.7 (d, 1H), 7.35 (t, 1H), 7.25 (dd, 1H), 7.2 (s, 1H), 6.95 (t, 1H), 3.9 (s, 3H)

Intermediate 268

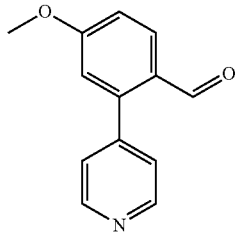 [SMILES: COc1ccc(C=O)c(-c2ccncc2)c1]

$^1$H NMR: (400 MHz, dmso-d6) δ ppm 9.75 (s, 1H), 8.69 (d, 2H), 7.97 (d, 1H), 7.7 (dd, 1H), 7.5 (d, 2H), 7 (d, 1H), 3.9 (s, 3H)

Intermediate 269

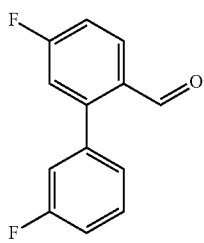 [SMILES: O=Cc1ccc(F)cc1-c1cccc(F)c1]

$^1$H NMR: (300/400 MHz, dmso-d6) δ ppm 9.8 (s, 1H), 8 (dd, 1H), 7.55 (m, 1H), 7.5 (m, 1H), 7.45 (d, 1H), 7.45 (d, 1H), 7.35 (m, 1H), 7.3 (dd, 1H)

$^{19}$F NMR: (300/400 MHz, dmso-d6) δ ppm −103.1, −111.7

Intermediate 270

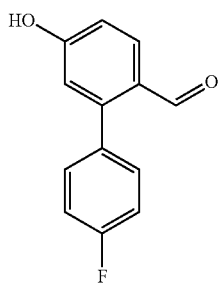

$^1$H NMR: (400 MHz, dmso-d6) δ ppm 10.75 (sl, 1H), 9.65 (s, 1H), 7.81 (d, 1H), 7.45 (dd, 2H), 7.3 (dd, 2H), 6.93 (dd, 1H), 6.75 (d, 1H)

Intermediate 271

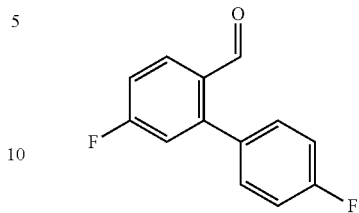

$^1$H NMR: (400 MHz, CDCl3) δ ppm 9.88 (s, 1H), 8.06 (dd, 1H), 7.36 (dd, 2H), 7.19 (m, 1H), 7.19 (dd, 2H), 7.11 (dd, 1H)

Intermediate 272

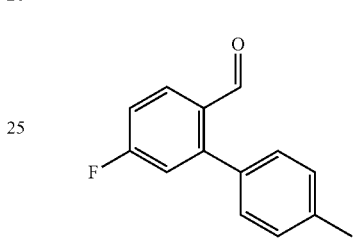

$^1$H NMR: (400 MHz, CDCl3) δ ppm 9.9 (s, 1H), 8.05 (dd, 1H), 7.28 (dd, 4H), 7.16 (td, 1H), 7.12 (dd, 1H), 2.44 (s, 3H)

Intermediate 273

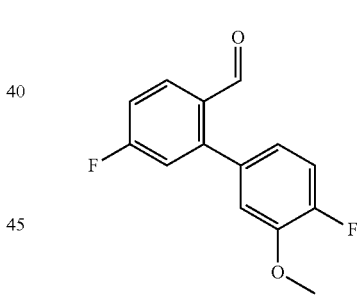

$^1$H NMR: (400 MHz, dmso-d6) δ ppm 9.82 (s, 1H), 8 (dd, 1H), 7.48-7.3 (m, 2H), 7.48-7.3 (m, 2H), 7 (ddd, 1H), 3.9 (s, 3H)

$^{19}$F NMR: (400 MHz, dmso-d6) δ ppm −104.4, −135.7

Intermediate 274

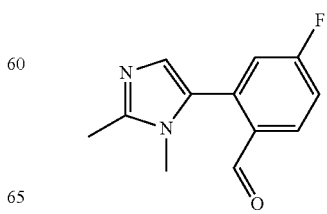

¹H NMR: (400 MHz, dmso-d6) δ ppm 9.8 (s, 1H), 8.05 (dd, 1H), 7.45 (m, 1H), 7.4 (d, 1H), 6.9 (s, 1H), 3.45 (s, 3H), 2.35 (s, 3H)
¹⁹F NMR: (400 MHz, dmso-d6) δ ppm −102.9

Intermediate 275

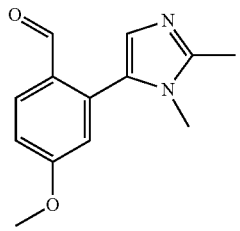 [SMILES: COc1ccc(C=O)c(-c2cnc(C)n2C)c1]

¹H NMR: (400 MHz, dmso-d6) δ ppm 9.7 (s, 1H), 7.95 (d, 1H), 7.15 (dd, 1H), 7 (s, 1H), 6.85 (s, 1H), 3.9 (s, 3H), 3.4 (s, 3H), 2.35 (s, 3H)

Intermediate 276

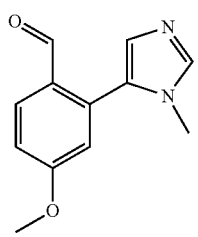 [SMILES: COc1ccc(C=O)c(-c2cncn2C)c1]

¹H NMR: (300/400 MHz, dmso-d6) δ ppm 9.7 (s, 1H), 7.93 (d, 1H), 7.8 (s, 1H), 7.18 (dd, 1H), 7.03 (d, 1H), 7 (s, 1H), 3.9 (s, 3H), 3.54 (s, 3H)

Intermediate 277

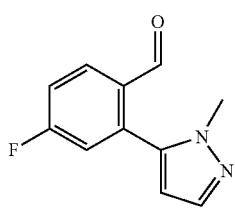

¹H NMR: (400 MHz, CDCl3) δ ppm 9.85 (s, 1H), 8.15 (dd, 1H), 7.6 (s, 1H), 7.3 (m, 1H), 7.15 (d, 1H), 6.35 (s, 1H), 3.75 (s, 3H)
¹⁹F NMR: (400 MHz, CDCl3) δ ppm −101.2

Intermediate 278

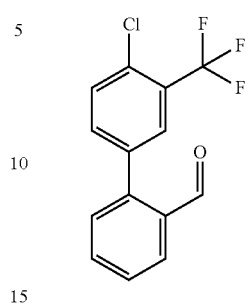

¹H NMR: (400 MHz, dmso-d6) δ ppm 9.9 (s, 1H), 7.98 (dd, 1H), 7.9 (d, 1H), 7.84 (d, 1H), 7.78 (td, 1H), 7.77 (dd, 1H), 7.67 (tl, 1H), 7.55 (dd, 1H)
DEI (70 eV): [M]+.=284

Intermediate 279

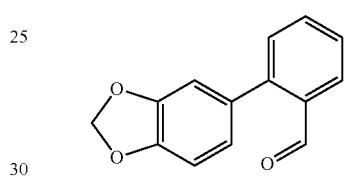

¹H NMR: (400 MHz, dmso-d6) δ ppm 9.9 (s, 1H), 7.9 (d, 1H), 7.75 (m, 1H), 7.55 (m, 1H), 7.5 (d, 1H), 7.1 (s, 1H), 7.05 (d, 1H), 6.85 (dd, 1H), 6.1 (s, 2H)

Intermediate 280

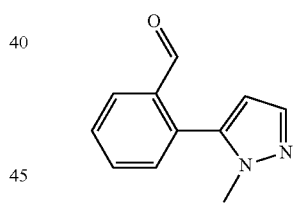

¹H NMR: (400 MHz, dmso-d6) δ ppm 9.8 (s, 1H), 7.99 (d, 1H), 7.8 (t, 1H), 7.69 (t, 1H), 7.58 (d, 1H), 7.55 (d, 1H), 6.41 (d, 1H), 3.69 (s, 3H)
¹³C NMR: (400 MHz, dmso-d6) δ ppm 191, 138, 138, 136, 134, 133, 132, 130, 128, 109, 37

Intermediate 281

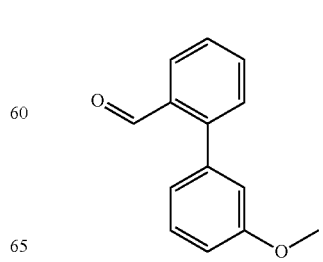

Intermediate 282

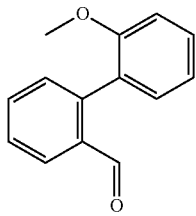 [SMILES: COc1ccccc1-c1ccccc1C=O]

¹H NMR: (400 MHz, dmso-d6) δ ppm 9.9 (s, 1H), 7.91 (d, 1H), 7.75 (t, 1H), 7.59 (t, 1H), 7.54 (d, 1H), 7.42 (t, 1H), 7.05 (dd, 1H), 7.01 (t, 1H), 6.98 (dd, 1H), 3.82 (s, 3H)

Intermediate 283

¹H NMR: (400 MHz, dmso-d6) δ ppm 9.66 (s, 1H), 7.86 (d, 1H), 7.73 (t, 1H), 7.54 (t, 1H), 7.46 (t, 1H), 7.38 (d, 1H), 7.31 (d, 1H), 7.14 (d, 1H), 7.11 (t, 1H), 3.69 (s, 3H)

Intermediate 284

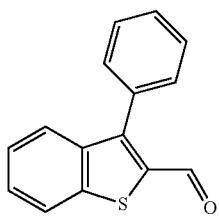 [SMILES: O=Cc1sc2ccccc2c1-c1ccccc1]

¹H NMR: (400 MHz, dmso-d6) δ ppm 9.86 (s, 1H), 8.17 (d, 1H), 7.78 (d, 1H), 7.7-7.55 (m, 1H), 7.7-7.55 (m, 5H), 7.52 (t, 1H)

Intermediate 285

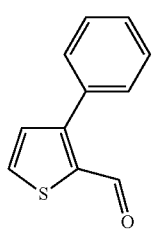 [SMILES: O=Cc1sccc1-c1ccccc1]

¹H NMR: (400 MHz, dmso-d6) δ ppm 9.82 (d, 1H), 8.17 (dd, 1H), 7.62 (d, 2H), 7.52 (m, 3H), 7.43 (d, 1H)

Intermediate 286

¹H NMR: (400 MHz, CDCl3) δ ppm 9.85 (s, 1H), 8.03 (d, 1H), 7.5-7.37 (m, 5H), 7 (dd, 1H), 6.89 (df, 1H), 3.9 (s, 3H)

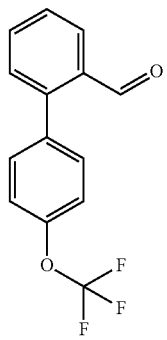

Intermediate 287

¹H NMR: (400 MHz, dmso-d6) δ ppm 9.89 (s, 1H), 7.95 (d, 1H), 7.77 (t, 1H), 7.62 (m, 3H), 7.53 (d, 1H), 7.49 (d, 2H)

¹⁹F NMR: (400 MHz, dmso-d6) δ ppm −55.59

Intermediate 288

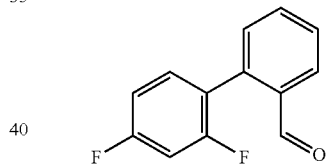

¹H NMR: (400 MHz, CDCl3) δ ppm 9.9 (d, 1H), 8.04 (dd, 1H), 7.68 (dt, 1H), 7.56 (t, 1H), 7.39 (d, 1H), 7.31 (dt, 1H), 7.01 (dt, 1H), 6.95 (dt, 1H)

¹⁹F NMR: (400 MHz, CDCl3) δ ppm −109/−110

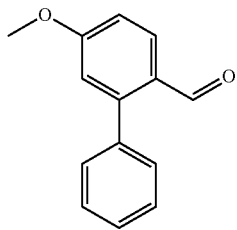 [SMILES: COc1ccc(C=O)c(-c2ccccc2)c1]

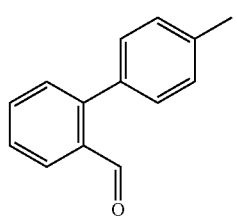

¹H NMR: (400 MHz, CDCl3) δ ppm 10 (d, 1H), 8.01 (dd, 1H), 7.63 (dt, 1H), 7.48 (t, 1H), 7.44 (d, 1H), 7.29 (s, 4H), 2.43 (s, 3H)

Intermediate 289

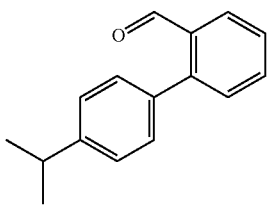 [SMILES: CC(C)c1ccc(-c2ccccc2C=O)cc1]

¹H NMR: (400 MHz, CDCl3) δ ppm 10 (s, 1H), 8.02 (d, 1H), 7.62 (t, 1H), 7.45 (d, 1H), 7.32 (2*d, 4H), 4.48 (t, 1H), 2.99 (hept., 1H), 1.31 (d, 6H)

Intermediate 290

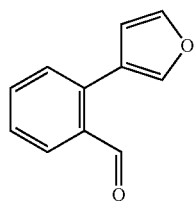 [SMILES: O=Cc1ccccc1-c1ccoc1]

¹H NMR: (400 MHz, CDCl3) δ ppm 10.27 (d, 1H), 7.99 (dd, 1H), 7.61 (dt, 1H), 7.55 (2*m, 2H), 7.46 (2*m, 2H), 6.59 (dd, 1H)

Intermediate 291

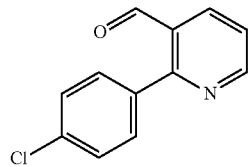 [SMILES: O=Cc1cccnc1-c1ccc(Cl)cc1]

¹H NMR: (300 MHz, dmso-d6) δ ppm 9.99 (s, 1H), 8.86 (d, 1H), 8.82 (df, 1H), 7.79 (dd, 1H), 7.6 (2*d, 4H)

Intermediate 292

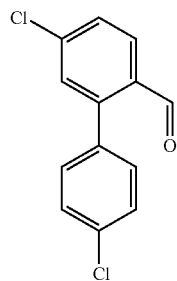

¹H NMR: (400 MHz, dmso-d6) δ ppm 9.85 (s, 1H), 7.95 (d, 1H), 7.65 (dd, 1H), 7.6 (s, 1H), 7.55 (d, 2H), 7.5 (d, 2H)

Intermediate 293

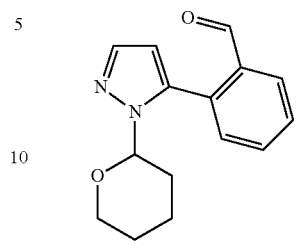

¹H NMR: (400 MHz, dmso-d6) δ ppm 9.7 (s, 1H), 8 (dd, 1H), 7.8 (td, 1H), 7.7 (td, 1H), 7.65 (d, 1H), 7.55 (dd, 1H), 6.5 (d, 1H), 5 (dd, 1H), 3.8/3.25 (2m, 2H), 2.25/1.8 (2m, 2H), 1.9/1.5 (2m, 2H), 1.4 (m, 2H)

Procedure F: Generic Procedure for Reductive Amination Starting from Intermediate 21 (Synthesis of Intermediates 22 to 127).

Intermediate 21 (14 g, 26.2 mmol), anhydrous DCM (280 mL), the aldehyde (intermediates 213 to 293) (39.3 mmol, 1.5 eq) and MgSO₄ (14 g) are introduced in succession into a 500 mL three-necked flask at ambient temperature and under a stream of argon. After stirring for 1 hour, NaBH(OAc)₃ (8.32 g, 39.3 mmol, 1.5 eq) is added in portions and the reaction mixture is maintained at ambient temperature for 16 hours. The reaction is monitored by LC/MS. The insoluble components are filtered off over microfibre and rinsed with DCM (100 mL). The filtrate is then washed with water (1×200 mL) and then with a saturated NaCl solution (2×200 mL). The organic phase is dried over MgSO₄ and concentrated under reduced pressure. The oil obtained is then purified by flash chromatography on silica gel (330 g) to yield intermediates 22 to 127.

EXAMPLE 31: 3-(4-AMINOBUTYL)-4-HYDROXY-4-OXO-1,4-AZAPHOSPHINANE-3-CARBOXYLIC ACID

Example 31 is obtained starting from intermediate 21 in accordance with procedure D described hereinbefore.

¹H NMR: (400 MHz, D2O) δ ppm 3.5-3.65 (2m, 2H), 3.2 (m, 1H), 3.05 (dd, 1H), 2.95 (m, 2H), 2.15 (m, 1H), 1.95 (m, 1H), 1.75 (m, 1H), 1.65 (m, 2H), 1.5 (m, 1H), 1.4 (m, 1H), 1.25 (m, 1H)

ESI/FIA/HR and MS/MS: [M+H]+=251.1154 (251.1160)

Elemental analysis: C=42.65 (43.20); H=7.23 (7.65); N=11.24 (11.20)

Intermediate 22: tert-Butyl 3-{4-[bis(tert-butoxycarbonyl)amino]butyl}-1-[(3-fluoro-4-hydroxyphenyl)methyl]-4-ethoxy-4-oxo-1,4-azaphosphinane-3-carboxylate Intermediate 22 is obtained starting from intermediate 21 and 3-fluoro-4-hydroxybenzaldehyde in accordance with procedure F described hereinbefore.

¹H NMR: (400 MHz, dmso-d6) δ ppm 7.0 (d, 1H), 6.88 (d, 2H), 3.95 (m, 2H), 3.5/3.33 (2*d, 2H), 3.4 (m, 2H), 2.85/2.3 (2*m, 2H), 2.8/2.45 (dd, 2H), 2-1.6 (m, 4H), 1.42/1.35 (2*s, 27H), 1.4 (m, 2H), 1.2 (t, 3H), 0.9 (m, 2H)

EXAMPLE 32: 3-(4-AMINOBUTYL)-1-[(3-FLUORO-4-HYDROXYPHENYL)METHYL]-4-HYDROXY-4-OXO-1,4-AZAPHOSPHINANE-3-CARBOXYLIC ACID

Example 32 is obtained starting from intermediate 22 in accordance with procedure D described hereinbefore.

$^{1}$H NMR: (300/400 MHz, D2O) δ ppm 7.24 (dd, 1H), 7.12 (dd, 1H), 7.03 (t, 1H), 4.32/4.12 (2*d, 2H), 3.68/3.3 (2*m, 2H), 3.45/3.07 (2*m, 2H), 2.92 (m, 2H), 2.22/1.78 (2*m, 2H), 1.92/1.58 (2*m, 2H), 1.58/1.46 (2*m, 2H), 1.23/1.1 (2*m, 2H)

$^{19}$F NMR: (300/400 MHz, D2O) δ ppm −135.8

ESI/FIA/HR and MS/MS: [M+H]+=375.1455 (375.1480)

Elemental analysis: C=51.71 (51.34); H=6.44 (6.46); N=7.64 (7.48)

Intermediate 23: tert-Butyl 3-{4-[bis(tert-butoxycarbonyl)amino]butyl}-1-[(2,4-difluorophenyl)methyl]-4-ethoxy-4-oxo-1,4-azaphosphinane-3-carboxylate Intermediate 23 is obtained starting from intermediate 21 and 2,4-difluorobenzaldehyde in accordance with procedure F described hereinbefore.

$^{1}$H NMR: (400 MHz, dmso-d6) δ ppm 7.44 (m, 1H), 7.19 (m, 1H), 7.07 (m, 1H), 4 (m, 2H), 3.57 (m, 2H), 3-2.6/2.35 (m, 2H), 3-2.6/2.52 (m, 2H), 2.78 (m, 2H), 2-1.6 (m, 2H), 2-1.6 (m, 2H), 1.39 (m, 27H), 1.39 (m, 2H), 1.2 (m, 3H), 0.82 (m, 2H)

EXAMPLE 33: 3-(4-AMINOBUTYL)-1-[(2,4-DIFLUOROPHENYL)METHYL]-4-HYDROXY-4-OXO-1,4-AZAPHOSPHINANE-3-CARBOXYLIC ACID

Example 33 is obtained starting from intermediate 23 in accordance with procedure D described hereinbefore.

$^{1}$H NMR: (400 MHz, D2O) δ ppm 7.51 (m, 1H), 7.07 (m, 2H), 4.37 (sl, 2H), 3.69/3.33 (m, 2H), 3.49/3.19 (m, 2H), 2.95 (m, 2H), 2.21/1.77 (m, 2H), 1.95/1.49 (m, 2H), 1.61 (m, 2H), 1.28/1.14 (m, 2H)

ESI/FIA/HR and MS/MS: [M+H]+=377.1419 (377.1441)

Elemental analysis: C=50.66 (51.06); H=5.79 (6.16); N=7.37 (7.44)

Intermediate 24: tert-Butyl 3-{4-[Bis(tert-butoxycarbonyl)amino]butyl}-1-[(3,5-difluoro-4-hydroxyphenyl)methyl]-4-ethoxy-4-oxo-1,4-azaphosphinane-3-carboxylate Intermediate 24 is obtained starting from intermediate 21 and 3,5-difluoro-4-hydroxy-benzaldehyde in accordance with procedure F described hereinbefore.

$^{1}$H NMR: (300 MHz, dmso-d6) δ ppm 10.1 (sl, 1H), 6.63 (d, 2H), 4.1-3.8 (m, 2H), 3.58-3.3 (m, 2H), 3.58-3.3 (m, 2H), 3-2.6/2.3 (2*m, 2H), 3-2.6/2.49 (2*m, 2H), 2-1.5 (m, 2H), 2-1.5 (m, 2H), 1.4 (m, 2H), 1.4/1.37 (2*s, 27H), 1.2 (t, 3H), 1.1-0.8 (m, 2H)

EXAMPLE 34: 3-(4-AMINOBUTYL)-1-[(3,5-DIFLUORO-4-HYDROXYPHENYL)METHYL]-4-HYDROXY-4-OXO-1,4-AZAPHOSPHINANE-3-CARBOXYLIC ACID

Example 34 is obtained starting from intermediate 24 in accordance with procedure D described hereinbefore.

$^{1}$H NMR: (300/400 MHz, D2O) δ ppm 7.1 (m, 2H), 4.33/4.12 (2*d, 2H), 3.69/3.31 (2*dd, 2H), 3.45/3.09 (2*dd, 2H), 2.94 (m, 2H), 2.24/1.78 (2*m, 2H), 1.93/1.6 (2*m, 2H), 1.6/1.47 (2*m, 2H), 1.25/1.13 (2*m, 2H)

$^{19}$F NMR: (300/400 MHz, D2O) δ ppm −132

ESI/FIA/HR and MS/MS: [M+H]+=393.1388 (393.1390)

Elemental analysis: C=48.74 (48.98); H=5.90 (5.91); N=7.10 (7.14)

Intermediate 25: tert-Butyl 3-{4-[bis(tert-butoxycarbonyl)amino]butyl}-1-[[4-(difluoromethyl)phenyl]methyl]-4-ethoxy-4-oxo-1,4-azaphosphinane-3-carboxylate Intermediate 25 is obtained starting from intermediate 21 and 4-(difluoromethyl)benzaldehyde in accordance with procedure F described hereinbefore.

$^{1}$H NMR: (400 MHz, dmso-d6) δ ppm 7.55-7.4 (dd, 4H), 7 (t, 1H), 4.1-3.85 (m, 2H), 3.7-3.5 (dd, 2H), 3.35 (m, 2H), 3-2.25 (m, 4H), 2-1.8 (m, 4H), 1.4 (m, 2H), 1.4 (s, 18H), 1.35 (s, 9H), 1.2 (t, 3H), 0.8 (m, 2H).

EXAMPLE 35: 3-(4-AMINOBUTYL)-1-[[4-(DIFLUOROMETHYL)PHENYL]METHYL]-4-HYDROXY-4-OXO-1,4-AZAPHOSPHINANE-3-CARBOXYLIC ACID

Example 35 is obtained starting from intermediate 25 in accordance with procedure D described hereinbefore.

$^{1}$H NMR: (400 MHz, D2O) δ ppm 7.7-7.6 (d, 4H), 6.85 (t, 1H), 4.5/4.3 (m, 2H), 3.8-3.65 (m, 1H), 3.55-3.35 (m, 2H), 3.15 (m, 1H), 2.95 (m, 2H), 2.25 (m, 1H), 2-1.75 (m, 2H), 1.65-1.5 (m, 3H), 1.3-1.1 (m, 2H)

$^{31}$P NMR: (400 MHz, D2O) δ ppm 26

$^{19}$F NMR: (400 MHz, D2O) δ ppm −110

ESI/FIA/HR and MS/MS: [M+H]+=391.1583 (391.1598)

Elemental analysis: C=51.85 (52.31); H=6.46 (6.45); N=7.04 (7.18)

Intermediate 26: tert-Butyl 3-{4-[bis(tert-butoxycarbonyl)amino]butyl}-4-ethoxy-1-[[4-hydroxy-3-(trifluoromethyl)phenyl]methyl]-4-oxo-1,4-azaphosphinane-3-carboxylate Intermediate 26 is obtained starting from intermediate 21 and 4-hydroxy-3-(trifluoromethyl)benzaldehyde in accordance with procedure F described hereinbefore.

$^{1}$H NMR: (400 MHz, dmso-d6) δ ppm 10.45 (unresolved peak, 1H), 7.4 (sl, 1H), 7.34 (dl, 1H), 6.96 (d, 1H), 4.1-3.85 (m, 2H), 3.65-3.3 (m, 2H), 3.65-3.3 (m, 2H), 3-2.2 (m, 4H), 2-1.6 (m, 4H), 1.38 (m, 29H), 1.2 (t, 3H), 0.88 (m, 2H)

EXAMPLE 36: 3-(4-AMINOBUTYL)-4-HYDROXY-1-[[4-HYDROXY-3-(TRIFLUOROMETHYL)PHENYL]-METHYL]-4-OXO-1,4-AZAPHOSPHINANE-3-CARBOXYLIC ACID

Example 36 is obtained starting from intermediate 26 in accordance with procedure D described hereinbefore.

$^{1}$H NMR: (400 MHz, D2O) δ ppm 7.68 (df, 1H), 7.55 (dd, 1H), 7.09 (d, 1H), 4.38/4.2 (2*d, 2H), 3.7/3.3 (2*dd, 2H), 3.45/3.09 (2*dd, 2H), 2.92 (m, 2H), 2.23/1.77 (2*m, 2H), 1.93/1.6 (2*m, 2H), 1.6/1.47 (2*m, 2H), 1.25/1.11 (2*m, 2H)

ESI/FIA/HR and MS/MS: [M+H]+=425.1453 (425.1453)

Elemental analysis: C=48.19 (48.12); H=5.16 (5.70); N=6.72 (6.60)

Intermediate 27: tert-Butyl 3-{4-[bis(tert-butoxycarbonyl)amino]butyl}-1-[(3-chloro-5-fluoro-4-hydroxyphenyl)methyl]-4-ethoxy-4-oxo-1,4-azaphosphinane-3-carboxylate Intermediate 27 is obtained starting from intermediate 21 and 3-chloro-5-fluoro-4-hydroxybenzaldehyde in accordance with procedure F described hereinbefore.

$^1$H NMR: (400 MHz, dmso-d6) δ ppm 10.26 (sl, 1H), 7.12 (sl, 1H), 7.07 (dl, 1H), 4.06/3.98 (2quad, 2H), 3.47 (AB, 2H), 3.42 (m, 2H), 3-2.26 (m, 4H), 1.94 (m, 4H), 1.41/1.37 (2s, 27H), 1.4 (m, 2H), 1.25/1.21 (2t, 3H), 0.92 (m, 2H)

$^{19}$F NMR: (400 MHz, dmso-d6) δ ppm −131.7

$^{31}$P NMR: (400 MHz, dmso-d6) δ ppm −43

ESI/FIA/HR and MS/MS: [M+H]+=693.308 (693.3083)

EXAMPLE 37: 3-(4-AMINOBUTYL)-1-[(3-CHLORO-5-FLUORO-4-HYDROXYPHENYL)METHYL]-4-HYDROXY-4-OXO-1,4-AZAPHOSPHINANE-3-CARBOXYLIC ACID

Example 37 is obtained starting from intermediate 27 in accordance with procedure D described hereinbefore.

$^1$H NMR: (400 MHz, D2O) δ ppm 7.3 (m, 1H), 7.21 (m, 1H), 4.31/4.12 (2*d, 2H), 3.69/3.3 (2*dd, 2H), 3.45/3.09 (2*dd, 2H), 2.93 (m, 2H), 2.24/1.77 (2*m, 2H), 1.93/1.6 (2*m, 2H), 1.6/1.47 (2*m, 2H), 1.27/1.13 (2*m, 2H)

$^{19}$F NMR: (400 MHz, D2O) δ ppm −131.6

ESI/FIA/HR and MS/MS: [M+H]+=409.1091 (409.1095)

Elemental analysis: C=47.25 (47.01); H=5.75 (5.67); N=6.92 (6.85)

Intermediate 28: tert-Butyl 3-{4-[bis(tert-butoxycarbonyl)amino]butyl}-1-(2,3-dihydro-1-benzofuran-5-ylmethyl)-4-ethoxy-4-oxo-1,4-azaphosphinane-3-carboxylate Intermediate 28 is obtained starting from intermediate 21 and 2,3-dihydrobenzofuran-5-carbaldehyde in accordance with procedure F described hereinbefore.

$^1$H NMR: (400 MHz, dmso-d6) δ ppm 7.13 (d, 1H), 6.97 (dd, 1H), 6.68 (d, 1H), 4.5 (t, 2H), 4 (m, 2H), 3.55-3.3 (m, 4H), 3.15 (m, 2H), 3-2.2 (m, 4H), 1.91 (m, 4H), 1.39 (m, 29H), 1.2 (t, 3H), 0.87 (m, 2H)

EXAMPLE 38: 3-(4-AMINOBUTYL)-1-(2,3-DIHYDRO-1-BENZOFURAN-5-YLMETHYL)-4-HYDROXY-4-OXO-1,4-AZAPHOSPHINANE-3-CARBOXYLIC ACID

Example 38 is obtained starting from intermediate 28 in accordance with procedure D described hereinbefore.

$^1$H NMR: (400 MHz, D2O) δ ppm 7.34 (d, 1H), 7.2 (dd, 1H), 6.85 (d, 1H), 4.59 (t, 2H), 4.14/3.68 (dd, 2H), 3.68/3.28 (m, 2H), 3.47/3.06 (m, 2H), 3.22 (t, 2H), 2.94 (m, 2H), 2.22/1.76 (m, 2H), 1.93/1.47 (m, 2H), 1.6 (m, 2H), 1.26/1.12 (m, 2H)

ESI/FIA/HR and MS/MS: [M+H]+=383.1725 (383.1735)

Elemental analysis: C=55.92 (56.54); H=6.71 (7.12); N=7.17 (7.33)

Intermediate 29: tert-Butyl 3-{4-[bis(tert-butoxycarbonyl)amino]butyl}-4-ethoxy-4-oxo-1-[(2-oxo-3H-1,3-benzoxazol-6-yl)methyl]-1,4-azaphosphinane-3-carboxylate Intermediate 29 is obtained starting from intermediate 21 and 3H-1,3-benzoxazole-carbaldehyde in accordance with procedure F described hereinbefore.

$^1$H NMR: (400 MHz, dmso-d6) δ ppm 12.55 (s, 1H), 7.15 (s, 1H), 7.05 (dd, 1H), 7 (d, 1H), 4 (m, 2H), 3.65 (d, 1H), 3.4 (d, 1H), 3.35 (m, 2H), 3.05-2.3 (m, 4H), 2.05-1.8 (m, 4H), 1.4 (m, 2H), 1.4 (3s, 27H), 1.25 (t, 3H), 0.9-0.7 (m, 2H)

ESI/FIA/HR and MS/MS: [M+H]+=682.3461 (682.3468)

EXAMPLE 39: 3-(4-AMINOBUTYL)-4-HYDROXY-4-OXO-1-[(2-OXO-3H-1,3-BENZOXAZOL-6-YL)METHYL]-1,4-AZAPHOSPHINANE-3-CARBOXYLIC ACID

Example 39 is obtained starting from intermediate 29 in accordance with procedure D described hereinbefore.

$^1$H NMR: (400 MHz, D2O) δ ppm 7.4 (s, 1H), 7.3 (dd, 1H), 7.25 (d, 1H), 4.45/4.25 (2dd, 2H), 3.8-3.6 (m, 1H), 3.45 (m, 1H), 3.35 (m, 1H), 3.1 (m, 1H), 2.95 (m, 2H), 2.25 (m, 2H), 1.95 (m, 1H), 1.65-1.4 (m, 3H), 1.25/1.1 (2*m, 2H)

ESI/FIA/HR and MS/MS: [M+H]+=398.1455 (398.1480)

Elemental analysis: C=51.17 (51.39); H=5.85 (6.09); N=10.49 (10.57)

Intermediate 30: tert-Butyl 3-{4-[bis(tert-butoxycarbonyl)amino]butyl}-1-(1H-benzimidazol-5-ylmethyl)-4-ethoxy-4-oxo-1,4-azaphosphinane-3-carboxylate Intermediate 30 is obtained starting from intermediate 21 and 1H-benzimidazole-5-carbaldehyde in accordance with procedure F described hereinbefore.

$^1$H NMR: (400 MHz, dmso-d6) δ ppm 12.4 (sl, 1H), 8.16 (s, 1H), 7.7-7.3 (m, 2H), 7.14 (d, 1H), 3.97 (m, 2H), 3.72/3.54 (2*d, 2H), 3.45-3.2 (m, 2H), 2.97/2.33 (2*m, 2H), 2.85/2.48 (2*m, 2H), 2.02-1.85 (m, 2H), 2.02-1.85 (m, 2H), 1.39/1.34 (2*s, 27H), 1.38 (m, 2H), 1.2 (t, 3H), 0.81 (m, 2H)

EXAMPLE 40: 3-(4-AMINOBUTYL)-1-(1H-BENZIMIDAZOL-5-YLMETHYL)-4-HYDROXY-4-OXO-1,4-AZAPHOSPHINANE-3-CARBOXYLIC ACID

Example 40 is obtained starting from intermediate 30 in accordance with procedure D described hereinbefore.

$^1$H NMR: (400 MHz, D2O) δ ppm 8.26 (s, 1H), 7.77 (df, 1H), 7.72 (d, 1H), 7.38 (dd, 1H), 4.53/4.34 (2*d, 2H), 3.73/3.36 (2*m, 2H), 3.47/3.12 (2*m, 2H), 2.88 (m, 2H), 2.23/1.78 (2*m, 2H), 1.91/1.55 (2*m, 2H), 1.55/1.45 (2*m, 2H), 1.18/1.04 (2*m, 2H)

ESI/FIA/HR and MS/MS: [M+H]+=381.1692 (381.1691)

Elemental analysis: C=54.46 (53.68); H=6.00 (6.62); N=14.67 (14.73)

Intermediate 31: tert-Butyl 3-{4-[bis(tert-butoxycarbonyl)amino]butyl}-1-[(2-fluoro-4-hydroxyphenyl)methyl]-4-ethoxy-4-oxo-1,4-azaphosphinane-3-carboxylate Intermediate 31 is obtained starting from intermediate 21 and 2-fluoro-4-methoxybenzaldehyde in accordance with procedure F described hereinbefore.

¹H NMR: (400 MHz, dmso-d6) δ ppm 7.25 (t, 1H), 6.78 (2*m, 2H), 4.1-3.9 (m, 2H), 3.76 (s, 3H), 3.57/3.46 (2*d, 2H), 3.36 (m, 2H), 2.93/2.32 (2*m, 2H), 2.81/2.47 (2*dd, 2H), 2-1.8 (m, 2H), 2-1.8 (m, 2H), 1.42/1.36 (2*s, 27H), 1.4 (m, 2H), 1.2 (t, 3H), 1-0.75 (m, 2H)

EXAMPLE 41: 3-(4-AMINOBUTYL)-1-[(2-FLUORO-4-HYDROXYPHENYL)METHYL]-4-HYDROXY-4-OXO-1,4-AZAPHOSPHINANE-3-CARBOXYLIC ACID

Example 41 is obtained starting from intermediate 31 in accordance with procedure D described hereinbefore.

¹H NMR: (400 MHz, D2O) δ ppm 7.21 (t, 1H), 6.63 (m, 1H), 6.63 (m, 1H), 4.19 (dd, 2H), 3.58/3.19 (m, 2H), 3.38/3.04 (dd, 2H), 2.84 (m, 2H), 2.1/1.65 (m, 2H), 1.84/1.5 (m, 2H), 1.5/1.38 (m, 2H), 1.17/1.04 (m, 2H)

ESI/FIA/HR and MS/MS: [M+H]+=375.1486 (375.1485)

Elemental analysis: C=51.05 (51.34); H=5.28 (6.46); N=7.76 (7.48)

Intermediate 32: tert-Butyl 3-{4-[bis(tert-butoxycarbonyl)amino]butyl}-4-ethoxy-4-oxo-1-[(6-oxo-1H-pyridin-3-yl)methyl]-1,4-azaphosphinane-3-carboxylate Intermediate 32 is obtained starting from intermediate 21 and 6-hydroxynicotinaldehyde in accordance with procedure F described hereinbefore.

¹H NMR: (400 MHz, dmso-d6) δ ppm 11.45 (s, 1H), 7.35 (dd, 1H), 7.21 (df, 1H), 6.31 (d, 1H), 4.1-3.9 (m, 2H), 3.4 (m, 2H), 3.32/3.19 (2*d, 2H), 2.9/2.28 (2*m, 2H), 2.8/2.44 (2*dd, 2H), 2-1.7 (m, 2H), 2-1.7 (m, 2H), 1.42/1.38 (2*s, 27H), 1.4 (m, 2H), 1.21 (t, 3H), 1.1-0.85 (m, 2H)

EXAMPLE 42: 3-(4-AMINOBUTYL)-4-HYDROXY-4-OXO-1-[(6-OXO-1H-PYRIDIN-3-YL)METHYL]-1,4-AZAPHOSPHINANE-3-CARBOXYLIC ACID

Example 42 is obtained starting from intermediate 32 in accordance with procedure D described hereinbefore.

¹H NMR: (300 MHz, D2O) δ ppm 7.74 (dd, 1H), 7.7 (d, 1H), 6.66 (d, 1H), 4.17 (AB, 2H), 3.69/3.31 (2m, 2H), 3.45/3.09 (2m, 2H), 2.94 (m, 2H), 2.24/1.79 (2m, 2H), 1.94/1.49 (2m, 2H), 1.61 (quint., 2H), 1.29/1.14 (2m, 2H)

³¹P NMR: (300 MHz, D2O) δ ppm 25.8

ESI/FIA/HR and MS/MS: [M+H]+=358.1537 (358.1531)

Elemental analysis: C=50.77 (50.42); H=6.41 (6.77); N=11.96 (11.76)

Intermediate 33: tert-Butyl 3-{4-[bis(tert-butoxycarbonyl)amino]butyl}-1-(1-benzofuran-5-ylmethyl)-4-ethoxy-4-oxo-1,4-azaphosphinane-3-carboxylate Intermediate 33 is obtained starting from intermediate 21 and 5-formylbenzofuran in accordance with procedure F described hereinbefore.

¹H NMR: (400 MHz, dmso-d6) δ ppm 7.98 (df, 1H), 7.55 (df, 1H), 7.53 (d, 1H), 7.25 (dd, 1H), 6.91 (df, 1H), 4.1-3.9 (m, 2H), 3.72/3.51 (2*d, 2H), 3.4-3.2 (m, 2H), 2.98/2.35 (2*dd, 2H), 2.81/2.48 (2*dd, 2H), 2-1.65 (m, 2H), 2-1.65 (m, 2H), 1.4/1.34 (2*s, 27H), 1.39 (m, 2H), 1.21 (t, 3H), 1-0.7 (m, 2H)

EXAMPLE 43: 3-(4-AMINOBUTYL)-1-(1-BENZOFURAN-5-YLMETHYL)-4-HYDROXY-4-OXO-1,4-AZAPHOSPHINANE-3-CARBOXYLIC ACID

Example 43 is obtained starting from intermediate 33 in accordance with procedure D described hereinbefore.

¹H NMR: (400 MHz, D2O) δ ppm 7.79 (df, 1H), 7.76 (df, 1H), 7.61 (d, 1H), 7.39 (dd, 1H), 7.31/4.5 (2*d, 2H), 6.91 (df, 1H), 3.72/3.33 (2*dd, 2H), 3.49/3.11 (2*dd, 2H), 2.9 (m, 2H), 2.23/1.77 (2*m, 2H), 1.91/1.57 (2*m, 2H), 1.57/1.45 (2*m, 2H), 1.2/1.15 (2*m, 2H)

ESI/FIA/HR and MS/MS: [M+H]+=381.1577 (381.1579)

Elemental analysis: C=56.67 (56.84); H=6.52 (6.62); N=7.42 (7.36)

Intermediate 34: tert-Butyl 3-{4-[bis(tert-butoxycarbonyl)amino]butyl}-4-ethoxy-1-[(4-hydroxy-2-methylphenyl)methyl]-4-oxo-1,4-azaphosphinane-3-carboxylate Intermediate 34 is obtained starting from intermediate 21 and 4-methoxy-2-methylbenzaldehyde in accordance with procedure F described hereinbefore.

¹H NMR: (400 MHz, dmso-d6) δ ppm 7.05 (d, 1H), 6.75 (df, 1H), 6.69 (dd, 1H), 4.1-3.9 (m, 2H), 3.72 (s, 3H), 3.5/3.3 (2*d, 2H), 3.3 (m, 2H), 2.9/2.41 (2*m, 2H), 2.8/2.29 (2*m, 2H), 2.3 (2*s, 3H), 2.02-1.79 (unresolved peak, 2H), 2.02-1.79 (unresolved peak, 2H), 1.42/1.36 (2*s, 27H), 1.32 (m, 2H), 1.21 (t, 3H), 0.68 (m, 2H)

EXAMPLE 44: 3-(4-AMINOBUTYL)-4-HYDROXY-1-[(4-HYDROXY-2-METHYLPHENYL)METHYL]-4-OXO-1,4-AZAPHOSPHINANE-3-CARBOXYLIC ACID

Example 44 is obtained starting from intermediate 34 in accordance with procedure D described hereinbefore.

¹H NMR: (400 MHz, D2O) δ ppm 7.25 (d, 1H), 6.81 (df, 1H), 6.77 (dd, 1H), 4.29/4.22 (2*d, 2H), 3.69/3.32 (2*dd, 2H), 3.49/3.18 (2*dd, 2H), 2.94 (m, 2H), 2.32 (s, 3H), 2.19/1.75 (2*m, 2H), 1.94/1.6 (2*m, 2H), 1.6/1.5 (2*m, 2H), 1.27/1.12 (2*m, 2H)

³¹P NMR: (400 MHz, D2O) δ ppm 26

ESI/FIA/HR and MS/MS: [M+H]+=371.1739 (371.1735)

Elemental analysis: C=54.81 (55.13); H=6.88 (7.35); N=7.52 (7.56)

Intermediate 35: tert-Butyl 3-{4-[bis(tert-butoxycarbonyl)amino]butyl}-1-[(2-chloro-4-fluorophenyl)methyl]-4-ethoxy-4-oxo-1,4-azaphosphinane-3-carboxylate Intermediate 35 is obtained starting from intermediate 21 and 2-chloro-4-fluorobenzaldehyde in accordance with procedure F described hereinbefore.

¹H NMR: (400 MHz, dmso-d6) δ ppm 7.5 (dd, 1H), 7.35 (dd, 1H), 7.2 (dd, 1H), 4.1-3.9 (quad., 2H), 3.65-3.55 (d, 2H), 3.4-3.3 (m, 2H), 2.9-2.35 (m, 4H), 1.9 (m, 4H), 1.55-1.35 (m, 2H), 1.4-1.35 (s, 27H), 1.2 (t, 3H), 0.85-0.75 (m, 2H)

$^{31}$P NMR: (400 MHz, dmso-d6) δ ppm 45
$^{19}$F NMR: (400 MHz, dmso-d6) δ ppm −112
ESI/FIA/HR and MS/MS: [M+H]+=677.3146 (677.3133)

EXAMPLE 45: 3-(4-AMINOBUTYL)-1-[(2-CHLORO-4-FLUOROPHENYL)METHYL]-4-HYDROXY-4-OXO-1,4-AZAPHOSPHINANE-3-CARBOXYLIC ACID

Example 45 is obtained starting from intermediate 35 in accordance with procedure D described hereinbefore.
$^1$H NMR: (400 MHz, D2O) δ ppm 7.56 (dd, 1H), 7.39 (dd, 1H), 7.18 (td, 1H), 4.43 (sl, 2H), 3.7/3.4 (m, 2H), 3.5/3.26 (m, 2H), 2.95 (m, 2H), 2.22/1.78 (m, 2H), 1.95/1.62 (m, 2H), 1.62/1.5 (m, 2H), 1.28/1.12 (m, 2H)
ESI/FIA/HR and MS/MS: [M+H]+=393.1149 (393.1146)
Elemental analysis: C=49.40 (48.93); H=5.31 (5.90); N=7.17 (7.13)

Intermediate 36: tert-Butyl 3-{4-[bis(tert-butoxycarbonyl)amino]butyl}-1-[[2-(4-fluorophenyl)phenyl]methyl]-4-ethoxy-4-oxo-1,4-azaphosphinane-3-carboxylate Intermediate 36 is obtained starting from intermediate 21 and 2-(4-fluorophenyl)benzaldehyde in accordance with procedure F described hereinbefore.
$^1$H NMR: (400 MHz, dmso-d6) δ ppm 7.5-7.2 (m, 4H), 7.5-7.2 (m, 4H), 4.08-3.73 (m, 2H), 3.52/3.3 (2*d, 2H), 3.3 (m, 2H), 2.8-2.62/2.33 (2*m, 2H), 2.8-2.62/2.2 (2*m, 2H), 1.98-1.63 (m, 2H), 1.98-1.63 (m, 2H), 1.4/1.32 (2*s, 27H), 1.38 (m, 2H), 1.21/1.18 (2*t, 3H), 0.9-0.6 (m, 2H)

EXAMPLE 46: 3-(4-AMINOBUTYL)-1-[[2-(4-FLUOROPHENYL)PHENYL]METHYL]-4-HYDROXY-4-OXO-1,4-AZAPHOSPHINANE-3-CARBOXYLIC ACID

Example 46 is obtained starting from intermediate 36 in accordance with procedure D described hereinbefore.
$^1$H NMR: (400 MHz, D2O) δ ppm 7.6 (d, 1H), 7.52 (m, 2H), 7.4 (d, 1H), 7.35 (dd, 2H), 7.24 (dd, 2H), 4.41/4.29 (dd, 2H), 3.39/3.1 (2*m, 2H), 3.19/2.88 (2*m, 2H), 2.93 (m, 2H), 2.09/1.65 (2*m, 2H), 1.85/1.59 (2*m, 2H), 1.59/1.35 (2*m, 2H), 1.2-1 (m, 2H)
ESI/FIA/HR and MS/MS: [M+H]+=435.1850 (435.1848)
Elemental analysis: C=60.73 (60.82); H=5.96 (6.50); N=6.73 (6.45)

Intermediate 37: tert-Butyl 3-{4-[bis(tert-butoxycarbonyl)amino]butyl}-1-[[2-(2-fluorophenyl)phenyl]methyl]-4-ethoxy-4-oxo-1,4-azaphosphinane-3-carboxylate Intermediate 37 is obtained starting from intermediate 21 and 2-(2-fluorophenyl)benzaldehyde in accordance with procedure F described hereinbefore.
$^1$H NMR: (400 MHz, dmso-d6) δ ppm 7.52 (d, 1H), 7.45/7.42 (t, 2H), 7.45 (m, 1H), 7.35 (m, 3H), 7.2 (d, 1H), 3.91 (m, 2H), 3.5-3.2 (m, 2H), 3.5-3.2 (m, 2H), 2.67/2.29 (m, 2H), 2.67/2.13 (m, 2H), 1.95-1.6 (m, 2H), 1.95-1.6 (m, 2H), 1.42 (s, 18H), 1.38 (m, 2H), 1.34 (s, 9H), 1.17 (t, 3H), 0.68 (m, 2H)

EXAMPLE 47: 3-(4-AMINOBUTYL)-1-[[2-(2-FLUOROPHENYL)PHENYL]METHYL]-4-HYDROXY-4-OXO-1,4-AZAPHOSPHINANE-3-CARBOXYLIC ACID

Example 47 is obtained starting from intermediate 37 in accordance with procedure D described hereinbefore.
$^1$H NMR: (400 MHz, D2O) δ ppm 7.66 (m, 1H), 7.57 (m, 1H), 7.57 (m, 1H), 7.51 (m, 1H), 7.42 (m, 1H), 7.34 (m, 1H), 7.34 (m, 1H), 7.28 (t, 1H), 4.6-4 (unresolved peak, 2H), 3.7-2.7 (unresolved peak, 2H), 3.7-2.7 (unresolved peak, 2H), 2.93 (m, 2H), 2.14/1.69 (m, 2H), 1.87/1.37 (m, 2H), 1.59 (m, 2H), 1.15/1.06 (m, 2H)
ESI/FIA/HR and MS/MS: [M+H]+=435.1855 (435.1848)
Elemental analysis: C=60.87 (60.82); H=6.12 (6.50); N=6.42 (6.45)

Intermediate 38: tert-Butyl 3-{4-[bis(tert-butoxycarbonyl)amino]butyl}-1-[[2-(2,5-dichlorophenyl)phenyl]methyl]-4-ethoxy-4-oxo-1,4-azaphosphinane-3-carboxylate Intermediate 38 is obtained starting from intermediate 21 and 2-(2,5-dichlorophenyl)benzaldehyde in accordance with procedure F described hereinbefore.
$^1$H NMR: (400 MHz, dmso-d6) δ ppm 7.65-7.1 (m, 7H), 4.05-3.85 (m, 2H), 3.5-3.2 (m, 4H), 2.8-2.3 (m, 4H), 2.2-1.65 (m, 4H), 1.5-1.3 (m, 2H), 1.45 (s, 18H), 1.35 (s, 9H), 1.2 (t, 3H), 0.8-0.5 (m, 2H)

EXAMPLE 48: 3-(4-AMINOBUTYL)-1-[[2-(2,5-DICHLOROPHENYL)PHENYL]METHYL]-4-HYDROXY-4-OXO-1,4-AZAPHOSPHINANE-3-CARBOXYLIC ACID

Example 48 is obtained starting from intermediate 38 in accordance with procedure D described hereinbefore.
$^1$H NMR: (300 MHz, D2O) δ ppm 7.7-7.3 (m, 7H), 4.45/4.21/4.02 (m, 2H), 3.75/3.1 (2*m, 2H), 3.75/3.1 (2*m, 2H), 2.98 (m, 2H), 2.2/1.65 (2*m, 2H), 1.95/1.65 (2*m, 2H), 1.65/1.15 (2*m, 2H), 1.45/1.15 (2*m, 2H)
ESI/FIA/HR and MS/MS: [M+H]+=485.1184 (485.1163)
Elemental analysis: C=54.33 (54.44); H=4.99 (5.61); N=5.86 (5.77)

Intermediate 39: tert-Butyl 3-{4-[bis(tert-butoxycarbonyl)amino]butyl}-4-ethoxy-4-oxo-1-[[2-(3-phenylphenyl)phenyl]methyl]-1,4-azaphosphinane-3-carboxylate Intermediate 39 is obtained starting from intermediates 21 and 241 in accordance with procedure F described hereinbefore.
$^1$H NMR: (400 MHz, dmso-d6) δ ppm 7.7 (d, 2H), 7.65 (d, 1H), 7.6 (s, 1H), 7.55 (m, 2H), 7.45 (m, 2H), 7.4-7.3 (m, 5H), 3.9 (m, 2H), 3.6/3.4 (2*d, 2H), 3.4-3.2 (m, 2H), 2.85-2.65 (m, 2H), 2.35 (m, 1H), 2.2 (m, 1H), 1.9 (m, 1H), 1.85-1.6 (m, 3H), 1.45-1.3 (m, 2H), 1.4/1.3 (2*s, 27H), 1.15 (t, 3H), 0.65 (m, 2H)

EXAMPLE 49: 3-(4-AMINOBUTYL)-4-HYDROXY-4-OXO-1-[[2-(3-PHENYLPHENYL)PHENYL]-METHYL]-1,4-AZAPHOSPHINANE-3-CARBOXYLIC ACID

Example 49 is obtained starting from intermediate 39 in accordance with procedure D described hereinbefore.

¹H NMR: (300 MHz, D2O) δ ppm 7.6-7.1 (m, 13H), 4.25 (d, 1H), 4.1 (d, 1H), 3.4-3.2 (m, 1H), 3.15-2.9 (m, 2H), 2.75-2.55 (m, 3H), 2.05 (m, 1H), 1.75 (m, 1H), 1.55 (m, 1H), 1.4 (m, 2H), 1.25 (m, 1H), 0.9 (m, 2H)

ESI/FIA/HR and MS/MS: [M+H]+=493.2256 (493.2256)

Elemental analysis: C=68.08 (68.28); H=6.02 (6.75); N=5.71 (5.69)

Intermediate 40: tert-Butyl 3-{4-[bis(tert-butoxycarbonyl)amino]butyl}-4-ethoxy-1-[(2-naphthalen-2-ylphenyl)methyl]-4-oxo-1,4-azaphosphinane-3-carboxylate Intermediate 40 is obtained starting from intermediates 21 and 240 in accordance with procedure F described hereinbefore.

¹H NMR: (400 MHz, dmso-d6) δ ppm 7.95 (d, 1H), 7.95 (m, 2H), 7.9 (s, 1H), 7.55 (m, 4H), 7.4 (m, 2H), 7.3 (d, 1H), 3.9 (m, 2H), 3.65/3.45 (2*d, 2H), 3.45-3.2 (m, 2H), 3.3-2.6 (m, 2H), 2.35 (dd, 2H), 2.2 (m, 1H), 1.9 (m, 1H), 1.85-1.65 (m, 3H), 1.8 (m, 2H), 1.4/1.3 (2*s, 27H), 1.15 (t, 3H), 0.7 (m, 2H)

EXAMPLE 50: 3-(4-AMINOBUTYL)-4-HYDROXY-1-[(2-NAPHTHALEN-2-YLPHENYL)METHYL]-4-OXO-1,4-AZAPHOSPHINANE-3-CARBOXYLIC ACID

Example 50 is obtained starting from intermediate 40 in accordance with procedure D described hereinbefore.

¹H NMR: (300 MHz, D2O) δ ppm 7.9 (d, 1H), 7.9/7.85 (2*m, 2H), 7.7 (s, 1H), 7.6-7.4 (m, 5H), 7.3 (m, 2H), 4.35/4.2 (2dd, 2H), 3.4-3.2 (m, 1H), 3.15-2.9 (m, 2H), 2.8 (m, 2H), 2.7 (dd, 1H), 2 (m, 1H), 1.75 (m, 1H), 1.65-1.35 (m, 3H), 1.25 (m, 1H), 0.85 (m, 2H)

ESI/FIA/HR and MS/MS: [M+H]+=467.2090 (467.2099)

Elemental analysis: C=67.58 (66.94); H=6.40 (6.70); N=5.73 (6.00)

Intermediate 41: tert-Butyl 3-{4-[bis(tert-butoxycarbonyl)amino]butyl}-1-[[2-(2,6-dichlorophenyl)phenyl]methyl]-4-ethoxy-4-oxo-1,4-azaphosphinane-3-carboxylate Intermediate 41 is obtained starting from intermediates 21 and 242 in accordance with procedure F described hereinbefore.

¹H NMR: (300 MHz, dmso-d6) δ ppm 7.65-7.5 (m, 3H), 7.5-7.3 (m, 3H), 7.1 (d, 1H), 4 (m, 2H), 3.45 (m, 2H), 3.25 (2*d, 2H), 2.85-2.1 (m, 4H), 2-1.75 (m, 4H), 1.6-1.15 (m, 2H), 1.45/1.4 (2*s, 27H), 1.25 (t, 3H), 0.95 (m, 2H)

EXAMPLE 51: 3-(4-AMINOBUTYL)-1-[[2-(2,6-DICHLOROPHENYL)PHENYL]METHYL]-4-HYDROXY-4-OXO-1,4-AZAPHOSPHINANE-3-CARBOXYLIC ACID

Example 51 is obtained starting from intermediate 41 in accordance with procedure D described hereinbefore.

¹H NMR: (300 MHz, D2O) δ ppm 7.6 (d, 1H), 7.5/7.2 (m, 3H), 7.5-7.3 (m, 2H), 7.12 (d, 1H), 3.38/3.21 (2*d, 2H), 2.82/2.38 (2*dd, 2H), 2.65/2.22 (2*m, 2H), 2.45 (t, 2H), 1.85/1.71 (2*m, 2H), 1.7/1.35 (2*m, 2H), 1.32/0.8 (2*m, 2H), 1.32/0.8 (2*m, 2H)

ESI/FIA/HR and MS/MS: [M+H]+=485.1169 (485.1163)

Elemental analysis: C=54.71 (54.44); H=5.14 (5.61); N=5.81 (5.77)

Intermediate 42: tert-Butyl 3-{4-[bis(tert-butoxycarbonyl)amino]butyl}-4-ethoxy-1-methyl-4-oxo-1,4-azaphosphinane-3-carboxylate Intermediate 42 is obtained starting from intermediate 21 and formaldehyde in accordance with procedure F described hereinbefore.

¹H NMR: (400 MHz, dmso-d6) δ ppm 3.98 (m, 2H), 3.48 (m, 2H), 2.75 (m, 2H), 2.49/2.2 (2m, 2H), 2.01 (s, 3H), 1.92 (m, 4H), 1.5 (m, 2H), 1.45/1.4 (2s, 27H), 1.25/1 (2m, 2H), 1.2 (t, 3H)

EXAMPLE 52: 3-(4-AMINOBUTYL)-4-HYDROXY-1-METHYL-4-OXO-1,4-AZAPHOSPHINANE-3-CARBOXYLIC ACID

Example 52 is obtained starting from intermediate 42 in accordance with procedure D described hereinbefore.

¹H NMR: (400 MHz, D2O) δ ppm 3.7-3.5 (m, 2H), 3.3 (t, 1H), 3.2 (dd, 1H), 3 (t, 2H), 2.9 (s, 3H), 2.3 (m, 1H), 2 (m, 1H), 1.75 (m, 1H), 1.7 (m, 2H), 1.5 (m, 1H), 1.4/1.25 (2m, 2H)

ESI/FIA/HR and MS/MS: [M+H]+=265.1300 (265.1317)

Elemental analysis: C=45.59 (45.45); H=7.97 (8.01); N=10.61 (10.60)

Intermediate 43: tert-Butyl 3-{4-[bis-(tert-butoxycarbonyl)amino]butyl}-4-ethoxy-4-oxo-1-(2-phenyl-ethyl)-1,4-azaphosphinane-3-carboxylate Intermediate 43 is obtained starting from intermediate 21 and phenylacetaldehyde in accordance with procedure F described hereinbefore.

¹H NMR: (400 MHz, dmso-d6) δ ppm 7.3-7.15 (m, 5H), 3.98 (m, 2H), 3.45 (t, 2H), 3.05-2.3 (m, 8H), 2-1.8 (m, 4H), 1.4 (m+2s, 29H), 1.2 (t, 3H), 1.18/0.9 (2m, 2H)

EXAMPLE 53: 3-(4-AMINOBUTYL)-4-HYDROXY-4-OXO-1-(2-PHENYLETHYL)-1,4-AZAPHOSPHINANE-3-CARBOXYLIC ACID

Example 53 is obtained starting from intermediate 43 in accordance with procedure D described hereinbefore.

¹H NMR: (400 MHz, D2O) δ ppm 7.4-7.25 (m, 5H), 3.7/3.3 (2m, 2H), 3.52 (m, 1H), 3.45 (t, 2H), 3.1 (m, 3H), 2.95 (m, 2H), 2.2/1.75 (2m, 2H), 1.95 (m, 1H), 1.62 (m, 2H), 1.5-1.1 (m, 3H)

ESI/FIA/HR and MS/MS: [M+H]+=355.1777 (355.1786)

Elemental analysis: C=57.63 (57.62); H=7.36 (7.68); N=7.90 (7.90)

Intermediate 44: tert-Butyl 3-{4-[bis(tert-butoxycarbonyl)amino]butyl}-4-ethoxy-4-oxo-1-pentyl-1,4-azaphosphinane-3-carboxylate Intermediate 44 is obtained starting from intermediate 21 and 1-pentanal in accordance with procedure F described hereinbefore.

¹H NMR: (400 MHz, dmso-d6) δ ppm 3.98 (m, 2H), 3.8 (m, 2H), 3.49 (t, 2H), 2.85 (m, 2H), 2.49/2.25 (2m, 2H), 1.9 (m, 4H), 1.45/1.4 (2s, 27H), 1.45 (m, 4H), 1.25/1 (2m, 6H), 1.2 (t, 3H), 0.85 (t, 3H)

EXAMPLE 54: 3-(4-AMINOBUTYL)-4-HYDROXY-4-OXO-1-PENTYL-1,4-AZAPHOSPHINANE-3-CARBOXYLIC ACID

Example 54 is obtained starting from intermediate 44 in accordance with procedure D described hereinbefore.

$^1$H NMR: (400 MHz, D2O) δ ppm 3.7-3.5 (m, 2H), 3.3 (m, 1H), 3.15/3 (2m, 5H), 2.27 (m, 1H), 2 (m, 1H), 1.85-1.6 (m, 5H), 1.5/1.41 (2m, 2H), 1.3 (m, 5H), 0.85 (t, 3H)

ESI/FIA/HR and MS/MS: [M+H]+=321.1923 (321.1943)

Elemental analysis: C=52.77 (52.49); H=8.93 (9.12); N=9.00 (8.74)

Intermediate 45: tert-Butyl 3-{4-[bis(tert-butoxycarbonyl)amino-butyl}-4-ethoxy-1-(naphthalen-1-ylmethyl)-4-oxo-1,4-azaphosphinane-3-carboxylate Intermediate 45 is obtained starting from intermediate 21 and 1-naphthaldehyde in accordance with procedure F described hereinbefore.

$^1$H NMR: (400 MHz, dmso-d6) δ ppm 8.29 (d, 1H), 7.9/7.85 (2d, 2H), 7.6-7.4 (m, 4H), 3.95 (AB, 2H), 4 (m, 2H), 3.6 (m, 2H), 3.2-2.8 (m, 4H), 2.4/2 (2m, 2H), 1.7 (m, 2H), 1.4/1.3 (2s, 27H), 1.22 (t, 3H), 1.05/0.75 (2m, 2H), 0.5/0.2 (2m, 2H)

EXAMPLE 55: 3-(4-AMINOBUTYL)-4-HYDROXY-1-(NAPHTHALEN-1-YLMETHYL)-4-OXO-1,4-AZAPHOSPHINANE-3-CARBOXYLIC ACID

Example 55 is obtained starting from intermediate 45 in accordance with procedure D described hereinbefore.

$^1$H NMR: (400 MHz, D2O) δ ppm 7.9 (m, 3H), 7.6-7.3 (m, 4H), 4.55 (s, 2H), 3.55/3.28 (2m, 2H), 3.4/3.15 (2dd, 2H), 2.75 (m, 2H), 2/1.6 (2m, 2H), 1.8 (m, 1H), 1.5-1.25 (m, 3H), 1/0.9 (2m, 2H)

ESI/FIA/HR and MS/MS: [M+H]+=391.1778 (391.1786)

Elemental analysis: C=61.34 (61.53); H=6.58 (6.97); N=7.01 (7.18)

Intermediate 46: tert-Butyl 3-{4-[bis(tert-butoxycarbonyl)amino]butyl}-1-(cyclohexylmethyl)-4-ethoxy-4-oxo-1,4-azaphosphinane-3-carboxylate Intermediate 46 is obtained starting from intermediate 21 and cyclohexanal in accordance with procedure F described hereinbefore.

$^1$H NMR: (400 MHz, dmso-d6) δ ppm 4 (m, 2H), 3.5 (t, 2H), 2.8 (m, 2H), 2.48/2.25 (2m, 2H), 2.15 (dd, 2H), 1.95 (m, 2H), 1.68 (m, 1H), 1.65/1.4/0.8 (3m, 10H), 1.45 (m, 3H), 1.45/1.4 (2s, 27H), 1.2 (m, 2H), 1.2 (t, 3H), 1 (m, 1H)

EXAMPLE 56: 3-(4-AMINOBUTYL)-1-(CYCLOHEXYLMETHYL)-4-HYDROXY-4-OXO-1,4-AZAPHOSPHINANE-3-CARBOXYLIC ACID

Example 56 is obtained starting from intermediate 46 in accordance with procedure D described hereinbefore.

$^1$H NMR: (400 MHz, D2O) δ ppm 3.7/3.25 (2m, 2H), 3.55/3.15 (2dd, 2H), 3.1-2.9 (t+2dd, 4H), 2.25 (m, 1H), 2 (m, 1H), 1.85-1.55 (m, 9H), 1.52/1.41 (2m, 2H), 1.3/1.1 (m, 4H), 1 (m, 2H)

ESI/FIA/HR and MS/MS: [M+H]+=347.2095 (347.2099)

Elemental analysis: C=55.29 (55.48); H=9.08 (9.02); N=7.95 (8.09)

Intermediate 47: tert-Butyl 3-{4-bis[tert-butoxycarbonyl)amino]butyl}-4-ethoxy-1-(naphthalen-2-ylmethyl)-4-oxo-1,4-azaphosphinane-3-carboxylate Intermediate 47 is obtained starting from intermediate 21 and 2-naphthaldehyde in accordance with procedure F described hereinbefore.

$^1$H NMR: (400 MHz, dmso-d6) δ ppm 7.9 (m, 3H), 7.8 (s, 1H), 7.5 (m, 3H), 3.98 (m, 2H), 3.8 (d, 1H), 3.6 (m, 3H), 3.35/3.2 (2m, 2H), 3.1-2.75 (2m, 2H), 2.4 (m, 1H), 2.05-1.8 (m, 3H), 1.4-0.7 (m, 4H), 1.38 (3s, 27H), 1.22 (t, 3H)

EXAMPLE 57: 3-(4-AMINOBUTYL)-4-HYDROXY-1-(NAPHTHALEN-2-YLMETHYL)-4-OXO-1,4-AZAPHOSPHINANE-3-CARBOXYLIC ACID

Example 57 is obtained starting from intermediate 47 in accordance with procedure D described hereinbefore.

$^1$H NMR: (400 MHz, D2O) δ ppm 7.95-7.9 (m, 4H), 7.6-7.5 (m, 3H), 4.5; 4.3 (d, 2*1H H), 3.65 (m, 1H), 3.45-3.3 (m, 2H), 3.15 (m, 1H), 2.8 (m, 2H), 2.25 (m, 1H), 1.9-1.7 (m, 2H), 1.55-1.4 (m, 3H), 1.15-0.95 (m, 2H)

ESI/FIA/HR and MS/MS: [M+H]+=391.1778 (391.1786)

Elemental analysis: C=61.31 (61.53); H=6.56 (6.97); N=7.15 (7.18)

Intermediate 48: tert-Butyl 3-{4-[bis(tert-butoxycarbonyl)amino]butyl}-1-[(4-chlorophenyl)methyl]-4-ethoxy-4-oxo-1,4-azaphosphinane-3-carboxylate Intermediate 48 is obtained starting from intermediate 21 and 4-chlorobenzaldehyde in accordance with procedure F described hereinbefore.

$^1$H NMR: (400 MHz, dmso-d6) δ ppm 7.4 (d, 2H), 7.31 (d, 2H), 3.98 (m, 2H), 3.65-3.3 (m, 4H), 3-2.3 (m, 4H), 2-1.8 (m, 4H), 1.4 (s+m, 29H), 1.22 (2t, 3H), 0.8 (m, 2H)

EXAMPLE 58: 3-(4-AMINOBUTYL)-1-[(4-CHLOROPHENYL)METHYL]-4-HYDROXY-4-OXO-1,4-AZAPHOSPHINANE-3-CARBOXYLIC ACID

Example 58 is obtained starting from intermediate 48 in accordance with procedure D described hereinbefore.

$^1$H NMR: (400 MHz, D2O) δ ppm 7.5/7.45 (2d, 4H), 4.41/4.21 (2d, 2H), 3.7/3.33 (2m, 2H), 3.45/3.1 (2dd, 2H), 2.95 (m, 2H), 2.25/1.78 (2m, 2H), 1.95/1.5 (2m, 2H), 1.6 (m, 2H), 1.25/1.1 (2m, 2H)

ESI/FIA/HR and MS/MS: [M+H]+=375.1242 (375.1240)

Elemental analysis: C=50.89 (51.27); H=6.01 (6.45); N=7.44 (7.47)

Intermediate 49: tert-Butyl 3-{4-[bis(tert-butoxycarbonyl)amino]butyl}-4-ethoxy-1-[(4-fluorophenyl)methyl]-4-oxo-1,4-azaphosphinane-3-carboxylate Intermediate 49 is obtained starting from intermediate 21 and 4-fluorobenzaldehyde in accordance with procedure F described hereinbefore.

$^1$H NMR: (400 MHz, dmso-d6) δ ppm 7.35 (m, 2H), 7.15 (t, 2H), 4 (m, 2H), 3.65-3.3 (m, 4H), 3-2.3 (m, 4H), 2-1.8 (m, 4H), 1.4 (s+m, 29H), 1.2 (2t, 3H), 0.9/0.8 (2m, 2H)

EXAMPLE 59: 3-(4-AMINOBUTYL)-1-[(4-FLUOROPHENYL)METHYL]-4-HYDROXY-4-OXO-1,4-AZAPHOSPHINANE-3-CARBOXYLIC ACID

Example 59 is obtained starting from intermediate 49 in accordance with procedure D described hereinbefore.

¹H NMR: (400 MHz, D2O) δ ppm 7.5 (dd, 2H), 7.2 (t, 2H), 4.41/4.21 (2d, 2H), 3.7/3.31 (2m, 2H), 3.45/3.1 (2dd, 2H), 2.95 (m, 2H), 2.25/1.78 (2m, 2H), 1.95/1.5 (2m, 2H), 1.6 (m, 2H), 1.25/1.1 (2m, 2H)

ESI/FIA/HR and MS/MS: [M+H]+=359.1532 (359.1535)

Elemental analysis: C=53.65 (53.63); H=6.20 (6.75); N=7.83 (7.82)

Intermediate 50: tert-Butyl 3-{4-[bis(tert-butoxycarbonyl)amino]butyl}-4-ethoxy-1-(furan-2-ylmethyl)-4-oxo-1,4-azaphosphinane-3-carboxylate Intermediate 50 is obtained starting from intermediate 21 and 2-furaldehyde in accordance with procedure F described hereinbefore.

¹H NMR: (400 MHz, CDCl3) δ ppm 7.41 (s, 1H), 6.32 (s, 1H), 6.2 (s, 1H), 4.09 (s, 2H), 3.62/3.52 (AB, 2H), 3.5 (m, 2H), 3/2.65 (m, 2H), 2.96/2.52 (m, 2H), 2.7-1.8 (m, 4H), 1.5/1.46 (m, 30H), 1.3 (t, 3H), 1.01 (m, 1H)

³¹P NMR: (400 MHz, CDCl3) δ ppm 46.14

EXAMPLE 60: 3-(4-AMINOBUTYL)-1-(FURAN-2-YLMETHYL)-4-HYDROXY-4-OXO-1,4-AZAPHOSPHINANE-3-CARBOXYLIC ACID

Example 60 is obtained starting from intermediate 50 in accordance with procedure D described hereinbefore.

¹H NMR: (400 MHz, D2O) δ ppm 7.6 (sl, 1H), 6.7 (tf, 1H), 6.5 (tf, 1H), 4.45/4.32 (2d, 2H), 3.7/3.3 (2*m, 2H), 3.52/3.12 (2*m, 2H), 2.98 (m, 2H), 2.25/1.8 (2*m, 2H), 1.95/1.5 (2*m, 2H), 1.62 (m, 2H), 1.32/1.2 (2*m, 2H)

ESI/FIA/HR and MS/MS: [M+H]+=331.1422 (331.1422)

Elemental analysis: C=50.48 (50.91); H=6.48 (7.02); N=8.37 (8.48)

Intermediate 51: tert-Butyl 3-{4-[bis(tert-butoxycarbonyl)amino]butyl}-4-ethoxy-4-oxo-1-[[4-(trifluoromethyl)phenyl]methyl]-1,4-azaphosphinane-3-carboxylate Intermediate 51 is obtained starting from intermediate 21 and 4-trifluoromethylbenzaldehyde in accordance with procedure F described hereinbefore.

¹H NMR: (400 MHz, dmso-d6) δ ppm 7.71 (d, 2H), 7.52 (d, 2H), 4.03 (m, 2H), 3.72/3.51 (2*d, 2H), 3.35 (m, 2H), 3-2.3 (m, 4H), 1.98 (m, 4H), 1.4 (s+m, 29H), 1.2 (t, 3H), 0.8 (m, 2H)

EXAMPLE 61: 3-(4-AMINOBUTYL)-4-HYDROXY-4-OXO-1-[[4-(TRIFLUOROMETHYL)PHENYL]-METHYL]-1,4-AZAPHOSPHINANE-3-CARBOXYLIC ACID

Example 61 is obtained starting from intermediate 51 in accordance with procedure D described hereinbefore.

¹H NMR: (400 MHz, D2O) δ ppm 7.8 (d, 2H), 7.65 (d, 2H), 4.5/4.3 (AB, 2H), 3.7/3.45 (m, 2H), 3.39/3.11 (m, 2H), 2.9 (m, 2H), 2.28/1.8 (m, 2H), 1.95/1.49 (m, 2H), 1.6 (m, 2H), 1.2/1.1 (m, 2H)

¹⁹F NMR: (400 MHz, D2O) δ ppm −62.5

³¹P NMR: (400 MHz, D2O) δ ppm 24

ESI/FIA/HR and MS/MS: [M+H]+=409.1510 (409.1504)

Elemental analysis: C=49.86 (50.00); H=5.32 (5.92); N=6.83 (6.86)

Intermediate 52: tert-Butyl 3-{4-[bis(tert-butoxycarbonyl)amino]butyl}-4-ethoxy-1-[(4-methoxyphenyl)methyl]-4-oxo-1,4-azaphosphinane-3-carboxylate Intermediate 52 is obtained starting from intermediate 21 and 4-methoxybenzaldehyde in accordance with procedure F described hereinbefore.

¹H NMR: (400 MHz, dmso-d6) δ ppm 7.2 (d, 2H), 6.9 (d, 2H), 3.98 (m, 2H), 3.72 (s, 3H), 3.6/3.32 (2*d, 2H), 3.4 (m, 2H), 3-2.25 (m, 4H), 1.9 (m, 4H), 1.4 (s+m, 29H), 1.2 (t, 3H), 0.8 (m, 2H)

EXAMPLE 62: 3-(4-AMINOBUTYL)-4-HYDROXY-1-[(4-METHOXYPHENYL)METHYL]-4-OXO-1,4-AZAPHOSPHINANE-3-CARBOXYLIC ACID

Example 62 is obtained starting from intermediate 52 in accordance with procedure D described hereinbefore.

¹H NMR: (400 MHz, D2O) δ ppm 7.41 (d, 2H), 7.02 (d, 2H), centred at 4.25 (AB, 2H), 3.8 (s, 3H), 3.7/3.3 (2m, 2H), 3.45/3.08 (2dd, 2H), 2.95 (m, 2H), 2.25/1.75 (2m, 2H), 1.95/1.45 (2m, 2H), 1.6 (m, 2H), 1.25/1.1 (2m, 2H)

ESI/FIA/HR and MS/MS: [M+H]+=371.1712 (371.1730)

Elemental analysis: C=54.93 (55.13); H=7.41 (7.35); N=7.56 (7.56)

Intermediate 53: tert-Butyl 3-{4-[bis(tert-butoxycarbonyl)amino]butyl}-4-ethoxy-4-oxo-1-(thiophen-3-ylmethyl)-1,4-azaphosphinane-3-carboxylate Intermediate 53 is obtained starting from intermediate 21 and 3-thiophenaldehyde in accordance with procedure F described hereinbefore.

¹H NMR: (400 MHz, dmso-d6) δ ppm 7.49 (m, 1H), 7.31 (m, 1H), 7.02 (m, 1H), 3.95 (m, 2H), 3.6/3.49 (AB, 2H), 3.4 (m, 2H), 3/2.8 (m, 2H), 2.8/2.45 (m, 2H), 1.9 (m, 4H), 1.4 (m, 29H), 1.2 (t, 3H), 0.95/0.85 (m, 2H)

³¹P NMR: (400 MHz, dmso-d6) δ ppm 47/45

EXAMPLE 63: 3-(4-AMINOBUTYL)-4-HYDROXY-4-OXO-1-(THIOPHEN-3-YLMETHYL)-1,4-AZAPHOSPHINANE-3-CARBOXYLIC ACID

Example 63 is obtained starting from intermediate 53 in accordance with procedure D described hereinbefore.

¹H NMR: (400 MHz, D2O) δ ppm 7.61 (d, 1H), 7.54 (dd, 1H), 7.2 (d, 1H), 4.42/4.28 (2*d, 2H), 3.71/3.32 (m, 2H), 3.48/3.06 (m, 2H), 2.94 (m, 2H), 2.25/1.77 (m, 2H), 1.93/1.46 (m, 2H), 1.6 (m, 2H), 1.26/1.13 (m, 2H)

ESI/FIA/HR and MS/MS: [M+H]+=347.1182 (347.1189)

Elemental analysis: C=48.14 (48.55); H=6.55 (6.69); N=7.87 (8.09); S=8.65 (9.26)

Intermediate 54: tert-Butyl 3-{4-[bis(tert-butoxycarbonyl)amino]butyl}-4-ethoxy-1-[(4-hydroxy-3-methoxyphenyl)methyl]-4-oxo-1,4-azaphosphinane-3-carboxylate Intermediate 54 is obtained starting from intermediate 21 and 4-hydroxy-3-methoxybenzaldehyde in accordance with procedure F described hereinbefore.

¹H NMR: (400 MHz, dmso-d6) δ ppm 8.8 (s, 1H), 6.8 (df, 1H), 6.7 (d, 1H), 6.62 (dd, 1H), 3.95 (m, 2H), 3.71 (s, 3H), 3.49/3.31 (2d, 2H), 3.4 (m, 2H), 3-2.2 (m, 4H), 2-1.8 (m, 4H), 1.4 (2s+m, 29H), 1.2 (2t, 3H), 1/0.85 (2m, 2H)

EXAMPLE 64: 3-(4-AMINOBUTYL)-4-HYDROXY-1-[(4-HYDROXY-3-METHOXYPHENYL)METHYL]-4-OXO-1,4-AZAPHOSPHINANE-3-CARBOXYLIC ACID

Example 64 is obtained starting from intermediate 54 in accordance with procedure D described hereinbefore.

$^1$H NMR: (300 MHz, D2O) δ ppm 7.09 (m, 1H), 6.94 (m, 2H), 4.3/4.13 (2*d, 2H), 3.7/3.3 (2*m, 2H), 3.65 (s, 3H), 3.45/3.07 (2*m, 2H), 2.92 (m, 2H), 2.22/1.77 (2*m, 2H), 1.92/1.6 (2*m, 2H), 1.6/1.48 (2*m, 2H), 1.23/1.11 (2*m, 2H)

ESI/FIA/HR and MS/MS: [M+H]+=387.1665 (387.1685)

Elemental analysis: C=53.10 (52.85); H=7.01 (7.04); N=7.30 (7.25)

Intermediate 55: tert-Butyl 3-{4-[bis(tert-butoxycarbonyl)amino]butyl}-1-[(2-carboxyphenyl)methyl]-4-ethoxy-4-oxo-1,4-azaphosphinane-3-carboxylate Intermediate 55 is obtained starting from intermediate 21 and methyl 2-formylbenzoate in accordance with procedure F described hereinbefore.

$^1$H NMR: (400 MHz, dmso-d6) δ ppm 7.65 (d, 1H), 7.5 (t, 1H), 7.38 (m, 2H), 4.05/3.4 (2d, 2H), 3.95 (m, 2H), 3.8 (2s, 3H), 3.3/3.2 (2m, 2H), 3-2.35 (m, 4H), 2 (m, 1H), 1.8-1.6 (m, 3H), 1.4/1.3 (2s+m, 29H), 1.2 (2t, 3H), 0.5/0.35 (2m, 2H)

EXAMPLE 65: 3-(4-AMINOBUTYL)-1-[(2-CARBOXYPHENYL)METHYL]-4-HYDROXY-4-OXO-1,4-AZAPHOSPHINANE-3-CARBOXYLIC ACID

Example 55 is obtained starting from intermediate 65 in accordance with procedure D described hereinbefore.

ESI/FIA/HR and MS/MS: [M+H]+=385.1504 (385.1523)

Elemental analysis: C=53.42 (53.12); H=6.25 (6.56); N=7.40 (7.29)

Intermediate 56: tert-Butyl 3-{4-[bis(tert-butoxycarbonyl)amino]butyl}-1-[(3-chloro-4-hydroxyphenyl)methyl]-4-ethoxy-4-oxo-1,4-azaphosphinane-3-carboxylate Intermediate 56 is obtained starting from intermediate 21 and 3-chloro-4-hydroxybenzaldehyde in accordance with procedure F described hereinbefore.

$^1$H NMR: (400 MHz, dmso-d6) δ ppm 10.05 (m, 1H), 7.22 (df, 1H), 7.02 (dd, 1H), 6.9 (d, 1H), 3.98 (m, 2H), 3.5/3.31 (2d, 2H), 3.4 (m, 2H), 3-2.25 (m, 4H), 2-1.8 (m, 4H), 1.4 (2s+m, 29H), 1.2 (2t, 3H), 1.1-0.8 (2m, 2H)

EXAMPLE 66: 3-(4-AMINOBUTYL)-1-[(3-CHLORO-4-HYDROXYPHENYL)METHYL]-4-HYDROXY-4-OXO-1,4-AZAPHOSPHINANE-3-CARBOXYLIC ACID

Example 66 is obtained starting from intermediate 56 in accordance with procedure D described hereinbefore.

$^1$H NMR: (400 MHz, D2O) δ ppm 7.42 (df, 1H), 7.2 (dd, 1H), 6.97 (d, 1H), 4.27/4.07 (2*d, 2H), 3.62/3.22 (2*m, 2H), 3.39/3 (2*m, 2H), 2.85 (m, 2H), 2.18/1.7 (2*m, 2H), 1.85/1.52 (2*m, 2H), 1.52/1.4 (2*m, 2H), 1.18/1.05 (2*m, 2H)

ESI/FIA/HR and MS/MS: [M+H]+=391.1189 (391.1189)

Elemental analysis: C=49.09 (49.17); H=6.02 (6.19); N=7.18 (7.17)

Intermediate 57: tert-Butyl 3-{4-[bis(tert-butoxycarbonyl)amino]butyl}-4-ethoxy-1-[[4-hydroxy-3-(trifluoromethoxy)phenyl]methyl]-4-oxo-1,4-azaphosphinane-3-carboxylate Intermediate 57 is obtained starting from intermediate 21 and 4-hydroxy-3-(trifluoromethoxy)benzaldehyde in accordance with procedure F described hereinbefore.

$^1$H NMR: (400 MHz, dmso-d6) δ ppm 10.1 (m, 1H), 7.15 (df, 1H), 7.08 (dd, 1H), 6.95 (d, 1H), 3.98 (m, 2H), 3.5/3.4 (2d, 2H), 3.4 (m, 2H), 3-2.2 (m, 4H), 2-1.8 (m, 4H), 1.4 (2s+m, 29H), 1.2 (2t, 3H), 1.1-0.8 (2m, 2H)

EXAMPLE 67: 3-(4-AMINOBUTYL)-4-HYDROXY-1-[[4-HYDROXY-3-(TRIFLUOROMETHOXY)-PHENYL]METHYL]-4-OXO-1,4-AZAPHOSPHINANE-3-CARBOXYLIC ACID

Example 67 is obtained starting from intermediate 57 in accordance with procedure D described hereinbefore.

$^1$H NMR: (400 MHz, D2O) δ ppm 7.44 (df, 1H), 7.33 (dd, 1H), 7.09 (d, 1H), 4.38/4.13 (2*d, 2H), 3.7/3.31 (2*dd, 2H), 3.44/3.07 (2*dd, 2H), 2.92 (m, 2H), 2.23/1.78 (2*m, 2H), 1.94/1.59 (2*m, 2H), 1.59/1.46 (2*m, 2H), 1.21/1.1 (2*m, 2H)

$^{19}$F NMR: (400 MHz, D2O) δ ppm −58.3

$^{31}$P NMR: (400 MHz, D2O) δ ppm 26

ESI/FIA/HR and MS/MS: [M+H]+=441.1403 (441.1402)

Elemental analysis: C=46.46 (46.37); H=4.98 (5.49); N=6.42 (6.36)

Intermediate 58: tert-Butyl 3-{4-[bis(tert-butoxycarbonyl)amino]butyl}-4-ethoxy-1-[(4-hydroxy-3,5-dimethylphenyl)methyl]-4-oxo-1,4-azaphosphinane-3-carboxylate Intermediate 58 is obtained starting from intermediate 21 and 3,5-dimethyl-4-hydroxybenzaldehyde in accordance with procedure F described hereinbefore.

$^1$H NMR: (400 MHz, dmso-d6) δ ppm 8.09 (s, 1H), 6.8 (s, 2H), 3.98 (m, 2H), 3.49/3.21 (2d, 2H), 3.35 (m, 2H), 3-2.2 (m, 4H), 2.15 (s, 6H), 2-1.8 (m, 4H), 1.4 (2s+m, 29H), 1.2 (2t, 3H), 0.95-0.82 (2m, 2H)

EXAMPLE 68: 3-(4-AMINOBUTYL)-4-HYDROXY-1-[(4-HYDROXY-3,5-DIMETHYLPHENYL)-METHYL]-4-OXO-1,4-AZAPHOSPHINANE-3-CARBOXYLIC ACID

Example 68 is obtained starting from intermediate 58 in accordance with procedure D described hereinbefore.

$^1$H NMR: (400 MHz, D2O) δ ppm 7.1 (s, 2H), 4.25-4.1 (d, 2H), 3.7-3.5 (m, 2H), 3.25 (m, 1H), 3.1 (m, 1H), 2.95 (t, 2H), 2.2 (s, 6H), 2.2/1.75 (m, 2H), 1.95 (m, 1H), 1.6 (m, 2H), 1.5 (m, 1H), 1.3-1.1 (m, 2H)

ESI/FIA/HR and MS/MS: [M+H]+=385.1889 (385.1892)

Elemental analysis: C=55.50 (56.24); H=7.07 (7.60); N=7.16 (7.29)

Intermediate 59: tert-Butyl 3-{4-[bis(tert-butoxycarbonyl)amino]butyl}-4-ethoxy-4-oxo-1-(pyridin-4-ylmethyl)-1,4-azaphosphinane-3-carboxylate Intermediate 59 is obtained starting from intermediate 21 and 4-formylpyridine in accordance with procedure F described hereinbefore.

¹H NMR: (400 MHz, dmso-d6) δ ppm 8.5 (d, 2H), 7.3 (d, 2H), 4.1-3.9 (2m, 2H), 3.65/3.52 (2×2d, 2H), 3.45 (2m, 2H), 2.95-2.3 (m, 4H), 1.98 (m, 4H), 1.5-1.35 (m+s, 29H), 1.22 (2t, 3H), 1.05 (m, 2H)

EXAMPLE 69: 3-(4-AMINOBUTYL)-4-HYDROXY-4-OXO-1-(PYRIDIN-4-YLMETHYL)-1,4-AZAPHOSPHINANE-3-CARBOXYLIC ACID

Example 69 is obtained starting from intermediate 59 in accordance with procedure D described hereinbefore.
¹H NMR: (400 MHz, dmso-d6) δ ppm 8.5 (d, 2H), 8.05 (m, 3H), 7.3 (d, 2H), 3.55 (AB, 2H), 3.05/2.3 (2m, 2H), 2.7 (m, 3H), 2.5 (m, 1H), 1.75 (m, 1H), 1.65-1.15 (m, 7H)
ESI/FIA/HR and MS/MS: [M+H]+=342.1577 (342.1582)
Elemental analysis: C=52.56 (52.78); H=6.70 (7.09); N=12.22 (12.31)

Intermediate 60: tert-Butyl 3-{4-[bis(tert-butoxycarbonyl)amino]butyl}-4-ethoxy-4-oxo-1-(pyridin-3-ylmethyl)-1,4-azaphosphinane-3-carboxylate Intermediate 60 is obtained starting from intermediate 21 and 3-formylpyridine in accordance with procedure F described hereinbefore.
¹H NMR: (400 MHz, dmso-d6) δ ppm 8.5 (d+s, 2H), 7.7 (2dd, 1H), 7.35 (m, 1H), 4.1-3.9 (2m, 2H), 3.65/3.52 (2×2d, 2H), 3.45 (2m, 2H), 3-2.3 (m, 4H), 1.9 (m, 4H), 1.4 (m+s, 30H), 1.22 (2t, 3H), 0.82 (m, 1H)

EXAMPLE 70: 3-(4-AMINOBUTYL)-4-HYDROXY-4-OXO-1-(PYRIDIN-3-YLMETHYL)-1,4-AZAPHOSPHINANE-3-CARBOXYLIC ACID

Example 70 is obtained starting from intermediate 60 in accordance with procedure D described hereinbefore.
¹H NMR: (400 MHz, D2O) δ ppm 8.6 (s+d, 2H), 8 (dd, 1H), 7.52 (dd, 1H), 4.4 (AB, 2H), 3.7 (m, 1H), 3.4 (m, 2H), 3.18 (dd, 1H), 2.9 (m, 2H), 2.28/1.8 (2m, 2H), 1.91 (m, 1H), 1.6 (m, 2H), 1.5 (m, 1H), 1.21/1.1 (2m, 2H)
ESI/FIA/HR and MS/MS: [M+H]+=342.1568 (342.1582)
Elemental analysis: C=52.32 (52.78); H=6.66 (7.09); N=12.32 (12.31)

Intermediate 61: tert-Butyl 3-{4-[bis(tert-butoxycarbonyl)amino]butyl}-4-ethoxy-4-oxo-1-(pyridin-2-ylmethyl)-1,4-azaphosphinane-3-carboxylate Intermediate 61 is obtained starting from intermediate 21 and 2-formylpyridine in accordance with procedure F described hereinbefore.
¹H NMR: (400 MHz, dmso-d6) δ ppm 8.5 (df, 1H), 7.75 (t, 1H), 7.42/7.25 (2dd, 2H), 4.1-3.9 (2m, 2H), 3.71/3.6 (2AB, 2H), 3.5-3.35 (m, 2H), 3-2.3 (m, 4H), 2.0-2.9 (m, 4H), 1.45/1.35 (3s, 27H), 1.4/1-0.8 (3m, 4H), 1.22 (2t, 3H)

EXAMPLE 71: 3-(4-AMINOBUTYL)-4-HYDROXY-4-OXO-1-(PYRIDIN-2-YLMETHYL)-1,4-AZAPHOSPHINANE-3-CARBOXYLIC ACID

Example 71 is obtained starting from intermediate 61 in accordance with procedure D described hereinbefore.
¹H NMR: (400 MHz, D2O) δ ppm 8.6 (dd, 1H), 7.91 (t, 1H), 7.55 (d, 1H), 7.45 (dd, 1H), centred at 4.41 (AB, 2H), 3.75/3.4 (2m, 2H), 3.55/3.3 (2dd, 2H), 2.95 (m, 2H), 2.3/1.78 (2m, 2H), 1.98 (m, 1H), 1.65 (m, 2H), 1.5 (m, 1H), 1.3/1.2 (2m, 2H)
ESI/FIA/HR and MS/MS: [M+H]+=342.1592 (342.1582)
Elemental analysis: C=52.72 (52.78); H=6.92 (7.09); N=12.25 (12.31)

Intermediate 63: tert-Butyl 3-{4-[bis(tert-butoxycarbonyl)amino]butyl}-1-(2-cyclohexylethyl)-4-ethoxy-4-oxo-1,4-azaphosphinane-3-carboxylate Intermediate 63 is obtained starting from intermediate 21 and 2-cyclohexylacetaldehyde in accordance with procedure F described hereinbefore.
¹H NMR: (400 MHz, dmso-d6) δ ppm 3.98 (m, 2H), 3.48 (t, 2H), 2.8 (m, 2H), 2.5-2.2 (m, 4H), 2-0.8 (m, 19H), 1.9 (m, 2H), 1.45/1.4 (2s, 27H), 1.2 (t, 3H)

EXAMPLE 73: 3-(4-AMINOBUTYL)-1-(2-CYCLOHEXYLETHYL)-4-HYDROXY-4-OXO-1,4-AZAPHOSPHINANE-3-CARBOXYLIC ACID

Example 73 is obtained starting from intermediate 63 in accordance with procedure D described hereinbefore.
¹H NMR: (400 MHz, D2O) δ ppm 3.7-3.5 (m, 2H), 3.3 (m, 1H), 3.15 (m, 3H), 3 (t, 2H), 2.22/1.8 (2m, 2H), 2 (m, 1H), 1.7-0.85 (m, 17H), 1.65 (m, 1H)
ESI/FIA/HR and MS/MS: [M+H]+=361.2257 (361.2256)
Elemental analysis: C=56.25 (56.65); H=8.92 (9.23); N=7.49 (7.77)

Intermediate 64: tert-Butyl 3-{4-[bis(tert-butoxycarbonyl)amino]butyl}-4-ethoxy-4-oxo-1-[(4-phenylphenyl)methyl]-1,4-azaphosphinane-3-carboxylate Intermediate 64 is obtained starting from intermediate 21 and 4-phenylbenzaldehyde in accordance with procedure F described hereinbefore.
¹H NMR: (400 MHz, dmso-d6) δ ppm 7.69 (2d, 4H), 7.5-7.3 (m, 5H), 4 (m, 2H), 3.7/3.45 (2d, 2H), 3.4 (m, 2H), 3.05-2.3 (m, 4H), 2.05-1.65 (m, 4H), 1.4 (m+2s, 29H), 1.22 (2t, 3H), 1-0.7 (m, 2H)

EXAMPLE 74: 3-(4-AMINOBUTYL)-4-HYDROXY-4-OXO-1-[(4-PHENYLPHENYL)METHYL]-1,4-AZAPHOSPHINANE-3-CARBOXYLIC ACID

Example 74 is obtained starting from intermediate 64 in accordance with procedure D described hereinbefore.
¹H NMR: (400 MHz, D2O) δ ppm 7.8 (d, 2H), 7.7 (d, 2H), 7.55 (d, 2H), 7.5 (t, 2H), 7.41 (t, 1H), 4.45/4.28 (2d, 2H), 3.75/3.35 (2m, 2H), 3.5/3.15 (2dd, 2H), 2.9 (m, 2H), 2.25/1.8 (2m, 2H), 1.95/1.45 (2m, 2H), 1.6 (m, 2H), 1.25/1.1 (2m, 2H)
ESI/FIA/HR and MS/MS: [M+H]+=417.1932 (417.1943)
Elemental analysis: C=63.25 (63.45); H=6.64 (7.02); N=6.55 (6.73)

Intermediate 65: tert-Butyl 3-{4-[bis(tert-butoxycarbonyl)amino]butyl}-4-ethoxy-4-oxo-1-[(3-phenoxyphenyl)methyl]-1,4-azaphosphinane-3-carboxylate Intermediate 65 is obtained starting from intermediate 21 and 3-phenoxybenzaldehyde in accordance with procedure F described hereinbefore.
¹H NMR: (400 MHz, dmso-d6) δ ppm 7.38 (2t, 3H), 7.15 (t, 1H), 7.05 (d, 1H), 7.05 (d, 2H), 6.95 (sl, 1H), 6.9 (d, 1H), 3.98 (m, 2H), 3.6/3.45 (2d, 2H), 3.4 (m, 2H), 3-2.3 (m, 4H), 2-1.6 (m, 6H), 1.4 (2s, 27H), 1.2 (2t, 3H), 1-0.75 (m, 2H)

EXAMPLE 75: 3-(4-AMINOBUTYL)-4-HYDROXY-4-OXO-1-[(3-PHENOXYPHENYL)METHYL]-1,4-AZAPHOSPHINANE-3-CARBOXYLIC ACID

Example 75 is obtained starting from intermediate 65 in accordance with procedure D described hereinbefore.
$^{1}$H NMR: (400 MHz, D2O) δ ppm 7.5-7.3 (2t, 3H), 7.2-6.95 (m, 6H), centred at 4.2 (AB, 2H), 3.65/3.25 (2m, 2H), 3.4/3 (2dd, 2H), 2.82 (m, 2H), 2.19/1.7 (2m, 2H), 1.88/1.4 (2m, 2H), 1.52 (m, 2H), 1.2-1 (2m, 2H)
ESI/FIA/HR and MS/MS: [M+H]+=433.1891 (433.1892)
Elemental analysis: C=60.90 (61.10); H=6.58 (6.76); N=6.34 (6.48)

Intermediate 66: tert-Butyl 3-{4-[bis(tert-butoxycarbonyl)amino]butyl}-4-ethoxy-4-oxo-1-(3-phenylpropyl)-1,4-azaphosphinane-3-carboxylate Intermediate 66 is obtained starting from intermediate 21 and 3-phenylpropanal in accordance with procedure F described hereinbefore.
$^{1}$H NMR: (400 MHz, dmso-d6) δ ppm 7.29 (t, 2H), 7.15 (d+t, 3H), 3.98 (m, 2H), 3.49 (t, 2H), 2.9-2.2 (m, 4H), 2.59 (t, 2H), 2.35 (m, 2H), 2-1.6 (m, 7H), 1.5 (m, 1H), 1.4 (2s, 27H), 1.25/1 (2m, 2H), 1.2 (2t, 3H)

EXAMPLE 76: 3-(4-AMINOBUTYL)-4-HYDROXY-4-OXO-1-(3-PHENYLPROPYL)-1,4-AZAPHOSPHINANE-3-CARBOXYLIC ACID

Example 76 is obtained starting from intermediate 66 in accordance with procedure D described hereinbefore.
$^{1}$H NMR: (400 MHz, D2O) δ ppm 7.38 (t, 2H), 7.27 (m, 3H), 3.62/3.28 (2m, 2H), 3.52 (dd, 1H), 3.11 (m, 3H), 3 (td, 2H), 2.7 (t, 2H), 2.25/1.75 (2m, 2H), 2.09 (m, 2H), 1.95/1.5 (2m, 2H), 1.65 (m, 2H), 1.38/1.22 (2m, 2H)
ESI/FIA/HR and MS/MS: [M+H]+=369.195 (369.1943)
Elemental analysis: C=58.46 (58.68); H=7.45 (7.93); N=7.54 (7.60)

Intermediate 68: tert-Butyl 3-{4-[bis(tert-butoxycarbonyl)amino]butyl}-4-ethoxy-4-oxo-1-[(4-phenoxyphenyl)methyl]-1,4-azaphosphinane-3-carboxylate Intermediate 68 is obtained starting from intermediate 21 and 4-phenoxybenzaldehyde in accordance with procedure F described hereinbefore.
$^{1}$H NMR: (400 MHz, dmso-d6) δ ppm 7.4 (t, 2H), 7.3 (d, 2H), 7.12 (t, 1H), 6.98 (2d, 4H), 3.99 (m, 2H), 3.6/3.4 (2d, 2H), 3.38 (m, 2H), 3-2.25 (m, 4H), 2-1.65 (m, 6H), 1.4 (2s, 27H), 1.2 (2t, 3H), 1-0.75 (m, 2H)

EXAMPLE 78: 3-(4-AMINOBUTYL)-4-HYDROXY-4-OXO-1-[(4-PHENOXYPHENYL)METHYL]-1,4-AZAPHOSPHINANE-3-CARBOXYLIC ACID

Example 78 is obtained starting from intermediate 68 in accordance with procedure D described hereinbefore.
$^{1}$H NMR: (400 MHz, D2O) δ ppm 7.44 (d, 2H), 7.41 (t, 2H), 7.21 (t, 1H), 7.08 (d, 2H), 7.08 (d, 2H), 4.38/4.21 (2d, 1+1H), 3.7/3.31 (m+m, 1+1H), 3.5/3.1 (2d, 2H), 2.93 (m, 2H), 2.23/1.77 (m+m, 1+1H), 1.93/1.48 (m+m, 1+1H), 1.6 (quint., 2H), 1.24/1.13 (m+m, 1+1H)
$^{13}$C NMR: (400 MHz, D2O) δ ppm 177.6, 158.2, 155.7, 132.1, 130, 124.3, 124.1, 119.3, 118.7, 59.4, 51.6, 50.9, 38.8, 27, 26.6, 24.8, 20
$^{31}$P NMR: (400 MHz, D2O) δ ppm 25
ESI/FIA/HR and MS/MS: [M+H]+=433.1884 (433.1892)
Elemental analysis: C=60.77 (61.10); H=6.27 (6.76); N=6.42 (6.48)

EXAMPLE 79: 3-(4-AMINOBUTYL)-4-HYDROXY-4-OXO-1-(2-PHENYLMETHOXYETHYL)-1,4-AZAPHOSPHINANE-3-CARBOXYLIC ACID

Example 79 is obtained starting from intermediate 21 and benzyloxyacetaldehyde in accordance with procedures F and D described hereinbefore.
$^{1}$H NMR: (400 MHz, D2O) δ ppm 7.42 (m, 5H), 4.63 (d, 1H), 4.55 (d, 1H), 3.82 (t, 2H), 3.61 (dd, 1H), 3.5 (m, 1H), 3.33 (m, 2H), 3.26 (m, 1H), 3.16 (dd, 1H), 2.92 (t, 2H), 2.24 (m, 1H), 1.94 (m, 1H), 1.71 (m, 1H), 1.61 (quint, 2H), 1.48 (m, 1H), 1.21 (m, 2H)
$^{31}$P NMR: (400 MHz, D2O) δ ppm 25.6
ESI/FIA/HR and MS/MS: [M+H]+=385.1883 (385.1892)

EXAMPLE 80: 3-(4-AMINOBUTYL)-4-HYDROXY-1-(2-HYDROXYETHYL)-4-OXO-1,4-AZAPHOSPHINANE-3-CARBOXYLIC ACID

Example 80 is obtained starting from Example 79 in accordance with procedure E described hereinbefore.
$^{1}$H NMR: (400 MHz, D2O) δ ppm 3.9 (m, 2H), 3.72 (dd, 1H), 3.62 (dd, 1H), 3.32 (m, 1H), 3.29 (t, 2H), 3.25 (dd, 1H), 2.99 (m, 2H), 2.29 (m, 1H), 1.99 (m, 1H), 1.79 (m, 1H), 1.67 (quint, 2H), 1.52 (m, 1H), 1.41 (m, 1H), 1.29 (m, 1H)
ESI/FIA/HR and MS/MS: [M+H]+=295.1424 (295.1422)
Elemental analysis: C=44.08 (44.90); H=7.66 (7.88); N=9.23 (9.52)

Intermediate 69: tert-Butyl 3-{4-[Bis(tert-butoxycarbonyl)amino]butyl}-1-[(3-chlorophenyl)methyl]-4-ethoxy-4-oxo-1,4-azaphosphinane-3-carboxylate Intermediate 69 is obtained starting from intermediate 21 and 3-chlorobenzaldehyde in accordance with procedure F described hereinbefore.
$^{1}$H NMR: (400 MHz, dmso-d6) δ ppm 7.4-7.2 (m, 4H), 3.99 (m, 2H), 3.62/3.43 (AB, 1+1H), 3.38 (m, 2H), 2.92/2.36 (m)+(m, 1+1H), 2.73/2.47 (m)+(m, 1+1H), 1.96 (m, 2H), 1.89 (m, 2H), 1.41 (m, 2H), 1.37/1.33 (2*(s, 27H), 1.2 (t, 3H), 0.81 (m, 2H)
$^{13}$C NMR: (400 MHz, dmso-d6) δ ppm 127-130, 152.3, 60.9, 60.6, 54.9, 51.6, 45.6, 28.9, 28.9, 27.6, 24.7, 20.6, 133.2, 81.8/81.1

EXAMPLE 81: 3-(4-AMINOBUTYL)-1-[(3-CHLOROPHENYL)METHYL]-4-HYDROXY-4-OXO-1,4-AZAPHOSPHINANE-3-CARBOXYLIC ACID

Example 81 is obtained starting from intermediate 69 in accordance with procedure D described hereinbefore.
$^{1}$H NMR: (400 MHz, D2O) δ ppm 7.52-7.35 (m, 4H), centred at 4.32 (AB, 2H), 3.7/3.32 (2m, 2H), 3.5/3.12 (2dd, 2H), 2.93 (m, 2H), 2.25/1.8 (2m, 2H), 1.95/1.48 (2m, 2H), 1.6 (m, 2H), 1.25/1.11 (2m, 2H)

ESI/FIA/HR and MS/MS: [M+H]+=375.1256 (375.1240)
Elemental analysis: C=51.26 (51.27); H=6.32 (6.45); N=7.43 (7.47)

Intermediate 70: tert-Butyl 3-{4-[bis(tert-butoxycarbonyl)amino]butyl}-4-ethoxy-1-[(3-hydroxyphenyl)methyl]-4-oxo-1,4-azaphosphinane-3-carboxylate Intermediate 70 is obtained starting from intermediate 21 and 3-hydroxybenzaldehyde in accordance with procedure F described hereinbefore.
$^1$H NMR: (400 MHz, dmso-d6) δ ppm 9.25 (s, 1H), 7.1 (t, 1H), 6.7-6.55 (m, 3H), 3.98 (m, 2H), 3.52/3.4 (2d, 2H), 3.4 (m, 2H), 3-2.2 (m, 4H), 2-1.65 (m, 6H), 1.4 (2s, 27H), 1.2 (2t, 3H), 0.95/0.82 (2m, 2H)

EXAMPLE 82: 3-(4-AMINOBUTYL)-4-HYDROXY-1-[(3-HYDROXYPHENYL)METHYL]-4-OXO-1,4-AZAPHOSPHINANE-3-CARBOXYLIC ACID

Example 82 is obtained starting from intermediate 70 in accordance with procedure D described hereinbefore.
$^1$H NMR: (400 MHz, D2O) δ ppm 7.38 (t, 1H), 7-6.9 (m, 3H), centred at 4.18 (AB, 2H), 3.7/3.32 (2m, 2H), 3.45/3.1 (2dd, 2H), 2.91 (m, 2H), 2.25/1.8 (2m, 2H), 1.92/1.48 (2m, 2H), 1.6 (m, 2H), 1.25/1.1 (2m, 2H)
ESI/FIA/HR and MS/MS: [M+H]+=357.1573 (357.1579)
Elemental analysis: C=53.22 (53.93); H=6.98 (7.07); N=7.72 (7.86)

Intermediate 71: tert-Butyl 3-{4-[bis(tert-butoxycarbonyl)amino]butyl}-4-ethoxy-1-[(4-hydroxyphenyl)methyl]-4-oxo-1,4-azaphosphinane-3-carboxylate Intermediate 71 is obtained starting from intermediate 21 and 4-hydroxybenzaldehyde in accordance with procedure F described hereinbefore.
$^1$H NMR: (400 MHz, dmso-d6) δ ppm 9.25 (s, 1H), 7.05 (d, 2H), 6.7 (d, 2H), 3.98 (m, 2H), 3.49/3.3 (2d, 2H), 3.4 (m, 2H), 3-2.2 (m, 4H), 2-1.8 (m, 4H), 1.4 (2s+m, 29H), 1.2 (2t, 3H), 0.95/0.82 (2m, 2H)

EXAMPLE 83: 3-(4-AMINOBUTYL)-4-HYDROXY-1-[(4-HYDROXYPHENYL)METHYL]-4-OXO-1,4-AZAPHOSPHINANE-3-CARBOXYLIC ACID

Example 83 is obtained starting from intermediate 71 in accordance with procedure D described hereinbefore.
$^1$H NMR: (400 MHz, D2O) δ ppm 7.38 (d, 2H), 6.95 (d, 2H), centred at 4.25 (AB, 2H), 3.7/3.3 (2m, 2H), 3.48/3.05 (2dd, 2H), 2.95 (m, 2H), 2.21/1.75 (2m, 2H), 1.95/1.5 (2m, 2H), 1.6 (m, 2H), 1.25/1.11 (2m, 2H)
ESI/FIA/HR and MS/MS: [M+H]+=357.1572 (357.1579)
Elemental analysis: C=53.24 (53.93); H=6.89 (7.07); N=7.57 (7.86)

Intermediate 72: tert-Butyl 3-{4-[bis(tert-butoxycarbonyl)amino]butyl}-1-(furan-3-ylmethyl)-4-ethoxy-4-oxo-1,4-azaphosphinane-3-carboxylate Intermediate 72 is obtained starting from intermediate 21 and 3-furaldehyde in accordance with procedure F described hereinbefore.
$^1$H NMR: (400 MHz, dmso-d6) δ ppm 7.61/7.55 (2sl, 2H), 6.39 (sl, 1H), 3.98 (m, 2H), 3.49/3.33 (2d, 2H), 3.45 (m, 2H), 3-2.2 (m, 4H), 2-1.8 (m, 4H), 1.4 (2s+m, 29H), 1.2 (2t, 3H), 1.05/0.9 (2m, 2H)

EXAMPLE 84: 3-(4-AMINOBUTYL)-1-(FURAN-3-YLMETHYL)-4-HYDROXY-4-OXO-1,4-AZAPHOSPHINANE-3-CARBOXYLIC ACID

Example 84 is obtained starting from intermediate 72 in accordance with procedure D described hereinbefore.
$^1$H NMR: (400 MHz, D2O) δ ppm 7.71 (sl, 1H), 7.59 (sl, 1H), 6.58 (sl, 1H), centred at 4.22 (AB, 2H), 3.7/3.35 (2m, 2H), 3.55/3.08 (2dd, 2H), 2.95 (m, 2H), 2.25/1.8 (2m, 2H), 1.95/1.5 (2m, 2H), 1.62 (m, 2H), 1.31/1.18 (2m, 2H)
ESI/FIA/HR and MS/MS: [M+H]+=331.1431 (331.1422)
Elemental analysis: C=50.45 (50.91); H=6.72 (7.02); N=8.39 (8.48)

Intermediate 73: tert-Butyl 3-{4-[bis(tert-butoxycarbonyl)amino]butyl}-4-ethoxy-1-[(2-hydroxyphenyl)methyl]-4-oxo-1,4-azaphosphinane-3-carboxylate Intermediate 73 is obtained starting from intermediate 21 and 2-hydroxybenzaldehyde in accordance with procedure F described hereinbefore.
$^1$H NMR: (400 MHz, dmso-d6) δ ppm 9.45 (s, 1H), 7.1 (d+t, 2H), 6.78 (d+t, 2H), 4 (m, 2H), 3.62/3.52 (2d, 2H), 3.4 (m, 2H), 3-2.3 (m, 4H), 2-1.8 (m, 4H), 1.42/1.38 (m+2s, 29H), 1.21 (2t, 3H), 0.98/0.85 (2m, 2H)

EXAMPLE 85: 3-(4-AMINOBUTYL)-4-HYDROXY-1-[(2-HYDROXYPHENYL)METHYL]-4-OXO-1,4-AZAPHOSPHINANE-3-CARBOXYLIC ACID

Example 85 is obtained starting from intermediate 73 in accordance with procedure D described hereinbefore.
$^1$H NMR: (400 MHz, D2O) δ ppm 7.39 (t, 1H), 7.3 (d, 1H), 6.95 (d+t, 2H), 4.28 (AB, 2H), 3.65/3.28 (2m, 2H), 3.52/3.2 (2dd, 2H), 2.95 (m, 2H), 2.2/1.72 (2m, 2H), 1.98/1.5 (2m, 2H), 1.62 (m, 2H), 1.3/1.18 (2m, 2H)
ESI/FIA/HR and MS/MS: [M+H]+=357.1591 (357.1579)
Elemental analysis: C=53.22 (53.93); H=6.97 (7.07); N=7.71 (7.86)

Intermediate 74: tert-Butyl 3-{4-[bis(tert-butoxycarbonyl)amino]butyl}-4-ethoxy-1-[[2-(4-hydroxyphenyl)phenyl]methyl]-4-oxo-1,4-azaphosphinane-3-carboxylate Intermediate 74 is obtained starting from intermediate 21 and 2-(4-hydroxyphenyl)benzaldehyde in accordance with procedure F described hereinbefore.
$^1$H NMR: (400 MHz, dmso-d6) δ ppm 9.45 (s, 1H), 7.45 (dd, 1H), 7.3 (td, 2H), 7.16 (dd, 1H), 7.13 (d, 2H), 6.81 (d, 2H), 3.93 (quad., 2H), 3.54/3.36 (d, 2H), 3.28 (t, 2H), 2.85-2.15 (m, 2H), 2.85-2.15 (m, 2H), 1.84 (m, 2H), 1.84 (m, 2H), 1.47-1.3 (s, 27H), 1.47-1.3 (s, 2H), 1.17 (t, 3H), 0.7 (m, 2H)
$^{31}$P NMR: (400 MHz, dmso-d6) δ ppm 45.3

EXAMPLE 86: 3-(4-AMINOBUTYL)-4-HYDROXY-1-[[2-(4-HYDROXYPHENYL)PHENYL]METHYL]-4-OXO-1,4-AZAPHOSPHINANE-3-CARBOXYLIC ACID

Example 86 is obtained starting from intermediate 74 in accordance with procedure D described hereinbefore.

¹H NMR: (400 MHz, D2O) δ ppm 7.56 (dd, 1H), 7.55-7.45 (2td, 2H), 7.37 (dd, 1H), 7.25 (d, 2H), 7 (d, 2H), 4.36 (dd, 2H), 3.35/3.1 (2m, 2H), 3.2/2.85 (2m, 2H), 2.95 (m, 2H), 2.05/1.65 (2m, 2H), 1.85/1.35 (2m, 2H), 1.6 (m, 2H), 1.2-0.95 (m, 2H)
ESI/FIA/HR and MS/MS: [M+H]+=433.1893 (433.1892)
Elemental analysis: C=61.11 (61.10); H=6.10 (6.76); N=6.68 (6.48)

Intermediate 75: tert-Butyl 3-{4-[bis(tert-butoxycarbonyl)amino]butyl}-4-ethoxy-4-oxo-1-[(3-phenyl-1H-pyrazol-4-yl)methyl]-1,4-azaphosphinane-3-carboxylate Intermediate 75 is obtained starting from intermediate 21 and 3-phenyl-1H-pyrazole-4-carboxaldehyde in accordance with procedure F described hereinbefore.
¹H NMR: (400 MHz, dmso-d6) δ ppm 13-12.5 (m, 1H), 7.9-7.3 (m, 6H), 4.05-3.9 (m, 2H), 3.45 (dd, 2H), 3.3 (m, 2H), 3.1-2.2 (m, 6H), 2-1.7 (m, 2H), 1.4 (s, 18H), 1.35 (s, 9H), 1.2 (m, 2H), 1.2 (t, 3H), 1-0.7 (m, 2H)
ESI/FIA/HR and MS/MS: [M+H]+=691.3829 (691.3835)

EXAMPLE 87: 3-(4-AMINOBUTYL)-4-HYDROXY-4-OXO-1-[(3-PHENYL-1H-PYRAZOL-4-YL)METHYL]-1,4-AZAPHOSPHINANE-3-CARBOXYLIC ACID

Example 87 is obtained starting from intermediate 75 in accordance with procedure D described hereinbefore.
¹H NMR: (400 MHz, D2O) δ ppm 7.95 (sl, 1H), 7.6-7.5 (m, 5H), 4.45 (dd, 2H), 3.55/3.15 (2m, 2H), 3.05/2.7 (2m, 2H), 2.9 (m, 2H), 2.2/1.7 (2m, 2H), 1.8/1.25 (m, 2H), 1.5 (m, 2H), 0.95/0.7 (2m, 2H)
ESI/FIA/HR and MS/MS: [M+H]+=407.1865 (407.1848)
Elemental analysis: C=55.99 (56.15); H=6.40 (6.70); N=13.79 (13.79)

Intermediate 76: tert-Butyl 3-{4-[bis(tert-butoxycarbonyl)amino]butyl}-4-ethoxy-1-[[2-(4-methoxyphenyl)phenyl]methyl]-4-oxo-1,4-azaphosphinane-3-carboxylate Intermediate 76 is obtained starting from intermediate 21 and 2-(4-methoxyphenyl)benzaldehyde in accordance with procedure F described hereinbefore.
¹H NMR: (400 MHz, dmso-d6) δ ppm 7.47 (d, 1H), 7.32 (m, 2H), 7.27 (d, 2H), 7.19 (d, 1H), 7 (d, 2H), 3.93 (m, 2H), 3.8 (s, 3H), 3.54/3.37 (2*d, 2H), 3.32 (m, 2H), 2.74/2.22 (m, 2H), 2.74/2.33 (m, 2H), 1.95-1.75 (m, 2H), 1.95-1.75 (m, 2H), 1.41 (s, 18H), 1.37 (m, 2H), 1.34 (s, 9H), 1.18 (t, 3H), 0.7 (m, 2H)

EXAMPLE 88: 3-(4-AMINOBUTYL)-4-HYDROXY-1-[[2-(4-METHOXYPHENYL)PHENYL]METHYL]-4-OXO-1,4-AZAPHOSPHINANE-3-CARBOXYLIC ACID

Example 88 is obtained starting from intermediate 76 in accordance with procedure D described hereinbefore.
¹H NMR: (400 MHz, D2O) δ ppm 7.59 (dd, 1H), 7.51 (m, 2H), 7.38 (dd, 2H), 7.31 (d, 2H), 7.1 (d, 2H), 4.44/4.29 (2*d, 2H), 3.36 (s, 3H), 3.19/2.94 (m, 2H), 3.19/2.84 (m, 2H), 2.94 (m, 2H), 2.08/1.65 (m, 2H), 1.85/1.35 (m, 2H), 1.58 (m, 2H), 1.13/1.05 (m, 2H)

ESI/FIA/HR and MS/MS: [M+H]+=447.2046 (447.2048)
Elemental analysis: C=62.04 (61.87); H=6.38 (7.00); N=6.05 (6.27)

Intermediate 77: tert-Butyl 3-{4-[bis(tert-butoxycarbonyl)amino]butyl}-4-ethoxy-4-oxo-1-[(4-phenyl-1H-pyrazol-3-yl)methyl]-1,4-azaphosphinane-3-carboxylate Intermediate 77 is obtained starting from intermediate 21 and 4-phenyl-1H-pyrazole-3-carboxaldehyde in accordance with procedure F described hereinbefore.
¹H NMR: (400 MHz, dmso-d6) δ ppm 13-12.5 (m, 1H), 8 (m, 1H), 7.62 (d, 2H), 7.35 (t, 2H), 7.2 (t, 1H), 4.1-3.9 (m, 2H), 3.8-3.35 (m, 2H), 3.25 (m, 2H), 3.15-2.3 (m, 4H), 2.1-1.9 (m, 2H), 1.8 (m, 2H), 1.4-1.2 (m, 2H), 1.4 (s, 18H), 1.35 (s, 9H), 1.2 (t, 3H), 0.7 (m, 2H)

EXAMPLE 89: 3-(4-AMINOBUTYL)-4-HYDROXY-4-OXO-1-[(4-PHENYL-1H-PYRAZOL-3-YL)METHYL]-1,4-AZAPHOSPHINANE-3-CARBOXYLIC ACID

Example 89 is obtained starting from intermediate 77 in accordance with procedure D described hereinbefore.
¹H NMR: (400 MHz, D2O) δ ppm 7.9 (s, 1H), 7.55-7.35 (m, 5H), 4.65-4.4 (dd, 2H), 3.55/3.15 (2m, 2H), 3.15/2.9 (2m, 2H), 2.9 (m, 2H), 2.15/1.65 (2m, 2H), 1.8/1.25 (m, 2H), 1.5 (m, 2H), 0.95/0.75 (2m, 2H)
ESI/FIA/HR and MS/MS: [M+H]+=407.1844 (407.1848)
Elemental analysis: C=56.58 (56.15); H=6.24 (6.70); N=13.79 (13.79)

Intermediate 78: tert-Butyl 3-{4-[bis(tert-butoxycarbonyl)amino]butyl}-4-ethoxy-4-oxo-1-[(5-phenyl-1,3-oxazol-4-yl)methyl]-1,4-azaphosphinane-3-carboxylate Intermediate 78 is obtained starting from intermediate 21 and 5-phenyl-1,3-oxazole-4-carboxaldehyde in accordance with procedure F described hereinbefore.
¹H NMR: (300 MHz, dmso-d6) δ ppm 8.29 (s, 1H), 7.78 (m, 2H), 7.5 (m, 2H), 7.4 (m, 1H), 4 (m, 2H), 3.68 (dd, 2H), 3.3 (m, 2H), 3.05/2.5 (2m, 2H), 2.95/2.65 (2m, 2H), 2.05-1.7 (m, 4H), 1.45 (s, 18H), 1.35 (s, 9H), 1.25 (m, 2H), 1.25 (t, 3H), 0.9 (m, 2H)

EXAMPLE 90: 3-(4-AMINOBUTYL)-4-HYDROXY-4-OXO-1-[(5-PHENYL-1,3-OXAZOL-4-YL)METHYL]-1,4-AZAPHOSPHINANE-3-CARBOXYLIC ACID

Example 90 is obtained starting from intermediate 78 in accordance with procedure D described hereinbefore.
¹H NMR: (400 MHz, D2O) δ ppm 8.28 (s, 1H), 7.68 (d, 2H), 7.6-7.5 (m, 3H), 4.55 (dd, 2H), 3.65/3.3 (2m, 2H), 3.4/3.1 (2dd, 2H), 2.9 (m, 2H), 2.2/1.71 (2m, 2H), 1.9/1.35 (2m, 2H), 1.55 (m, 2H), 1.05/0.95 (2m, 2H)
ESI/FIA/HR and MS/MS: [M+H]+=408.1689 (408.1688)
Elemental analysis: C=55.52 (56.02); H=6.16 (6.43); N=10.20 (10.31)

Intermediate 79: tert-Butyl 3-{4-[bis(tert-butoxycarbonyl)amino]butyl}-4-ethoxy-1-[[2-(1,2-oxazol-5-yl)phenyl]methyl]-4-oxo-1,4-azaphosphinane-3-carboxylate Intermediate 79 is obtained starting from intermediates 21 and 218 in accordance with procedure F described hereinbefore.

¹H NMR: (300 MHz, dmso-d6) δ ppm 8.6 (d, 1H), 7.65 (m, 1H), 7.55-7.4 (m, 3H), 6.75 (d, 1H), 4 (m, 2H), 3.85/3.5 (dd, 2H), 3.3 (m, 2H), 2.95/2.4 (2m, 2H), 2.8/2.55 (2m, 2H), 2.1-1.6 (2m, 4H), 1.45 (s, 18H), 1.35 (m, 2H), 1.35 (s, 9H), 1.22 (t, 3H), 0.9-0.5 (m, 2H)

EXAMPLE 91: 3-(4-AMINOBUTYL)-4-HYDROXY-1-[[2-(1,2-OXAZOL-5-YL)PHENYL]METHYL]-4-OXO-1,4-AZAPHOSPHINANE-3-CARBOXYLIC ACID

Example 91 is obtained starting from intermediate 79 in accordance with procedure D described hereinbefore.

¹H NMR: (400 MHz, D2O) δ ppm 8.55 (d, 1H), 7.85 (m, 1H), 7.65-7.55 (m, 3H), 6.85 (d, 1H), 4.7/4.4 (dd, 2H), 3.85/3.2 (2m, 2H), 3.5/3.2 (2dd, 2H), 2.9 (m, 2H), 2.3/1.8 (2m, 2H), 1.9/1.45 (2m, 2H), 1.6 (m, 2H), 1.2/1.05 (2m, 2H)

ESI/FIA/HR and MS/MS: [M+H]+=408.1685 (408.1688)

Elemental analysis: C=55.14 (56.02); H=5.95 (6.43); N=10.14 (10.31)

Intermediate 80: tert-Butyl 3-{4-[bis(tert-butoxycarbonyl)amino]butyl}-4-ethoxy-4-oxo-1-[(2-pyrazol-1-ylphenyl)methyl]-1,4-azaphosphinane-3-carboxylate Intermediate 80 is obtained starting from intermediate 21 and 2-(1H-pyrazol-1-yl)-benzaldehyde in accordance with procedure F described hereinbefore.

¹H NMR: (400 MHz, dmso-d6) δ ppm 8.04 (d, 1H), 7.7 (d, 1H), 7.55-7.35 (m, 4H), 6.5 (m, 1H), 3.95 (m, 2H), 3.65/3.35 (dd, 2H), 3.3 (m, 2H), 2.8-2.6 (2m, 2H), 2.4-2.15 (2m, 2H), 2-1.65 (m, 4H), 1.5-1.3 (m, 2H), 1.41 (s, 18H), 1.35 (s, 9H), 1.19 (t, 3H), 0.7 (m, 2H)

EXAMPLE 92: 3-(4-AMINOBUTYL)-4-HYDROXY-4-OXO-1-[(2-PYRAZOL-1-YLPHENYL)METHYL]-1,4-AZAPHOSPHINANE-3-CARBOXYLIC ACID

Example 92 is obtained starting from intermediate 80 in accordance with procedure D described hereinbefore.

¹H NMR: (400 MHz, D2O) δ ppm 8.05 (d, 1H), 7.9 (d, 1H), 7.7-7.45 (m, 4H), 6.6 (t, 1H), 4.25 (dd, 2H), 3.5/3.1 (2dd, 2H), 3.35/3.15 (2m, 2H), 2.95 (m, 2H), 2.3/1.8 (2m, 2H), 1.9/1.5 (2m, 2H), 1.6 (m, 2H), 1.3/1.1 (2m, 2H)

ESI/FIA/HR and MS/MS: [M+H]+=407.1869 (407.1848)

Elemental analysis: C=56.00 (56.15); H=6.16 (6.70); N=13.77 (13.79)

Intermediate 81: tert-Butyl 3-{4-[bis(tert-butoxycarbonyl)amino]butyl}-4-ethoxy-1-[[2-fluoro-6-(4-methoxyphenyl)phenyl]methyl]-4-oxo-1,4-azaphosphinane-3-carboxylate Intermediate 81 is obtained starting from intermediate 21 and 2-fluoro-6-(4-methoxyphenyl)benzaldehyde in accordance with procedure F described hereinbefore.

¹H NMR: (400 MHz, D2O) δ ppm 7.4 (d, 2H), 7.4 (dd, 1H), 7.18 (t, 1H), 7.08 (d, 1H), 7 (d, 2H), 3.92 (m, 2H), 3.8 (s, 3H), 3.46 (s, 2H), 3.22 (m, 2H), 2.7/2.38 (dd, 2H), 2.65/2.25 (2*m, 2H), 2-1.6 (m, 4H), 1.4 (s, 18H), 1.34 (s, 9H), 1.25 (m, 2H), 1.18 (t, 3H), 0.63/0.5 (2*m, 2H)

EXAMPLE 93: 3-(4-AMINOBUTYL)-1-[[2-FLUORO-6-(4-METHOXYPHENYL)PHENYL]METHYL]-4-HYDROXY-4-OXO-1,4-AZAPHOSPHINANE-3-CARBOXYLIC ACID

Example 93 is obtained starting from intermediate 81 in accordance with procedure D described hereinbefore.

¹H NMR: (400 MHz, D2O) δ ppm 7.54 (m, 1H), 7.3 (d, 2H), 7.28 (m, 1H), 7.21 (d, 1H), 7.11 (d, 2H), 4.42 (dd, 2H), 3.86 (s, 3H), 3.46/3.09 (m, 2H), 3.2/2.9 (m, 2H), 2.95 (m, 2H), 2.11/1.67 (m, 2H), 1.87/1.37 (m, 2H), 1.6 (m, 2H), 1.11 (m, 2H)

ESI/FIA/HR and MS/MS: [M+H]+=465.1955 (465.1954)

Elemental analysis: C=59.31 (59.48); H=5.75 (6.51); N=6.10 (6.03)

Intermediate 82: tert-Butyl 3-{4-[bis(tert-butoxycarbonyl)amino]butyl}-4-ethoxy-1-[[2-(1-methylpyrazol-4-yl)phenyl]methyl]-4-oxo-1,4-azaphosphinane-3-carboxylate Intermediate 82 is obtained starting from intermediates 21 and 235 in accordance with procedure F described hereinbefore.

¹H NMR: (400 MHz, dmso-d6) δ ppm 7.9 (s, 1H), 7.65 (s, 1H), 7.4-7.35 (m, 2H), 7.3-7.2 (m, 2H), 4 (m, 2H), 3.9 (s, 3H), 3.61/3.4 (dd, 2H), 3.3-3.15 (m, 2H), 2.9/2.35 (2m, 2H), 2.8/2.45 (2dd, 2H), 2.05-1.9 (m, 2H), 1.8 (m, 2H), 1.4 (s, 18H), 1.35 (s, 9H), 1.25 (m, 2H), 1.2 (t, 3H), 0.65 (m, 2H)

EXAMPLE 94: 3-(4-AMINOBUTYL)-4-HYDROXY-1-[[2-(1-METHYLPYRAZOL-4-YL)PHENYL]-METHYL]-4-OXO-1,4-AZAPHOSPHINANE-3-CARBOXYLIC ACID

Example 94 is obtained starting from intermediate 82 in accordance with procedure D described hereinbefore.

¹H NMR: (400 MHz, D2O) δ ppm 7.75 (s, 1H), 7.6 (s, 1H), 7.55-7.35 (m, 4H), 4.4 (dd, 2H), 3.9 (s, 3H), 3.6-3.1 (m, 3H), 3-2.8 (m, 3H), 2.05/1.7 (m, 2H), 1.85/1.35 (m, 2H), 1.55 (m, 2H), 1.1 (m, 2H)

ESI/FIA/HR and MS/MS: [M+H]+=421.2016 (421.2004)

Elemental analysis: C=56.61 (57.13); H=6.36 (6.95); N=13.08 (13.33)

Intermediate 83: tert-Butyl 3-{4-[bis(tert-butoxycarbonyl)amino]butyl}-4-ethoxy-4-oxo-1-[(2-pyrimidin-5-ylphenyl)methyl]-1,4-azaphosphinane-3-carboxylate Intermediate 83 is obtained starting from intermediates 21 and 236 in accordance with procedure F described hereinbefore.

¹H NMR: (400 MHz, dmso-d6) δ ppm 9.2 (s, 1H), 8.86 (s, 2H), 7.5-7.3 (m, 4H), 3.93 (m, 2H), 3.46 (dd, 2H), 3.3 (m, 2H), 2.78-2.6 (2m, 2H), 2.4 (dd, 1H), 2.2 (m, 1H), 2-1.75 (m, 2H), 1.65 (m, 2H), 1.4 (m, 2H), 1.4 (s, 18H), 1.33 (s, 9H), 1.18 (t, 3H), 0.6 (m, 2H)

EXAMPLE 95: 3-(4-AMINOBUTYL)-4-HYDROXY-4-OXO-1-[(2-PYRIMIDIN-5-YLPHENYL)METHYL]-1,4-AZAPHOSPHINANE-3-CARBOXYLIC ACID

Example 95 is obtained starting from intermediate 83 in accordance with procedure D described hereinbefore.

¹H NMR: (400 MHz, D2O) δ ppm 9.19 (s, 1H), 8.85 (s, 2H), 7.7 (m, 1H), 7.68-7.59 (m, 2H), 7.45 (m, 1H), 4.38 (dd, 2H), 3.52/3.15 (2m, 2H), 3.25/2.9 (2m, 2H), 2.9 (m, 2H), 2.1/1.7 (2m, 2H), 1.85/1.4 (2m, 2H), 1.6 (m, 2H), 1.1 (m, 2H)

ESI/FIA/HR and MS/MS: [M+H]+=419.1856 (419.1848)
Elemental analysis: C=57.94 (57.41); H=6.37 (6.50); N=13.40 (13.39)

Intermediate 84: tert-Butyl 3-{4-[bis(tert-butoxycarbonyl)amino]butyl}-4-ethoxy-1-[[2-(2-methylpyrazol-3-yl)phenyl]methyl]-4-oxo-1,4-azaphosphinane-3-carboxylate Intermediate 84 is obtained starting from intermediates 21 and 280 in accordance with procedure F described hereinbefore.

¹H NMR: (400 MHz, dmso-d6) δ ppm 7.56 (dd, 1H), 7.5 (d, 1H), 7.47 (td, 1H), 7.39 (td, 1H), 7.28 (dd, 1H), 6.25 (d, 1H), 3.95 (m, 2H), 3.58 (s, 3H), 3.45-3.25 (m, 4H), 2.8/2.2 (2m, 2H), 2.7/2.35 (2dd, 2H), 2-1.75 (m, 4H), 1.4 (m, 2H), 1.4 (s, 18H), 1.35 (s, 9H), 1.2 (t, 3H), 0.7 (m, 2H)

EXAMPLE 96: 3-(4-AMINOBUTYL)-4-HYDROXY-1-[[2-(2-METHYLPYRAZOL-3-YL)PHENYL]-METHYL]-4-OXO-1,4-AZAPHOSPHINANE-3-CARBOXYLIC ACID

Example 96 is obtained starting from intermediate 84 in accordance with procedure D described hereinbefore.

¹H NMR: (400 MHz, D2O) δ ppm 7.7-7.4 (m, 4H), 7.63 (d, 1H), 6.45 (d, 1H), 4.2 (dd, 2H), 3.58 (s, 3H), 3.55-3.05 (m, 4H), 2.8 (m, 2H), 2.1/1.7 (2m, 2H), 1.85/1.4 (2m, 2H), 1.6 (m, 2H), 1.3-1 (m, 2H)

ESI/FIA/HR and MS/MS: [M+H]+=421.2019 (421.2004)
Elemental analysis: C=57.47 (57.13); H=6.44 (6.95); N=13.24 (13.33)

Intermediate 85: tert-Butyl 3-{4-[bis(tert-butoxycarbonyl)amino]butyl}-1-[[2-(2-chlorophenyl)phenyl]methyl]-4-ethoxy-4-oxo-1,4-azaphosphinane-3-carboxylate Intermediate 85 is obtained starting from intermediates 21 and 214 in accordance with procedure F described hereinbefore.

¹H NMR: (400 MHz, dmso-d6) δ ppm 7.56 (m, 1H), 7.56/7.49 (d, 1H), 7.42 (m, 2H), 7.42 (m, 1H), 7.34 (m, 1H), 7.27 (m, 1H), 7.12 (m, 1H), 3.92 (m, 2H), 3.5-3.15 (m, 2H), 3.5-3.15 (m, 2H), 2.68/2.1 (m, 2H), 2.68/2.31 (m, 2H), 2-1.7 (m, 2H), 2-1.7 (m, 2H), 1.42 (s, 18H), 1.39 (m, 2H), 1.34 (s, 9H), 1.16 (2*t, 3H), 0.73 (m, 2H)

EXAMPLE 97: 3-(4-AMINOBUTYL)-1-[[2-(2-CHLOROPHENYL)PHENYL]METHYL]-4-HYDROXY-4-OXO-1,4-AZAPHOSPHINANE-3-CARBOXYLIC ACID

Example 97 is obtained starting from intermediate 85 in accordance with procedure D described hereinbefore.

¹H NMR: (400 MHz, D2O) δ ppm 7.7-7.25 (m, 4H), 7.7-7.25 (m, 4H), 4.45-3.9 (m, 2H), 3.75-3 (m, 2H), 3.45-2.75 (m, 2H), 2.95 (m, 2H), 2.15/1.69 (m, 2H), 1.87/1.38 (m, 2H), 1.59 (m, 2H), 1.3-1 (m, 2H)

ESI/FIA/HR and MS/MS: [M+H]+=451.1545 (451.1553)
Elemental analysis: C=58.81 (58.60); H=6.24 (6.26); N=6.36 (6.21)

Intermediate 86: tert-Butyl 3-{4-[bis(tert-butoxycarbonyl)amino]butyl}-4-ethoxy-1-[(2-imidazol-1-ylphenyl)methyl]-4-oxo-1,4-azaphosphinane-3-carboxylate Intermediate 86 is obtained starting from intermediate 21 and 2-imidazol-1-ylbenzaldehyde in accordance with procedure F described hereinbefore.

¹H NMR: (400 MHz, dmso-d6) δ ppm 7.81 (t, 1H), 7.53 (m, 1H), 7.5-7.42 (2m, 2H), 7.41 (t, 1H), 7.35 (m, 1H), 7.1 (t, 1H), 4.05-4 (m, 2H), 3.4 (dd, 2H), 3.3 (m, 2H), 2.9/2.4 (2m, 2H), 2.68/2.6 (2dd, 2H), 1.9-1.6 (m, 4H), 1.45 (s, 18H), 1.35 (m, 2H), 1.35 (s, 9H), 1.21 (t, 3H), 1-0.65 (2m, 2H)

EXAMPLE 98: 3-(4-AMINOBUTYL)-4-HYDROXY-1-[(2-IMIDAZOL-1-YLPHENYL) METHYL]-4-OXO-1,4-AZAPHOSPHINANE-3-CARBOXYLIC ACID

Example 98 is obtained starting from intermediate 86 in accordance with procedure D described hereinbefore.

¹H NMR: (400 MHz, D2O) δ ppm 7.9 (sl, 1H), 7.7-7.45 (m, 4H), 7.36 (sl, 1H), 7.25 (sl, 1H), 4.25 (dd, 2H), 3.5-3 (m, 4H), 2.95 (m, 2H), 2.1/1.7 (2m, 2H), 1.85/1.4 (2m, 2H), 1.6 (m, 2H), 1.15 (m, 2H)

ESI/FIA/HR and MS/MS: [M+H]+=407.1852 (407.1848)
Elemental analysis: C=56.41 (56.15); H=5.89 (6.70); N=13.55 (13.79)

Intermediate 87: tert-Butyl 3-{4-[bis(tert-butoxycarbonyl)amino]butyl}-4-ethoxy-4-oxo-1-[(2-piperazin-1-ylphenyl)methyl]-1,4-azaphosphinane-3-carboxylate Intermediate 87 is obtained starting from intermediate 21 and 1-Boc-4 (2-formylphenyl)piperazine in accordance with procedure F described hereinbefore.

¹H NMR: (400 MHz, dmso-d6) δ ppm 7.35 (dd, 1H), 7.24 (td, 1H), 7.11 (dd, 1H), 7.07 (td, 1H), 4.1-4 (m, 2H), 3.58 (dd, 2H), 3.46 (m, 4H), 3.3 (m, 2H), 2.9-2.5 (m, 8H), 1.9 (m, 2H), 1.75 (m, 2H), 1.4 (s, 18H), 1.4 (s, 9H), 1.35 (s, 9H), 1.35 (m, 2H), 1.25 (t, 3H), 0.85 (m, 2H)

EXAMPLE 99: 3-(4-AMINOBUTYL)-4-HYDROXY-4-OXO-1-[(2-PIPERAZIN-1-YLPHENYL) METHYL]-1,4-AZAPHOSPHINANE-3-CARBOXYLIC ACID

Example 99 is obtained starting from intermediate 87 in accordance with procedure D described hereinbefore.

¹H NMR: (400 MHz, D2O) δ ppm 7.6-7.25 (m, 4H), 4.3 (dd, 2H), 3.75-3.05 (m, 12H), 2.9 (m, 2H), 2.2/1.75 (2m, 2H), 1.9/1.5 (2m, 2H), 1.6 (m, 2H), 1.3/1.15 (2m, 2H)

ESI/FIA/HR and MS/MS: [M+H]+=425.2317 (425.231768)
Elemental analysis: C=47.64 (47.53); H=6.01 (6.78); N=11.07 (11.09); Br——15.70 (15.81)

Intermediate 88: tert-Butyl 3-{4-[bis(tert-butoxycarbonyl)amino]butyl}-4-ethoxy-4-oxo-1-[[2-(2-oxo-1,3-oxazolidin-3-yl)phenyl]methyl]-1,4-azaphosphinane-3-carboxylate Intermediate 88 is obtained starting from intermediate 21 and 2-(2-oxooxazolidin-3-yl)benzaldehyde in accordance with procedure F described hereinbefore.

¹H NMR: (400 MHz, dmso-d6) δ ppm 7.5-7.3 (m, 4H), 4.5 (t, 2H), 4.15-4 (m, 2H), 4-3.85 (2m, 2H), 3.5 (dd, 2H), 3.35 (m, 2H), 2.9-2.5 (m, 4H), 2-1.7 (m, 4H), 1.42 (s, 18H), 1.4 (m, 2H), 1.38 (s, 9H), 1.25 (t, 3H), 0.85 (m, 2H)

EXAMPLE 100: 3-(4-AMINOBUTYL)-4-HYDROXY-4-OXO-1-[[2-(2-OXO-1,3-OXAZOLIDIN-3-YL)PHENYL]METHYL]-1,4-AZAPHOSPHINANE-3-CARBOXYLIC ACID

Example 100 is obtained starting from intermediate 88 in accordance with procedure D described hereinbefore.
¹H NMR: (400 MHz, D2O) δ ppm 7.71-7.42 (m, 4H), 4.64 (t, 2H), 4.38 (s, 2H), 4.12/4.03 (m, 2H), 3.65/3.38 (dd, 2H), 3.46/3.16 (dd, 2H), 2.94 (t, 2H), 2.24/1.76 (m, 2H), 1.93/1.47 (m, 2H), 1.6 (t, 2H), 1.26/1.12 (m, 2H)
ESI/FIA/HR and MS/MS: [M+H]+=426.1782 (426.1793)
Elemental analysis: C=53.51 (53.64); H=6.34 (6.63); N=9.71 (9.88)

Intermediate 89: tert-Butyl 3-{4-[bis(tert-butoxycarbonyl)amino]butyl}-4-ethoxy-1-[[2-(3-methylimidazol-4-yl)phenyl]methyl]-4-oxo-1,4-azaphosphinane-3-carboxylate Intermediate 89 is obtained starting from intermediate 21 and 3-(methylimidazol-4-yl)benzaldehyde in accordance with procedure F described hereinbefore.
¹H NMR: (400 MHz, dmso-d6) δ ppm 7.7 (s, 1H), 7.52 (dd, 1H), 7.4/7.35 (2t, 2H), 7.25 (dd, 1H), 6.86 (s, 1H), 4.1-4 (m, 2H), 3.45-3.25 (m, 2H), 3.4 (s, 3H), 3.35 (m, 2H), 2.95/2.4 (2m, 2H), 2.85-2.6 (2m, 2H), 1.95-1.8 (m, 2H), 1.75 (m, 2H), 1.45 (s, 18H), 1.4 (m, 2H), 1.35 (s, 9H), 1.25 (t, 3H), 0.9-0.7 (2m, 2H)

EXAMPLE 101: 3-(4-AMINOBUTYL)-4-HYDROXY-1-[[2-(3-METHYLIMIDAZOL-4-YL)PHENYL]-METHYL]-4-OXO-1,4-AZAPHOSPHINANE-3-CARBOXYLIC ACID

Example 101 is obtained starting from intermediate 89 in accordance with procedure D described hereinbefore.
¹H NMR: (400 MHz, D2O) δ ppm 7.8 (s, 1H), 7.65 (m, 1H), 7.59 (m, 2H), 7.45 (m, 1H), 7.08 (d, 1H), 4.24 (dl, 2H), 3.43 (s, 3H), 3.36/3.02 (dd, 2H), 3.19 (m, 2H), 2.94 (m, 2H), 2.15/1.73 (m, 2H), 1.9/1.44 (m, 2H), 1.6 (m, 2H), 1.15 (dl, 2H)
ESI/FIA/HR and MS/MS: [M+H]+=421.1999 (421.2004)
Elemental analysis: C=58.05 (57.13); H=6.09 (6.95); N=13.62 (13.33)

Intermediate 90: tert-Butyl 3-{4-[bis(tert-butoxycarbonyl)amino]butyl}-4-ethoxy-1-[[2-(1-methylimidazol-2-yl)phenyl]methyl]-4-oxo-1,4-azaphosphinane-3-carboxylate Intermediate 90 is obtained starting from intermediates 21 and 223 in accordance with procedure F described hereinbefore.
¹H NMR: (400 MHz, dmso-d6) δ ppm 7.55 (dd, 1H), 7.45/7.35 (2t, 2H), 7.31 (dd, 1H), 7.25 (d, 1H), 6.98 (d, 1H), 4 (m, 2H), 3.5 (dd, 2H), 3.48 (s, 3H), 3.4 (m, 2H), 2.95/2.35 (2m, 2H), 2.7-2.4 (2m, 2H), 1.85-1.75 (m, 2H), 1.7 (m, 2H), 1.45 (s, 18H), 1.4 (m, 2H), 1.35 (s, 9H), 1.2 (t, 3H), 0.85 (m, 2H)

EXAMPLE 102: 3-(4-AMINOBUTYL)-4-HYDROXY-1-[[2-(1-METHYLIMIDAZOL-2-YL)PHENYL]-METHYL]-4-OXO-1,4-AZAPHOSPHINANE-3-CARBOXYLIC ACID

Example 102 is obtained starting from intermediate 90 in accordance with procedure D described hereinbefore.
¹H NMR: (400 MHz, D2O) δ ppm 7.7-7.5 (m, 4H), 7.23 (d, 1H), 7.16 (d, 1H), 4.17 (dd, 2H), 3.61 (s, 3H), 3.46/3.26 (2m, 2H), 3.37/3.09 (dd, 2H), 2.8 (m, 2H), 2.11/1.83 (2m, 2H), 1.94/1.4 (2m, 2H), 1.5 (m, 2H), 1 (m, 2H)
ESI/FIA/HR and MS/MS: [M+H]+=421.2013 (421.2004)
Elemental analysis: C=57.28 (57.13); H=7.10 (6.95); N=13.21 (13.33)

Intermediate 91: tert-Butyl 3-{4-[bis(tert-butoxycarbonyl)amino]butyl}-4-ethoxy-1-[[4-fluoro-2-(4-methoxyphenyl)phenyl]methyl]-4-oxo-1,4-azaphosphinane-3-carboxylate Intermediate 91 is obtained starting from intermediates 21 and 221 in accordance with procedure F described hereinbefore.
¹H NMR: (400 MHz, dmso-d6) δ ppm 7.48 (dd, 1H), 7.33 (d, 2H), 7.16 (td, 1H), 7.02 (dd, 1H), 7.02 (d, 2H), 4.03 (m, 2H), 3.8 (s, 3H), 3.4 (AB, 2H), 3.32 (m, 2H), 2.66/2.51/2.41 (3m, 4H), 1.91-1.66 (m, 4H), 1.41 (s, 18H), 1.37 (m, 2H), 1.34 (s, 9H), 1.22 (t, 3H), 0.88/0.76 (2m, 2H)

EXAMPLE 103: 3-(4-AMINOBUTYL)-1-[[4-FLUORO-2-(4-METHOXYPHENYL)PHENYL]METHYL]-4-HYDROXY-4-OXO-1,4-AZAPHOSPHINANE-3-CARBOXYLIC ACID

Example 103 is obtained starting from intermediate 91 in accordance with procedure D described hereinbefore.
¹H NMR: (300 MHz, D2O) δ ppm 7.62 (dd, 1H), 7.35 (d, 2H), 7.24 (td, 1H), 7.17 (dd, 1H), 7.13 (d, 2H), 4.36 (AB, 2H), 3.89 (s, 3H), 3.37/3.14 (2m, 2H), 3.14/2.85 (2m, 2H), 2.97 (m, 2H), 2.09/1.66 (2m, 2H), 1.88/1.38 (2m, 2H), 1.62 (m, 2H), 1.09 (m, 2H)
ESI/FIA/HR and MS/MS: [M+H]+=465.1965 (465.1954)
Elemental analysis: C=59.91 (59.48); H=6.23 (6.51); N=6.25 (6.03)

EXAMPLE 104: 3-(4-AMINOBUTYL)-1-[[4-FLUORO-2-(4-HYDROXYPHENYL)PHENYL]METHYL]-4-HYDROXY-4-OXO-1,4-AZAPHOSPHINANE-3-CARBOXYLIC ACID

Example 104 is obtained starting from intermediate 91 in accordance with procedure D described hereinbefore.
¹H NMR: (300 MHz, D2O) δ ppm 7.62 (dd, 1H), 7.3 (d, 2H), 7.25 (td, 1H), 7.18 (dd, 1H), 7.03 (d, 2H), 4.39 (AB, 2H), 3.4/3.13 (2m, 2H), 3.18/2.88 (2m, 2H), 2.99 (m, 2H), 2.12/1.68 (2m, 2H), 1.89/1.38 (2m, 2H), 1.63 (m, 2H), 1.12 (m, 2H)
ESI/FIA/HR and MS/MS: [M+H]+=451.1816 (451.1798)
Elemental analysis: C=58.99 (58.66); H=6.33 (6.27); N=6.27 (6.22)

Intermediate 92: tert-Butyl 3-{4-[bis(tert-butoxycarbonyl)amino]butyl}-4-ethoxy-4-oxo-1-[(2-phenylthiophen-3-yl)methyl]-1,4-azaphosphinane-3-carboxylate Intermediate 92 is obtained starting from intermediates 21 and 224 in accordance with procedure F described hereinbefore.

¹H NMR: (400 MHz, dmso-d6) δ ppm 7.55-7.34 (m, 5H), 7.55-7.34 (m, 1H), 7.09 (d, 1H), 4.04 (m, 2H), 3.51 (dd, 2H), 3.34 (m, 2H), 2.88-2.52 (m, 4H), 1.91 (m, 2H), 1.74 (m, 2H), 1.41 (s, 18H), 1.38 (m, 2H), 1.35 (s, 9H), 1.23 (t, 3H), 0.89 (m, 2H)

EXAMPLE 105: 3-(4-AMINOBUTYL)-4-HYDROXY-4-OXO-1-[(2-PHENYLTHIOPHEN-3-YL)METHYL]-1,4-AZAPHOSPHINANE-3-CARBOXYLIC ACID

Example 105 is obtained starting from intermediate 92 in accordance with procedure D described hereinbefore.
¹H NMR: (300 MHz, D2O) δ ppm 7.52 (d, 1H), 7.4 (m, 5H), 7.2 (d, 1H), 4.4-4.25 (m, 2H), 3.6-3.4 (m, 1H), 3.2-3.1 (m, 2H), 2.9 (m, 2H), 2.7 (m, 1H), 2.15 (m, 1H), 1.85 (m, 1H), 1.65-1.5 (m, 3H), 1.3 (m, 1H), 1 (m, 2H)
ESI/FIA/HR and MS/MS: [M+H]+=423.1511 (423.1507)
Elemental analysis: C=56.99 (56.86); H=6.31 (6.44); N=6.79 (6.63); S=7.29 (7.59)

Intermediate 93: tert-Butyl 3-{4-[bis(tert-butoxycarbonyl)amino]butyl}-4-ethoxy-4-oxo-1-[(4-phenylthiophen-3-yl)methyl]-1,4-azaphosphinane-3-carboxylate Intermediate 93 is obtained starting from intermediates 21 and 252 in accordance with procedure F described hereinbefore.
¹H NMR: (400 MHz, dmso-d6) δ ppm 7.53 (d, 2H), 7.5/7.47 (2d, 2H), 7.41 (t, 2H), 7.33 (t, 1H), 4.04 (m, 2H), 3.47 (AB, 2H), 3.32 (m, 2H), 2.92-2.4 (m, 4H), 1.94-1.6 (m, 4H), 1.43/1.41 (2s, 18H), 1.34 (2s, 9H), 1.33 (m, 2H), 1.22 (t, 3H), 0.8 (m, 2H)

EXAMPLE 106: 3-(4-AMINOBUTYL)-4-HYDROXY-4-OXO-1-[(4-PHENYLTHIOPHEN-3-YL)METHYL]-1,4-AZAPHOSPHINANE-3-CARBOXYLIC ACID

Example 106 is obtained starting from intermediate 93 in accordance with procedure D described hereinbefore.
¹H NMR: (300 MHz, D2O) δ ppm 7.75 (d, 1H), 7.45 (m, 5H), 7.42 (d, 1H), 4.4-4.3 (2*d, 2H), 3.45/3.15 (m, 2H), 3.15/2.75 (m, 2H), 2.9 (m, 2H), 2.1 (m, 1H), 1.8 (m, 1H), 1.7-1.5 (m, 3H), 1.25 (m, 1H), 0.95 (m, 2H)
ESI/FIA/HR and MS/MS: [M+H]+=423.1503 (423.1507)
Elemental analysis: C=57.35 (56.86); H=6.30 (6.44); N=6.53 (6.63); S=7.56 (7.59)

Intermediate 94: tert-Butyl 3-{4-[bis(tert-butoxycarbonyl)amino]butyl}-4-ethoxy-4-oxo-1-(thiophen-2-ylmethyl)-1,4-azaphosphinane-3-carboxylate Intermediate 94 is obtained starting from intermediate 21 and 2-formylthiophene in accordance with procedure F described hereinbefore.
¹H NMR: (400 MHz, dmso-d6) δ ppm 7.43 (m, 1H), 6.97 (m, 2H), 4.05 (m, 2H), 3.77 (AB, 2H), 3.41 (m, 2H), 2.85/2.55 (2m, 2H), 2.85/2.66 (2m, 2H), 2-1.7 (m, 4H), 1.43 (s, 18H), 1.41 (m, 2H), 1.39 (s, 9H), 1.24 (t, 3H), 1.01 (m, 2H)

EXAMPLE 107: 3-(4-AMINOBUTYL)-4-HYDROXY-4-OXO-1-(THIOPHEN-2-YLMETHYL)-1,4-AZAPHOSPHINANE-3-CARBOXYLIC ACID

Example 107 is obtained starting from intermediate 94 in accordance with procedure D described hereinbefore.
¹H NMR: (400 MHz, D2O) δ ppm 7.6 (dl, 1H), 7.25 (dl, 1H), 7.12 (t, 1H), 4.6/4.5 (d, 2H), 3.75/3.3 (m, 2H), 3.6/3.12 (m, 2H), 2.95 (m, 2H), 2.25/1.8 (m, 2H), 1.95/1.5 (m, 2H), 1.6 (m, 2H), 1.3-1.1 (m, 2H)
ESI/FIA/HR and MS/MS: [M+H]+=347.1205 (347.1194)
Elemental analysis: C=48.94 (48.55); H=5.79 (6.69); N=7.90 (8.09); S=9.22 (9.26)

Intermediate 95: tert-Butyl 3-{4-[bis(tert-butoxycarbonyl)amino]butyl}-4-ethoxy-4-oxo-1-[[2-(1,3-thiazol-2-yl)phenyl]methyl]-1,4-azaphosphinane-3-carboxylate Intermediate 95 is obtained starting from intermediates 21 and 225 in accordance with procedure F described hereinbefore.
¹H NMR: (400 MHz, dmso-d6) δ ppm 7.98 (d, 1H), 7.85 (d, 1H), 7.7 (d, 1H), 4.45 (m, 3H), 4.05 (quad., 2H), 3.45/3.35 (d, 2H), 3.4/2.5 (m, 2H), 3.3 (m, 2H), 2.7/2.5 (m, 2H), 1.8-1.55 (m, 4H), 1.45-1.35 (m, 2H), 1.4/1.3 (s, 27H), 1.2 (t, 3H), 0.65-0.3 (m, 2H)
ESI/FIA/HR and MS/MS: [M+H]+=708.3453 (708.3447)

EXAMPLE 108: 3-(4-AMINOBUTYL)-4-HYDROXY-4-OXO-1-[[2-(1,3-THIAZOL-2-YL)PHENYL]-METHYL]-1,4-AZAPHOSPHINANE-3-CARBOXYLIC ACID

Example 108 is obtained starting from intermediate 95 in accordance with procedure D described hereinbefore.
¹H NMR: (300 MHz, D2O) δ ppm 7.98 (m, 2H), 7.85 (m, 4H), 4.6 (d, 1H), 4.2 (d, 1H), 3.85 (m, 1H), 3.45 (m, 2H), 3.15 (dd, 1H), 2.9 (m, 2H), 2.3 (m, 1H), 1.85 (m, 2H), 1.55 (m, 3H), 1.2 (m, 1H), 1.0 (m, 1H)
ESI/FIA/HR and MS/MS: [M+H]+=424.1443 (424.1459)
Elemental analysis: C=54.17 (53.89); H=5.57 (6.19); N=9.91 (9.92); S=7.38 (7.57)

Intermediate 96: tert-Butyl 3-{4-[bis(tert-butoxycarbonyl)amino]butyl}-4-ethoxy-1-[(2-naphthalen-1-ylphenyl)methyl]-4-oxo-1,4-azaphosphinane-3-carboxylate Intermediate 96 is obtained starting from intermediates 21 and 228 in accordance with procedure F described hereinbefore.
¹H NMR: (400 MHz, dmso-d6) δ ppm 8-7.15 (m, 11H), 4.05-3.8 (m, 2H), 3.5-3.3 (m, 2H), 3.3-3 (dd, 2H), 2.7-2.1 (m, 4H), 2-1.5 (m, 4H), 1.5-1.3 (m, 2H), 1.45 (s, 18H), 1.35 (s, 9H), 1.2 (t, 3H), 1-0.5 (m, 2H)

EXAMPLE 109: 3-(4-AMINOBUTYL)-4-HYDROXY-1-[(2-NAPHTHALEN-1-YLPHENYL)METHYL]-4-OXO-1,4-AZAPHOSPHINANE-3-CARBOXYLIC ACID

Example 109 is obtained starting from intermediate 96 in accordance with procedure D described hereinbefore.
¹H NMR: (400 MHz, D2O) δ ppm 8 (d, 2H), 7.75-7.3 (m, 9H), 4.3/4.05 (2*d, 1H), 3.95/3.8 (2*d, 1H), 3.55-2.8 (m, 5H), 2.65 (m, 1H), 2.2-1.9 (m, 1H), 1.75 (m, 1H), 1.7-1.4 (m, 3H), 1.35-0.7 (m, 3H)
ESI/FIA/HR and MS/MS: [M+H]+=467.2109 (467.2099)
Elemental analysis: C=67.08 (66.94); H=6.21 (6.70); N=5.75 (6.00)

Intermediate 97: tert-Butyl 3-{4-[bis(tert-butoxycarbonyl)amino]butyl}-4-ethoxy-4-oxo-1-[(4-phenylthiophen-2-yl)methyl]-1,4-azaphosphinane-3-carboxylate Intermediate 97 is obtained starting from intermediate 21 and 4-phenyl-2-thiophenecarboxaldehyde in accordance with procedure F described hereinbefore.

$^1$H NMR: (500 MHz, dmso-d6) δ ppm 7.75 (d, 1H), 7.67 (d, 2H), 7.41 (d, 1H), 7.39 (t, 2H), 7.27 (t, 1H), 4.07 (m, 2H), 3.8 (AB, 2H), 3.4 (m, 2H), 2.95/2.58 (2m, 2H), 2.89/2.71 (2m, 2H), 2-1.74 (m, 4H), 1.43/1.4/1.39/1.37 (5s, 27H), 1.4 (m, 2H), 1.24/1.2 (2t, 3H), 1.1/1 (2m, 2H)

EXAMPLE 110: 3-(4-AMINOBUTYL)-4-HYDROXY-4-OXO-1-[(4-PHENYLTHIOPHEN-2-YL)METHYL]-1,4-AZAPHOSPHINANE-3-CARBOXYLIC ACID

Example 110 is obtained starting from intermediate 97 in accordance with procedure D described hereinbefore.

$^1$H NMR: (400 MHz, D2O) δ ppm 7.75 (s, 1H), 7.65 (d, 2H), 7.6 (s, 1H), 7.42 (d, 2H), 7.3 (t, 1H), 4.6/4.5 (2*d, 2H), 3.8-3.35 (m, 3H), 3.1 (m, 1H), 2.85 (m, 2H), 2.25/1.8 (m, 2H), 1.95/1.45 (m, 2H), 1.55 (m, 2H), 1.25-1.05 (m, 2H)

ESI/FIA/HR and MS/MS: [M+H]+=423.151 (423.1507)

Elemental analysis: C=57.05 (56.86); H=6.10 (6.44); N=6.67 (6.63); S=7.51 (7.59)

Intermediate 98: tert-Butyl 3-{4-[bis(tert-butoxycarbonyl)amino]butyl}-1-[(2-bromo-4-hydroxyphenyl)methyl]-4-ethoxy-4-oxo-1,4-azaphosphinane-3-carboxylate Intermediate 98 is obtained starting from intermediate 21 and 2-bromo-4-methoxybenzaldehyde in accordance with procedure F described hereinbefore.

$^1$H NMR: (300 MHz, dmso-d6) δ ppm 7.3 (d, 1H), 7.2 (s, 1H), 6.95 (dd, 1H), 4.05 (m, 2H), 3.75 (s, 3H), 3.6-3.5 (d, 2H), 3.4-3.3 (m, 2H), 3-2.6 (m, 4H), 2.9-1.5 (m, 4H), 1.42/1.35 (s, 27H), 1.4 (m, 2H), 1.22 (t, 3H), 0.75 (m, 2H)

$^{31}$P NMR: (300 MHz, dmso-d6) δ ppm 47.5

EXAMPLE 111: 3-(4-AMINOBUTYL)-1-[(2-BROMO-4-HYDROXYPHENYL)METHYL]-4-HYDROXY-4-OXO-1,4-AZAPHOSPHINANE-3-CARBOXYLIC ACID

Example 111 is obtained starting from intermediate 98 in accordance with procedure D described hereinbefore.

$^1$H NMR: (400 MHz, D2O) δ ppm 7.38 (d, 1H), 7.2 (s, 1H), 6.9 (dd, 1H), 4.4-4.3 (2*d, 2H), 3.8-3.7 (m, 1H), 3.6-3.4 (m, 2H), 3.25 (dd, 1H), 2.95 (m, 2H), 2.25 (m, 1H), 1.95 (m, 1H), 1.8 (m, 1H), 1.65-1.5 (m, 3H), 1.3 (m, 1H), 1.15 (m, 1H)

ESI/FIA/HR and MS/MS: [M+H]+=435.067 (435.0684)

Elemental analysis: C=44.16 (44.15); H=5.06 (5.56); N=6.05 (6.44)

Intermediate 99: tert-Butyl 3-{4-[bis(tert-butoxycarbonyl)amino]butyl}-1-[[2-(4-chlorophenyl)pyridin-3-yl]methyl]-4-ethoxy-4-oxo-1,4-azaphosphinane-3-carboxylate Intermediate 99 is obtained starting from intermediates 21 and 291 in accordance with procedure F described hereinbefore.

$^1$H NMR: (400 MHz, dmso-d6) δ ppm 8.58 (m, 1H), 7.9/7.89 (2dd, 1H), 7.63/7.61 (2d, 2H), 7.53 (d, 2H), 7.4 (dd, 1H), 4.04/3.94 (2m, 2H), 3.56/3.53 (2AB, 2H), 3.32 (m, 2H), 2.76-2.25 (m, 4H), 1.95-1.65 (m, 4H), 1.43/1.41 (2s, 18H), 1.35 (m, 2H), 1.33/1.32 (2s, 9H), 1.23/1.18 (2t, 3H), 0.9/0.74 (2m, 2H)

EXAMPLE 112: 3-(4-AMINOBUTYL)-1-[[2-(4-CHLOROPHENYL)PYRIDIN-3-YL]METHYL]-4-HYDROXY-4-OXO-1,4-AZAPHOSPHINANE-3-CARBOXYLIC ACID

Example 112 is obtained starting from intermediate 99 in accordance with procedure D described hereinbefore.

$^1$H NMR: (300 MHz, D2O) δ ppm 8.61 (dd, 1H), 8.09 (dd, 1H), 7.56/7.43 (2d, 4H), 7.55 (dd, 1H), 4.42 (AB, 2H), 3.45/3.1 (2m, 2H), 3.1/2.87 (2m, 2H), 2.9 (m, 2H), 2.1/1.65 (2m, 2H), 1.82/1.33 (2m, 2H), 1.55 (m, 2H), 1.03 (m, 2H)

ESI/FIA/HR and MS/MS: [M+H]+=452.1508 (452.1505)

Elemental analysis: C=55.90 (55.82); H=6.11 (6.02); N=8.95 (9.30)

Intermediate 100: tert-Butyl 3-{4-[bis(tert-butoxycarbonyl)amino]butyl}-1-[[4-chloro-2-(4-chlorophenyl)phenyl]methyl]-4-ethoxy-4-oxo-1,4-azaphosphinane-3-carboxylate Intermediate 100 is obtained starting from intermediates 21 and 292 in accordance with procedure F described hereinbefore.

$^1$H NMR: (300 MHz, dmso-d6) δ ppm 7.55-7.35 (m, 6H), 7.25 (s, 1H), 4.15-4 (m, 2H), 3.5-3.3 (m, 4H), 2.95-2.4 (m, 4H), 1.95-1.6 (m, 6H), 1.5-1.3 (3t, 27H), 1.25 (t, 3H), 1.15-0.75 (m, 2H)

EXAMPLE 113: 3-(4-AMINOBUTYL)-1-[[4-CHLORO-2-(4-CHLOROPHENYL)PHENYL]METHYL]-4-HYDROXY-4-OXO-1,4-AZAPHOSPHINANE-3-CARBOXYLIC ACID

Example 113 is obtained starting from intermediate 100 in accordance with procedure D described hereinbefore.

$^1$H NMR: (400 MHz, D2O) δ ppm 7.58 (d, 1H), 7.54 (d, 2H), 7.54 (dd, 1H), 7.45 (d, 1H), 7.33 (d, 2H), 4.33 (dd, 2H), 3.41/3.1 (2m, 2H), 3.15/2.85 (dd, 2H), 2.95 (m, 2H), 2.1/1.65 (2m, 2H), 1.85/1.35 (2m, 2H), 1.6 (m, 2H), 1.1 (m, 2H)

ESI/FIA/HR and MS/MS: [M+H]+=485.1172 (485.1163)

Elemental analysis: C=54.57 (54.44); H=5.31 (5.61); N=5.84 (5.77)

Intermediate 101: tert-Butyl 3-{4-[bis(tert-butoxycarbonyl)amino]butyl}-4-ethoxy-4-oxo-1-[[2-(2-phenylphenyl)phenyl]methyl]-1,4-azaphosphinane-3-carboxylate Intermediate 101 is obtained starting from intermediates 21 and 238 in accordance with procedure F described hereinbefore.

$^1$H NMR: (300 MHz, dmso-d6) δ ppm 7.6-7 (m, 13H), 4.15-3.9 (m, 2H), 3.5-3.3 (m, 2H), 3.3-2.9 (m, 2H), 2.75-2.2 (m, 4H), 1.95-1.65 (m, 4H), 1.6-1.3 (m, 2H), 1.45 (3s, 27H), 1.25 (t, 3H), 1.2-0.7 (m, 2H)

EXAMPLE 114: 3-(4-AMINOBUTYL)-4-HYDROXY-4-OXO-1-[[2-(2-PHENYLPHENYL)PHENYL]-METHYL]-1,4-AZAPHOSPHINANE-3-CARBOXYLIC ACID

Example 114 is obtained starting from intermediate 101 in accordance with procedure D described hereinbefore.

¹H NMR: (300 MHz, D2O) δ ppm 7.6-7.1 (m, 13H), 3.8/3.6/3.55 (2*d, 2H), 3.3/3 (2*m, 2H), 3.15/2.6 (2*m, 2H), 2.92 (m, 2H), 2.05/1.6 (2*m, 2H), 1.8/1.3 (2*m, 2H), 1.6 (m, 2H), 1.02 (m, 2H)

ESI/FIA/HR and MS/MS: [M+H]+=493.2273 (493.2256)
Elemental analysis: C=68.12 (68.28); H=6.31 (6.75); N=5.77 (5.69)

Intermediate 102: tert-Butyl 3-{4-[bis(tert-butoxycarbonyl)amino]butyl}-4-ethoxy-4-oxo-1-[[2-[3-(trifluoromethoxy)phenyl]phenyl]methyl]-1,4-azaphosphinane-3-carboxylate Intermediate 102 is obtained starting from intermediate 21 and 2-[3-(trifluoromethoxyphenyl)]benzaldehyde in accordance with procedure F described hereinbefore.

¹H NMR: (400 MHz, dmso-d6) δ ppm 7.59 (t, 1H), 7.42 (m, 3H), 7.42 (m, 3H), 7.28 (m, 1H), 3.99 (m, 2H), 3.54/3.32 (m, 2H), 3.32 (m, 2H), 3.1-2.2 (m, 2H), 3.1-2.2 (m, 2H), 2-1.6 (m, 2H), 2-1.6 (m, 2H), 1.5-1.3 (m, 27H), 1.3 (m, 2H), 1.21 (t, 3H), 0.9-0.5 (m, 2H)

EXAMPLE 115: 3-(4-AMINOBUTYL)-4-HYDROXY-4-OXO-1-[[2-[3-(TRIFLUOROMETHOXY)PHENYL]-PHENYL]METHYL]-1,4-AZAPHOSPHINANE-3-CARBOXYLIC ACID

Example 115 is obtained starting from intermediate 102 in accordance with procedure D described hereinbefore.

¹H NMR: (400 MHz, dmso-d6) δ ppm 7.63 (m, 1H), 7.59 (t, 1H), 7.55 (m, 2H), 7.41 (m, 1H), 7.41 (m, 1H), 7.34 (m, 2H), 4.41/3.2 (2*d, 2H), 3.43/3.1 (m, 2H), 3.2/2.84 (m, 2H), 2.94 (m, 2H), 2.11/1.64 (m, 2H), 1.86/1.36 (m, 2H), 1.59 (m, 2H), 1.13/1.06 (m, 2H)

ESI/FIA/HR and MS/MS: [M+H]+=501.1759 (501.1766)
Elemental analysis: C=54.63 (55.20); H=5.24 (5.64); N=5.43 (5.60)

Intermediate 103: tert-Butyl 3-{4-[bis(tert-butoxycarbonyl)amino]butyl}-4-ethoxy-1-[(4-fluoro-2-phenylphenyl)methyl]-4-oxo-1,4-azaphosphinane-3-carboxylate Intermediate 103 is obtained starting from intermediates 21 and 257 in accordance with procedure F described hereinbefore.

¹H NMR: (400 MHz, dmso-d6) δ ppm 22/2.7 (2*m, 2H), 7.52 (dd, 1H), 7.47 (t, 2H), 7.4 (t, 1H), 7.37 (d, 2H), 7.2 (dt, 1H), 7.04 (dd, 1H), 4-3.7 (m, 2H), 3.52/3.32 (2*d, 2H), 3.32 (m, 2H), 2.7/2.32 (2*m, 2H), 1.95-1.72 (m, 2H), 1.95-1.72 (m, 2H), 1.41/1.35 (2*s, 27H), 1.38 (m, 2H), 1.17 (t, 3H), 0.8-0.6 (m, 2H)

EXAMPLE 116: 3-(4-AMINOBUTYL)-1-[(4-FLUORO-2-PHENYLPHENYL)METHYL]-4-HYDROXY-4-OXO-1,4-AZAPHOSPHINANE-3-CARBOXYLIC ACID

Example 116 is obtained starting from intermediate 103 in accordance with procedure D described hereinbefore.

¹H NMR: (300 MHz, D2O) δ ppm 7.6 (dd, 1H), 7.49 (m, 3H), 7.34 (m, 2H), 7.22 (td, 1H), 7.15 (dd, 1H), 4.31 (AB, 2H), 3.32/3.06 (2m, 2H), 3.16/2.8 (2m, 2H), 2.92 (m, 2H), 2.05/1.6 (2m, 2H), 1.82/1.33 (2m, 2H), 1.56 (m, 2H), 1.07 (m, 2H)

¹⁹F NMR: (300 MHz, D2O) δ ppm −111.5
ESI/FIA/HR and MS/MS: [M+H]+=435.1854 (435.1848)
Elemental analysis: C=60.79 (60.82); H=6.07 (6.50); N=6.19 (6.45)

Intermediate 104: tert-Butyl 3-{4-[bis(tert-butoxycarbonyl)amino]butyl}-4-ethoxy-1-[(4-hydroxy-2-phenylphenyl)methyl]-4-oxo-1,4-azaphosphinane-3-carboxylate Intermediate 104 is obtained starting from intermediates 21 and 285 in accordance with procedure F described hereinbefore.

¹H NMR: (400 MHz, dmso-d6) δ ppm 7.45-7.32 (m, 5H), 7.42 (d, 1H), 6.95 (dd, 1H), 6.74 (df, 1H), 3.92 (m, 2H), 3.77 (s, 3H), 3.46/3.27 (2*d, 2H), 3.34 (m, 2H), 2.75/2.15 (2*m, 2H), 2.68/2.28 (2*m, 2H), 1.85-1.65 (m, 2H), 1.85-1.65 (m, 2H), 1.69 (m, 2H), 1.41/1.34 (2*s, 27H), 1.39 (m, 2H), 1.17 (t, 3H)

EXAMPLE 117: 3-(4-AMINOBUTYL)-4-HYDROXY-1-[(4-HYDROXY-2-PHENYLPHENYL)METHYL]-4-OXO-1,4-AZAPHOSPHINANE-3-CARBOXYLIC ACID

Example 117 is obtained starting from intermediate 104 in accordance with procedure D described hereinbefore.

¹H NMR: (400 MHz, D2O) δ ppm 7.5-7.25 (m, 5H), 7.3 (d, 1H), 6.92 (dd, 1H), 6.82 (d, 1H), 4.3/4.15 (2*d, 2H), 3.3/3 (2*m, 2H), 3.15/2.72 (dd, 2H), 2.9 (m, 2H), 2/1.55 (2*m, 2H), 1.8/1.55 (2*m, 2H), 1.55/1.3 (2*m, 2H), 1.05 (m, 2H)

ESI/FIA/HR and MS/MS: [M+H]+=433.1888 (433.1892)
Elemental analysis: C=60.92 (61.10); H=6.44 (6.76); N=6.43 (6.48)

Intermediate 105: tert-Butyl 3-{4-[bis(tert-butoxycarbonyl)amino]butyl}-4-ethoxy-1-[[2-(furan-2-yl)phenyl]methyl]-4-oxo-1,4-azaphosphinane-3-carboxylate Intermediate 105 is obtained starting from intermediate 21 and 2-(2-furyl)benzaldehyde in accordance with procedure F described hereinbefore.

¹H NMR: (400 MHz, dmso-d6) δ ppm 7.77 (d, 1H), 7.62 (d, 1H), 7.41 (d, 1H), 7.37/7.31 (2*m, 2H), 6.77 (d, 1H), 6.61 (dd, 1H), 3.96 (m, 2H), 3.84/3.49 (2*d, 2H), 3.3-3.15 (m, 2H), 2.95/2.38 (2*m, 2H), 2.77/2.45 (2*m, 2H), 2.05-1.6 (m, 2H), 2.05-1.6 (m, 2H), 1.4/1.32 (2*s, 27H), 1.3-1.15 (m, 2H), 1.2 (t, 3H), 0.7-0.48 (4*m, 2H)

EXAMPLE 118: 3-(4-AMINOBUTYL)-1-[[2-(FURAN-2-YL)PHENYL]METHYL]-4-HYDROXY-4-OXO-1,4-AZAPHOSPHINANE-3-CARBOXYLIC ACID

Example 118 is obtained starting from intermediate 105 in accordance with procedure D described hereinbefore.

¹H NMR: (400 MHz, D2O) δ ppm 7.75 (d, 1H), 7.73 (s, 1H), 7.52 (t, 1H), 7.48 (d, 1H), 7.4 (t, 1H), 6.88 (d, 1H), 6.63 (d, 1H), 4.63/4.33 (2*d, 2H), 3.82/3.5 (2*m, 2H), 3.48/3.18 (dd, 2H), 2.9 (m, 2H), 2.26/1.8 (2*m, 2H), 1.9/1.48 (2*m, 2H), 1.6 (m, 2H), 1.2/1.05 (2*m, 2H)

ESI/FIA/HR and MS/MS: [M+H]+=407.1729 (407.1735)
Elemental analysis: C=59.18 (59.11); H=6.65 (6.70); N=6.86 (6.89)

Intermediate 106: tert-Butyl 3-{4-[bis(tert-butoxycarbonyl)amino]butyl}-4-ethoxy-4-oxo-1-[(2-thiophen-2-ylphenyl)methyl]-1,4-azaphosphinane-3-carboxylate Intermediate 106 is obtained starting from intermediate 21 and 2-(2-thienyl)benzaldehyde in accordance with procedure F described hereinbefore.

$^1$H NMR: (400 MHz, dmso-d6) δ ppm 7.62 (dd, 1H), 7.46-7.33 (m, 4H), 7.23 (dd, 1H), 7.14 (dd, 1H), 4.03-3.88 (m, 2H), 3.65/3.42 (2*d, 2H), 3.32-3.15 (m, 2H), 3-2.7/2.4 (2*m, 2H), 3-2.7/2.4 (2*m, 2H), 2.05-1.75 (m, 2H), 2.05-1.75 (m, 2H), 1.4/1.34 (2*s, 27H), 1.39 (m, 2H), 1.2 (t, 3H), 0.7-0.45 (m, 2H)

EXAMPLE 119: 3-(4-AMINOBUTYL)-4-HYDROXY-4-OXO-1-[(2-THIOPHEN-2-YLPHENYL)-METHYL]-1,4-AZAPHOSPHINANE-3-CARBOXYLIC ACID

Example 119 is obtained starting from intermediate 106 in accordance with procedure D described hereinbefore.

$^1$H NMR: (400 MHz, D2O) δ ppm 7.6 (m, 1H), 7.57 (d, 1H), 7.52 (m, 2H), 7.52 (m, 1H), 7.2 (d, 1H), 7.15 (d, 1H), 4.52/4.42 (2*d, 2H), 3.48/3.22 (2*m, 2H), 3.3/2.98 (dd, 2H), 2.93 (m, 2H), 2.13/1.68 (2*m, 2H), 1.88/1.4 (2*m, 2H), 1.6 (m, 2H), 1.2/1.05 (2*m, 2H)

ESI/FIA/HR and MS/MS: [M+H]+=423.1493 (423.1507)
Elemental analysis: C=56.66 (56.86); H=6.32 (6.44); N=6.64 (6.63); S=7.48 (7.59)

Intermediate 107: tert-Butyl 3-{4-[bis(tert-butoxycarbonyl)amino]butyl}-4-ethoxy-4-oxo-1-[(2-pyridin-4-ylphenyl)methyl]-1,4-azaphosphinane-3-carboxylate Intermediate 107 is obtained starting from intermediates 21 and 258 in accordance with procedure F described hereinbefore.

$^1$H NMR: (400 MHz, dmso-d6) δ ppm 8.62 (d, 2H), 7.5 (dd, 1H), 7.46-7.37 (m, 2H), 7.4 (d, 2H), 7.26 (dd, 1H), 3.92 (m, 2H), 3.58/3.38 (2*d, 2H), 3.3 (m, 2H), 2.82/2.22 (2*m, 2H), 2.68/2.37 (2*m, 2H), 1.85-1.65 (m, 2H), 1.85-1.65 (m, 2H), 1.41/1.33 (2*s, 27H), 1.38 (m, 2H), 1.18 (t, 3H), 0.63 (m, 2H)

$^{13}$C NMR: (400 MHz, dmso-d6) δ ppm 107, 67, 29/23

EXAMPLE 120: 3-(4-AMINOBUTYL)-4-HYDROXY-4-OXO-1-[(2-PYRIDIN-4-YLPHENYL)METHYL]-1,4-AZAPHOSPHINANE-3-CARBOXYLIC ACID

Example 120 is obtained starting from intermediate 107 in accordance with procedure D described hereinbefore.

$^1$H NMR: (400 MHz, D2O) δ ppm 8.59 (d, 2H), 7.62 (m, 1H), 7.55 (m, 2H), 7.41 (d, 2H), 7.41 (m, 1H), 4.4/4.29 (2*d, 2H), 3.42/3.09 (2*m, 2H), 3.18/2.85 (2*m, 2H), 2.91 (m, 2H), 2.08/1.65 (2*m, 2H), 1.82/1.55 (2*m, 2H), 1.55/1.32 (2*m, 2H), 1.05 (m, 2H)

ESI/FIA/HR and MS/MS: [M+H]+=418.1891 (418.1895)
Elemental analysis: C=59.87 (60.42); H=6.51 (6.76); N=9.86 (10.07)

Intermediate 108: tert-Butyl 3-{4-[bis(tert-butoxycarbonyl)amino]butyl}-4-ethoxy-4-oxo-1-[(2-pyridin-3-ylphenyl)methyl]-1,4-azaphosphinane-3-carboxylate Intermediate 108 is obtained starting from intermediate 21 and 2-(3-pyridyl)benzaldehyde in accordance with procedure F described hereinbefore.

$^1$H NMR: (400 MHz, dmso-d6) δ ppm 8.58 (dd, 1H), 8.56 (d, 1H), 7.81 (dt, 1H), 7.48 (m, 1H), 7.48 (m, 1H), 7.41 (m, 2H), 7.27 (d, 1H), 3.93 (m, 2H), 3.55/3.35 (2*d, 2H), 3.29 (m, 2H), 2.71/2.2 (m, 2H), 2.71/2.35 (m, 2H), 1.95-1.7 (m, 2H), 1.95-1.7 (m, 2H), 1.41 (s, 18H), 1.36 (m, 2H), 1.34 (s, 9H), 1.18 (t, 3H), 0.64 (m, 2H)

EXAMPLE 121: 3-(4-AMINOBUTYL)-4-HYDROXY-4-OXO-1-[(2-PYRIDIN-3-YLPHENYL)METHYL]-1,4-AZAPHOSPHINANE-3-CARBOXYLIC ACID

Example 121 is obtained starting from intermediate 108 in accordance with procedure D described hereinbefore.

$^1$H NMR: (400 MHz, D2O) δ ppm 8.58 (dd, 1H), 8.51 (d, 1H), 7.86 (dt, 1H), 7.67 (m, 1H), 7.58 (m, 1H), 7.58 (m, 2H), 7.43 (m, 1H), 4.42/4.3 (2*d, 2H), 3.46/3.11 (m, 2H), 3.2/2.87 (m, 2H), 2.94 (m, 2H), 2.11/1.65 (m, 2H), 1.86/1.36 (m, 2H), 1.59 (m, 2H), 1.08 (m, 2H)

ESI/FIA/HR and MS/MS: [M+H]+=418.1898 (418.1895)
Elemental analysis: C=60.58 (60.42); H=6.51 (6.76); N=10.09 (10.07)

Intermediate 109: tert-Butyl 3-{4-[bis(tert-butoxycarbonyl)amino]butyl}-4-ethoxy-4-oxo-1-[[2-[4-(trifluoromethyl)phenyl]phenyl]methyl]-1,4-azaphosphinane-3-carboxylate Intermediate 109 is obtained starting from intermediate 21 and 2-[4-(trifluoromethyl)phenyl]benzaldehyde in accordance with procedure F described hereinbefore.

$^1$H NMR: (400 MHz, dmso-d6) δ ppm 7.81 (d, 2H), 7.62 (d, 2H), 7.5 (d, 1H), 7.41 (m, 2H), 7.27 (d, 1H), 3.93 (m, 2H), 3.58/3.34 (2*d, 2H), 3.28 (m, 2H), 2.74/2.36 (m, 2H), 2.74/2.24 (m, 2H), 2-1.7 (m, 2H), 2-1.7 (m, 2H), 1.4 (s, 18H), 1.36 (m, 2H), 1.34 (s, 9H), 1.17 (t, 3H), 0.65 (m, 2H)

EXAMPLE 122: 3-(4-AMINOBUTYL)-4-HYDROXY-4-OXO-1-[[2-[4-(TRIFLUOROMETHYL)PHENYL]-PHENYL]METHYL]-1,4-AZAPHOSPHINANE-3-CARBOXYLIC ACID

Example 122 is obtained starting from intermediate 109 in accordance with procedure D described hereinbefore.

$^1$H NMR: (400 MHz, D2O) δ ppm 7.83 (d, 2H), 7.64 (m, 1H), 7.56 (m, 2H), 7.53 (d, 2H), 7.43 (m, 1H), 4.42/4.28 (2*d, 2H), 3.42/3.09 (m, 2H), 3.18/2.84 (m, 2H), 2.94 (m, 2H), 2.1/1.64 (m, 2H), 1.85/1.35 (m, 2H), 1.59 (m, 2H), 1.13/1.05 (m, 2H)

ESI/FIA/HR and MS/MS: [M+H]+=485.1800 (485.1817)
Elemental analysis: C=56.24 (57.02); H=5.26 (5.83); N=5.65 (5.78)

Intermediate 110: tert-Butyl 3-{4-[bis(tert-butoxycarbonyl)amino]butyl}-1-[(2-cyclohexylphenyl)methyl]-4-ethoxy-4-oxo-1,4-azaphosphinane-3-carboxylate Intermediate 110 is obtained starting from intermediate 21 and 2-cyclohexylbenzaldehyde in accordance with procedure F described hereinbefore.

$^1$H NMR: (400 MHz, dmso-d6) δ ppm 7.28/7.17 (2*d, 2H), 7.22/7.1 (2*m, 2H), 3.98 (m, 2H), 3.5 (s, 2H), 3.31 (m, 2H), 3-2.8/2.28 (2*m, 2H), 3-2.8/2.5 (2*m, 2H), 3-2.8 (m, 1H), 2-1.78 (2*m, 2H), 1.9-1.65 (m, 2H), 1.9-1.65 (m, 6H), 1.45-1.25 (m, 2H), 1.45-1.25 (m, 4H), 1.41/1.37 (2*s, 27H), 1.21 (t, 3H), 0.85-0.65 (m, 2H)

EXAMPLE 123: 3-(4-AMINOBUTYL)-1-[(2-CYCLOHEXYLPHENYL)METHYL]-4-HYDROXY-4-OXO-1,4-AZAPHOSPHINANE-3-CARBOXYLIC ACID

Example 123 is obtained starting from intermediate 110 in accordance with procedure D described hereinbefore.
$^1$H NMR: (400 MHz, D2O) δ ppm 7.52-7.4 (m, 2H), 7.52-7.4/7.3 (2*m, 2H), 4.4 (t, 2H), 3.6/3.4 (2*m, 2H), 3.49/3.24 (2*m, 2H), 2.93 (m, 2H), 2.66 (m, 1H), 2.21/1.75 (2*m, 2H), 1.95/1.5 (2*m, 2H), 1.85-1.1 (m, 10H), 1.85-1.1 (m, 4H)
ESI/FIA/HR and MS/MS: [M+H]+=423.2408 (423.2412)
Elemental analysis: C=62.46 (62.54); H=8.23 (8.35); N=6.61 (6.63)

Intermediate 111: tert-Butyl 3-{4-[bis(tert-butoxycarbonyl)amino]butyl}-4-ethoxy-1-(1H-indazol-5-ylmethyl)-4-oxo-1,4-azaphosphinane-3-carboxylate Intermediate 111 is obtained starting from intermediate 21 and 1H-indazole-5-carbaldehyde in accordance with procedure F described hereinbefore.
$^1$H NMR: (400 MHz, dmso-d6) δ ppm 13 (sl, 1H), 8 (s, 1H), 7.62 (df, 1H), 7.48 (d, 1H), 7.3 (dd, 1H), 3.97 (m, 2H), 3.72/3.52 (2*d, 2H), 3.4-3.2 (m, 2H), 2.96/2.32 (2*m, 2H), 2.83/2.47 (2*m, 2H), 2-1.8 (m, 2H), 2-1.8 (m, 2H), 1.39/1.33 (2*s, 27H), 1.36 (m, 2H), 1.2 (t, 3H), 0.9-0.7 (m, 2H)

EXAMPLE 124: 3-(4-AMINOBUTYL)-4-HYDROXY-1-(1H-INDAZOL-5-YLMETHYL)-4-OXO-1,4-AZAPHOSPHINANE-3-CARBOXYLIC ACID

Example 124 is obtained starting from intermediate 111 in accordance with procedure D described hereinbefore.
$^1$H NMR: (400 MHz, D2O) δ ppm 8.16 (s, 1H), 7.91 (s, 1H), 7.68 (d, 1H), 7.49 (d, 1H), 4.51/4.32 (2*d, 2H), 3.64/3.35 (2*m, 2H), 3.48/3.11 (2*m, 2H), 2.89 (m, 2H), 2.25/1.77 (2*m, 2H), 1.91/1.55 (2*m, 2H), 1.55/1.45 (2*m, 2H), 1.19/1.05 (2*m, 2H)
ESI/FIA/HR and MS/MS: [M+H]+=381.1697 (381.1691)
Elemental analysis: C=53.27 (53.68); H=6.55 (6.62); N=14.52 (14.73)

Intermediate 112: tert-Butyl 3-{4-[bis(tert-butoxycarbonyl)amino]butyl}-4-ethoxy-4-oxo-1-[(2-thiophen-3-ylphenyl)methyl]-1,4-azaphosphinane-3-carboxylate Intermediate 112 is obtained starting from intermediates 21 and 259 in accordance with procedure F described hereinbefore.
$^1$H NMR: (400 MHz, dmso-d6) δ ppm 7.61 (dd, 1H), 7.59 (dd, 1H), 7.44/7.32 (2*m, 4H), 7.25 (dd, 1H), 3.95 (m, 2H), 3.6/3.4 (2*d, 2H), 3.3 (m, 2H), 2.8/2.29 (2*m, 2H), 2.8/2.4 (2*m, 2H), 2-1.79 (m, 2H), 2-1.79 (m, 2H), 1.7 (m, 2H), 1.4/1.34 (2*s, 27H), 1.35 (m, 2H), 1.19 (t, 3H)

EXAMPLE 125: 3-(4-AMINOBUTYL)-4-HYDROXY-4-OXO-1-[(2-THIOPHEN-3-YLPHENYL)-METHYL]-1,4-AZAPHOSPHINANE-3-CARBOXYLIC ACID

Example 125 is obtained starting from intermediate 112 in accordance with procedure D described hereinbefore.
$^1$H NMR: (400 MHz, D2O) δ ppm 7.63-7.43 (m, 2H), 7.63-7.43 (m, 4H), 7.19 (dd, 1H), 4.49/4.34 (2*d, 2H), 3.39/3.17 (2*m, 2H), 3.25/2.94 (2*m, 2H), 2.94 (m, 2H), 2.1/1.68 (2*m, 2H), 1.87/1.59 (2*m, 2H), 1.59/1.39 (2*m, 2H), 1.18/1.05 (2*m, 2H)
ESI/FIA/HR and MS/MS: [M+H]+=423.1504 (423.1507)
Elemental analysis: C=57.17 (56.86); H=6.48 (6.44); N=6.67 (6.63); S=7.11 (7.59)

Intermediate 113: tert-Butyl 3-{4-[bis(tert-butoxycarbonyl)amino]butyl}-4-ethoxy-1-[[2-(3-fluorophenyl)phenyl]methyl]-4-oxo-1,4-azaphosphinane-3-carboxylate Intermediate 113 is obtained starting from intermediate 21 and 2-(3-fluorophenyl)benzaldehyde in accordance with procedure F described hereinbefore.
$^1$H NMR: (400 MHz, dmso-d6) δ ppm 7.48 (m, 1H), 7.48 (m, 1H), 7.38 (m, 2H), 7.23 (m, 3H), 7.23 (m, 1H), 3.93 (m, 2H), 3.56/3.36 (2*d, 2H), 3.29 (m, 2H), 2.73/2.36 (m, 2H), 2.73/2.23 (m, 2H), 2-1.7 (m, 2H), 2-1.7 (m, 2H), 1.41 (s, 18H), 1.36 (m, 2H), 1.33 (s, 9H), 1.17 (t, 3H), 0.66 (m, 2H)

EXAMPLE 126: 3-(4-AMINOBUTYL)-1-[[2-(3-FLUOROPHENYL)PHENYL]METHYL]-4-HYDROXY-4-OXO-1,4-AZAPHOSPHINANE-3-CARBOXYLIC ACID

Example 126 is obtained starting from intermediate 113 in accordance with procedure D described hereinbefore.
$^1$H NMR: (400 MHz, D2O) δ ppm 7.62 (m, 1H), 7.54 (m, 2H), 7.5 (m, 1H), 7.41 (m, 1H), 7.21 (m, 1H), 7.16 (m, 1H), 7.14 (m, 1H), 4.44/4.31 (2*d, 2H), 3.43/3.11 (m, 2H), 3.21/2.86 (m, 2H), 2.94 (m, 2H), 2.11/1.64 (m, 2H), 1.86/1.36 (m, 2H), 1.59 (m, 2H), 1.09 (m, 2H)
ESI/FIA/HR and MS/MS: [M+H]+=435.1841 (435.1848)
Elemental analysis: C=61.58 (60.82); H=5.84 (6.50); N=6.51 (6.45)

Intermediate 114: tert-Butyl 3-{4-[bis(tert-butoxycarbonyl)amino]butyl}-4-ethoxy-4-oxo-1-[(5-phenyl-1,2-oxazol-4-yl)methyl]-1,4-azaphosphinane-3-carboxylate Intermediate 114 is obtained starting from intermediates 21 and 219 in accordance with procedure F described hereinbefore.
$^1$H NMR: (400 MHz, dmso-d6) δ ppm 8.6 (s, 1H), 7.9 (m, 2H), 7.55 (m, 3H), 4 (m, 2H), 3.6 (dd, 2H), 3.3 (m, 2H), 3/2.35 (2m, 2H), 2.8/2.5 (2dd, 2H), 2 (m, 2H), 1.8 (m, 2H), 1.4 (s, 18H), 1.35 (s, 9H), 1.35 (m, 2H), 1.2 (t, 3H), 0.8 (m, 2H)

EXAMPLE 127: 3-(4-AMINOBUTYL)-4-HYDROXY-4-OXO-1-[(5-PHENYL-1,2-OXAZOL-4-YL)METHYL]-1,4-AZAPHOSPHINANE-3-CARBOXYLIC ACID

Example 127 is obtained starting from intermediate 114 in accordance with procedure D described hereinbefore.

¹H NMR: (400 MHz, D2O) δ ppm 8.66 (s, 1H), 7.75-7.55 (m, 5H), 4.5 (dd, 2H), 3.6/3.28 (2m, 2H), 3.2/2.9 (dd, 2H), 2.85 (m, 2H), 2.2/1.7 (2m, 2H), 1.85/1.25 (2m, 2H), 1.5 (m, 2H), 0.9/0.7 (2m, 2H)
ESI/FIA/HR and MS/MS: [M+H]+=408.1661 (408.1688)

Intermediate 115: tert-Butyl 3-{4-[bis(tert-butoxycarbonyl)amino]butyl}-1-[(5-bromo-2-phenylphenyl)methyl]-4-ethoxy-4-oxo-1,4-azaphosphinane-3-carboxylate Intermediate 115 is obtained starting from intermediate 21 and 5-bromo-2-phenylbenzaldehyde in accordance with procedure F described hereinbefore.
¹H NMR: (400 MHz, dmso-d6) δ ppm 7.71 (df, 1H), 7.53 (dd, 1H), 7.45 (t, 2H), 7.4 (dd, 1H), 7.3 (d, 2H), 7.16 (t, 1H), 3.92 (m, 2H), 3.58/3.35 (2*d, 2H), 3.4 (m, 2H), 2.74/2.22 (2*m, 2H), 2.67/2.34 (2*m, 2H), 2-1.7 (m, 2H), 2-1.7 (m, 2H), 1.42 (m, 2H), 1.4/1.35 (2*s, 27H), 1.17 (t, 3H), 0.78 (m, 2H)

EXAMPLE 128: 3-(4-AMINOBUTYL)-1-[(5-BROMO-2-PHENYLPHENYL)METHYL]-4-HYDROXY-4-OXO-1,4-AZAPHOSPHINANE-3-CARBOXYLIC ACID

Example 128 is obtained starting from intermediate 115 in accordance with procedure D described hereinbefore.
¹H NMR: (400 MHz, D2O) δ ppm 7.81 (d, 1H), 7.7 (dd, 1H), 7.52 (t, 2H), 7.49 (t, 1H), 7.37 (d, 2H), 7.31 (d, 1H), 4.4/4.28 (2*d, 2H), 3.32/2.88 (2*m, 2H), 3.2/3.1 (2*m, 2H), 2.95 (m, 2H), 2.08/1.67 (2*m, 2H), 1.88/1.6 (2*m, 2H), 1.6/1.37 (2*m, 2H), 1.17/1.08 (2*m, 2H)
ESI/FIA/HR and MS/MS: [M+H]+=495.1041 (495.1048)
Elemental analysis: C=53.71 (53.34); H=5.72 (5.70); N=5.89 (5.66)

Intermediate 116: tert-Butyl 3-{4-[bis(tert-butoxycarbonyl)amino]butyl}-4-ethoxy-4-oxo-1-[[2-[4-(trifluoromethoxy)phenyl]phenyl]methyl]-1,4-azaphosphinane-3-carboxylate Intermediate 116 is obtained starting from intermediates 21 and 286 in accordance with procedure F described hereinbefore.
¹H NMR: (400 MHz, dmso-d6) δ ppm 7.65-7.33 (m, 4H), 7.65-7.33 (m, 3H), 7.25 (dd, 1H), 3.94 (m, 2H), 3.57/3.3 (2*d, 2H), 3.3 (m, 2H), 2.72/2.23 (2*m, 2H), 2.72/2.37 (2*m, 2H), 2-1.7 (m, 2H), 2-1.7 (m, 2H), 1.4/1.34 (2*s, 24H), 1.35 (m, 2H), 1.17 (t, 3H), 0.65 (m, 2H)

EXAMPLE 129: 3-(4-AMINOBUTYL)-4-HYDROXY-4-OXO-1-[[2-[4-(TRIFLUOROMETHOXY)-PHENYL]PHENYL]METHYL]-1,4-AZAPHOSPHINANE-3-CARBOXYLIC ACID

Example 129 is obtained starting from intermediate 116 in accordance with procedure D described hereinbefore.
¹H NMR: (400 MHz, D2O) δ ppm 7.62 (m, 1H), 7.54 (m, 2H), 7.44 (s, 4H), 7.4 (m, 1H), 4.42/4.28 (2*d, 2H), 3.4/3.12 (2*m, 2H), 3.2/2.88 (2*m, 2H), 2.94 (m, 2H), 2.1/1.64 (2*m, 2H), 1.86/1.59 (2*m, 2H), 1.59/1.38 (2*m, 2H), 1.15/1.05 (2*m, 2H)
ESI/FIA/HR and MS/MS: [M+H]+=501.1773 (501.1766)
Elemental analysis: C=55.71 (55.20); H=5.27 (5.64); N=5.62 (5.60)

Intermediate 117: tert-Butyl 3-{4-[bis(tert-butoxycarbonyl)amino]butyl}-4-ethoxy-1-[[4-fluoro-2-(4-fluorophenyl)phenyl]methyl]-4-oxo-1,4-azaphosphinane-3-carboxylate Intermediate 117 is obtained starting from intermediates 21 and 271 in accordance with procedure F described hereinbefore.
¹H NMR: (400 MHz, dmso-d6) δ ppm 7.49 (dd, 1H), 7.42 (dd, 2H), 7.29 (t, 2H), 7.21 (dt, 1H), 7.06 (dd, 1H), 3.93 (m, 2H), 3.49/3.3 (2*d, 2H), 3.3 (m, 2H), 2.72/2.21 (2*m, 2H), 2.69/2.34 (2*m, 2H), 1.95-1.7 (unresolved peak, 2H), 1.95-1.7 (unresolved peak, 2H), 1.68 (m, 2H), 1.41/1.33 (2*s, 27H), 1.38 (m, 2H), 1.18 (t, 3H)

EXAMPLE 130: 3-(4-AMINOBUTYL)-1-[[4-FLUORO-2-(4-FLUOROPHENYL)PHENYL]METHYL]-4-HYDROXY-4-OXO-1,4-AZAPHOSPHINANE-3-CARBOXYLIC ACID

Example 130 is obtained starting from intermediate 117 in accordance with procedure D described hereinbefore.
¹H NMR: (400 MHz, D2O) δ ppm 7.66 (dd, 1H), 7.38 (dd, 2H), 7.27 (t, 2H), 7.25 (df, 1H), 7.18 (dd, 1H), 4.39/4.28 (2*d, 2H), 3.38/3.09 (2*m, 2H), 3.18/2.87 (2*m, 2H), 2.95 (m, 2H), 2.09/1.68 (2*m, 2H), 1.86/1.6 (2*m, 2H), 1.6/1.37 (2*m, 2H), 1.15/1.07 (2*m, 2H)
ESI/FIA/HR and MS/MS: [M+H]+=453.1741 (453.1754)
Elemental analysis: C=58.67 (58.40); H=5.99 (6.01); N=6.46 (6.19)

Intermediate 118: tert-Butyl 3-{4-[bis(tert-butoxycarbonyl)amino]butyl}-1-[[2-[4-chloro-3-(trifluoromethyl)phenyl]phenyl]methyl]-4-ethoxy-4-oxo-1,4-azaphosphinane-3-carboxylate Intermediate 118 is obtained starting from intermediates 21 and 278 in accordance with procedure F described hereinbefore.
¹H NMR: (400 MHz, dmso-d6) δ ppm 7.9 (d, 1H), 7.81 (d, 1H), 7.75 (dd, 1H), 7.42/7.32 (2m, 3H), 3.95 (m, 2H), 3.41 (AB, 2H), 3.2 (m, 2H), 2.79/2.37 (2m, 2H), 2.69/2.27 (2m, 2H), 1.95/1.7 (2m, 2H), 1.8/1.7 (2m, 2H), 1.39 (s, 18H), 1.33 (s, 9H), 1.27 (m, 2H), 1.19 (t, 3H), 0.61/0.48 (2m, 2H)

EXAMPLE 131: 3-(4-AMINOBUTYL)-1-[[2-[4-CHLORO-3-(TRIFLUOROMETHYL)PHENYL]PHENYL]-METHYL]-4-HYDROXY-4-OXO-1,4-AZAPHOSPHINANE-3-CARBOXYLIC ACID

Example 131 is obtained starting from intermediate 118 in accordance with procedure D described hereinbefore.
¹H NMR: (300 MHz, D2O) δ ppm 7.76 (sl, 1H), 7.71 (d, 1H), 7.63 (m, 1H), 7.54 (dl, 1H), 7.54 (m, 2H), 7.38 (m, 1H), 4.31 (AB, 2H), 3.46/3.08 (2m, 2H), 3.13/2.83 (2m, 2H), 2.92 (m, 2H), 2.11/1.64 (2m, 2H), 1.83/1.34 (2m, 2H), 1.57 (m, 2H), 1.06 (m, 2H)
¹⁹F NMR: (300 MHz, D2O) δ ppm −62.3
ESI/FIA/HR and MS/MS: [M+H]+=519.1442 (519.1427)
Elemental analysis: C=53.40 (53.24); H=4.76 (5.24); N=5.43 (5.40)

Intermediate 119: tert-Butyl 3-{4-[bis(tert-butoxycarbonyl)amino]butyl}-1-[[2-(3-chlorophenyl)phenyl]methyl]-4-ethoxy-4-oxo-1,4-azaphosphinane-3-carboxylate Intermediate 119 is obtained starting from intermediates 21 and 213 in accordance with procedure F described hereinbefore.

¹H NMR: (400 MHz, dmso-d6) δ ppm 7.52 (t, 1H), 7.45 (m, 3H), 7.4/7.37 (2td, 2H), 7.33 (dt, 1H), 7.25 (dd, 1H), 3.94 (m, 2H), 3.53/3.32 (AB, 2H), 3.25 (m, 2H), 2.76/2.37 (2m, 2H), 2.7/2.25 (2m, 2H), 1.95/1.78 (2m, 2H), 1.82/1.75 (2m, 2H), 1.41 (s, 18H), 1.33 (s, 9H), 1.33 (m, 2H), 1.18 (t, 3H), 0.66/0.57 (2m, 2H)

EXAMPLE 132: 3-(4-AMINOBUTYL)-1-[[2-(3-CHLOROPHENYL)PHENYL]METHYL]-4-HYDROXY-4-OXO-1,4-AZAPHOSPHINANE-3-CARBOXYLIC ACID

Example 132 is obtained starting from intermediate 119 in accordance with procedure D described hereinbefore.

¹H NMR: (300 MHz, D2O) δ ppm 7.6 (m, 1H), 7.52 (m, 2H), 7.5-7.35 (m, 4H), 7.26 (m, 1H), 4.33 (AB, 2H), 3.41/3.09 (2m, 2H), 3.16/2.81 (2m, 2H), 2.92 (m, 2H), 2.09/1.64 (2m, 2H), 1.83/1.34 (2m, 2H), 1.56 (m, 2H), 1.05 (m, 2H)

ESI/FIA/HR and MS/MS: [M+H]+=451.1556 (451.1553)

Elemental analysis: C=58.91 (58.60); H=5.83 (6.26); N=6.32 (6.21)

Intermediate 120: tert-Butyl 3-{4-[bis(tert-butoxycarbonyl)amino]butyl}-4-ethoxy-1-[[2-(4-methylphenyl)phenyl]methyl]-4-oxo-1,4-azaphosphinane-3-carboxylate Intermediate 120 is obtained starting from intermediates 21 and 288 in accordance with procedure F described hereinbefore.

¹H NMR: (400 MHz, dmso-d6) δ ppm 7.49 (dd, 1H), 7.33 (2*m, 2H), 7.23 (2*d, 4H), 7.18 (dd, 1H), 3.92 (m, 2H), 3.54/3.35 (2*d, 2H), 3.3 (m, 2H), 2.74/2.2 (2*m, 2H), 2.74/2.32 (2*m, 2H), 2.36 (s, 3H), 1.95-1.75 (m, 2H), 1.95-1.75 (m, 2H), 1.41/1.33 (2*s, 27H), 1.38 (m, 2H), 1.17 (t, 3H), 0.71 (m, 2H)

EXAMPLE 133: 3-(4-AMINOBUTYL)-4-HYDROXY-1-[[2-(4-METHYLPHENYL)PHENYL]METHYL]-4-OXO-1,4-AZAPHOSPHINANE-3-CARBOXYLIC ACID

Example 133 is obtained starting from intermediate 120 in accordance with procedure D described hereinbefore.

¹H NMR: (400 MHz, D2O) δ ppm 7.6 (dd, 1H), 7.52/7.5 (2*m, 2H), 7.39 (dd, 1H), 7.35 (d, 2H), 7.25 (d, 2H), 4.43/4.28 (2*d, 2H), 3.36/3.1 (2*dd, 2H), 3.22/2.83 (2*dd, 2H), 2.94 (m, 2H), 2.38 (s, 3H), 2.09/1.64 (2*m, 2H), 1.86/1.6 (2*m, 2H), 1.6/1.35 (2*m, 2H), 1.15/1.05 (2*m, 2H)

ESI/FIA/HR and MS/MS: [M+H]+=431.2103 (431.2099)

Elemental analysis: C=64.12 (64.17); H=7.45 (7.26); N=6.50 (6.51)

Intermediate 121: tert-Butyl 3-{4-[bis(tert-butoxycarbonyl)amino]butyl}-1-[[2-(2,4-dichlorophenyl)phenyl]methyl]-4-ethoxy-4-oxo-1,4-azaphosphinane-3-carboxylate Intermediate 121 is obtained starting from intermediates 21 and 251 in accordance with procedure F described hereinbefore.

¹H NMR: (400 MHz, dmso-d6) δ ppm 7.73 (m, 1H), 7.51 (m, 1H), 7.51 (m, 1H), 7.42/7.35 (m, 2H), 7.31 (m, 1H), 7.12 (m, 1H), 3.92 (m, 2H), 3.5-3.2 (m, 2H), 3.5-3.2 (m, 2H), 2.68/2.12 (m, 2H), 2.68/2.35 (m, 2H), 1.81 (m, 2H), 1.81 (m, 2H), 1.42 (2*s, 18H), 1.38 (m, 2H), 1.35 (2*s, 9H), 1.17 (2*t, 3H), 0.74 (m, 2H)

EXAMPLE 134: 3-(4-AMINOBUTYL)-1-[[2-(2,4-DICHLOROPHENYL)PHENYL]METHYL]-4-HYDROXY-4-OXO-1,4-AZAPHOSPHINANE-3-CARBOXYLIC ACID

Example 134 is obtained starting from intermediate 121 in accordance with procedure D described hereinbefore.

¹H NMR: (400/500 MHz, D2O) δ ppm 7.7-7.63 (m, 2H), 7.6-7.5 (m, 2H), 7.46 (dd, 1H), 7.33 (m, 1H), 7.3/7.28 (2*d, 1H), 4.42/4.19/3.99 (m, 2H), 3.64/3.41/3.14 (m, 2H), 3.38/3.12/2.99/2.84 (m, 2H), 2.95 (m, 2H), 2.14/1.67 (m, 2H), 1.9/1.4 (m, 2H), 1.58 (m, 2H), 1.19/1.11 (m, 2H)

¹³C NMR: (400/500 MHz, D2O) δ ppm 132.1, 130.6, 129.5, 127.3, 57, 57, 51.8, 38.6, 27, 26.4, 24.5, 20

ESI/FIA/HR and MS/MS: [M+H]+=485.1166 (485.1163)

Elemental analysis: C=54.26 (54.44); H=5.33 (5.61); N=5.83 (5.77)

Intermediate 122: tert-Butyl 3-{4-[bis(tert-butoxycarbonyl)amino]butyl}-4-ethoxy-1-[[2-(2-methoxyphenyl)phenyl]methyl]-4-oxo-1,4-azaphosphinane-3-carboxylate Intermediate 122 is obtained starting from intermediates 21 and 282 in accordance with procedure F described hereinbefore.

¹H NMR: (300 MHz, dmso-d6) δ ppm 7.5 (d, 1H), 7.4-7.2 (m, 2H), 7.4-7.2 (m, 1H), 7.09 (m, 1H), 7.09 (m, 2H), 7.01 (t, 1H), 3.96 (m, 2H), 3.7 (s, 3H), 3.42 (m, 2H), 3.34 (dd, 2H), 2.73/2.23 (m, 2H), 2.73/2.46 (m, 2H), 2-1.7 (m, 2H), 2-1.7 (m, 2H), 1.47 (s, 18H), 1.42 (m, 2H), 1.4 (s, 9H), 1.21 (t, 3H), 0.96 (m, 2H)

EXAMPLE 135: 3-(4-AMINOBUTYL)-4-HYDROXY-1-[[2-(2-METHOXYPHENYL)PHENYL]METHYL]-4-OXO-1,4-AZAPHOSPHINANE-3-CARBOXYLIC ACID

Example 135 is obtained starting from intermediate 122 in accordance with procedure D described hereinbefore.

¹H NMR: (400 MHz, D2O) δ ppm 7.7-7.1 (m, 4H), 7.7-7.1 (m, 4H), 4.4-3.9 (m, 2H), 3.74 (s, 3H), 3.7-3 (m, 2H), 3.25-2.65 (m, 2H), 2.94 (m, 2H), 2.3-1.3 (m, 2H), 2.3-1.3 (m, 2H), 1.61 (m, 2H), 1.3-0.9 (m, 2H)

ESI/FIA/HR and MS/MS: [M+H]+=447.2031 (447.2048)

Elemental analysis: C=62.34 (61.87); H=6.65 (7.00); N=6.46 (6.27)

Intermediate 123: tert-Butyl 3-{4-[bis(tert-butoxy-carbonyl)amino]butyl}-4-ethoxy-1-[[2-(3-methoxyphenyl)phenyl]methyl]-4-oxo-1,4-azaphosphinane-3-carboxylate Intermediate 123 is obtained starting from intermediates 21 and 281 in accordance with procedure F described hereinbefore.
$^1$H NMR: (400 MHz, dmso-d6) δ ppm 7.49 (d, 1H), 7.35 (m, 2H), 7.35 (m, 1H), 7.21 (d, 1H), 6.95 (dd, 1H), 6.89 (d, 1H), 6.86 (sl, 1H), 3.93 (m, 2H), 3.79 (s, 3H), 3.55/3.37 (2*d, 2H), 3.29 (m, 2H), 2.74/2.21 (m, 2H), 2.74/2.33 (m, 2H), 2-1.7 (m, 2H), 2-1.7 (m, 2H), 1.41 (s, 18H), 1.37 (m, 2H), 1.33 (s, 9H), 1.17 (t, 3H), 0.68 (m, 2H)

EXAMPLE 136: 3-(4-AMINOBUTYL)-4-HYDROXY-1-[[2-(3-METHOXYPHENYL)PHENYL]-METHYL]-4-OXO-1,4-AZAPHOSPHINANE-3-CARBOXYLIC ACID

Example 136 is obtained starting from intermediate 123 in accordance with procedure D described hereinbefore.
$^1$H NMR: (400 MHz, D2O) δ ppm 7.6 (m, 1H), 7.53 (m, 2H), 7.46 (t, 1H), 7.4 (m, 1H), 7.07 (dd, 1H), 6.95 (m, 2H), 4.43/4.28 (2*d, 2H), 3.84 (s, 3H), 3.38/3.1 (m, 2H), 3.2/2.85 (m, 2H), 2.94 (m, 2H), 2.1/1.64 (m, 2H), 1.86/1.36 (m, 2H), 1.59 (m, 2H), 1.13/1.06 (m, 2H)
ESI/FIA/HR and MS/MS: [M+H]+=447.2064 (447.2048)
Elemental analysis: C=61.90 (61.87); H=6.25 (7.00); N=6.35 (6.27)

Intermediate 124: tert-Butyl 3-{4-[bis(tert-butoxy-carbonyl)amino]butyl}-4-ethoxy-4-oxo-1-[[2-(4-propan-2-ylphenyl)phenyl]methyl]-1,4-azaphosphinane-3-carboxylate Intermediate 124 is obtained starting from intermediates 21 and 289 in accordance with procedure F described hereinbefore.
$^1$H NMR: (400 MHz, dmso-d6) δ ppm 7.49 (dd, 1H), 7.33 (2*m, 2H), 7.31 (d, 2H), 7.27 (d, 2H), 7.21 (dd, 1H), 3.93 (m, 2H), 3.6/3.35 (2*d, 2H), 3.33 (m, 2H), 2.95 (hept., 1H), 2.73/2.23 (2*m, 2H), 2.73/2.34 (2*m, 2H), 1.9-1.75 (m, 2H), 1.9-1.75 (m, 2H), 1.41/1.32 (2*s, 27H), 1.38 (m, 2H), 1.25 (d, 6H), 1.18 (t, 3H), 0.7 (m, 2H)

EXAMPLE 137: 3-(4-AMINOBUTYL)-4-HYDROXY-4-OXO-1-[[2-(4-PROPAN-2-YLPHENYL)-PHENYL]METHYL]-1,4-AZAPHOSPHINANE-3-CARBOXYLIC ACID

Example 137 is obtained starting from intermediate 124 in accordance with procedure D described hereinbefore.
$^1$H NMR: (400 MHz, D2O) δ ppm 7.61 (dd, 1H), 7.52 (2*t, 2H), 7.43 (d, 2H), 7.38 (dd, 1H), 7.29 (d, 2H), 4.42/4.24 (2*d, 2H), 3.35/3.11 (2*m, 2H), 3.22/2.83 (2*m, 2H), 2.97 (m, 1H), 2.95 (m, 2H), 2.09/1.67 (2*m, 2H), 1.85/1.6 (2*m, 2H), 1.6/1.35 (2*m, 2H), 1.24 (d, 6H), 1.15/1.05 (2*m, 2H)
ESI/FIA/HR and MS/MS: [M+H]+=459.2418 (459.2412)
Elemental analysis: C=65.54 (65.49); H=7.39 (7.69); N=6.12 (6.11)

Intermediate 125: tert-Butyl 3-{4-[bis(tert-butoxy-carbonyl)amino]butyl}-4-ethoxy-1-(1H-indazol-4-ylmethyl)-4-oxo-1,4-azaphosphinane-3-carboxylate Intermediate 125 is obtained starting from intermediate 21 and 1H-indazole-4-carbaldehyde in accordance with procedure F described hereinbefore.
$^1$H NMR: (400 MHz, dmso-d6) δ ppm 13.01 (s, 1H), 8.19 (s, 1H), 7.44 (d, 1H), 7.27 (dd, 1H), 6.99 (d, 1H), 3.98 (m, 2H), 3.93/3.71 (2*d, 2H), 3.29/3.16 (m, 2H), 3.03/2.37 (m, 2H), 2.83/2.52 (m, 2H), 2-1.7 (m, 2H), 2-1.7 (m, 2H), 1.38 (s, 18H), 1.33 (s, 9H), 1.24/1.1 (m, 2H), 1.21 (t, 3H), 0.65/0.51 (m, 2H)

EXAMPLE 138: 3-(4-AMINOBUTYL)-4-HYDROXY-1-(1H-INDAZOL-4-YLMETHYL)-4-OXO-1,4-AZAPHOSPHINANE-3-CARBOXYLIC ACID

Example 138 is obtained starting from intermediate 125 in accordance with procedure D described hereinbefore.
$^1$H NMR: (300 MHz, D2O) δ ppm 8.29 (s, 1H), 7.71 (dl, 1H), 7.49 (dd, 1H), 7.3 (dl, 1H), 4.65 (AB, 2H), 3.71/3.39 (2m, 2H), 3.56/3.21 (2m, 2H), 2.87 (m, 2H), 2.19/1.74 (2m, 2H), 1.91/1.45 (2m, 2H), 1.54 (quint., 2H), 1.08 (m, 2H)
ESI/FIA/HR and MS/MS: [M+H]+=381.1707 (381.1691)
Elemental analysis: C=53.52 (53.68); H=6.73 (6.62); N=14.77 (14.73)

Intermediate 126: tert-Butyl 3-{4-[bis(tert-butoxy-carbonyl)amino]butyl}-1-[[3-(4-chlorophenyl)pyridin-4-yl]methyl]-4-ethoxy-4-oxo-1,4-azaphosphinane-3-carboxylate Intermediate 126 is obtained starting from intermediate 21 and 3-(4-chlorophenyl)pyridine-4-carbaldehyde in accordance with procedure F described hereinbefore.
$^1$H NMR: (400 MHz, dmso-d6) δ ppm 8.57 (d, 1H), 8.42 (s, 1H), 7.56 (d, 2H), 7.54 (d, 1H), 7.44 (d, 2H), 3.94 (m, 2H), 3.53 (AB, 2H), 3.36 (m, 2H), 2.7/2.45 (2m, 2H), 2.7/2.26 (2m, 2H), 1.89 (m, 4H), 1.41 (s, 18H), 1.41 (m, 2H), 1.35 (s, 9H), 1.17 (t, 3H), 0.78 (m, 2H)

EXAMPLE 139: 3-(4-AMINOBUTYL)-1-[[3-(4-CHLOROPHENYL)PYRIDIN-4-YL]METHYL]-4-HYDROXY-4-OXO-1,4-AZAPHOSPHINANE-3-CARBOXYLIC ACID

Example 139 is obtained starting from intermediate 126 in accordance with procedure D described hereinbefore.
$^1$H NMR: (400 MHz, D2O) δ ppm 8.62 (d, 1H), 8.54 (s, 1H), 7.67 (d, 1H), 7.58 (d, 2H), 7.38 (d, 2H), 4.46/4.35 (2*d, 2H), 3.47/3.12 (2*m, 2H), 3.17/2.95 (2*m, 2H), 2.95 (m, 2H), 2.15/1.68 (2*m, 2H), 1.87/1.61 (2*m, 2H), 1.59/1.38 (2*m, 2H), 1.08 (m, 2H)
$^{31}$P NMR: (400 MHz, D2O) δ ppm 25.1
$^{13}$C NMR: (400 MHz, D2O) δ ppm 147.4, 146.1, 128.3, 126.4, 122.2, 55, 53.2, 49.9, 36, 24.3, 23.9, 22.1, 17.3
ESI/FIA/HR and MS/MS: [M+H]+=452.1516 (452.1505)
Elemental analysis: C=55.97 (55.82); H=5.86 (6.02); N=9.28 (9.30)

Intermediate 127: tert-Butyl 3-{4-[bis(tert-butoxy-carbonyl)amino]butyl}-4-ethoxy-4-oxo-1-[(3-phenyl-1-benzothiophen-2-yl)methyl]-1,4-azaphosphinane-3-carboxylate Intermediate 127 is obtained starting from intermediates 21 and 283 in accordance with procedure F described hereinbefore.
$^1$H NMR: (400 MHz, dmso-d6) δ ppm 7.95 (m, 1H), 7.55 (t, 2H), 7.47 (t, 1H), 7.45-7.3 (m, 3H), 7.45-7.3 (m, 2H), 4.05 (m, 2H), 3.81 (dd, 2H), 3.42/3.33 (m, 2H), 2.88/2.53

(m, 2H), 2.88/2.7 (m, 2H), 2-1.7 (m, 2H), 2-1.7 (m, 2H), 1.49 (m, 2H), 1.39 (s, 27H), 1.23 (t, 3H), 1.14/1.02 (m, 2H)

EXAMPLE 140: 3-(4-AMINOBUTYL)-4-HYDROXY-4-OXO-1-[(3-PHENYL-1-BENZOTHIOPHEN-2-YL)METHYL]-1,4-AZAPHOSPHINANE-3-CARBOXYLIC ACID

Example 140 is obtained starting from intermediate 127 in accordance with procedure D described hereinbefore.
$^1$H NMR: (400 MHz, D2O) δ ppm 7.97 (d, 1H), 7.56 (m, 3H), 7.49 (d, 1H), 7.45 (t, 1H), 7.35 (m, 1H), 7.35 (m, 2H), 4.6/4.51 (dd, 2H), 3.55/3.18 (m, 2H), 3.26/2.9 (m, 2H), 2.9 (m, 2H), 2.18/1.68 (m, 2H), 1.86/1.34 (m, 2H), 1.56 (m, 2H), 1.04 (m, 2H)
ESI/FIA/HR and MS/MS: [M+H]+=473.1669 (473.1663)
Elemental analysis: C=61.52 (61.00); H=5.76 (6.19); N=5.51 (5.93); S=6.56 (6.79)

EXAMPLE 141: 3-(4-AMINOBUTYL)-4-HYDROXY-4-OXO-1-[(3-PHENYLPHENYL)METHYL]-1,4-AZAPHOSPHINANE-3-CARBOXYLIC ACID

Example 141 is obtained starting from intermediate 21 and 3-phenylbenzaldehyde in accordance with procedures F and D described hereinbefore.
$^1$H NMR: (400 MHz, D2O) δ ppm 7.79-7.4 (m, 9H), 4.49 (m, 1H), 4.29 (d, 1H), 3.76 (m, 1H), 3.51 (dd, 1H), 3.39 (m, 1H), 3.13 (dd, 1H), 2.89 (m, 2H), 2.27 (m, 1H), 1.92 (m, 1H), 1.79 (m, 1H), 1.58 (unresolved peak, 2H), 1.48 (m, 1H), 1.21 (m, 1H), 1.09 (m, 1H)
ESI/FIA/HR and MS/MS: [M+H]+=417.1937 (417.1943)
Elemental analysis: C=64.07 (63.45); H=6.72 (7.02); N=6.86 (6.73)

EXAMPLE 142: 3-(4-AMINOBUTYL)-4-HYDROXY-4-OXO-1-(4-PHENYLBUTYL)-1,4-AZAPHOSPHINANE-3-CARBOXYLIC ACID

Example 142 is obtained starting from intermediate 21 and 4-phenylbutanal in accordance with procedures F and D described hereinbefore.
$^1$H NMR: (400 MHz, D2O) δ ppm 7.29 (t, 2H), 7.21 (d, 2H), 7.19 (t, 1H), 3.5 (m, 1H), 3.41 (dd, 1H), 3.2 (m, 1H), 3.07 (m, 2H), 3 (m, 1H), 2.92 (m, 2H), 2.61 (m, 2H), 2.19 (m, 1H), 1.9 (m, 1H), 1.75-1.1 (m, 10H)
ESI/FIA/HR and MS/MS: [M+H]+=383.2092 (383.2099)
Elemental analysis: C=59.51 (59.67); H=8.12 (8.17); N=7.34 (7.33)

EXAMPLE 143: 3-(4-AMINOBUTYL)-4-HYDROXY-4-OXO-1-(5-PHENYLPENTYL)-1,4-AZAPHOSPHINANE-3-CARBOXYLIC ACID

Example 143 is obtained starting from intermediate 21 and 5-phenylpentanal in accordance with procedures F and D described hereinbefore.
$^1$H NMR: (400 MHz, D2O) δ ppm 7.33 (t, 2H), 7.26 (d, 1H), 7.21 (t, 1H), 3.6 (m, 1H), 3.52 (dd, 1H), 3.28 (m, 1H), 3.1 (m, 3H), 2.99 (m, 2H), 2.62 (t, 2H), 2.22 (m, 1H), 1.98 (m, 1H), 1.8-1.6 (unresolved peak, 2H), 1.8-1.15 (m, 10H)
ESI/FIA/HR and MS/MS: [M+H]+=397.2251 (397.2256)
Elemental analysis: C=61.01 (60.59); H=7.98 (8.39); N=7.12 (7.07)

EXAMPLE 145: 3-(4-AMINOBUTYL)-4-HYDROXY-1-[(4-METHYLSULPHANYLPHENYL)METHYL]-4-OXO-1,4-AZAPHOSPHINANE-3-CARBOXYLIC ACID

Example 145 is obtained starting from intermediate 21 and 4-formylthioanisole in accordance with procedures F and D described hereinbefore.
$^1$H NMR: (400 MHz, D2O) δ ppm 7.41/7.37 (2*d, 4H), 4.38/4.17 (2*d, 2H), 3.7/3.31 (2*m, 2H), 3.45/3.09 (2*m, 2H), 2.92 (m, 2H), 2.49 (s, 3H), 2.22/1.78 (2*m, 2H), 1.92/1.59 (2*m, 2H), 1.58/1.47 (2*m, 2H), 1.22/1.1 (2*m, 2H)
$^{31}$P NMR: (400 MHz, D2O) δ ppm 25.9
ESI/FIA/HR and MS/MS: [M+H]+=387.1512 (387.1507)
Elemental analysis: C=52.52 (52.84); H=6.70 (7.04); N=7.35 (7.25); S=8.34 (8.30)

EXAMPLE 146: 3-(4-AMINOBUTYL)-1-[(3-CARBOXYPHENYL)METHYL]-4-HYDROXY-4-OXO-1,4-AZAPHOSPHINANE-3-CARBOXYLIC ACID

Example 146 is obtained starting from intermediate 21 and methyl 3-formylbenzoate in accordance with procedures F and D described hereinbefore.
$^1$H NMR: (400 MHz, D2O) δ ppm 8.03 (2*m, 2H), 7.7 (d, 1H), 7.59 (t, 1H), 4.52/4.3 (2*d, 2H), 3.75/3.4 (2*m, 2H), 3.4/3.12 (2*m, 2H), 2.9 (m, 2H), 2.25/1.81 (2*m, 2H), 1.95/1.58 (2*m, 2H), 1.62-1.43 (unresolved peak, 2H), 1.2/1.1 (2*m, 2H)
$^{31}$P NMR: (400 MHz, D2O) δ ppm 25
ESI/FIA/HR and MS/MS: [M+H]+=385.1522 (385.1528)
Elemental analysis: C=53.60 (53.12); H=6.54 (6.56); N=7.42 (7.29)

EXAMPLE 147: 3-(4-AMINOBUTYL)-1-[(4-CARBOXYPHENYL)METHYL]-4-HYDROXY-4-OXO-1,4-AZAPHOSPHINANE-3-CARBOXYLIC ACID

Example 147 is obtained starting from intermediate 21 and methyl 4-formylbenzoate in accordance with procedures F and D described hereinbefore.
$^1$H NMR: (400 MHz, D2O) δ ppm 8 (d, 2H), 7.6 (d, 2H), 4.52/4.3 (2*d, 2H), 3.75/3.4 (2*m, 2H), 3.45/3.13 (dd, 2H), 2.9 (m, 2H), 2.28/1.8 (2*m, 2H), 1.9/1.55 (2*m, 2H), 1.55/1.5 (m, 2H), 1.2/1.1 (m, 2H)
ESI/FIA/HR and MS/MS: [M+H]+=385.1524 (385.1528)
Elemental analysis: C=52.66 (53.12); H=6.04 (6.56); N=7.33 (7.29)

EXAMPLE 148: 3-(4-AMINOBUTYL)-1-[[4-(DIFLUOROMETHOXY)PHENYL]METHYL]-4-HYDROXY-4-OXO-1,4-AZAPHOSPHINANE-3-CARBOXYLIC ACID

Example 148 is obtained starting from intermediate 21 and 4-(difluoromethoxy)benzaldehyde in accordance with procedures F and D described hereinbefore.
$^1$H NMR: (400 MHz, D2O) δ ppm 7.5 (d, 2H), 7.25 (d, 2H), 6.83 (t, 1H), 4.4/4.22 (2*d, 2H), 3.7/3.32 (dd, 2H), 3.45/3.1 (dd, 2H), 2.92 (m, 2H), 2.25/1.78 (2*m, 2H), 1.9/1.6 (2*m, 2H), 1.6/1.46 (2*m, 2H), 1.22/1.1 (2*m, 2H)
ESI/FIA/HR and MS/MS: [M+H]+=407.1551 (407.1547)
Elemental analysis: C=50.33 (50.25); H=5.97 (6.20); N=7.02 (6.89)

EXAMPLE 149: 3-(4-AMINOBUTYL)-4-HYDROXY-4-OXO-1-[(1S)-1-PHENYLETHYL]-1,4-AZAPHOSPHINANE-3-CARBOXYLIC ACID

Example 149 is obtained starting from intermediate 21 and acetophenone in accordance with procedures F and D described hereinbefore.

$^1$H NMR: (400 MHz, D2O) δ ppm 7.5 (m, 5H), 4.67 (quad., 1H), 3.72/3.53 (2*m, 1H), 3.62/3.41 (2*m, 1H), 3.29/3.13 (2*m, 1H), 3.09-2.9 (m, 1H), 3.09-2.9 (m, 2H), 2.28/2.11 (2*m, 1H), 2-1.65 (m, 1H), 2-1.65 (m, 2H), 1.7 (2*d, 3H), 1.7-1.05 (m, 2H), 1.7-1.05 (m, 2H)

$^{31}$P NMR: (400 MHz, D2O) δ ppm 26.4/26.2

ESI/FIA/HR and MS/MS: [M+H]+=355.1807 (355.1781)

Elemental analysis: C=57.43 (57.62); H=7.57 (7.68); N=7.96 (7.90)

EXAMPLE 150: 3-(4-AMINOBUTYL)-1-[(3,4-DIFLUOROPHENYL)METHYL]-4-HYDROXY-4-OXO-1,4-AZAPHOSPHINANE-3-CARBOXYLIC ACID

Example 150 is obtained starting from intermediate 21 and 3,4-difluorobenzaldehyde in accordance with procedures F and D described hereinbefore.

$^1$H NMR: (300 MHz, D2O) δ ppm 7.46-7.22 (m, 3H), 4.28 (AB, 2H), 3.69/3.42 (2m, 2H), 3.34/3.1 (m+dd, 2H), 2.92 (m, 2H), 2.23/1.77 (2m, 2H), 1.92/1.46 (2m, 2H), 1.59 (quint., 2H), 1.22/1.09 (2m, 2H)

$^{19}$F NMR: (300 MHz, D2O) δ ppm −135.5

$^{31}$P NMR: (300 MHz, D2O) δ ppm 23

ESI/FIA/HR and MS/MS: [M+H]+=377.1416 (377.1441)

Elemental analysis: C=50.40 (51.06); H=6.20 (6.16); N=7.38 (7.44)

EXAMPLE 151: 3-(4-AMINOBUTYL)-1-[[3-[(DIMETHYLAMINO)METHYL]-4-HYDROXYPHENYL]-METHYL]-4-HYDROXY-4-OXO-1,4-AZAPHOSPHINANE-3-CARBOXYLIC ACID

Example 151 is obtained starting from intermediate 21 and 3-(dimethylaminomethyl)-4-hydroxy-benzaldehyde in accordance with procedures F and D described hereinbefore.

$^1$H NMR: (400 MHz, D2O) δ ppm 7.45 (d, 1H), 7.43 (s, 1H), 7.02 (d, 1H), 4.35/4.18 (2*d, 2H), 4.32/4.28 (2*d, 2H), 3.7/3.3 (2*m, 2H), 3.44/3.08 (dd, 2H), 2.9 (m, 2H), 2.8 (d, 6H), 2.2/1.75 (2*m, 2H), 1.9/1.45 (2*m, 2H), 1.6 (m, 2H), 1.25/1.1 (2*m, 2H)

ESI/FIA/HR and MS/MS: [M+H]+=414.2155 (414.2157)

Elemental analysis: C=46.97 (47.82); H=5.90 (6.31); N=7.67 (7.97)

EXAMPLE 152: 3-(4-AMINOBUTYL)-1-[(2-FLUOROPHENYL)METHYL]-4-HYDROXY-4-OXO-1,4-AZAPHOSPHINANE-3-CARBOXYLIC ACID

Example 152 is obtained starting from intermediate 21 and 2-fluorobenzaldehyde in accordance with procedures F and D described hereinbefore.

$^1$H NMR: (300 MHz, D2O) δ ppm 7.5 (m, 2H), 7.26 (m, 2H), 4.41 (sl, 2H), 3.7/3.35 (2m, 2H), 3.52/3.21 (2m, 2H), 2.94 (m, 2H), 2.22/1.77 (2m, 2H), 1.95/1.49 (2m, 2H), 1.61 (quint., 2H), 1.28/1.14 (2m, 2H)

$^{19}$F NMR: (300 MHz, D2O) δ ppm −115

$^{31}$P NMR: (300 MHz, D2O) δ ppm 25.6

ESI/FIA/HR and MS/MS: [M+H]+=359.1530 (359.1535)

Elemental analysis: C=53.34 (53.63); H=6.46 (6.75); N=7.77 (7.82)

EXAMPLE 153: 3-(4-AMINOBUTYL)-1-[(3-FLUOROPHENYL)METHYL]-4-HYDROXY-4-OXO-1,4-AZAPHOSPHINANE-3-CARBOXYLIC ACID

Example 153 is obtained starting from intermediate 21 and 3-fluorobenzaldehyde in accordance with procedures F and D described hereinbefore.

$^1$H NMR: (300 MHz, D2O) δ ppm 7.48 (m, 1H), 7.24 (m, 3H), 4.31 (AB, 2H), 3.71/3.35 (2m, 2H), 3.45/3.12 (2m, 2H), 2.92 (m, 2H), 2.24/1.77 (2m, 2H), 1.93/1.46 (2m, 2H), 1.58 (quint., 2H), 1.22/1.1 (2m, 2H)

$^{19}$F NMR: (300 MHz, D2O) δ ppm −112

$^{31}$P NMR: (300 MHz, D2O) δ ppm 22.9

ESI/FIA/HR and MS/MS: [M+H]+=359.1536 (359.1535)

Elemental analysis: C=53.15 (53.63); H=6.41 (6.75); N=7.83 (7.82)

EXAMPLE 154: 3-(4-AMINOBUTYL)-1-[(6-AMINOPYRIDIN-3-YL)METHYL]-4-HYDROXY-4-OXO-1,4-AZAPHOSPHINANE-3-CARBOXYLIC ACID

Example 154 is obtained starting from intermediate 21 and 2-(Boc-amino)pyridine-5-carboxaldehyde in accordance with procedures F and D described hereinbefore.

$^1$H NMR: (400 MHz, D2O) δ ppm 7.97 (d, 1H), 7.61 (dd, 1H), 6.71 (d, 1H), 4.18 (AB, 2H), 3.67/3.29 (2m, 2H), 3.42/3.05 (2m, 2H), 2.93 (m, 2H), 2.22/1.77 (2m, 2H), 1.93/1.47 (2m, 2H), 1.59 (quint., 2H), 1.25/1.11 (2m, 2H)

$^{31}$P NMR: (400 MHz, D2O) δ ppm 23.2

ESI/FIA/HR and MS/MS: [M+H]+=357.1696 (357.1691)

Elemental analysis: C=51.09 (50.56); H=6.51 (7.07); N=15.78 (15.72)

EXAMPLE 155: 3-(4-AMINOBUTYL)-4-HYDROXY-4-OXO-1-[(2-PHENOXYPHENYL)-METHYL]-1,4-AZAPHOSPHINANE-3-CARBOXYLIC ACID

Example 155 is obtained starting from intermediate 21 and 2-phenoxybenzaldehyde in accordance with procedures F and D described hereinbefore.

$^1$H NMR: (300 MHz, D2O) δ ppm 7.47 (t, 1H), 7.41 (t, 2H), 7.27-7.09 (m, 4H), 7.05 (d, 2H), 4.27 (AB, 2H), 3.68/3.3 (2m, 2H), 3.46/3.07 (2m, 2H), 2.91 (m, 2H), 2.23/1.76 (2m, 2H), 1.93/1.46 (2m, 2H), 1.6 (quint., 2H), 1.15 (m, 2H)

$^{31}$P NMR: (300 MHz, D2O) δ ppm 25.8

ESI/FIA/HR and MS/MS: [M+H]+=433.1894 (433.1892)

Elemental analysis: C=61.51 (61.10); H=6.57 (6.76); N=6.61 (6.48)

EXAMPLE 156: 3-(4-AMINOBUTYL)-1-[[2-(4-CHLOROPHENYL)PHENYL]METHYL]-4-HYDROXY-4-OXO-1,4-AZAPHOSPHINANE-3-CARBOXYLIC ACID

Example 156 is obtained starting from intermediate 21 and 2-(4-chlorophenyl)benzaldehyde in accordance with procedures F and D described hereinbefore.

$^1$H NMR: (300 MHz, D2O) δ ppm 7.6/7.52/7.4 (m, 3H), 7.52/7.34 (2d, 4H), 4.35 (AB, 2H), 3.4/3.1 (2m, 2H), 3.17/

2.86 (2m, 2H), 2.94 (m, 2H), 2.09/1.64 (2m, 2H), 1.85/1.35 (2m, 2H), 1.58 (m, 2H), 1.08 (m, 2H)
ESI/FIA/HR and MS/MS: [M+H]+=451.1559 (451.1553)
Elemental analysis: C=58.24 (58.60); H=5.82 (6.26); N=6.48 (6.21)

EXAMPLE 157: 3-(4-AMINOBUTYL)-1-[(2-BROMOPHENYL)METHYL]-4-HYDROXY-4-OXO-1,4-AZAPHOSPHINANE-3-CARBOXYLIC ACID

Example 157 is obtained starting from intermediate 21 and 2-bromobenzaldehyde in accordance with procedures F and D described hereinbefore.
$^1$H NMR: (300 MHz, D2O) δ ppm 7.75 (dl, 1H), 7.53 (dd, 1H), 7.45 (tl, 1H), 7.39 (td, 1H), 4.44 (AB, 2H), 3.74/3.43 (2m, 2H), 3.5/3.28 (2m, 2H), 2.94 (m, 2H), 2.24/1.79 (2m, 2H), 1.95/1.5 (2m, 2H), 1.6 (m, 2H), 1.26/1.1 (2m, 2H)
ESI/FIA/HR and MS/MS: [M+H]+=419.0732 (419.0735)
Elemental analysis: C=45.33 (45.84); H=5.29 (5.77); N=7.00 (6.68)

EXAMPLE 159: 3-(4-AMINOBUTYL)-4-HYDROXY-4-OXO-1-[(2-OXO-1,3-DIHYDROINDOL-5-YL)METHYL]-1,4-AZAPHOSPHINANE-3-CARBOXYLIC ACID

Example 159 is obtained starting from intermediate 21 and oxindole-5-carboxaldehyde in accordance with procedures F and D described hereinbefore.
$^1$H NMR: (300 MHz, D2O) δ ppm 7.35 (d, 1H), 7.3 (dd, 1H), 7 (d, 1H), 4.35/4.15 (dd, 2H), 3.7/3.3 (2m, 2H), 3.6 (dd, 2H), 3.4/3.1 (2dd, 2H), 2.9 (m, 2H), 2.2/1.75 (2m, 2H), 1.9/1.45 (2m, 2H), 1.58 (m, 2H), 1.3-1 (2m, 2H)
ESI/FIA/HR and MS/MS: [M+H]+=396.1692 (396.1688)
Elemental analysis: C=54.70 (54.68); H=6.42 (6.63); N=10.57 (10.63)

EXAMPLE 160: 3-(4-AMINOBUTYL)-4-HYDROXY-1-[[2-(3-METHYL-1,2,4-OXADIAZOL-5-YL)PHENYL]METHYL]-4-OXO-1,4-AZAPHOSPHINANE-3-CARBOXYLIC ACID

Example 160 is obtained starting from intermediate 21 and 2-(3-methyl-1,2,4-oxadiazol-5-yl)benzaldehyde in accordance with procedures F and D described hereinbefore.
$^1$H NMR: (400 MHz, D2O) δ ppm 8.26 (d, 1H), 7.72 (m, 2H), 7.65 (d, 1H), 4.78/4.36 (2*d, 2H), 4/3.55 (m, 2H), 3.44/3.25 (m, 2H), 2.91 (m, 2H), 2.5 (s, 3H), 2.31/1.88 (m, 2H), 1.88/1.49 (m, 2H), 1.58 (m, 2H), 1.22/1.02 (m, 2H)
ESI/FIA/HR and MS/MS: [M+H]+=423.1801 (423.1797)
Elemental analysis: C=53.57 (54.02); H=6.25 (6.44); N=12.77 (13.26)

EXAMPLE 161: 3-(4-AMINOBUTYL)-4-HYDROXY-1-[[2-[2-METHYL-5-(TRIFLUOROMETHYL)-PYRAZOL-3-YL]PHENYL]METHYL]-4-OXO-1,4-AZAPHOSPHINANE-3-CARBOXYLIC ACID

Example 156 is obtained starting from intermediate 21 and 2-[1-methyl-3(trifluoromethyl)-1H-pyrazol-5-yl]benzaldehyde in accordance with procedures F and D described hereinbefore.
$^1$H NMR: (400 MHz, D2O) δ ppm 7.71 (d, 1H), 7.67 (t, 1H), 7.63 (t, 1H), 7.48 (d, 1H), 6.83 (s, 1H), 4.3/4.18 (dl, 2H), 3.53/3.21 (m, 2H), 3.27 (s, 3H), 3.27/3.03 (m, 2H), 2.94 (m, 2H), 2.18/1.71 (m, 2H), 2.18/1.43 (m, 2H), 1.6 (m, 2H), 1.18/1.1 (m, 2H)
ESI/FIA/HR and MS/MS: [M+H]+=489.1903 (489.1878)
Elemental analysis: C=51.66 (51.64); H=5.61 (5.78); N=11.25 (11.47)

EXAMPLE 162: 3-(4-AMINOBUTYL)-1-[[2-(2,4-DIFLUOROPHENYL)PHENYL]METHYL]-4-HYDROXY-4-OXO-1,4-AZAPHOSPHINANE-3-CARBOXYLIC ACID

Example 162 is obtained starting from intermediates 21 and 287 in accordance with procedures F and D described hereinbefore.
$^1$H NMR: (400 MHz, D2O) δ ppm 7.65 (m, 1H), 7.57 (m, 2H), 7.4 (m, 1H), 7.34 (m, 1H), 7.1 (2*m, 2H), 4.45-4 (m, 2H), 3.7-2.8 (m, 2H), 3.7-2.8 (m, 2H), 2.93 (m, 2H), 2.15/1.66 (2*m, 2H), 1.88/1.6 (2*m, 2H), 1.6/1.38 (2*m, 2H), 1.15/1.05 (2*m, 2H)
ESI/FIA/HR and MS/MS: [M+H]+=453.1745 (453.1754)
Elemental analysis: C=58.27 (58.40); H=6.09 (6.01); N=6.17 (6.19)

EXAMPLE 163: 3-(4-AMINOBUTYL)-1-[[2-FLUORO-6-(4-HYDROXYPHENYL)PHENYL]-METHYL]-4-HYDROXY-4-OXO-1,4-AZAPHOSPHINANE-3-CARBOXYLIC ACID

Example 163 is obtained starting from intermediate 21 and 2-fluoro-6-(4-hydroxyphenyl)benzaldehyde in accordance with procedures F and D described hereinbefore.
$^1$H NMR: (400 MHz, D2O) δ ppm 7.52 (m, 1H), 7.27 (m, 1H), 7.22 (d, 2H), 7.19 (m, 1H), 6.98 (d, 2H), 4.41 (dd, 2H), 3.45/3.09 (m, 2H), 3.16/2.9 (m, 2H), 2.94 (m, 2H), 2.09/1.64 (m, 2H), 1.86/1.35 (m, 2H), 1.59 (m, 2H), 1.08 (m, 2H)
ESI/FIA/HR and MS/MS: [M+H]+=451.1813 (451.1798)
Elemental analysis: C=58.33 (58.66); H=5.35 (6.27); N=6.49 (6.22)

EXAMPLE 164: 3-(4-AMINOBUTYL)-1-[[2-(1,3-BENZODIOXOL-5-YL)PHENYL]METHYL]-4-HYDROXY-4-OXO-1,4-AZAPHOSPHINANE-3-CARBOXYLIC ACID

Example 164 is obtained starting from intermediates 21 and 279 in accordance with procedures F and D described hereinbefore.
$^1$H NMR: (400 MHz, dmso-d6) δ ppm 8.2-7.9 (s, 3H), 7.45 (d, 1H), 7.3 (m, 2H), 7.15 (d, 1H), 6.95 (dd, 1H), 6.95 (s, 1H), 6.8 (dd, 1H), 6.05 (s, 2H), 3.5 (d, 1H), 3.4 (d, 1H), 2.9 (m, 1H), 2.7 (t, 2H), 2.55 (m, 1H), 2.35 (m, 1H), 2.25 (m, 1H), 1.7 (m, 1H), 1.6-1 (m, 7H)
ESI/FIA/HR and MS/MS: [M+H]+=461.1854 (461.1841)
Elemental analysis: C=60.04 (59.99); H=6.06 (6.35); N=5.62 (6.08)

EXAMPLE 165: 3-(4-AMINOBUTYL)-4-HYDROXY-1-[[2-(6-METHOXYPYRIDIN-3-YL)PHENYL]-METHYL]-4-OXO-1,4-AZAPHOSPHINANE-3-CARBOXYLIC ACID

Example 165 is obtained starting from intermediate 21 and 2-(6-methoxy-3-pyridinyl)benzaldehyde in accordance with procedures F and D described hereinbefore.
$^1$H NMR: (300 MHz, D2O) δ ppm 8.05 (s, 1H), 7.75 (dd, 1H), 7.6 (m, 1H), 7.5 (m, 2H), 7.35 (m, 1H), 6.95 (d, 1H), 4.4 (d, 1H), 4.25 (d, 1H), 3.9 (s, 3H), 3.55-3.3 (m, 1H), 3.3-3.1 (m, 1H), 3.1 (m, 1H), 2.95 (t, 2H), 2.85 (m, 1H), 2.1 (m, 1H), 1.85 (m, 1H), 1.75-1.5 (m, 3H), 1.35 (m, 1H), 1.2-0.95 (m, 2H)

ESI/FIA/HR and MS/MS: [M+H]+=448.1996 (448.2001)

Elemental analysis: C=59.45 (59.05); H=6.75 (6.76); N=9.12 (9.39)

EXAMPLE 166: 3-(4-AMINOBUTYL)-4-HYDROXY-4-OXO-1-[[2-(6-OXO-1H-PYRIDIN-3-YL)PHENYL]METHYL]-1,4-AZAPHOSPHINANE-3-CARBOXYLIC ACID

Example 166 is obtained starting from intermediates 21 and 237 in accordance with procedures F and D described hereinbefore.

$^1$H NMR: (300/400 MHz, D2O) δ ppm 7.7 (dd, 1H), 7.6 (s, 1H), 7.6-7.3 (2*m, 2H), 6.7 (d, 1H), 4.35 (m, 2H), 3.6-3.4 (m, 1H), 3.4-3.05 (m, 2H), 3 (m, 1H), 2.9 (t, 2H), 2.1 (m, 1H), 1.85 (m, 1H), 1.7 (m, 1H), 1.6 (m, 2H), 1.4 (m, 1H), 1.25-0.95 (m, 2H)

ESI/FIA/HR and MS/MS: [M+H]+=434.1860 (434.1844)

Elemental analysis: C=58.86 (58.19); H=6.27 (6.51); N=9.89 (9.69)

EXAMPLE 167: 3-(4-AMINOBUTYL)-4-HYDROXY-1-[(2-IMIDAZO[1,2-A]PYRIDIN-3-YL-PHENYL)-METHYL]-4-OXO-1,4-AZAPHOSPHINANE-3-CARBOXYLIC ACID

Example 167 is obtained starting from intermediates 21 and 227 in accordance with procedures F and D described hereinbefore.

$^1$H NMR: (300 MHz, D2O) δ ppm 7.98 (d, 1H), 7.68 (s, 1H), 7.65 (d, 1H), 7.65 (m, 2H), 7.52 (m, 1H), 7.45 (dd, 1H), 7.22 (m, 1H), 6.98 (t, 1H), 4.25 (m, 2H), 3.45/3.1 (2*m, 2H), 2.9 (m, 2H), 2.85 (m, 2H), 2.12/1.55 (2*m, 2H), 1.8/1.55 (2*m, 2H), 1.55/0.95 (2*m, 2H), 1.28/0.95 (2*m, 2H)

ESI/FIA/HR and MS/MS: [M+H]+=457.2004 (457.20046)

Elemental analysis: C=59.82 (60.52); H=5.48 (6.40); N=11.98 (12.27)

EXAMPLE 168: 3-(4-AMINOBUTYL)-1-[(2-CHLOROPHENYL)METHYL]-4-HYDROXY-4-OXO-1,4-AZAPHOSPHINANE-3-CARBOXYLIC ACID

Example 168 is obtained starting from intermediate 21 and 2-chlorobenzaldehyde in accordance with procedures F and D described hereinbefore.

$^1$H NMR: (400 MHz, D2O) δ ppm 7.58/7.53 (2*d, 2H), 7.48/7.4 (2*m, 2H), 4.44 (m, 2H), 3.71/3.41 (2*m, 2H), 3.51/3.28 (2*m, 2H), 2.94 (m, 2H), 2.22/1.78 (2*m, 2H), 1.95/1.61 (2*m, 2H), 1.6/1.49 (2*m, 2H), 1.28/1.11 (2*m, 2H)

$^{31}$P NMR: (400 MHz, D2O) δ ppm −25.5

ESI/FIA/HR and MS/MS: [M+H]+=375.1235 (375.1240)

Elemental analysis: C=51.58 (51.27); H=6.22 (6.45); N=7.65 (7.47)

EXAMPLE 169: 3-(4-AMINOBUTYL)-4-HYDROXY-4-OXO-1-[(1R)-1-PHENYLETHYL]-1,4-AZAPHOSPHINANE-3-CARBOXYLIC ACID

Example 169 is obtained starting from intermediate 21 and acetophenone in accordance with procedures F and D described hereinbefore.

$^1$H NMR: (400 MHz, D2O) δ ppm 7.5 (m, 5H), 4.67 (quad., 1H), 3.72/3.53 (2*m, 1H), 3.62/3.41 (2*m, 1H), 3.29/3.13 (2*m, 1H), 3.09-2.9 (m, 1H), 3.09-2.9 (m, 2H), 2.28/2.11 (2*m, 1H), 2-1.65 (m, 1H), 2-1.65 (m, 2H), 1.7 (2*d, 3H), 1.7-1.05 (m, 2H), 1.7-1.05 (m, 2H)

$^{31}$P NMR: (400 MHz, D2O) δ ppm 26.4/26.2

ESI/FIA/HR and MS/MS: [M+H]+=355.1783 (355.1786)

Elemental analysis: C=58.22 (57.62); H=7.85 (7.68); N=8.04 (7.90)

EXAMPLE 170: 3-(4-AMINOBUTYL)-4-HYDROXY-4-OXO-1-[(2-PHENYLPHENYL)METHYL]-4-AZAPHOSPHINANE-3-CARBOXYLIC ACID

Example 170 is obtained starting from intermediate 21 and 2-phenylbenzaldehyde in accordance with procedures F and D described hereinbefore.

$^1$H NMR: (400 MHz, dmso-d6) δ ppm 7.65-7.3 (m, 6H), 4.33 (AB, 2H), 3.43-3 (m, 3H), 2.92 (dd, 1H), 2.82 (m, 2H), 2.06/1.57 (2m, 2H), 1.83/1.33 (2m, 2H), 1.57 (m, 2H), 1.08 (m, 2H)

ESI/FIA/HR and MS/MS: [M+H]+=417.1945 (417.1943)

Elemental analysis: C=63.68 (63.45); H=6.84 (7.02); N=6.85 (6.73)

EXAMPLE 171: 3-(4-AMINOBUTYL)-1-[[2-(FURAN-3-YL)PHENYL]METHYL]-4-HYDROXY-4-OXO-1,4-AZAPHOSPHINANE-3-CARBOXYLIC ACID

Example 171 is obtained starting from intermediates 21 and 290 in accordance with procedures F and D described hereinbefore.

$^1$H NMR: (400 MHz, D2O) δ ppm 7.68 (m, 1H), 7.65 (m, 1H), 7.58-7.44 (m, 4H), 6.63 (m, 1H), 4.49/4.4 (2*d, 2H), 3.5/3.22 (2*m, 2H), 3.34/3.01 (2*m, 2H), 2.94 (m, 2H), 2.1/1.68 (2*m, 2H), 1.69/1.6 (2*m, 2H), 1.59/1.41 (2*m, 2H), 1.18/1.08 (2*m, 2H)

ESI/FIA/HR and MS/MS: [M+H]+=407.1736 (407.1735)

Elemental analysis: C=59.20 (59.11); H=7.12 (6.70); N=7.00 (6.89)

EXAMPLE 172: 3-(4-AMINOBUTYL)-4-HYDROXY-1-[[2-(3-HYDROXYPHENYL)PHENYL]METHYL]-4-OXO-1,4-AZAPHOSPHINANE-3-CARBOXYLIC ACID

Example 172 is obtained starting from intermediates 21 and 281 in accordance with procedures F and D described hereinbefore.

$^1$H NMR: (400 MHz, D2O) δ ppm 7.52 (m, 2H), 7.39 (m, 1H), 7.39 (m, 1H), 7.29 (d, 1H), 6.95 (dd, 1H), 6.9 (dl, 1H), 6.85 (sl, 1H), 4.44/4.29 (d, 2H), 3.38/3.13 (m, 2H), 3.2/2.85 (m, 2H), 3.13/1.36 (m, 2H), 2.94 (m, 2H), 2.1-1.65 (m, 2H), 1.59 (m, 2H), 1.13/1.05 (m, 2H)

ESI/FIA/HR and MS/MS: [M+H]+=433.1895 (433.1892)

Elemental analysis: C=61.64 (61.10); H=6.51 (6.76); N=6.73 (6.48)

EXAMPLE 173: 3-(4-AMINOBUTYL)-1-[[2-(4-CHLOROPHENYL)-4-FLUOROPHENYL]METHYL]-4-HYDROXY-4-OXO-1,4-AZAPHOSPHINANE-3-CARBOXYLIC ACID

Example 173 is obtained starting from intermediates 21 and 220 in accordance with procedures F and D described hereinbefore.

¹H NMR: (400 MHz, D2O) δ ppm 7.59 (dd, 1H), 7.51 (d, 2H), 7.32 (d, 2H), 7.23 (td, 1H), 7.14 (dd, 1H), 4.3 (AB, 2H), 3.37/3.06 (2m, 2H), 3.11/2.81 (2m, 2H), 2.92 (m, 2H), 2.06/1.62 (2m, 2H), 1.83/1.33 (2m, 2H), 1.56 (m, 2H), 1.05 (m, 2H)
ESI/FIA/HR and MS/MS: [M+H]+=469.1470 (469.1459)
Elemental analysis: C=56.07 (56.35); H=5.39 (5.80); N=6.03 (5.97)

EXAMPLE 174: 3-(4-AMINOBUTYL)-4-HYDROXY-4-OXO-1-[(2-PROPAN-2-YLPHENYL)METHYL]-1,4-AZAPHOSPHINANE-3-CARBOXYLIC ACID

Example 174 is obtained starting from intermediate 21 and 2-isopropylbenzaldehyde in accordance with procedures F and D described hereinbefore.
¹H NMR: (500 MHz, D2O) δ ppm 7.49 (d, 1H), 7.45 (t, 1H), 7.38 (d, 1H), 7.28 (t, 1H), 4.39 (dd, 2H), 3.65 (dd, 1H), 3.5 (dd, 1H), 3.35 (m, 1H), 3.21 (dd, 1H), 3.09 (m, 1H), 2.91 (m, 2H), 2.17 (m, 1H), 1.93 (m, 1H), 1.74 (m, 1H), 1.58 (m, 2H), 1.47 (m, 1H), 1.24 (m, 1H), 1.2/1.18 (2*s, 6H), 1.1 (m, 1H)
ESI/FIA/HR and MS/MS: [M+H]+=383.2097 (383.2099)
Elemental analysis: C=59.45 (59.67); H=8.00 (8.17); N=7.60 (7.33)

EXAMPLE 175: 3-(4-AMINOBUTYL)-1-[[2-(3,4-DICHLOROPHENYL)PHENYL]METHYL]-4-HYDROXY-4-OXO-1,4-AZAPHOSPHINANE-3-CARBOXYLIC ACID

Example 175 is obtained starting from intermediates 21 and 215 in accordance with procedures F and D described hereinbefore.
¹H NMR: (300 MHz, D2O) δ ppm 7.62 (d, 1H), 7.6 (m, 1H), 7.54 (d, 1H), 7.52 (m, 2H), 7.37 (m, 1H), 7.24 (dd, 1H), 4.34 (AB, 2H), 3.45/3.07 (2m, 2H), 3.12/2.83 (2m, 2H), 2.93 (m, 2H), 2.1/1.63 (2m, 2H), 1.84/1.33 (2m, 2H), 1.57 (m, 2H), 1.04 (m, 2H)
ESI/FIA/HR and MS/MS: [M+H]+=485.1158 (485.1163)
Elemental analysis: C=54.91 (54.44); H=5.37 (5.61); N=5.35 (5.77)

EXAMPLE 176: 3-(4-AMINOBUTYL)-4-HYDROXY-4-OXO-1-[(3-PHENYLTHIOPHEN-2-YL)METHYL]-1,4-AZAPHOSPHINANE-3-CARBOXYLIC ACID

Example 176 is obtained starting from intermediates 21 and 284 in accordance with procedures F and D described hereinbefore.
¹H NMR: (300 MHz, D2O) δ ppm 7.62 (d, 1H), 7.49 (t, 2H), 7.44 (t, 1H), 7.4 (d, 2H), 7.17 (d, 1H), 4.6 (AB, 2H), 3.52/3.13 (2m, 2H), 3.13/2.73 (2m, 2H), 2.91 (m, 2H), 2.12/1.66 (2m, 2H), 1.81/1.26 (2m, 2H), 1.55 (m, 2H), 0.97 (m, 2H)
ESI/FIA/HR and MS/MS: [M+H]+=423.1525 (423.1507)
Elemental analysis: C=56.76 (56.86); H=6.46 (6.44); N=7.19 (6.63); S=7.30 (7.59)

Procedure G: Chiral Separation of the Diastereoisomers of Intermediate 20b

Intermediate 128: tert-Butyl (3S)-3-{4-[bis(tert-butoxycarbonyl)amino]butyl}-1-benzyl-4-ethoxy-4-oxo-1,4-azaphosphinane-3-carboxylate DMSO (30 mL) and 60% NaH (6.78 g, 186.6 mmol, 1.6 eq) are introduced in succession under an argon atmosphere into a 1 L three-necked flask equipped with mechanical stirring. The flask is maintained at ambient temperature by means of a water bath. A solution of intermediate 204 (41.1 g, 116.7 mmol, 1.1 eq) in DMSO (25 mL) is then added dropwise over a period of 5 minutes. A solution of intermediate 19 (37.54 g, 106 mmol) in DMSO (100 mL) is then added dropwise, the temperature being maintained below 20° C. The addition in fact causes pronounced heating as well as pronounced thickening of the reaction mixture. When the addition is complete, 100 mL of anhydrous THF are then added in order that stirring can be maintained. After 3 hours, the reaction mixture is cooled by means of an ice-water bath and hydrolysed by addition of 500 mL of a saturated NH4Cl solution. The mixture is then extracted with AcOEt (3×300 mL). The organic phases are then combined, washed with a saturated NaCl solution (2×300 mL) and dried over MgSO4, before being concentrated under reduced pressure to yield a yellowish solid (69.94 g), a mixture of 4 diastereoisomers. The 4 diastereoisomers of intermediate 20b are separated on a 2.5 kg chiral column of type (R,R)-Whelk-O-1 in batches of 8 g, each batch requiring 2 passes under the following conditions:

1st Pass:
The mixture containing the 4 diastereoisomers of intermediate 20b (8 g of crude product) is applied to a chiral column of type (R,R)-Whelk-O-1 of 2.5 kg using as mobile phase DCM/heptane (55:45)+10% NEt3 in order to isolate diastereoisomer 4 (number allocated according to the order of discharge from the column) of intermediate 20b.

2nd Pass:
The mixture containing the remaining 3 diastereoisomers of intermediate 20b is applied to a 2.5 kg chiral column of type (R,R)-Whelk-O-1 using as mobile phase MTBE+10% DEA in order to isolate diastereoisomer 2.

After 9 injections, the fractions containing diastereoisomers 2 and 4 of intermediate 20b are then collected and evaporated under reduced pressure to yield intermediate 128 (25.2 g, 40.3 mmol), quaternary carbon of the (S) configuration with a yield of 38%.
¹H NMR: (400 MHz, dmso-d6) δ ppm 7.3 (m, 5H), 4 (m, 2H), 3.6 (d, 1H), 3.4 (d, 1H), 3.35 (m, 2H), 2.9 (m, 1H), 2.8 (dd, 1H), 2.45 (dd, 1H), 2.3 (m, 1H), 1.9 (m, 4H), 1.4 (m, 2H), 1.38 (s, 18H), 1.35 (s, 9H), 1.2 (t, 3H), 0.8 (3, 2H).
IR (cm⁻¹): 1760-1680 cm⁻¹ (C=O), 1124 cm⁻¹ (P=O), 1124 cm⁻¹ (C—O—C).

Intermediate 129: tert-Butyl (3S)-3-{4-[bis(tert-butoxycarbonyl)amino]butyl}-4-ethoxy-4-oxo-1,4-azaphosphinane-3-carboxylate Intermediate 128 (30.35 g, 48.6 mol), ethanol (200 mL), Pd/C (3.03 g, 10% by mass) and 37% HCl (3 mL, 0.8 eq) are introduced in succession into a 500 mL flask at ambient temperature and under a stream of argon. The argon is then replaced by a hydrogen atmosphere. The reaction is monitored by LC/MS. After 4 hours, the reaction is complete and the catalyst is filtered off over glass fibre. The filtrate is evaporated to dryness in order to obtain a yellow oil, which is taken up in AcOEt (200 mL) and in a 10% NaHCO3 solution (200 mL). After decantation, the aqueous phase is extracted with AcOEt (3×100 mL). The organic phases are combined and then washed with a saturated NaCl solution (400 mL), dried over MgSO4 and concentrated to yield intermediate 129 in the form of a white solid (23.12 g, 43.24 mmol) with a yield of 89%.
¹H NMR: (DMSO-d6, 400 MHz) δ 4.01 to 3.88 (m, 2H), 3.47 (m, 2H), 2.95-2.68 (2m, 2H), 2.95 (m, 2H), 2.23 (m, 1H), 1.92-1.68 (m, 4H), 1.48 (m, 2H), 1.44 (s, 9H), 1.41 (s, 9H), 1.3 (s, 9H), 1.27/0.97 (2m, 2H), 1.24/0.97 (2t, 3H).

IR (cm$^{-1}$): 1715-1692 cm$^{-1}$ (C=O), 1125 cm$^{-1}$ (C—O—C).

EXAMPLE 177: (3S)-3-(4-AMINOBUTYL)-1-BENZYL-4-HYDROXY-4-OXO-1,4-AZAPHOSPHINANE-3-CARBOXYLIC ACID

Example 177 is obtained starting from intermediate 128 in accordance with procedure D described hereinbefore.

$^1$H NMR: (400 MHz, D2O) δ ppm 7.49 (m, 5H), 4.41/4.21 (2d, 2H), 3.7/3.32 (2m, 2H), 3.5/3.1 (2m, 2H), 2.91 (m, 2H), 2.22/1.78 (2m, 2H), 1.92 (m, 1H), 1.6 (m, 2H), 1.45 (m, 1H), 1.22/1.1 (2m, 2H)

ESI/FIA/HR and MS/MS: [M+H]+=341.1638 (341.1630)

Elemental analysis: C=56.43 (56.46); H=7.33 (7.40); N=8.20 (8.23)

RP: −45.630 (589 nm, T=20° C., C=1.1)

Intermediate 131: tert-Butyl (3S)-3-{4-[bis(tert-butoxycarbonyl)amino]butyl}-1-[[2-(3,4-dimethoxyphenyl)-4-fluorophenyl]methyl]-4-ethoxy-4-oxo-1,4-azaphosphinane-3-carboxylate Intermediate 131 is obtained starting from intermediates 129 and 229 in accordance with procedure F described hereinbefore.

$^1$H NMR: (400 MHz, dmso-d6) δ ppm 7.5 (dd, 1H), 7.15 (m, 1H), 7.05 (m, 2H), 6.9 (m, 2H), 3.95 (m, 2H), 3.8 (2s, 6H), 3.55 (d, 1H), 3.35 (d, 1H), 3.3 (m, 2H), 2.85-2.65 (m, 2H), 2.35 (dd, 1H), 2.25 (m, 1H), 2-1.75 (m, 4H), 1.45-1.3 (m, 2H), 1.4 (s, 18H), 1.35 (s, 9H), 1.2 (t, 3H), 0.8-0.6 (m, 2H).

EXAMPLE 179: (3S)-3-(4-AMINOBUTYL)-1-[[2-(3,4-DIMETHOXYPHENYL)-4-FLUOROPHENYL]-METHYL]-4-HYDROXY-4-OXO-1,4-AZAPHOSPHINANE-3-CARBOXYLIC ACID

Example 179 is obtained starting from intermediate 131 in accordance with procedure D described hereinbefore.

$^1$H NMR: (300 MHz, D2O) δ ppm 7.6 (dd, 1H), 7.2 (td, 1H), 7.1 (m, 1H), 7 (dd, 1H), 6.9 (dd, 1H), 4.4/4.25 (2 d, 2H), 3.8 (2 s, 6H), 3.35 (m, 1H), 3.2-2.75 (m, 5H), 2.05 (m, 1H), 1.8 (m, 1H), 1.6 (m, 3H), 1.3 (m, 1H), 1 (m, 2H)

ESI/FIA/HR and MS/MS: [M+H]+=495.2056 (495.2060)

Elemental analysis: C=58.64 (58.29); H=6.44 (6.52); N=5.72 (5.67)

RP: −23.170 (589 nm, T=21° C., C=0.8)

Intermediate 132: tert-Butyl (3S)-3-{4-[bis(tert-butoxycarbonyl)amino]butyl}-4-ethoxy-1-[[4-fluoro-2-(4-methylphenyl)phenyl]methyl]-4-oxo-1,4-azaphosphinane-3-carboxylate Intermediate 132 is obtained starting from intermediates 129 and 272 in accordance with procedure F described hereinbefore.

$^1$H NMR: (400 MHz, dmso-d6) δ ppm 7.51 (dd, 1H), 7.26 (s, 4H), 7.18 (td, 1H), 7.01 (dd, 1H), 3.93 (m, 2H), 3.42 (AB, 2H), 3.34 (m, 2H), 2.72/2.2 (2m, 2H), 2.72/2.32 (2m, 2H), 2.36 (s, 3H), 1.9-1.7 (m, 4H), 1.41 (s, 18H), 1.37 (m, 2H), 1.34 (s, 9H), 1.17 (t, 3H), 0.7 (m, 2H)

EXAMPLE 180: (3S)-3-(4-AMINOBUTYL)-1-[[4-FLUORO-2-(4-METHYLPHENYL)PHENYL]-METHYL]-4-HYDROXY-4-OXO-1,4-AZAPHOSPHINANE-3-CARBOXYLIC ACID

Example 180 is obtained starting from intermediate 132 in accordance with procedure D described hereinbefore.

$^1$H NMR: (400 MHz, D2O) δ ppm 7.61 (dd, 1H), 7.36 (d, 2H), 7.26 (d, 2H), 7.23 (td, 1H), 7.15 (dd, 1H), 4.41/4.26 (2*d, 2H), 3.35/3.09 (m, 2H), 3.17/2.81 (m, 2H), 2.95 (m, 2H), 2.37 (s, 3H), 2.08/1.64 (m, 2H), 1.85/1.35 (m, 2H), 1.6 (m, 2H), 1.13/1.05 (m, 2H)

ESI/FIA/HR and MS/MS: [M+H]+=449.2005 (449.2005)

Elemental analysis: C=61.57 (61.60); H=6.53 (6.74); N=6.45 (6.25)

RP: −15.640 (589 nm, T=20° C., C=1.0)

Intermediate 133: tert-Butyl (3S)-3-{4-[bis(tert-butoxycarbonyl)amino]butyl}-4-ethoxy-4-oxo-1-[(2-phenylphenyl)methyl]-1,4-azaphosphinane-3-carboxylate Intermediate 133 is obtained starting from intermediate 129 and 2-phenylbenzaldehyde in accordance with procedure F described hereinbefore.

$^1$H NMR: (400 MHz, dmso-d6) δ ppm 7.52-7.2 (m, 9H), 4.06-3.86 (m, 2H), 3.55/3.36 (AB, 2H), 3.36 (m, 2H), 2.71/2.32/2.19 (3m, 4H), 1.95-1.65 (m, 4H), 1.42/1.34 (2s, 27H), 1.37 (m, 2H), 1.21/1.17 (2t, 3H), 0.68 (m, 2H)

EXAMPLE 181: (3S)-3-(4-AMINOBUTYL)-4-HYDROXY-4-OXO-1-[(2-PHENYLPHENYL)METHYL]-1,4-AZAPHOSPHINANE-3-CARBOXYLIC ACID

Example 181 is obtained starting from intermediate 133 in accordance with procedure D described hereinbefore.

$^1$H NMR: (400 MHz, dmso-d6) δ ppm 7.65-7.3 (m, 9H), 4.3 (AB, 2H), 3.43/3 (m, 3H), 2.92 (dd, 1H), 2.82 (m, 2H), 2.06-1.57 (2m, 2H), 1.83/1.33 (2m, 2H) 1.57 (m, 2H), 1.08 (m, 2H)

ESI/FIA/HR and MS/MS: [M+H]+=417.1938 (417.1943)

Elemental analysis: C=62.99 (63.45); H=6.45 (7.02); N=6.93 (6.73)

Intermediate 134: tert-Butyl (3S)-3-{4-[bis(tert-butoxycarbonyl)amino]butyl}-4-ethoxy-4-oxo-1-[(2-pyrimidin-5-ylphenyl)methyl]-1,4-azaphosphinane-3-carboxylate Intermediate 134 is obtained starting from intermediates 129 and 236 in accordance with procedure F described hereinbefore.

$^1$H NMR: (300 MHz, dmso-d6) δ ppm 9.2 (s, 1H), 8.85 (s, 2H), 7.45 (m, 3H), 7.35 (d, 1H), 3.95 (m, 2H), 3.55 (d, 1H), 3.4 (d, 1H), 3.3 (m, 2H), 2.8-2.55 (m, 2H), 2.45-2.15 (2*m, 2H), 2.15-1.7 (m, 2H), 2-1.55 (m, 4H), 1.5-1.25 (3s, 27H), 1.2 (t, 3H), 0.6 (m, 2H)

EXAMPLE 182: (3S)-3-(4-AMINOBUTYL)-4-HYDROXY-4-OXO-1-[(2-PYRIMIDIN-5-YLPHENYL)-METHYL]-1,4-AZAPHOSPHINANE-3-CARBOXYLIC ACID

Example 182 is obtained starting from intermediate 134 in accordance with procedure D described hereinbefore.

¹H NMR: (400 MHz, D2O) δ ppm 9.15 (s, 1H), 8.82 (s, 2H), 7.7-7.55 (m, 3H), 7.43 (d, 1H), 4.4/4.3 (2d, 2H), 3.6-3.35 (m, 1H), 3.3-3.1 (m, 1H), 3.1 (m, 1H), 2.95 (m, 3H), 2.1 (m, 1H), 1.85 (m, 1H), 1.65 (m, 1H), 1.62-1.45 (m, 2H), 1.35 (m, 1H), 1.15-1 (m, 2H)
ESI/FIA/HR and MS/MS: [M+H]+=419.1855 (419.1848)
Elemental analysis: C=57.01 (57.41); H=6.57 (6.50); N=13.45 (13.39)
RP: −20.520 (589 nm, T=20° C., C=1.0)

Intermediate 135: tert-Butyl (3S)-3-{4-[bis(tert-butoxycarbonyl)amino]butyl}-4-ethoxy-4-oxo-1-[(2-thiophen-2-ylphenyl)methyl]-1,4-azaphosphinane-3-carboxylate Intermediate 135 is obtained starting from intermediate 129 and 2-(2-thienyl)benzaldehyde in accordance with procedure F described hereinbefore.
¹H NMR: (300 MHz, dmso-d6) δ ppm 7.62 (d, 1H), 7.45-4.3 (m, 4H), 7.25 (d, 1H), 7.15 (t, 1H), 4.1-3.9 (quad., 2H), 3.65/3.45 (d, 2H), 3.4-3.2 (m, 2H), 2.9-2.7 (m, 2H), 2.4-2.3 (m, 2H), 1.9-1.7 (m, 4H), 1.5-1.3 (m, 2H), 1.4/1.35 (2*s, 27H), 1.2 (t, 3H), 0.7-0.5 (m, 2H)

EXAMPLE 183: (3S)-3-(4-AMINOBUTYL)-4-HYDROXY-4-OXO-1-[(2-THIOPHEN-2-YLPHENYL)-METHYL]-1,4-AZAPHOSPHINANE-3-CARBOXYLIC ACID

Example 183 is obtained starting from intermediate 135 in accordance with procedure D described hereinbefore.
¹H NMR: (400 MHz, D2O) δ ppm 7.6 (d, 1H), 7.55 (d, 1H), 7.48 (m, 2H), 7.45 (d, 1H), 7.15 (dd, 1H), 7.1 (t, 1H), 4.5/1.4 (2*d, 2H), 3.5-3.2 (m, 3H), 3-2.85 (m, 3H), 2.15/1.7 (m, 4H), 1.88 (m, 1H), 1.55 (m, 2H), 1.2-1 (m, 2H)
ESI/FIA/HR and MS/MS: [M+H]+=423.1505 (423.1507)
Elemental analysis: C=57.14 (56.86); H=6.12 (6.44); N=6.61 (6.63); S=7.33 (7.59)
RP: −18.340 (589 nm, T=20° C., C=0.9)

Intermediate 136: tert-Butyl (3S)-3-{4-[bis(tert-butoxycarbonyl)amino]butyl}-4-ethoxy-4-oxo-1-[(2-pyridin-3-ylphenyl)methyl]-1,4-azaphosphinane-3-carboxylate Intermediate 136 is obtained starting from intermediates 129 and 260 in accordance with procedure F described hereinbefore.
¹H NMR: (400 MHz, dmso-d6) δ ppm 8.59 (dd, 1H), 8.56 (dd, 1H), 7.82 (dt, 1H), 7.49 (dd, 1H), 7.48 (ddd, 1H), 7.42/7.39 (2td, 2H), 7.27 (dd, 1H), 3.92 (m, 2H), 3.44 (AB, 2H), 3.3 (m, 2H), 2.7/2.2 (2m, 2H), 2.7/2.35 (2m, 2H), 1.95-1.66 (m, 4H), 1.42 (s, 18H), 1.35 (m, 2H), 1.33 (s, 9H), 1.17 (t, 3H), 0.63 (m, 2H)

EXAMPLE 184: (3S)-3-(4-AMINOBUTYL)-4-HYDROXY-4-OXO-1-[(2-PYRIDIN-3-YLPHENYL)-METHYL]-1,4-AZAPHOSPHINANE-3-CARBOXYLIC ACID

Example 184 is obtained starting from intermediate 136 in accordance with procedure D described hereinbefore.
¹H NMR: (400 MHz, dmso-d6) δ ppm 8.57 (d, 1H), 8.48 (s, 1H), 7.83 (d, 1H), 7.65 (m, 1H), 7.57 (m, 1H), 7.57 (m, 2H), 7.4 (m, 1H), 4.41/4.29 (dd, 2H), 3.44/3.12 (dd, 2H), 3.2/2.86 (dd, 2H), 2.93 (m, 2H), 2.1/1.67 (2*m, 2H), 1.85/1.35 (2*m, 2H), 1.59 (m, 2H), 1.08 (m, 2H)

ESI/FIA/HR and MS/MS: [M+H]+=418.1871 (418.1895)
Elemental analysis: C=60.35 (60.42); H=6.74 (6.76); N=9.70 (10.07)
RP: −20.940 (589 nm, T=28° C., C=0.9)

Intermediate 137: tert-Butyl (3S)-3-{4-[bis(tert-butoxycarbonyl)amino]butyl}-4-ethoxy-1-[[4-fluoro-2-(3-methoxyphenyl)phenyl]methyl]-4-oxo-1,4-azaphosphinane-3-carboxylate Intermediate 137 is obtained starting from intermediates 129 and 222 in accordance with procedure F described hereinbefore.
¹H NMR: (400 MHz, dmso-d6) δ ppm 7.51 (dd, 1H), 7.36 (t, 1H), 7.2 (td, 1H), 7.05 (dd, 1H), 6.97 (d, 1H), 6.91 (m, 1H), 6.9 (m, 1H), 3.93 (m, 2H), 3.79 (s, 3H), 3.52/3.33 (2*d, 2H), 3.33 (m, 2H), 2.72/2.21 (m, 2H), 2.72/2.32 (m, 2H), 2-1.75 (m, 4H), 1.4 (s, 18H), 1.37 (m, 2H), 1.34 (s, 9H), 1.17 (t, 3H), 0.69 (m, 2H)

EXAMPLE 185: (3S)-3-(4-AMINOBUTYL)-1-[[4-FLUORO-2-(3-METHOXYPHENYL)PHENYL]-METHYL]-4-HYDROXY-4-OXO-1,4-AZAPHOSPHINANE-3-CARBOXYLIC ACID

Example 185 is obtained starting from intermediate 137 in accordance with procedure D described hereinbefore.
¹H NMR: (400 MHz, D2O) δ ppm 7.62 (dd, 1H), 7.46 (t, 1H), 7.25 (td, 1H), 7.16 (dd, 1H), 7.08 (dd, 1H), 6.97 (dl, 1H), 6.96 (sl, 1H), 4.41/4.27 (2*d, 2H), 3.84 (s, 3H), 3.37/3.09 (m, 2H), 3.16/2.83 (m, 2H), 2.95 (m, 2H), 2.09/1.66 (m, 2H), 1.86/1.35 (m, 2H), 1.66 (m, 2H), 1.13/1.06 (m, 2H)
ESI/FIA/HR and MS/MS: [M+H]+=465.1941 (465.1949)
Elemental analysis: C=59.94 (59.48); H=6.44 (6.51); N=6.11 (6.03)
RP: −19.240 (589 nm, T=20° C., C=0.6)

Intermediate 138: tert-Butyl (3S)-3-{4-[bis(tert-butoxycarbonyl)amino]butyl}-1-[[3-(4-chlorophenyl)pyridin-2-yl]methyl]-4-ethoxy-4-oxo-1,4-azaphosphinane-3-carboxylate Intermediate 138 is obtained starting from intermediates 129 and 291 in accordance with procedure F described hereinbefore.
¹H NMR: (400 MHz, dmso-d6) δ ppm 8.55 (d, 1H), 7.68 (d, 1H), 7.55 (m, 4H), 7.42 (dd, 1H), 3.94 (m, 2H), 3.63/3.44 (2*d, 2H), 3.19 (m, 2H), 2.98/2.51 (2*m, 2H), 2.64/2.36 (2*m, 2H), 1.91/1.75 (2*m, 2H), 1.75/1.62 (2*m, 2H), 1.4 (s, 18H), 1.33 (s, 9H), 1.23 (m, 2H), 1.18 (t, 3H), 0.59/0.34 (m, 2H)

EXAMPLE 186: (3S)-3-(4-AMINOBUTYL)-1-[[3-(4-CHLOROPHENYL)PYRIDIN-2-YL]METHYL]-4-HYDROXY-4-OXO-1,4-AZAPHOSPHINANE-3-CARBOXYLIC ACID

Example 186 is obtained starting from intermediate 138 in accordance with procedure D described hereinbefore.
¹H NMR: (400 MHz, D2O) δ ppm 8.6 (d, 1H), 7.8 (d, 1H), 7.5 (m, 3H), 7.3 (d, 2H), 4.4 (m, 2H), 3.5-3.3 (m, 2H), 3.2 (m, 2H), 2.95 (m, 2H), 2.2 (m, 1H), 1.9 (m, 1H), 1.65 (m, 1H), 1.6 (m, 2H), 1.45 (m, 1H), 1.3-1.1 (m, 2H)

ESI/FIA/HR and MS/MS: [M+H]+=452.1502 (452.1500)
Elemental analysis: C=55.89 (55.82); H=5.56 (6.02); N=9.17 (9.30)
RP: −5.260 (589 nm, T=20° C., C=1.0)

Intermediate 139: tert-Butyl (3S)-3-{4-[bis(tert-butoxycarbonyl)amino]butyl}-4-ethoxy-1-[[4-fluoro-2-(4-methoxyphenyl)phenyl]methyl]-4-oxo-1,4-azaphosphinane-3-carboxylate Intermediate 139 is obtained starting from intermediates 129 and 221 in accordance with procedure F described hereinbefore.

$^1$H NMR: (400 MHz, dmso-d6) δ ppm 7.49 (dd, 1H), 7.31 (d, 2H), 7.17 (m, 1H), 7.01 (m, 1H), 7.01 (d, 2H), 3.93 (m, 2H), 3.8 (s, 3H), 3.5/3.32 (2*d, 2H), 3.32 (m, 2H), 2.75/2.21 (2*m, 2H), 2.72/2.33 (2*m, 2H), 2-1.78 (unresolved peak, 2H), 2-1.78 (unresolved peak, 2H), 1.4/1.33 (2*s, 27H), 1.38 (m, 2H), 1.18 (t, 3H), 0.7 (m, 2H)

EXAMPLE 187: (3S)-3-(4-AMINOBUTYL)-1-[[4-FLUORO-2-(4-METHOXYPHENYL)PHENYL]-METHYL]-4-HYDROXY-4-OXO-1,4-AZAPHOSPHINANE-3-CARBOXYLIC ACID

Example 187 is obtained starting from intermediate 139 in accordance with procedure D described hereinbefore.

$^1$H NMR: (300 MHz, D2O) δ ppm 7.57 (dd, 1H), 7.3 (d, 2H), 7.19 (td, 1H), 7.12 (dd, 1H), 7.08 (d, 2H), 4.32 (AB, 2H), 3.84 (s, 3H), 3.33/3.07 (2m, 2H), 3.13/2.8 (2m, 2H), 2.92 (m, 2H), 2.05/1.62 (2m, 2H), 1.83/1.32 (2m, 2H), 1.57 (m, 2H), 1.05 (m, 2H)
ESI/FIA/HR and MS/MS: [M+H]+=465.1960 (465.1954)
Elemental analysis: C=59.41 (59.48); H=6.76 (6.51); N=6.09 (6.03)
RP: −13.770 (589 nm, T=20° C., C=0.9)

Intermediate 140: tert-Butyl (3S)-3-{4-[bis(tert-butoxycarbonyl)amino]butyl}-4-ethoxy-1-[[2-(4-methylphenyl)phenyl]methyl]-4-oxo-1,4-azaphosphinane-3-carboxylate Intermediate 140 is obtained starting from intermediates 129 and 288 in accordance with procedure F described hereinbefore.

$^1$H NMR: (400 MHz, dmso-d6) δ ppm 7.49 (dd, 1H), 7.33 (2*m, 2H), 7.23 (2*d, 4H), 7.18 (dd, 1H), 3.92 (m, 2H), 3.54/3.35 (2*d, 2H), 3.3 (m, 2H), 2.74/2.2 (2*m, 2H), 2.74/2.32 (2*m, 2H), 2.36 (s, 3H), 1.95-1.75 (m, 2H), 1.95-1.75 (m, 2H), 1.41/1.33 (2*s, 27H), 1.38 (m, 2H), 1.17 (t, 3H), 0.71 (m, 2H)

EXAMPLE 188: (3S)-3-(4-AMINOBUTYL)-4-HYDROXY-1-[[2-(4-METHYLPHENYL)PHENYL]-METHYL]-4-OXO-1,4-AZAPHOSPHINANE-3-CARBOXYLIC ACID

Example 188 is obtained starting from intermediate 140 in accordance with procedure D described hereinbefore.

$^1$H NMR: (300 MHz, D2O) δ ppm 7.6-7.35 (m, 4H), 7.33/7.22 (2d, 4H), 4.33 (AB, 2H), 3.33/3.07 (2m, 2H), 3.19/2.8 (2m, 2H), 2.91 (m, 2H), 2.35 (s, 3H), 2.06/1.58 (2m, 2H), 1.82/1.32 (2m, 2H), 1.57 (m, 2H), 1.07 (m, 2H)
ESI/FIA/HR and MS/MS: [M+H]+=431.2097 (431.2099)
Elemental analysis: C=64.03 (64.17); H=6.92 (7.26); N=6.45 (6.51)
RP: −13.150 (589 nm, T=20° C., C=0.9)

Intermediate 141: tert-Butyl (3S)-3-{4-[bis(tert-butoxycarbonyl)amino]butyl}-4-ethoxy-1-[[4-fluoro-2-(4-fluorophenyl)phenyl]methyl]-4-oxo-1,4-azaphosphinane-3-carboxylate Intermediate 141 is obtained starting from intermediates 129 and 271 in accordance with procedure F described hereinbefore.

$^1$H NMR: (400 MHz, dmso-d6) δ ppm 7.49 (dd, 1H), 7.42 (dd, 2H), 7.29 (t, 2H), 7.21 (td, 1H), 7.06 (dd, 1H), 3.92 (m, 2H), 3.49/3.32 (2*d, 2H), 3.32 (m, 2H), 2.71/2.2 (2*m, 2H), 2.7/2.34 (2*m, 2H), 1.9-1.65 (m, 2H), 1.9-1.65 (m, 2H), 1.4/1.33 (2*s, 27H), 1.38 (m, 2H), 1.18 (t, 3H), 0.67 (m, 2H)

EXAMPLE 189: (3S)-3-(4-AMINOBUTYL)-1-[[4-FLUORO-2-(4-FLUOROPHENYL)PHENYL] METHYL]-4-HYDROXY-4-OXO-1,4-AZAPHOSPHINANE-3-CARBOXYLIC ACID

Example 189 is obtained starting from intermediate 141 in accordance with procedure D described hereinbefore.

$^1$H NMR: (300 MHz, D2O) δ ppm 7.59 (dd, 1H), 7.35 (m, 2H), 7.23 (td, 1H), 7.23 (t, 2H), 7.14 (dd, 1H), 4.31 (AB, 2H), 3.36/3.07 (2m, 2H), 3.16/2.83 (2m, 2H), 2.92 (m, 2H), 2.06/1.58 (2m, 2H), 1.84/1.33 (2m, 2H), 1.58 (m, 2H), 1.07 (m, 2H)
$^{19}$F NMR: (300 MHz, D2O) δ ppm −111.4/−114.1
ESI/FIA/HR and MS/MS: [M+H]+=453.1750 (453.1754)
Elemental analysis: C=58.26 (58.40); H=5.79 (6.01); N=6.18 (6.19)
RP: −17.770 (589 nm, T=20° C., C=1.2)

Intermediate 142: tert-Butyl (3S)-3-{4-[bis(tert-butoxycarbonyl)amino]butyl}-4-ethoxy-1-[(4-fluoro-2-pyridin-3-ylphenyl)methyl]-4-oxo-1,4-azaphosphinane-3-carboxylate Intermediate 142 is obtained starting from intermediates 129 and 261 in accordance with procedure F described hereinbefore.

$^1$H NMR: (400 MHz, dmso-d6) δ ppm 8.6 (dd, 1H), 8.58 (dl, 1H), 7.84 (dt, 1H), 7.51 (m, 2H), 7.26 (td, 1H), 7.15 (dd, 1H), 3.93 (m, 2H), 3.42 (AB, 2H), 3.33 (m, 2H), 2.67/2.2 (2m, 2H), 2.67/2.35 (2m, 2H), 1.96-1.62 (m, 4H), 1.41 (s, 18H), 1.36 (m, 2H), 1.34 (s, 9H), 1.17 (t, 3H), 0.65 (m, 2H)

EXAMPLE 190: (3S)-3-(4-AMINOBUTYL)-1-[(4-FLUORO-2-PYRIDIN-3-YLPHENYL)METHYL]-4-HYDROXY-4-OXO-1,4-AZAPHOSPHINANE-3-CARBOXYLIC ACID

Example 190 is obtained starting from intermediate 142 in accordance with procedure D described hereinbefore.

$^1$H NMR: (300 MHz, D2O) δ ppm 8.62 (dd, 1H), 8.54 (d, 1H), 7.89 (dt, 1H), 7.7 (dd, 1H), 7.6 (dd, 1H), 7.34 (td, 1H), 7.23 (dd, 1H), 4.35 (AB, 2H), 3.46/3.12 (2m, 2H), 3.18/2.87 (2m, 2H), 2.97 (m, 2H), 2.12/1.67 (2m, 2H), 1.88/1.37 (2m, 2H), 1.61 (m, 2H), 1.11 (m, 2H)
$^{19}$F NMR: (300 MHz, D2O) δ ppm −111
ESI/FIA/HR and MS/MS: [M+H]+=436.1794 (436.1801)
Elemental analysis: C=57.69 (57.93); H=5.69 (6.25); N=9.60 (9.65)
RP: −19.680 (589 nm, T=20° C., C=0.7)

Intermediate 143: tert-Butyl (3S)-3-{4-[bis(tert-butoxycarbonyl)amino]butyl}-4-ethoxy-1-[(4-methoxy-2-phenylphenyl)methyl]-4-oxo-1,4-azaphosphinane-3-carboxylate Intermediate 143 is obtained starting from intermediates 129 and 285 in accordance with procedure F described hereinbefore.
$^1$H NMR: (400 MHz, dmso-d6) δ ppm 7.47-7.32 (m, 5H), 7.35 (d, 1H), 6.95 (dd, 1H), 6.75 (d, 1H), 3.92 (quad., 2H), 3.77 (s, 3H), 3.47/3.27 (dd, 2H), 3.32 (t, 2H), 2.75/2.28 (dd, 2H), 2.67/2.16 (dd, 2H), 1.85/1.72 (dd, 2H), 1.79 (t, 2H), 1.41 (s, 18H), 1.36 (m, 2H), 1.34 (s, 9H), 1.16 (t, 3H), 0.68 (m, 2H)

EXAMPLE 191: (3S)-3-(4-AMINOBUTYL)-4-HYDROXY-1-[(4-HYDROXY-2-PHENYLPHE-NYL)-METHYL]-4-OXO-1,4-AZAPHOSPHI-NANE-3-CARBOXYLIC ACID

Example 191 is obtained starting from intermediate 143 in accordance with procedure D described hereinbefore.
$^1$H NMR: (400 MHz, D2O) δ ppm 7.54-7.44 (m, 3H), 7.54-7.44 (m, 1H), 7.34 (d, 2H), 6.97 (dd, 1H), 6.86 (df, 1H), 4.34/4.19 (2*d, 2H), 3.33/3.05 (2*m, 2H), 3.19/2.78 (2*m, 2H), 2.95 (m, 2H), 2.07/1.63 (2*m, 2H), 1.85/1.35 (2*m, 2H), 1.59 (m, 2H), 1.2-1 (2*m, 2H)
ESI/FIA/HR and MS/MS: [M+H]+=433.1887 (433.1887)
Elemental analysis: C=60.81 (61.10); H=6.31 (6.76); N=6.49 (6.48)
RP: −39.130 (589 nm, T=20° C., C=0.9)

Intermediate 144: tert-Butyl (3S)-3-{4-[bis(tert-butoxycarbonyl)amino]butyl}-4-ethoxy-1-[(4-fluoro-2-pyridin-4-ylphenyl)methyl]-4-oxo-1,4-azaphosphinane-3-carboxylate Intermediate 144 is obtained starting from intermediates 129 and 262 in accordance with procedure F described hereinbefore.
$^1$H NMR: (400 MHz, dmso-d6) δ ppm 8.65 (m, 2H), 7.53 (dd, 1H), 7.44 (m, 2H), 7.28 (td, 1H), 7.14 (dd, 1H), 3.93 (m, 2H), 3.44 (AB, 2H), 3.32 (m, 2H), 2.69/2.21 (2m, 2H), 2.69/2.35 (2m, 2H), 1.96-1.62 (m, 4H), 1.41 (s, 18H), 1.36 (m, 2H), 1.33 (s, 9H), 1.17 (t, 3H), 0.66/0.58 (2m, 2H)

EXAMPLE 192: (3S)-3-(4-AMINOBUTYL)-1-[(4-FLUORO-2-PYRIDIN-4-YLPHENYL)METHYL]-4-HYDROXY-4-OXO-1,4-AZAPHOSPHINANE-3-CARBOXYLIC ACID

Example 192 is obtained starting from intermediate 144 in accordance with procedure D described hereinbefore.
$^1$H NMR: (400 MHz, D2O) δ ppm 8.63 (d, 2H), 7.67 (dd, 1H), 7.45 (d, 2H), 7.33 (td, 1H), 7.21 (dd, 1H), 4.4/4.29 (2*d, 2H), 3.44/3.08 (m, 2H), 3.16/2.88 (m, 2H), 2.95 (m, 2H), 2.1/1.65 (m, 2H), 1.86/1.36 (m, 2H), 1.6 (m, 2H), 1.08 (m, 2H)
ESI/FIA/HR and MS/MS: [M+H]+=436.1804 (436.1801)
Elemental analysis: C=58.11 (57.93); H=5.71 (6.25); N=9.79 (9.65)
RP: −16.250 (589 nm, T=20° C., C=1.0)

Intermediate 146: tert-Butyl (3S)-3-{4-[bis(tert-butoxycarbonyl)amino]butyl}-1-[[2-(3-chlorophenyl)phenyl]methyl]-4-ethoxy-4-oxo-1,4-azaphosphinane-3-carboxylate Intermediate 146 is obtained starting from intermediates 129 and 213 in accordance with procedure F described hereinbefore.
$^1$H NMR: (400 MHz, dmso-d6) δ ppm 7.52 (sl, 1H), 7.45 (m, 2H), 7.45/7.38/7.25 (3m, 4H), 7.33 (dt, 1H), 3.94 (m, 2H), 3.53/3.32 (AB, 2H), 3.25 (m, 2H), 2.76/2.37 (2m, 2H), 2.7/2.25 (2m, 2H), 1.95/1.78 (2m, 2H), 1.82/1.75 (2m, 2H), 1.41 (s, 18H), 1.33 (s, 9H), 1.33 (m, 2H), 1.18 (t, 3H), 0.66/0.57 (2m, 2H)

EXAMPLE 194: (3S)-3-(4-AMINOBUTYL)-1-[[2-(3-CHLOROPHENYL)PHENYL]METHYL]-4-HYDROXY-4-OXO-1,4-AZAPHOSPHINANE-3-CARBOXYLIC ACID

Example 194 is obtained starting from intermediate 146 in accordance with procedure D described hereinbefore.
$^1$H NMR: (300 MHz, D2O) δ ppm 7.63-7.23 (m, 8H), 4.33 (AB, 2H), 3.42/3.1 (2m, 2H), 3.17/2.82 (2m, 2H), 2.93 (m, 2H), 2.1/1.63 (2m, 2H), 1.84/1.34 (2m, 2H), 1.57 (m, 2H), 1.07 (m, 2H)
ESI/FIA/HR and MS/MS: [M+H]+=451.1539 (451.1548)
Elemental analysis: C=58.76 (58.60); H=6.46 (6.26); N=6.38 (6.21)
RP: −15.780 (589 nm, T=20° C., C=1.2)

Intermediate 147: tert-Butyl (3S)-3-{4-[bis(tert-butoxycarbonyl)amino]butyl}-1-[[4-chloro-2-(4-chlorophenyl)phenyl]methyl]-4-ethoxy-4-oxo-1,4-azaphosphinane-3-carboxylate Intermediate 147 is obtained starting from intermediates 129 and 292 in accordance with procedure F described hereinbefore.
$^1$H NMR: (400 MHz, dmso-d6) δ ppm 7.52 (d, 2H), 7.5 (d, 1H), 7.45 (dd, 1H), 7.41 (d, 2H), 7.27 (d, 1H), 3.94 (m, 2H), 3.5/3.33 (dd, 2H), 3.3 (m, 2H), 2.8-2.6 (2m, 2H), 2.35 (dd, 1H), 2.2 (m, 1H), 2-1.7 (m, 4H), 1.41 (s, 18H), 1.4-1.3 (m, 2H), 1.33 (s, 9H), 1.18 (t, 3H), 0.68 (m, 2H)

EXAMPLE 195: (3S)-3-(4-AMINOBUTYL)-1-[[4-CHLORO-2-(4-CHLOROPHENYL)PHENYL]METHYL]-4-HYDROXY-4-OXO-1,4-AZAPHOSPHINANE-3-CARBOXYLIC ACID

Example 195 is obtained starting from intermediate 147 in accordance with procedure D described hereinbefore.
$^1$H NMR: (300 MHz, D2O) δ ppm 7.55-7.5 (2d, 2H), 7.5 (d, 2H), 7.4 (d, 1H), 7.28 (d, 2H), 4.3 (dd, 2H), 3.35/3.05 (2m, 2H), 3.15/2.8 (2m, 2H), 2.9 (m, 2H), 2.05/1.65 (2m, 2H), 1.8/1.3 (2m, 2H), 1.55 (m, 2H), 1.05 (m, 2H)
ESI/FIA/HR and MS/MS: [M+H]+=485.1162 (485.1163)
Elemental analysis: C=55.11 (54.44); H=5.26 (5.61); N=5.87 (5.77)
RP: −17.410 (589 nm, T=19° C., C=1.0)

Intermediate 148: tert-Butyl (3S)-3-{4-[bis(tert-butoxycarbonyl)amino]butyl}-4-ethoxy-1-[2-(6-methoxypyridin-3-yl)benzyl]-4-oxo-1,4-azaphosphinane-3-carboxylate Intermediate 148 is obtained starting from intermediates 129 and 237 in accordance with procedure F described hereinbefore.

¹H NMR: (400 MHz, dmso-d6) δ ppm 8.1 (d, 1H), 7.75 (dd, 1H), 7.5-7.2 (m, 4H), 6.9 (d, 1H), 3.9 (s, 3H), 3.9 (m, 2H), 3.55/3.35 (dd, 2H), 3.3 (m, 2H), 2.75/2.2 (2m, 2H), 2.7/2.35 (2dd, 2H), 1.9/1.8 (2m, 2H), 1.8 (m, 2H), 1.4 (s, 18H), 1.35 (m, 2H), 1.35 (s, 9H), 1.2 (t, 3H), 0.65 (m, 2H)

EXAMPLE 196: (3S)-3-(4-AMINOBUTYL)-4-HYDROXY-1-[2-(6-METHOXYPYRIDIN-3-YL)BENZYL]-4-OXO-1,4-AZAPHOSPHINANE-3-CARBOXYLIC ACID

Example 196 is obtained starting from intermediate 148 in accordance with procedure D described hereinbefore.

¹H NMR: (400 MHz, D2O) δ ppm 8.05 (d, 1H), 7.75 (dd, 1H), 7.6 (m, 1H), 7.5 (m, 2H), 7.4 (m, 1H), 7 (d, 1H), 4.3 (dd, 2H), 3.9 (s, 3H), 3.45/3.15 (2m, 2H), 3.2/2.85 (2dd, 2H), 2.9 (m, 2H), 2.1/1.7 (2m, 2H), 1.8/1.35 (2m, 2H), 1.6 (m, 2H), 1.1 (m, 2H)

ESI/FIA/HR and MS/MS: [M+H]+=448.2009 (448.2001)

Elemental analysis: C=58.81 (59.05); H=6.79 (6.76); N=9.31 (9.39)

RP: −11.510 (589 nm, T=19° C., C=0.9)

Intermediate 149: tert-Butyl (3S)-3-{4-[bis(tert-butoxycarbonyl)amino]butyl}-4-ethoxy-1-[[2-(4-fluorophenyl)phenyl]methyl]-4-oxo-1,4-azaphosphinane-3-carboxylate Intermediate 149 is obtained starting from intermediate 129 and 2-(4-fluorophenyl)benzaldehyde in accordance with procedure F described hereinbefore.

¹H NMR: (400 MHz, dmso-d6) δ ppm 7.47 (dd, 1H), 7.39/7.33 (2*m, 2H), 7.39 (dd, 2H), 7.27 (t, 2H), 7.21 (dd, 1H), 3.93 (m, 2H), 3.52/3.34 (2*d, 2H), 3.38-3.22 (m, 2H), 2.75/2.21 (2*m, 2H), 2.7/2.35 (2*m, 2H), 1.98-1.72 (m, 2H), 1.98-1.72 (m, 2H), 1.41/1.34 (2*s, 27H), 1.37 (m, 2H), 1.19 (t, 3H), 0.68 (m, 2H)

EXAMPLE 197: (3S)-3-(4-AMINOBUTYL)-1-[[2-(4-FLUOROPHENYL)PHENYL]METHYL]-4-HYDROXY-4-OXO-1,4-AZAPHOSPHINANE-3-CARBOXYLIC ACID

Example 197 is obtained starting from intermediate 149 in accordance with procedure D described hereinbefore.

¹H NMR: (400 MHz, D2O) δ ppm 7.6 (d, 1H), 7.52 (m, 2H), 7.4 (d, 1H), 7.35 (dd, 2H), 7.24 (dd, 2H), 4.41/4.29 (dd, 2H), 3.39/3.1 (2*m, 2H), 3.19/2.88 (2*m, 2H), 2.93 (m, 2H), 2.09/1.65 (2*m, 2H), 1.85/1.59 (2*m, 2H), 1.59/1.35 (2*m, 2H), 1.2-1 (m, 2H)

ESI/FIA/HR and MS/MS: [M+H]+=435.1843 (435.1843)

Elemental analysis: C=60.70 (60.82); H=6.56 (6.50); N=6.49 (6.45)

RP: −23.350 (589 nm, T=20° C., C=0.7)

Intermediate 150: tert-Butyl (3S)-3-{4-[bis(tert-butoxycarbonyl)amino]butyl}-1-[[2-(4-chlorophenyl)-4-fluorophenyl]methyl]-4-ethoxy-4-oxo-1,4-azaphosphinane-3-carboxylate Intermediate 150 is obtained starting from intermediates 129 and 220 in accordance with procedure F described hereinbefore.

¹H NMR: (400 MHz, dmso-d6) δ ppm 7.52 (d, 2H), 7.5 (m, 1H), 7.42 (d, 2H), 7.22 (dt, 1H), 7.07 (dd, 1H), 4-3.86 (m, 2H), 3.5/3.32 (2*d, 2H), 3.4-3.25 (m, 2H), 2.71/2.21 (2*m, 2H), 2.71/2.35 (2*m, 2H), 1.99-1.72 (m, 2H), 1.99-1.72 (m, 2H), 1.41/1.33 (2*s, 27H), 1.38 (m, 2H), 1.19 (t, 3H), 0.68 (m, 2H)

EXAMPLE 198: (3S)-3-(4-AMINOBUTYL)-1-[[2-(4-CHLOROPHENYL)-4-FLUOROPHENYL]METHYL]-4-HYDROXY-4-OXO-1,4-AZAPHOSPHINANE-3-CARBOXYLIC ACID

Example 198 is obtained starting from intermediate 150 in accordance with procedure D described hereinbefore.

¹H NMR: (400 MHz, D2O) δ ppm 7.62 (dd, 1H), 7.54 (d, 2H), 7.35 (d, 2H), 7.25 (td, 1H), 7.17 (dd, 1H), 4.39/4.28 (2*d, 2H), 3.4/3.09 (2*m, 2H), 3.13/2.84 (2*m, 2H), 2.95 (m, 2H), 2.09/1.65 (2*m, 2H), 1.86/1.36 (2*m, 2H), 1.6 (m, 2H), 1.09 (m, 2H)

ESI/FIA/HR and MS/MS: [M+H]+=469.1452 (469.1454)

Elemental analysis: C=56.19 (56.35); H=5.57 (5.80); N=5.97 (5.97)

RP: −12.560 (589 nm, T=20° C., C=0.7)

Intermediate 151: tert-Butyl (3S)-3-{4-[bis(tert-butoxycarbonyl)amino]butyl}-4-ethoxy-1-[(2-naphthalen-1-ylphenyl)methyl]-4-oxo-1,4-azaphosphinane-3-carboxylate Intermediate 151 is obtained starting from intermediates 129 and 228 in accordance with procedure F described hereinbefore.

¹H NMR: (400 MHz, dmso-d6) δ ppm 8 (m, 2H), 7.65-7.2 (m, 9H), 3.85 (m, 2H), 3.4 (m, 2H), 3.35-3 (2dd, 2H), 2.65/2.2 (2m, 2H), 2.5/2 (2m, 2H), 1.9-1.5 (m, 4H), 1.4 (2s, 18H), 1.35 (m, 2H), 1.3 (2s, 9H), 1.1 (t, 3H), 0.65 (m, 2H)

EXAMPLE 199: (3S)-3-(4-AMINOBUTYL)-4-HYDROXY-1-[(2-NAPHTHALEN-1-YLPHENYL)-METHYL]-4-OXO-1,4-AZAPHOSPHINANE-3-CARBOXYLIC ACID

Example 199 is obtained starting from intermediate 151 in accordance with procedure D described hereinbefore.

¹H NMR: (400 MHz, D2O) δ ppm 8 (m, 2H), 7.75-7.3 (m, 9H), 4.35-3.8 (2dd, 2H), 3.4/2.95 (2m, 2H), 3.2/2.7 (2m, 2H), 2.9 (m, 2H), 2.05/1.55 (2m, 2H), 1.75/1.25 (2m, 2H), 1.5 (m, 2H), 1.2-0.7 (m, 2H)

ESI/FIA/HR and MS/MS: [M+H]+=467.2109 (467.2099)

Elemental analysis: C=66.50 (66.94); H=6.26 (6.70); N=6.08 (6.00)

RP: −25.420 (589 nm, T=19° C., C=1.0)

Intermediate 152: tert-Butyl (3S)-3-{4-[bis(tert-butoxycarboxy)amino]butyl}-1-[(2-tert-butylphenyl)methyl]-4-ethoxy-4-oxo-1,4-azaphosphinane-3-carboxylate Intermediate 152 is obtained starting from intermediate 129 and 2-tert-butylbenzaldehyde in accordance with procedure F described hereinbefore.

¹H NMR: (400 MHz, dmso-d6) δ ppm 7.6-7.15 (3m, 4H), 4 (m, 2H), 3.75 (dd, 2H), 3.45-3.3 (m, 2H), 3-2.75 (2m, 2H), 2.5 (dd, 2H), 2.4 (m, 2H), 2-1.85 (m, 2H), 1.4 (m, 2H), 1.4 (s, 18H), 1.4 (t, 9H), 1.35 (s, 9H), 1.2 (t, 3H), 0.95-0.7 (m, 2H)

EXAMPLE 200: (3S)-3-(4-AMINOBUTYL)-1-[(2-TERT-BUTYLPHENYL)METHYL]-4-HYDROXY-4-OXO-1,4-AZAPHOSPHINANE-3-CARBOXYLIC ACID

Example 200 is obtained starting from intermediate 152 in accordance with procedure D described hereinbefore.

$^1$H NMR: (300 MHz, D2O) δ ppm 7.57/7.46 (2m, 2H), 7.36 (m, 2H), 4.65 (AB, 2H), 3.68/3.41 (2m, 2H), 3.46/3.22 (2m, 2H), 2.89 (m, 2H), 2.25/1.75 (2m, 2H), 1.9/1.46 (2m, 2H), 1.56 (quint., 2H), 1.35 (s, 9H), 1.13 (m, 2H)

ESI/FIA/HR and MS/MS: [M+H]+=397.2253 (397.2256)

Elemental analysis: C=61.19 (60.59); H=8.40 (8.39); N=7.29 (7.07)

RP: −41.120 (589 nm, T=19° C., C=0.9)

Intermediate 153: tert-Butyl (3S)-3-{4-[bis(tert-butoxycarbonyl)amino]butyl}-4-ethoxy-1-[[4-fluoro-2-(4-fluoro-3-methoxyphenyl)phenyl]methyl]-4-oxo-1,4-azaphosphinane-3-carboxylate Intermediate 153 is obtained starting from intermediates 129 and 273 in accordance with procedure F described hereinbefore.

$^1$H NMR: (400 MHz, dmso-d6) δ ppm 7.51 (dd, 1H), 7.28 (dd, 1H), 7.21 (dt, 1H), 7.09 (m, 1H), 7.09 (m, 1H), 6.93 (m, 1H), 3.93 (m, 2H), 3.88 (s, 3H), 3.52/3.35 (2*d, 2H), 3.4-3.25 (m, 2H), 2.72/2.21 (2*m, 2H), 2.72/2.34 (2*m, 2H), 1.9-1.65 (m, 2H), 1.9-1.65 (m, 2H), 1.41/1.33 (2*s, 27H), 1.38 (m, 2H), 1.18 (t, 3H), 0.7 (m, 2H)

EXAMPLE 201: (3S)-3-(4-AMINOBUTYL)-1-[[4-FLUORO-2-(4-FLUORO-3-METHOXYPHENYL)-PHENYL]METHYL]-4-HYDROXY-4-OXO-1,4-AZAPHOSPHINANE-3-CARBOXYLIC ACID

Example 201 is obtained starting from intermediate 153 in accordance with procedure D described hereinbefore.

$^1$H NMR: (400 MHz, dmso-d6) δ ppm 7.6 (dd, 1H), 7.25 (m, 2H), 7.15 (m, 2H), 6.95 (m, 1H), 4.4/4.3 (2*d, 2H), 3.9 (s, 3H), 3.5-3.3 (m, 1H), 3.2-3.05 (m, 2H), 2.95 (m, 2H), 2.9 (dd, 1H), 2.05 (m, 1H), 1.85 (m, 1H), 1.65 (m, 1H), 1.6 (m, 2H), 1.35 (m, 1H), 1.2-1 (m, 2H)

ESI/FIA/HR and MS/MS: [M+H]+=483.1854 (483.1855)

Elemental analysis: C=57.37 (57.26); H=5.95 (6.06); N=5.86 (5.81)

RP: −21.910 (589 nm, T=21° C., C=1.1)

Intermediate 154: tert-Butyl (3S)-3-{4-[bis(tert-butoxycarbonyl)amino]butyl}-4-ethoxy-1-[(2-isoquinolin-4-ylphenyl)methyl]-4-oxo-1,4-azaphosphinane-3-carboxylate Intermediate 154 is obtained starting from intermediates 129 and 264 in accordance with procedure F described hereinbefore.

$^1$H NMR: (400 MHz, dmso-d6) δ ppm 9.35 (d, 1H), 8.32 (d, 1H), 8.21 (m, 1H), 7.71 (m, 2H), 7.6 (2*d, 1H), 7.5 (2*t, 1H), 7.42 (t, 1H), 7.31 (m, 1H), 7.25 (m, 2H), 3.87 (m, 2H), 3.45-3.3 (m, 2H), 3.32/3.2/3.05 (m, 2H), 2.62/2.2 (m, 2H), 2.58/2 (m, 2H), 1.8-1.25 (m, 6H), 1.6 (m, 2H), 1.42/1.4 (2*s, 18H), 1.32/1.3 (2*s, 9H), 1.1 (m, 3H)

$^{31}$P NMR: (400 MHz, dmso-d6) δ ppm 44.94

EXAMPLE 202: (3S)-3-(4-AMINOBUTYL)-4-HYDROXY-1-[(2-ISOQUINOLIN-4-YLPHENYL)-METHYL]-4-OXO-1,4-AZAPHOSPHINANE-3-CARBOXYLIC ACID

Example 202 is obtained starting from intermediate 154 in accordance with procedure D described hereinbefore.

$^1$H NMR: (400 MHz, D2O) δ ppm 9.3 (s, 1H), 8.35/8 (2*s, 1H), 8.2 (m, 1H), 7.8-7.4 (m, 7H), 4.4-3.8 (2AB, 2H), 3.6-3.2/3 (m, 2H), 3.1/2.7 (m, 2H), 2.91 (m, 2H), 2.1/1.55 (m, 2H), 1.75/1.25 (m, 2H), 1.6 (m, 2H), 1.15-0.75 (m, 2H)

$^{31}$P NMR: (400 MHz, D2O) δ ppm 25.29

ESI/FIA/HR and MS/MS: [M+H]+=468.2046 (468.2047)

Elemental analysis: C=64.83 (64.23); H=5.86 (6.47); N=9.17 (8.99)

Intermediate 155: tert-Butyl (3S)-3-{4-[bis(tert-butoxycarbonyl)amino]butyl}-4-ethoxy-1-[[2-(2-methoxypyridin-4-yl)phenyl]methyl]-4-oxo-1,4-azaphosphinane-3-carboxylate Intermediate 155 is obtained starting from intermediates 129 and 244 in accordance with procedure F described hereinbefore.

$^1$H NMR: (400 MHz, dmso-d6) δ ppm 8.2 (d, 1H), 7.5 (m, 1H), 7.45-7.3 (2m, 2H), 7.25 (m, 1H), 7 (dd, 1H), 6.8 (sl, 1H), 3.9 (m, 2H), 3.9 (s, 3H), 3.6/3.35 (dd, 2H), 3.3 (m, 2H), 2.75/2.35 (dd, 2H), 2.7/2.25 (2m, 2H), 1.95/1.75 (2m, 2H), 1.75 (m, 2H), 1.4 (s, 18H), 1.35 (s, 9H), 1.3 (m, 2H), 1.2 (t, 3H), 0.7-0.5 (m, 2H)

EXAMPLE 203: (3S)-3-(4-AMINOBUTYL)-4-HYDROXY-1-[[2-(2-METHOXYPYRIDIN-4-YL)PHENYL]METHYL]-4-OXO-1,4-AZAPHOSPHINANE-3-CARBOXYLIC ACID

Example 203 is obtained starting from intermediate 155 in accordance with procedure D described hereinbefore.

$^1$H NMR: (400 MHz, D2O) δ ppm 8.18 (d, 1H), 7.65-7.35 (m, 4H), 7.02 (d, 1H), 6.85 (s, 1H), 4.35 (dd, 2H), 3.9 (s, 3H), 3.65-3 (m, 3H), 3-2.8 (m, 3H), 2.1/1.7 (2m, 2H), 1.85/1.35 (2m, 2H), 1.6 (m, 2H), 1.1 (m, 2H)

ESI/FIA/HR and MS/MS: [M+H]+=448.1989 (448.2001)

Elemental analysis: C=59.15 (59.05); H=6.25 (6.76); N=9.64 (9.39)

RP: −11.440 (589 nm, T=19.5° C., C=0.9)

EXAMPLE 204: (3S)-3-(4-AMINOBUTYL)-4-HYDROXY-4-OXO-1-[[2-(2-OXO-1H-PYRIDIN-4-YL)PHENYL]METHYL]-1,4-AZAPHOSPHINANE-3-CARBOXYLIC ACID

Example 204 is obtained starting from intermediate 155 in accordance with procedure D described hereinbefore.

$^1$H NMR: (300 MHz, D2O) δ ppm 7.65-7.3 (m, 4H), 7.6 (d, 1H), 6.55 (s, 1H), 6.5 (d, 1H), 4.35 (dd, 2H), 3.5 (2m, 2H), 3.25/2.9 (2m, 2H), 2.9 (m, 2H), 2.15/1.7 (2m, 2H), 1.85/1.4 (2m, 2H), 1.6 (m, 2H), 1.1 (m, 2H)

ESI/FIA/HR and MS/MS: [M+H]+=434.1838 (434.1839)

Elemental analysis: C=58.88 (58.19); H=6.31 (6.51); N=9.95 (9.69)

RP: −10.530 (589 nm, T=19° C., C=1.0)

Intermediate 156: tert-Butyl (3S)-3-{4-[bis(tert-butoxycarbonyl)amino]butyl}-4-ethoxy-4-oxo-1-{2-[1-(tetrahydro-2H-pyran-2-yl)-1H-pyrazol-5-yl]benzyl}-1,4-azaphosphinane-3-carboxylate Intermediate 156 is obtained starting from intermediates 129 and 293 in accordance with procedure F described hereinbefore.

$^1$H NMR: (400 MHz, dmso-d6) δ ppm 7.6 (d, 1H), 7.6-7.2 (m, 4H), 6.3 (d, 1H), 4.9-4.8 (dd, 1H), 4-3.8 (m, 4H), 3.5-3.2 (m, 4H), 2.85-2.6 (m, 2H), 2.5-2.1 (m, 3H), 2-1.65 (m, 6H), 1.5-1.25 (m, 5H), 1.4 (s, 18H), 1.35 (s, 9H), 1.2 (t, 3H), 0.85-0.6 (m, 2H)

EXAMPLE 205: (3S)-3-(4-AMINOBUTYL)-4-HYDROXY-4-OXO-1-[2-(1H-PYRAZOL-3-YL)BENZYL]-1,4-AZAPHOSPHINANE-3-CARBOXYLIC ACID

Example 205 is obtained starting from intermediate 156 in accordance with procedure D described hereinbefore.

$^1$H NMR: (300/400/500 MHz, dmso-d6) δ ppm 7.62 (d, 1H), 7.6 (d, 1H), 7.38 (t, 1H), 7.33 (d, 1H), 7.26 (t, 1H), 6.55 (d, 1H), 4.32/4.05 (dd, 2H), 3.59/3.19 (dd, 2H), 3.33/2.93 (dd, 2H), 2.74 (m, 2H), 2.11/1.61 (2*m, 2H), 1.73/1.29 (2*m, 2H), 1.41 (m, 2H), 1.04/0.88 (2*m, 2H)

ESI/FIA/HR and MS/MS: [M+H]+=407.1843 (407.1848)

Elemental analysis: C=56.28 (56.15); H=6.42 (6.70); N=13.82 (13.79)

RP: −84.390 (589 nm, T=19° C., C=1.1)

Intermediate 157: tert-Butyl (3S)-3-{4-[bis(tert-butoxycarbonyl)amino]butyl}-1-[[2-(2-chlorophenyl)-4-fluorophenyl]methyl]-4-ethoxy-4-oxo-1,4-azaphosphinane-3-carboxylate Intermediate 157 is obtained starting from intermediates 129 and 253 in accordance with procedure F described hereinbefore.

$^1$H NMR: (300/400 MHz, dmso-d6) δ ppm 7.65-7.4 (m, 4H), 7.25 (m, 2H), 7 (m, 1H), 3.9 (m, 2H), 3.35 (d, 1H), 3.3 (m, 2H), 3.15 (d, 1H), 2.8-2.55 (m, 2H), 2.3 (m, 1H), 2.1 (m, 1H), 1.95-1.7 (m, 4H), 1.45 (m, 2H), 1.45/1.35 (2*s, 27H), 1.15 (t, 3H), 0.75 (m, 2H)

$^{19}$F NMR: (300/400 MHz, dmso-d6) δ ppm −114.5

ESI/FIA/HR and MS/MS: [M+H]+=753.3436 (753.3441)

EXAMPLE 206: (3S)-3-(4-AMINOBUTYL)-1-[[2-(2-CHLOROPHENYL)-4-FLUOROPHENYL]METHYL]-4-HYDROXY-4-OXO-1,4-AZAPHOSPHINANE-3-CARBOXYLIC ACID

Example 206 is obtained starting from intermediate 157 in accordance with procedure D described hereinbefore.

$^1$H NMR: (300/400 MHz, dmso-d6) δ ppm 7.7-7.35 (m, 4H), 7.35-7.2 (m, 2H), 7.1 (m, 1H), 4.1 (sl, 2H), 3.7-3 (m, 3H), 3-2.7 (m, 3H), 2.2-2 (m, 1H), 1.8 (m, 1H), 1.65 (m, 1H), 1.55 (m, 2H), 1.45-1 (m, 3H)

ESI/FIA/HR and MS/MS: [M+H]+=469.1456 (469.1454)

Elemental analysis: C=56.86 (56.35); H=5.21 (5.80); N=5.91 (5.97)

RP: −15.060 (589 nm, T=20° C., C=1.0)

Intermediate 158: tert-Butyl (3S)-3-{4-[bis(tert-butoxycarbonyl)amino]butyl}-1-[[2-(2,3-dimethoxyphenyl)phenyl]methyl]-4-hydroxy-4-oxo-1,4-azaphosphinane-3-carboxylate Intermediate 158 is obtained starting from intermediate 129 and 2-(2,3-dimethoxyphenylbezaldehyde) in accordance with procedure F described hereinbefore.

$^1$H NMR: (400 MHz, dmso-d6) δ ppm 7.5 (m, 1H), 7.35-7.2 (2m, 2H), 7.1 (m, 1H), 7.05-7 (2m, 2H), 6.7 (dd, 1H), 3.9 (m, 2H), 3.85 (s, 3H), 3.45 (s, 3H), 3.4 (m, 2H), 3.35 (dd, 2H), 2.7/2.4 (2m, 2H), 2.65/2.2 (2m, 2H), 1.95-1.7 (m, 4H), 1.45 (s, 18H), 1.4 (m, 2H), 1.35 (s, 9H), 1.2 (t, 3H), 0.9 (m, 2H)

ESI/FIA/HR and MS/MS: [M+H]+=761.4136 (761.4142)

EXAMPLE 207: (3S)-3-(4-AMINOBUTYL)-1-[[2-(2,3-DIMETHOXYPHENYL)PHENYL]METHYL]-4-HYDROXY-4-OXO-1,4-AZAPHOSPHINANE-3-CARBOXYLIC ACID

Example 207 is obtained starting from intermediate 158 in accordance with procedure D described hereinbefore.

$^1$H NMR: (400 MHz, D2O) δ ppm 7.65-7.35 (m, 4H), 7.25 (m, 1H), 7.2 (m, 1H), 6.9-6.8 (2dd, 1H), 4.35-3.9 (2dd, 2H), 3.86 (s, 3H), 3.7-2.65 (m, 4H), 3.4-3.35 (2s, 3H), 2.9 (m, 2H), 2.5-1.6 (m, 4H), 1.6 (m, 2H), 1.5-0.9 (m, 2H)

ESI/FIA/HR and MS/MS: [M+H]+=477.2149 (477.2154)

Elemental analysis: C=61.06 (60.50); H=6.99 (6.98); N=5.97 (5.88)

Intermediate 159: tert-Butyl (3S)-3-{4-[bis(tert-butoxycarbonyl)amino]butyl)-4-hydroxy-1-[[2-(2-methylsulphonylphenyl)phenyl]methyl]-4-oxo-1,4-azaphosphinane-3-carboxylate Intermediate 159 is obtained starting from intermediate 129 and 2-(2-methylsulphonylphenyl)benzaldehyde in accordance with procedure F described hereinbefore.

$^1$H NMR: (300/400 MHz, dmso-d6) δ ppm 8.1 (d, 1H), 7.8-7.65 (2*m, 2H), 7.55 (d, 1H), 7.45 (m, 1H), 7.3 (d, 1H), 7.25 (d, 1H), 7.25 (m, 1H), 3.95 (m, 2H), 3.5-3.25 (m, 4H), 3.1 (dd, 1H), 2.9-2.6 (2*m, 2H), 2.85 (2*s, 3H), 2.45 (m, 1H), 2.3 (m, 1H), 2.1 (m, 1H), 2-1.65 (m, 4H), 1.5-1.3 (4s, 27H), 1.2 (m, 3H), 0.75 (m, 2H)

ESI/FIA/HR and MS/MS: [M+H]+=779.3696 (779.3701)

EXAMPLE 208: (3S)-3-(4-AMINOBUTYL)-4-HYDROXY-1-[[2-(2-METHYLSULPHONYLPHENYL)-PHENYL]METHYL]-4-OXO-1,4-AZAPHOSPHINANE-3-CARBOXYLIC ACID

Example 208 is obtained starting from intermediate 159 in accordance with procedure D described hereinbefore.

$^1$H NMR: (400 MHz, dmso-d6) δ ppm 8.2 (d, 1H), 7.9/7.8 (2*m, 2H), 7.8-7.4 (m, 4H), 7.55 (d, 1H), 4.4-3.8 (4d, 2H), 3.8-3.5 (m, 1H), 3.5-2.85 (m, 5H), 3.1/3 (2*s, 3H), 2.4-1.85 (m, 2H), 1.8 (m, 1H), 1.7 (m, 2H), 1.6-1.1 (m, 3H)

ESI/FIA/HR and MS/MS: [M+H]+=495.1716 (495.1713)

Elemental analysis: C=55.39 (55.86); H=5.77 (6.32); N=5.61 (5.66); S=6.24 (6.48)

Intermediate 160: tert-Butyl (3S)-3-{4-[bis(tert-butoxycarbonyl)amino]butyl}-4-ethoxy-1-[(2-naphthalen-2-ylphenyl)methyl]-4-oxo-1,4-azaphosphinane-3-carboxylate Intermediate 160 is obtained starting from intermediates 129 and 240 in accordance with procedure F described hereinbefore.
$^1$H NMR: (400 MHz, dmso-d6) δ ppm 8-7.3 (m, 11H), 3.9 (m, 2H), 3.6/3.4 (dd, 2H), 3.3 (m, 2H), 2.75/2.3 (2dd, 2H), 2.7/2.2 (2m, 2H), 1.9/1.7 (2m, 2H), 1.75 (m, 2H), 1.4 (s, 18H), 1.3 (m, 2H), 1.3 (s, 9H), 1.15 (t, 3H), 0.65 (m, 2H)

EXAMPLE 209: (3S)-3-(4-AMINOBUTYL)-4-HYDROXY-1-[(2-NAPHTHALEN-2-YLPHENYL)-METHYL]-4-OXO-1,4-AZAPHOSPHINANE-3-CARBOXYLIC ACID

Example 209 is obtained starting from intermediate 160 in accordance with procedure D described hereinbefore.
$^1$H NMR: (300 MHz, D2O) δ ppm 8-7.4 (m, 11H), 4.35 (dd, 2H), 3.35/3 (2m, 2H), 3.1/2.7 (2dd, 2H), 2.8 (m, 2H), 2/1.6 (2m, 2H), 1.75/1.2 (2m, 2H), 1.5 (m, 2H), 0.9 (m, 2H)
ESI/FIA/HR and MS/MS: [M+H]+=467.2095 (467.2099)
Elemental analysis: C=67.07 (66.94); H=6.46 (6.70); N=5.88 (6.00)
RP: −8.570 (589 nm, T=19° C., C=0.8)

Intermediate 161: tert-Butyl (3S)-3-{4-[bis(tert-butoxycarbonyl)amino]butyl}-1-[[4-chloro-2-(4-fluorophenyl)phenyl]methyl]-4-ethoxy-4-oxo-1,4-azaphosphinane-3-carboxylate Intermediate 161 is obtained starting from intermediate 129 and 4-chloro-2-(4-fluorophenyl)benzaldehyde in accordance with procedure F described hereinbefore.
$^1$H NMR: (400 MHz, dmso-d6) δ ppm 7.5 (d, 1H), 7.45 (dd, 1H), 7.4 (dd, 2H), 7.29 (t, 2H), 7.25 (d, 1H), 3.92 (m, 2H), 3.5/3.3 (AB, 2H), 3.3 (m, 2H), 2.72/2.2 (2*m, 2H), 2.67/2.35 (2*m, 2H), 2-1.7 (m, 2H), 1.8 (m, 2H), 1.4 (s, 18H), 1.35 (m, 2H), 1.32 (s, 9H), 1.18 (t, 3H), 0.7 (m, 2H)
$^{31}$P NMR: (400 MHz, dmso-d6) δ ppm 44.88, −113.8

EXAMPLE 210: (3S)-3-(4-AMINOBUTYL)-1-[[4-CHLORO-2-(4-FLUOROPHENYL)PHENYL]METHYL]-4-HYDROXY-4-OXO-1,4-AZAPHOSPHINANE-3-CARBOXYLIC ACID

Example 210 is obtained starting from intermediate 161 in accordance with procedure D described hereinbefore.
$^1$H NMR: (400 MHz, D2O) δ ppm 7.57 (d, 1H), 7.51 (dd, 1H), 7.45 (d, 1H), 7.36 (m, 2H), 7.24 (t, 2H), 4.4/4.27 (AB, 2H), 3.38/3.1 (m, 2H), 3.2/2.85 (m, 2H), 2.94 (m, 2H), 2.09/1.65 (m, 2H), 1.85/1.35 (m, 2H), 1.59 (m, 2H), 1.1 (m, 2H)
$^{31}$P NMR: (400 MHz, D2O) δ ppm 25.4, −110.5
ESI/FIA/HR and MS/MS: [M+H]+=469.1455 (469.1454)
Elemental analysis: C=56.27 (56.35); H=5.43 (5.80); N=5.97 (5.97); Cl=7.28 (7.56)
RP: −28.440 (589 nm, T=20° C., C=0.9)

Intermediate 162: tert-Butyl (3S)-3-{4-[bis(tert-butoxycarbonyl)amino]butyl}-4-ethoxy-1-[[4-fluoro-2-(4-hydroxyphenyl)phenyl]methyl]-4-oxo-1,4-azaphosphinane-3-carboxylate Intermediate 162 is obtained starting from intermediates 129 and 265 in accordance with procedure F described hereinbefore.
$^1$H NMR: (400 MHz, dmso-d6) δ ppm 9.6 (sl, 1H), 7.49 (dd, 1H), 7.18 (d, 2H), 7.12 (td, 1H), 6.98 (dd, 1H), 6.81 (d, 2H), 3.92 (m, 2H), 3.5/3.3 (AB, 2H), 3.3 (m, 2H), 2.72/2.2 (2*m, 2H), 2.67/2.35 (2*m, 2H), 2-1.7 (m, 2H), 1.8 (m, 2H), 1.4 (s, 18H), 1.35 (m, 2H), 1.32 (s, 9H), 1.18 (t, 3H), 0.7 (m, 2H)
$^{31}$P NMR: (400 MHz, dmso-d6) δ ppm 45.1, −114.8

EXAMPLE 211: (3S)-3-(4-AMINOBUTYL)-1-[[4-FLUORO-2-(4-HYDROXYPHENYL)PHENYL]-METHYL]-4-HYDROXY-4-OXO-1,4-AZAPHOSPHINANE-3-CARBOXYLIC ACID

Example 211 is obtained starting from intermediate 162 in accordance with procedure D described hereinbefore.
$^1$H NMR: (400 MHz, D2O) δ ppm 7.47 (dd, 1H), 7.12 (d, 2H), 7.09 (td, 1H), 7.01 (dd, 1H), 6.88 (d, 2H), 4.3/4.16 (AB, 2H), 3.23/2.98 (m, 2H), 3/2.7 (m, 2H), 2.81 (m, 2H), 1.96/1.55 (m, 2H), 1.72/1.21 (m, 2H), 1.49 (m, 2H), 0.95 (m, 2H)
$^{31}$P NMR: (400 MHz, D2O) δ ppm 25.4, −113
ESI/FIA/HR and MS/MS: [M+H]+=451.1794 (451.1793)
Elemental analysis: C=58.16 (58.66); H=5.71 (6.27); N=6.30 (6.22)
RP: −16.520 (589 nm, T=20° C., C=0.9)

Intermediate 163: tert-Butyl (3S)-3-{4-[bis(tert-butoxycarbonyl)amino]butyl}-4-ethoxy-1-[4-fluoro-2-(1-methyl-1H-pyrazol-4-yl)benzyl]-4-oxo-1,4-azaphosphinane-3-carboxylate Intermediate 163 is obtained starting from intermediates 129 and 250 in accordance with procedure F described hereinbefore.
$^1$H NMR: (300 MHz, dmso-d6) δ ppm 8 (s, 1H), 7.7 (s, 1H), 7.4 (dd, 1H), 7.2 (dd, 1H), 7.05 (td, 1H), 3.97 (m, 2H), 3.9 (s, 3H), 3.6/3.4 (dd, 2H), 3.25 (m, 2H), 3/2.35 (2m, 2H), 2.8/2.45 (2m, 2H), 2 (m, 2H), 1.8 (m, 2H), 1.4 (s, 18H), 1.35 (s, 9H), 1.3 (m, 2H), 1.2 (t, 3H), 0.65 (m, 2H)

EXAMPLE 212: (3S)-3-(4-AMINOBUTYL)-1-[4-FLUORO-2-(1-METHYL-1H-PYRAZOL-4-YL)BENZYL]-4-HYDROXY-4-OXO-1,4-AZAPHOSPHINANE-3-CARBOXYLIC ACID

Example 212 is obtained starting from intermediate 163 in accordance with procedure D described hereinbefore.
$^1$H NMR: (300 MHz, D2O) δ ppm 7.81 (s, 1H), 7.7 (s, 1H), 7.6 (dd, 1H), 7.2 (m, 2H), 4.45 (dd, 2H), 3.95 (s, 3H), 3.5/3.25 (2m, 2H), 3.3/3 (2m, 2H), 3 (m, 2H), 2.1/1.75 (2m, 2H), 1.9/1.4 (2m, 2H), 1.65 (m, 2H), 1.15 (m, 2H)
$^{19}$F NMR: (300 MHz, D2O) δ ppm −110.5
ESI/FIA/HR and MS/MS: [M+H]+=439.1905 (439.1910)
Elemental analysis: C=54.79 (54.79); H=6.05 (6.44); N=12.61 (12.78)
RP: −18.620 (589 nm, T=19° C., C=0.9)

Intermediate 164: tert-Butyl (3S)-3-{4-[bis(tert-butoxycarbonyl)amino]butyl}-4-ethoxy-1-[(4-fluoro-2-thiophen-2-ylphenyl)methyl]-4-oxo-1,4-azaphosphinane-3-carboxylate Intermediate 164 is obtained starting from intermediates 129 and 246 in accordance with procedure F described hereinbefore.
$^1$H NMR: (300 MHz, dmso-d6) δ ppm 7.66 (dd, 1H), 7.47 (dd, 1H), 7.31 (dd, 1H), 7.25 (dd, 1H), 7.2 (dd, 1H), 7.16 (td, 1H), 3.97 (m, 2H), 3.63/3.4 (dd, 2H), 3.25 (m, 2H), 2.88/2.32 (2m, 2H), 2.79/2.42 (dd, 2H), 2.05-1.9 (m, 2H), 1.82 (m, 2H), 1.39 (s, 18H), 1.33 (s, 9H), 1.3 (m, 2H), 1.2 (t, 3H), 0.7-0.4 (2m, 2H)
$^{19}$F NMR: (300 MHz, dmso-d6) δ ppm −113.9

EXAMPLE 213: (3S)-3-(4-AMINOBUTYL)-1-[(4-FLUORO-2-THIOPHEN-2-YLPHENYL)METHYL]-4-HYDROXY-4-OXO-1,4-AZAPHOSPHINANE-3-CARBOXYLIC ACID

Example 213 is obtained starting from intermediate 164 in accordance with procedure D described hereinbefore.
$^{1}$H NMR: (300 MHz, dmso-d6) δ ppm 7.65 (dd, 1H), 7.55 (dd, 1H), 7.29 (dd, 1H), 7.2 (td, 1H), 7.15 (m, 2H), 4.5 (dd, 2H), 3.5/3.2 (2m, 2H), 3.3/2.9 (2m, 2H), 2.9 (m, 2H), 2.1/1.75 (2m, 2H), 1.85/1.4 (2m, 2H), 1.6 (m, 2H), 1.1 (m, 2H)
$^{19}$F NMR: (300 MHz, dmso-d6) δ ppm −110
ESI/FIA/HR and MS/MS: [M+H]+=441.1405 (441.1413)
Elemental analysis: C=54.66 (54.54); H=5.90 (5.95); N=6.35 (6.36); S=7.27 (7.28)
RP: −13.110 (589 nm, T=19.5° C., C=0.7)

Intermediate 165: tert-Butyl (3S)-3-{4-bis(tert-butoxycarbonyl)amino]butyl}-4-ethoxy-1-[(2-isoquinolin-5-ylphenyl)methyl]-4-oxo-1,4-azaphosphinane-3-carboxylate Intermediate 165 is obtained starting from intermediates 129 and 216 in accordance with procedure F described hereinbefore.
$^{1}$H NMR: (400 MHz, dmso-d6) δ ppm 9.4 (s, 1H), 8.45 (d, 1H), 8.2 (m, 1H), 7.75 (m, 1H), 7.65 (m, 1H), 7.6-7.4 (m, 3H), 7.2 (m, 1H), 7.15 (2*d, 1H), 3.95-3.7 (m, 2H), 3.5-3 (m, 4H), 3.5-3.3 (m, 2H), 2.7-2.4 (m, 2H), 2.2 (m, 1H), 2 (m, 1H), 1.85 (m, 1H), 1.8 (m, 2H), 1.7-1.5 (m, 1H), 1.5-1.25 (4s, 27H), 1.1 (t, 3H), 0.75-0.5 (m, 2H)

EXAMPLE 214: (3S)-3-(4-AMINOBUTYL)-4-HYDROXY-1-[(2-ISOQUINOLIN-5-YLPHENYL)-METHYL]-4-OXO-1,4-AZAPHOSPHINANE-3-CARBOXYLIC ACID

Example 214 is obtained starting from intermediate 165 in accordance with procedure D described hereinbefore.
$^{1}$H NMR: (400 MHz, D2O) δ ppm 9.25 (s, 1H), 8.3 (dd, 1H), 8.2 (m, 1H), 7.85-7.55 (m, 5H), 7.35 (m, 1H), 7.3 (d, 1H), 4.45-3.8 (4d, 2H), 3.65-3.05 (m, 2H), 3.05-2.8 (m, 3H), 2.7 (m, 1H), 2.1 (m, 1H), 1.75 (m, 1H), 1.7-1.5 (m, 3H), 1.35-0.6 (m, 3H)
ESI/FIA/HR and MS/MS: [M+H]+=468.2051 (468.2047)
Elemental analysis: C=64.96 (64.23); H=6.08 (6.47); N=9.03 (8.99)

Intermediate 166: tert-Butyl (3S)-3-{4-[bis(tert-butoxycarbonyl)amino]butyl}-4-ethoxy-1-[(4-fluoro-2-naphthalen-2-ylphenyl)methyl]-4-oxo-1,4-azaphosphinane-3-carboxylate Intermediate 166 is obtained starting from intermediates 129 and 247 in accordance with procedure F described hereinbefore.
$^{1}$H NMR: (400 MHz, dmso-d6) δ ppm 8-7.9 (m, 3H), 7.9 (sl, 1H), 7.6-7.5 (m, 4H), 7.25 (td, 1H), 7.15 (dd, 1H), 3.9 (m, 2H), 3.6/3.4 (dd, 2H), 3.3 (m, 2H), 2.75/2.3 (2m, 2H), 2.7/2.2 (2m, 2H), 1.9/1.75 (2m, 2H), 1.75 (m, 2H), 1.4 (s, 18H), 1.3 (s, 9H), 1.3 (m, 2H), 1.15 (t, 3H), 0.7 (m, 2H)

EXAMPLE 215: (3S)-3-(4-AMINOBUTYL)-1-[(4-FLUORO-2-NAPHTHALEN-2-YLPHENYL)METHYL]-4-HYDROXY-4-OXO-1,4-AZAPHOSPHINANE-3-CARBOXYLIC ACID

Example 215 is obtained starting from intermediate 166 in accordance with procedure D described hereinbefore.
$^{1}$H NMR: (400 MHz, D2O) δ ppm 8.08 (d, 1H), 8 (m, 2H), 7.95 (d, 1H), 7.7 (dd, 1H), 7.65 (m, 2H), 7.54 (dd, 1H), 7.3 (m, 1H), 7.3 (dd, 1H), 4.65-4.2 (m, 2H), 3.35/3.05 (2m, 2H), 3.05/2.8 (2m, 2H), 2.85 (m, 2H), 2/1.65 (2m, 2H), 1.85/1.35 (2m, 2H), 1.55 (m, 2H), 0.9 (m, 2H)
ESI/FIA/HR and MS/MS: [M+H]+=485.2002 (485.2005)
Elemental analysis: C=63.97 (64.45); H=6.21 (6.24); N=5.93 (5.78)
RP: −6.790 (589 nm, T=19° C., C=0.7)

Intermediate 167: tert-Butyl (3S)-3-{4-[bis(tert-butyloxycarbonyl)amino]butyl}-1-[[2-(1-benzothiophen-2-yl)-4-fluorophenyl]methyl]-4-ethoxy-4-oxo-1,4-azaphosphinane-3-carboxylate Intermediate 167 is obtained starting from intermediates 129 and 217 in accordance with procedure F described hereinbefore.
$^{1}$H NMR: (400 MHz, dmso-d6) δ ppm 8.05 (d, 1H), 7.9 (d, 1H), 7.6 (s, 1H), 7.55 (dd, 1H), 7.4 (m, 2H), 7.35 (d, 1H), 7.3 (m, 1H), 3.95 (m, 2H), 3.75 (d, 1H), 3.5 (d, 1H), 3.25 (m, 2H), 2.95 (m, 1H), 2.8 (m, 1H), 2.45 (dd, 1H), 2.35 (m, 1H), 2.05-1.6 (m, 4H), 1.42 (m, 2H), 1.4 (s, 18H), 1.35 (s, 9H), 1.2 (t, 3H), 0.65 (m, 1H), 0.55 (m, 1H)

EXAMPLE 216: (3S)-3-(4-AMINOBUTYL)-1-[[2-(1-BENZOTHIOPHEN-2-YL)-4-FLUOROPHENYL]-METHYL]-4-HYDROXY-4-OXO-1,4-AZAPHOSPHINANE-3-CARBOXYLIC ACID

Example 216 is obtained starting from intermediate 167 in accordance with procedure D described hereinbefore.
$^{1}$H NMR: (400 MHz, D2O) δ ppm 7.95/7.9 (2*d, 2H), 7.65 (m, 1H), 7.45 (m, 2H), 7.4 (s, 1H), 7.3 (m, 2H), 4.55/4.4 (2*d, 2H), 3.6-3.4 (m, 1H), 3.25 (m, 1H), 3.15 (m, 1H), 2.9 (dd, 1H), 2.85 (m, 2H), 2.1 (m, 1H), 1.85 (m, 1H), 1.65 (m, 1H), 1.6-0.85 (m, 5H)
ESI/FIA/HR and MS/MS: [M+H]+=491.1565 (491.1564)
Elemental analysis: C=59.10 (58.77); H=5.38 (5.75); N=5.84 (5.71); S=6.42 (6.54)
RP: 0.930 (589 nm, T=20.5° C., C=1.0)

Intermediate 168: tert-Butyl (3S)-3-{4-[bis(tert-butoxycarbonyl)amino]butyl}-4-ethoxy-1-[4-fluoro-2-(1-methyl-1H-imidazol-5-yl)benzyl]-4-oxo-1,4-azaphosphinane-3-carboxylate Intermediate 168 is obtained starting from intermediates 129 and 248 in accordance with procedure F described hereinbefore.
$^{1}$H NMR: (400 MHz, dmso-d6) δ ppm 7.75 (s, 1H), 7.56 (2d, 1H), 7.29 (2t, 1H), 7.15 (2d, 1H), 6.9 (s, 1H), 3.95 (m, 2H), 3.5-3.25 (m, 4H), 3.4 (s, 3H), 2.9/2.2 (2m, 2H), 2.65/2.3 (2m, 2H), 1.95/1.85 (2m, 2H), 1.85 (m, 2H), 1.4 (m, 2H), 1.4 (2s, 18H), 1.35 (2s, 9H), 1.2 (t, 3H), 1.1-0.65 (m, 2H)

EXAMPLE 217: (3S)-3-(4-AMINOBUTYL)-1-[4-FLUORO-2-(1-METHYL-1H-IMIDAZOL-5-YL)BENZYL]-4-HYDROXY-4-OXO-1,4-AZAPHOSPHINANE-3-CARBOXYLIC ACID

Example 217 is obtained starting from intermediate 168 in accordance with procedure D described hereinbefore.
$^1$H NMR: (400 MHz, D2O) δ ppm 7.8 (s, 1H), 7.68 (dd, 1H), 7.33 (td, 1H), 7.22 (dd, 1H), 7.1 (s, 1H), 4.25/4.18 (AB, 2H), 3.6/3.2 (2m, 2H), 3.45 (s, 3H), 3.3/3 (2m, 2H), 2.95 (m, 2H), 2.12/1.71 (2m, 2H), 1.9/1.42 (2m, 2H), 1.6 (m, 2H), 1.3-1 (m, 2H)
$^{19}$F NMR: (400 MHz, D2O) δ ppm −109.75
ESI/FIA/HR and MS/MS: [M+H]+=439.1905 (439.1905)
Elemental analysis: C=54.41 (54.79); H=6.12 (6.44); N=12.74 (12.78)
RP: −27.720 (589 nm, T=20° C., C=0.7)

Intermediate 169: tert-Butyl (3S)-3-{4-[bis(tert-butoxycarbonyl)amino]butyl}-1-[[4-chloro-2-(4-methylphenyl)phenyl]methyl]-4-ethoxy-4-oxo-1,4-azaphosphinane-3-carboxylate Intermediate 169 is obtained starting from intermediate 129 and 4-chloro-2-(4-methylphenyl)benzaldehyde in accordance with procedure F described hereinbefore.
$^1$H NMR: (400 MHz, dmso-d6) δ ppm 7.52 (d, 1H), 7.4 (dd, 1H), 7.25 (dd, 4H), 7.2 (d, 1H), 3.9 (m, 2H), 3.5/2.8 (dd, 2H), 2.8 (m, 2H), 2.75/2.2 (2m, 2H), 2.65/2.3 (2dd, 2H), 2.35 (s, 3H), 1.95/1.8 (2m, 2H), 1.8 (m, 2H), 1.4 (s, 18H), 1.35 (m, 2H), 1.35 (s, 9H), 1.18 (t, 3H), 0.7 (m, 2H)

EXAMPLE 218: (3S)-3-(4-AMINOBUTYL)-1-[[4-CHLORO-2-(4-METHYLPHENYL)PHENYL]METHYL]-4-HYDROXY-4-OXO-1,4-AZAPHOSPHINANE-3-CARBOXYLIC ACID

Example 218 is obtained starting from intermediate 169 in accordance with procedure D described hereinbefore.
$^1$H NMR: (400 MHz, D2O) δ ppm 7.58 (d, 1H), 7.5 (dd, 1H), 7.42 (d, 1H), 7.38 (d, 2H), 7.23 (d, 2H), 4.4/4.25 (AB, 2H), 3.35/3.1 (2m, 2H), 3.2/2.81 (2m, 2H), 2.95 (m, 2H), 2.39 (s, 3H), 2.09/1.68 (2m, 2H), 1.85/1.35 (2m, 2H), 1.6 (m, 2H), 1.2-1 (m, 2H)
ESI/FIA/HR and MS/MS: [M+H]+=465.1707 (465.1704)
Elemental analysis: C=60.11 (59.42); H=6.34 (6.50); N=6.09 (6.03)
RP: −26.100 (589 nm, T=20° C., C=0.3)

Intermediate 170: tert-Butyl (3S)-3-{4-[bis(tert-butoxycarbonyl)amino]butyl}-1-[2-(1,2-dimethyl-1H-imidazol-5-yl)-4-fluorobenzyl]-4-ethoxy-4-oxo-1,4-azaphosphinane-3-carboxylate Intermediate 170 is obtained starting from intermediates 129 and 274 in accordance with procedure F described hereinbefore.
$^1$H NMR: (300/400 MHz, dmso-d6) δ ppm 7.55 (dd, 1H), 7.2 (m, 1H), 7 (d, 1H), 6.75 (s, 1H), 4.05-3.7 (m, 4H), 3.5-3.3 (2*d, 2H), 3.25 (s, 3H), 3-2.2 (m, 4H), 2.35 (s, 3H), 2-1.3 (m, 6H), 1.4 (3s, 27H), 1.25 (m, 3H), 0.85 (m, 2H)

EXAMPLE 219: (3S)-3-(4-AMINOBUTYL)-1-[2-(1,2-DIMETHYL-1H-IMIDAZOL-5-YL)-4-FLUOROBENZYL]-4-HYDROXY-4-OXO-1,4-AZAPHOSPHINANE-3-CARBOXYLIC ACID

Example 219 is obtained starting from intermediate 170 in accordance with procedure D described hereinbefore.
$^1$H NMR: (400 MHz, D2O) δ ppm 7.75 (dd, 1H), 7.55 (s, 1H), 7.5 (m, 1H), 7.3 (dd, 1H), 4.25 (s, 2H), 3.55 (m, 1H), 3.45 (s, 3H), 3.4 (m, 1H), 3.25 (m, 1H), 3.15 (dd, 1H), 2.95 (t, 2H), 2.65 (s, 3H), 2.15 (m, 1H), 1.9 (m, 1H), 1.75 (m, 1H), 1.65 (m, 2H), 1.45 (m, 1H), 1.3 (m, 1H), 1.15 (m, 1H)
ESI/FIA/HR and MS/MS: [M+H]+=453.2058 (453.2061)
Elemental analysis: C=46.18 (47.29); H=5.24 (5.86); N=10.02 (10.50)
RP: −28.200 (589 nm, T=20° C., C=1.0)

Intermediate 171: tert-Butyl (3S)-3-{4-[bis(tert-butoxycarbonyl)amino]butyl}-4-ethoxy-1-[(4-fluoro-2-imidazo[1,2-a]pyridin-3-ylphenyl)methyl]-4-oxo-1,4-azaphosphinane-3-carboxylate Intermediate 171 is obtained starting from intermediates 129 and 234 in accordance with procedure F described hereinbefore.
$^1$H NMR: (300 MHz, dmso-d6) δ ppm 7.9 (d, 1H), 7.65 (m, 2H), 7.65 (s, 1H), 7.35-7.2 (m, 3H), 6.9 (m, 1H), 3.9 (quad., 2H), 3.35 (t, 2H), 3.35/3.25 (2*d, 2H), 2.8-2.4 (m, 3H), 2.4 (dd, 1H), 2.2 (m, 1H), 1.9-1.6 (m, 3H), 1.5-1.3 (m, 2H), 1.45 (s, 18H), 1.35 (s, 9H), 1.15 (t, 3H), 1-0.75 (m, 2H)

EXAMPLE 220: (3S)-3-(4-AMINOBUTYL)-1-[(4-FLUORO-2-IMIDAZO[1,2-A]PYRIDIN-3-YLPHENYL)METHYL]-4-HYDROXY-4-OXO-1,4-AZAPHOSPHINANE-3-CARBOXYLIC ACID

Example 220 is obtained starting from intermediate 171 in accordance with procedure D described hereinbefore.
$^1$H NMR: (400 MHz, D2O) δ ppm 8.05 (d, 1H), 7.75 (dd, 1H), 7.7 (d, 1H), 7.7 (s, 1H), 7.45 (m, 1H), 7.4 (m, 1H), 7.3 (d, 1H), 7 (m, 1H), 4.6-4 (m, 2H), 3.45 (m, 1H), 3.05 (m, 2H), 2.9 (m, 2H), 2.8 (dd, 1H), 2.1 (m, 1H), 1.8 (m, 1H), 1.65 (m, 1H), 1.55 (m, 2H), 1.3 (m, 1H), 0.95 (m, 2H)
ESI/FIA/HR and MS/MS: [M+H]+=475.1906 (475.1905)
Elemental analysis: C=58.69 (58.22); H=5.71 (5.95); N=11.94 (11.81)
RP: −27.190 (589 nm, T=20° C., C=1.0)

Intermediate 172: tert-Butyl (3S)-3-{4-[bis(tert-butoxycarbonyl)amino]butyl}-4-ethoxy-1-[[4-fluoro-2-(2-methoxypyridin-4-yl)phenyl]methyl]-4-oxo-1,4-azaphosphinane-3-carboxylate Intermediate 172 is obtained starting from intermediates 129 and 249 in accordance with procedure F described hereinbefore.
$^1$H NMR: (400 MHz, dmso-d6) δ ppm 8.23 (d, 1H), 7.52 (dd, 1H), 7.26 (td, 1H), 7.11 (dd, 1H), 7.01 (dd, 1H), 6.85 (sl, 1H), 3.94 (m, 2H), 3.9 (s, 3H), 3.53/3.34 (dd, 2H), 3.31 (m, 2H), 2.74/2.24 (2m, 2H), 2.68/2.37 (2dd, 2H), 1.93/1.75 (2m, 2H), 1.86-1.66 (m, 2H), 1.41 (s, 18H), 1.36 (m, 2H), 1.35 (s, 9H), 1.19 (2m, 2H), 0.69/0.61 (t, 3H)

EXAMPLE 221: (3S)-3-(4-AMINOBUTYL)-1-[[4-FLUORO-2-(2-METHOXYPYRIDIN-4-YL)PHENYL]-METHYL]-4-HYDROXY-4-OXO-1,4-AZAPHOSPHINANE-3-CARBOXYLIC ACID

Example 221 is obtained starting from intermediate 172 in accordance with procedure D described hereinbefore.
$^1$H NMR: (400 MHz, D2O) δ ppm 8.17 (d, 1H), 7.64 (dd, 1H), 7.29 (td, 1H), 7.17 (dd, 1H), 7.01 (dd, 1H), 6.86 (s, 1H), 4.32 (dd, 2H), 3.9 (s, 3H), 3.45/3.07 (2m, 2H), 3.17/2.84

(2m, 2H), 2.9 (m, 2H), 2.1/1.68 (2m, 2H), 1.85/1.35 (2m, 2H), 1.6 (m, 2H), 1.07 (m, 2H)

ESI/FIA/HR and MS/MS: [M+H]+=466.1905 (466.1902)
Elemental analysis: C=56.79 (56.77); H=6.15 (6.28); N=8.94 (9.03)
RP: −9.530 (589 nm, T=19° C., C=1.0)

EXAMPLE 222: (3S)-3-(4-AMINOBUTYL)-1-[[4-FLUORO-2-(2-OXO-1H-PYRIDIN-4-YL)PHENYL]-METHYL]-4-HYDROXY-4-OXO-1,4-AZAPHOSPHINANE-3-CARBOXYLIC ACID

Example 222 is obtained starting from intermediate 172 in accordance with procedure D described hereinbefore.
$^1$H NMR: (400 MHz, D2O) δ ppm 7.64 (dd, 1H), 7.62 (d, 1H), 7.29 (td, 1H), 7.18 (dd, 1H), 6.57 (d, 1H), 6.53 (dd, 1H), 4.3 (dd, 2H), 3.51/3.15 (2m, 2H), 3.24/2.95 (2m, 2H), 2.92 (m, 2H), 2.13/1.7 (2m, 2H), 1.86/1.38 (2m, 2H), 1.58 (m, 2H), 1.1 (m, 2H)
$^{19}$F NMR: (400 MHz, D2O) δ ppm −109.6
ESI/FIA/HR and MS/MS: [M+H]+=452.1745 (452.1745)
Elemental analysis: C=56.06 (55.87); H=5.96 (6.03); N=9.21 (9.31)
RP: −10.270 (589 nm, T=19° C., C=0.9)

Intermediate 173: tert-Butyl (3S)-3-{4-[bis(tert-butoxycarbonyl)amino]butyl}-4-ethoxy-1-[[4-hydroxy-2-(4-methylphenyl)phenyl]methyl]-4-oxo-1,4-azaphosphinane-3-carboxylate Intermediate 173 is obtained starting from intermediates 129 and 266 in accordance with procedure F described hereinbefore.
$^1$H NMR: (400 MHz, dmso-d6) δ ppm 9.4 (s, 1H), 7.2 (s, 4H), 7.2 (d, 1H), 6.75 (dd, 1H), 6.7 (t, 1H), 6.55 (s, 1H), 3.95 (m, 2H), 3.4 (d, 1H), 3.25 (d, 1H), 2.8 (m, 3H), 2.7 (dd, 1H), 2.35 (s, 3H), 2.25 (dd, 1H), 2.15 (m, 1H), 1.9 (m, 1H), 1.85-1.7 (m, 3H), 1.35 (2s, 18H), 1.25 (m, 2H), 1.2 (t, 3H), 0.75 (m, 2H)

EXAMPLE 223: (3S)-3-(4-AMINOBUTYL)-4-HYDROXY-1-[[4-HYDROXY-2-(4-METHYLPHENYL)-PHENYL]METHYL]-4-OXO-1,4-AZAPHOSPHINANE-3-CARBOXYLIC ACID

Example 223 is obtained starting from intermediate 173 in accordance with procedure D described hereinbefore.
$^1$H NMR: (400 MHz, D2O) δ ppm 7.47 (d, 1H), 7.35 (d, 2H), 7.22 (d, 2H), 6.95 (dd, 1H), 6.83 (d, 1H), 4.32/4.19 (AB, 2H), 3.32/3.05 (2m, 2H), 3.18/2.77 (2m, 2H), 2.95 (m, 2H), 2.38 (s, 3H), 2.09/1.68 (2m, 2H), 1.85/1.35 (2m, 2H), 1.6 (m, 2H), 1.2-1 (m, 2H)
ESI/FIA/HR and MS/MS: [M+H]+=447.2045 (447.2043)
Elemental analysis: C=62.20 (61.87); H=6.77 (7.00); N=6.19 (6.27)
RP: −32.320 (589 nm, T=20° C., C=0.7)

Intermediate 174: tert-Butyl (3S)-3-{4-[bis(tert-butoxycarbonyl)amino]butyl}-4-ethoxy-1-[4-methoxy-2-(imidazo[1,2-a]pyridin-3-yl)benzyl]-4-oxo-1,4-azaphosphinane-3-carboxylate Intermediate 174 is obtained starting from intermediates 129 and 267 in accordance with procedure F described hereinbefore.
$^1$H NMR: (400 MHz, dmso-d6) δ ppm 7.98 (d, 1H), 7.66 (d, 1H), 7.63 (d, 1H), 7.5 (s, 1H), 7.29 (t, 1H), 7.1 (dd, 1H), 6.98 (d, 1H), 6.9 (t, 1H), 3.9 (m, 2H), 3.8 (s, 3H), 3.35 (m, 2H), 3.35/3.19 (AB, 2H), 2.7/2.25 (m, 2H), 2.62/2.1 (m, 2H), 1.85/1.7 (m, 2H), 1.65 (m, 2H), 1.4 (s, 18H), 1.35 (m, 2H), 1.3 (s, 9H), 1.15 (t, 3H), 0.65 (m, 2H)

EXAMPLE 224: (3S)-3-(4-AMINOBUTYL)-4-HYDROXY-1-[4-HYDROXY-2-(IMIDAZO[1,2-A]-PYRIDIN-3-YL)BENZYL]-4-OXO-1,4-AZAPHOSPHINANE-3-CARBOXYLIC ACID

Example 224 is obtained starting from intermediate 174 in accordance with procedure D described hereinbefore.
$^1$H NMR: (400 MHz, D2O) δ ppm 8 (d, 1H), 7.67 (s, 1H), 7.65 (d, 1H), 7.59 (d, 1H), 7.42 (t, 1H), 7.09 (dd, 1H), 6.99 (t, 1H), 6.96 (df, 1H), 4.15 (m, 2H), 3.4/3.02 (m, 2H), 3.02/2.72 (m, 2H), 2.9 (m, 2H), 2.1/1.6 (m, 2H), 1.75/1.22 (m, 2H), 1.5 (m, 2H), 0.92 (m, 2H)
ESI/FIA/HR and MS/MS: [M+H]+=473.1950 (473.1948)
Elemental analysis: C=58.82 (58.47); H=6.00 (6.19); N=11.80 (11.86)
RP: −34.930 (589 nm, T=18° C., C=0.9)

Intermediate 175: tert-Butyl (3S)-3-{4-[bis(tert-butoxycarbonyl)amino]butyl}-4-ethoxy-1-[(4-methoxy-2-pyridin-4-ylphenyl)methyl]-4-oxo-1,4-azaphosphinane-3-carboxylate Intermediate 175 is obtained starting from intermediates 129 and 268 in accordance with procedure F described hereinbefore.
$^1$H NMR: (400 MHz, dmso-d6) δ ppm 8.61 (d, 2H), 7.41 (d, 2H), 7.38 (d, 1H), 7 (dd, 1H), 6.8 (d, 1H), 3.92 (m, 2H), 3.79 (s, 3H), 3.49/3.3 (AB, 2H), 2.73/2.18 (m, 2H), 2.73 (m, 2H), 2.67/2.3 (m, 2H), 1.95-1.8 (m, 2H), 1.7 (m, 2H), 1.35 (2s, 18H), 1.22 (m, 2H), 1.18 (t, 3H), 0.69/0.55 (m, 2H)

EXAMPLE 225: (3S)-3-(4-AMINOBUTYL)-4-HYDROXY-1-[(4-HYDROXY-2-PYRIDIN-4-YL-PHENYL)METHYL]-4-OXO-1,4-AZAPHOSPHINANE-3-CARBOXYLIC ACID

Example 225 is obtained starting from intermediate 175 in accordance with procedure D described hereinbefore.
$^1$H NMR: (400 MHz, D2O) δ ppm 8.6 (d, 2H), 7.5 (d, 1H), 7.41 (d, 2H), 7.01 (dd, 1H), 6.88 (d, 1H), 4.31/4.2 (AB, 2H), 3.41/3.05 (m, 2H), 3.15/2.8 (m, 2H), 2.97 (m, 2H), 2.09/1.65 (m, 2H), 1.85/1.35 (m, 2H), 1.6 (m, 2H), 1.09 (m, 2H)
ESI/FIA/HR and MS/MS: [M+H]+=434.1841 (434.1839)
Elemental analysis: C=58.51 (58.19); H=5.87 (6.51); N=9.77 (9.69)
RP: −28.730 (589 nm, T=18° C., C=0.6)

Intermediate 176: tert-Butyl (3S)-3-{4-[bis(tert-butoxycarbonyl)amino]butyl}-4-ethoxy-1-[[4-fluoro-2-(3-fluorophenyl)phenyl]methyl]-4-oxo-1,4-azaphosphinane-3-carboxylate Intermediate 176 is obtained starting from intermediates 129 and 269 in accordance with procedure F described hereinbefore.
$^1$H NMR: (400 MHz, dmso-d6) δ ppm 7.52-7.08 (m, 7H), 3.92 (m, 2H), 3.51/3.32 (AB, 2H), 3.3 (m, 2H), 2.72/2.21

(m, 2H), 2.69/2.36 (m, 2H), 2-1.85 (m, 2H), 1.78 (m, 2H), 1.4 (s, 18H), 1.34 (m, 2H), 1.31 (s, 9H), 1.18 (m, 3H), 0.65 (t, 2H)
$^{19}$F NMR: (400 MHz, dmso-d6) δ ppm −112/−114

EXAMPLE 226: (3S)-3-(4-AMINOBUTYL)-1-[[4-FLUORO-2-(3-FLUOROPHENYL)PHENYL]METHYL]-4-HYDROXY-4-OXO-1,4-AZAPHOSPHINANE-3-CARBOXYLIC ACID

Example 226 is obtained starting from intermediate 176 in accordance with procedure D described hereinbefore.
$^{1}$H NMR: (400 MHz, D2O) δ ppm 7.65 (dd, 1H), 7.5 (m, 1H), 7.25 (m, 1H), 7.25 (d, 1H), 7.25-7.1 (m, 3H), 4.4 (d, 1H), 4.3 (d, 1H), 3.5-3.35 (m, 1H), 3.2 (m, 1H), 3.15 (m, 1H), 2.95 (m, 2H), 2.85 (dd, 1H), 2.1 (m, 1H), 1.85 (m, 1H), 1.7 (m, 1H), 1.6 (m, 2H), 1.35 (m, 1H), 1.2-1 (m, 2H)
ESI/FIA/HR and MS/MS: [M+H]+=453.1748 (453.1749)
Elemental analysis: C=58.06 (58.40); H=6.00 (6.01); N=6.14 (6.19)
RP: −15.830 (589 nm, T=20.5° C., C=1.0)

Intermediate 177: tert-Butyl (3S)-3-{4-[Bis(tert-butoxycarbonyl)amino]butyl}-4-ethoxy-1-[(4-hydroxy-2-thiophen-2-ylphenyl)methyl]-4-oxo-1,4-azaphosphinane-3-carboxylate Intermediate 177 is obtained starting from intermediates 129 and 255 in accordance with procedure F described hereinbefore.
$^{1}$H NMR: (400 MHz, dmso-d6) δ ppm 9.55 (s, 1H), 7.55 (d, 1H), 7.25 (d, 1H), 7.2 (d, 1H), 7.1 (m, 1H), 6.8 (s, 1H), 6.75 (dd, 1H), 4 (m, 2H), 3.5 (d, 1H), 3.3 (d, 1H), 3.25 (m, 2H), 2.95-2.8 (m, 2H), 2.4 (dd, 1H), 2.25 (m, 1H), 2.05-1.8 (m, 4H), 1.4 (s, 18H), 1.35 (s, 9H), 1.3 (m, 2H), 1.2 (t, 3H), 0.65 (m, 2H)

EXAMPLE 227: (3S)-3-(4-AMINOBUTYL)-4-HYDROXY-1-[(4-HYDROXY-2-THIOPHEN-2-YLPHENYL)METHYL]-4-OXO-1,4-AZAPHOSPHINANE-3-CARBOXYLIC ACID

Example 227 is obtained starting from intermediate 177 in accordance with procedure D described hereinbefore.
$^{1}$H NMR: (400 MHz, D2O) δ ppm 7.55 (d, 1H), 7.45 (d, 1H), 7.2 (m, 1H), 7.15 (d, 1H), 6.95 (m, 2H), 4.45 (d, 1H), 4.35 (d, 1H), 3.55-3.4 (m, 1H), 3.35-3.25 (m, 1H), 3.15 (m, 1H), 2.95 (m, 2H), 2.9 (dd, 1H), 2.15 (m, 1H), 1.85 (m, 1H), 1.7 (m, 1H), 1.6 (m, 2H), 1.4 (m, 1H), 1.2 (m, 1H), 1.1 (m, 1H)
ESI/FIA/HR and MS/MS: [M+H]+=439.1450 (439.1451)
Elemental analysis: C=55.29 (54.78); H=6.41 (6.21); N=6.46 (6.39); S=7.06 (7.31)
RP: −36.090 (589 nm, T=20.5° C., C=1.0)

Intermediate 178: tert-Butyl (3S)-3-{4-[bis(tert-butoxycarbonyl)amino]butyl}-4-ethoxy-1-[[2-(4-fluorophenyl)-4-hydroxyphenyl]methyl]-4-oxo-1,4-azaphosphinane-3-carboxylate Intermediate 178 is obtained starting from intermediates 129 and 270 in accordance with procedure F described hereinbefore.
$^{1}$H NMR: (400 MHz, dmso-d6) δ ppm 9.5 (sl, 1H), 7.39 (dd, 1H), 7.24 (dd, 1H), 7.2 (d, 1H), 6.75 (dd, 2H), 6.6 (d, 2H), 3.92 (m, 2H), 3.31/3.21 (AB, 2H), 3.3 (m, 2H), 2.72/2.12 (2*m, 2H), 2.67/2.3 (2*m, 2H), 2-1.8 (m, 2H), 1.8 (m, 2H), 1.4 (s, 18H), 1.35 (m, 2H), 1.32 (s, 9H), 1.18 (t, 3H), 0.7 (m, 2H).
$^{31}$P NMR: (400 MHz, dmso-d6) δ ppm −114.8

EXAMPLE 228: (3S)-3-(4-AMINOBUTYL)-1-[[2-(4-FLUOROPHENYL)-4-HYDROXYPHENYL]METHYL]-4-HYDROXY-4-OXO-1,4-AZAPHOSPHINANE-3-CARBOXYLIC ACID

Example 228 is obtained starting from intermediate 178 in accordance with procedure D described hereinbefore.
$^{1}$H NMR: (400 MHz, D2O) δ ppm 7.47 (d, 1H), 7.32 (dd, 2H), 7.22 (dd, 2H), 6.98 (dd, 1H), 6.85 (d, 1H), 4.32/4.2 (AB, 2H), 3.37/3.05 (m, 2H), 3.15/2.8 (m, 2H), 2.95 (m, 2H), 2.09/1.65 (m, 2H), 1.85/1.35 (m, 2H), 1.59 (m, 2H), 1.1 (m, 2H)
$^{19}$F NMR: (400 MHz, D2O) δ ppm −113.5
ESI/FIA/HR and MS/MS: [M+H]+=451.1792 (451.1793)
Elemental analysis: C=58.29 (58.66); H=6.12 (6.27); N=6.20 (6.22)
RP: −36.630 (589 nm, T=21° C., C=1.0)

Intermediate 179: tert-Butyl (3S)-3-{4-[bis(tert-butoxycarbonyl)amino]butyl}-1-[[2-(3,4-dimethoxyphenyl)-4-hydroxyphenyl]methyl]-4-ethoxy-4-oxo-1,4-azaphosphinane-3-carboxylate Intermediate 179 is obtained starting from intermediates 129 and 256 in accordance with procedure F described hereinbefore.
$^{1}$H NMR: (400 MHz, dmso-d6) δ ppm 9.4 (m, 1H), 7.2 (d, 1H), 7 (d, 1H), 6.85 (m, 2H), 6.7 (dd, 1H), 6.6 (dd, 1H), 3.95 (m, 2H), 3.8 (2s, 6H), 3.4/3.25 (2d, 2H), 3.3 (m, 2H), 2.8 (m, 1H), 2.7 (m, 1H), 2.3 (dd, 1H), 2.15 (m, 1H), 1.9 (m, 1H), 1.8 (m, 3H), 1.4/1.25 (2m, 2H), 1.4 (s, 18H), 1.35 (s, 9H), 1.2 (t, 3H), 0.75 (quint, 2H)

EXAMPLE 229: (3S)-3-(4-AMINOBUTYL)-1-[[2-(3,4-DIMETHOXYPHENYL)-4-HYDROXYPHENYL]-METHYL]-4-HYDROXY-4-OXO-1,4-AZAPHOSPHINANE-3-CARBOXYLIC ACID

Example 229 is obtained starting from intermediate 179 in accordance with procedure D described hereinbefore.
$^{1}$H NMR: (400 MHz, dmso-d6) δ ppm 7.05 (s, 1H), 7-6.85 (dd; d, 2H), 6.85 (d, 1H), 6.25 (dd, 1H), 6.15 (s, 1H), 3.75 (s, 6H), 3.2 (d, 1H), 3.05 (d, 1H), 3-2.85 (m, 1H), 2.8-2.65 (m, 1H), 2.45-2.25 (m, 3H), 2.15 (m, 1H), 1.85-1.7 (m, 2H), 1.65 (m, 1H), 1.3-1.15 (m, 3H), 0.9 (m, 1H), 0.8 (m, 1H)
ESI/FIA/HR and MS/MS: ESI-HR+/−: [M+H]+=493.2098 (493.2098)
Elemental analysis: C=58.52 (58.53); H=6.32 (6.75); N=5.48 (5.69)
RP: −32.470 (589 nm, T=20° C., C=0.9)

EXAMPLE 230: (3S)-3-(4-AMINOBUTYL)-4-HYDROXY-1-[(4-HYDROXYPHENYL)METHYL]-4-OXO-1,4-AZAPHOSPHINANE-3-CARBOXYLIC ACID

Example 230 is obtained starting from intermediate 129 and 4-hydroxybenzaldehyde in accordance with procedures F and D described hereinbefore.
$^{1}$H NMR: (400 MHz, D2O) δ ppm 7.32 (d, 2H), 6.9 (d, 2H), centred at 4.2 (AB, 2H), 3.7/3.28 (2m, 2H), 3.45/3.05

(2dd, 2H), 2.9 (m, 2H), 2.21/1.75 (2m, 2H), 1.9/1.45 (2m, 2H), 1.59 (m, 2H), 1.22/1.1 (2m, 2H)

ESI/FIA/HR and MS/MS: [M+H]+=357.1577 (357.1574)

Elemental analysis: C=54.12 (53.93); H=6.96 (7.07); N=7.93 (7.86)

RP: −56.580 (589 nm, T=20° C., C=1.0)

EXAMPLE 231: (3S)-3-(4-AMINOBUTYL)-1-[[2-(4-CHLOROPHENYL)PHENYL]METHYL]-4-HYDROXY-4-OXO-1,4-AZAPHOSPHINANE-3-CARBOXYLIC ACID

Example 231 is obtained starting from intermediate 129 and 2-(4-chlorophenyl)benzaldehyde in accordance with procedures F and D described hereinbefore.

$^1$H NMR: (300 MHz, D2O) δ ppm 7.59 (m, 1H), 7.51 (m, 2H), 7.51 (d, 2H), 7.38 (m, 1H), 7.31 (d, 2H), 4.33 (AB, 2H), 3.39/3.08 (2m, 2H), 3.15/2.83 (2m, 2H), 2.92 (m, 2H), 2.07/1.62 (2m, 2H), 1.83/1.34 (2m, 2H), 1.56 (m, 2H), 1.06 (m, 2H)

ESI/FIA/HR and MS/MS: [M+H]+=451.1541 (451.1553)

Elemental analysis: C=58.91 (58.60); H=6.12 (6.26); N=5.85 (6.21)

RP: −10.140 (589 nm, T=20° C., C=0.8)

EXAMPLE 232: (3S)-3-(4-AMINOBUTYL)-4-HYDROXY-1-[[2-[2-METHYL-5-(TRIFLUOROMETHYL)-PYRAZOL-3-YL]PHENYL]METHYL]-4-OXO-1,4-AZAPHOSPHINANE-3-CARBOXYLIC ACID

Example 232 is obtained starting from intermediate 129 and 2-[1-methyl-3-(trifluoromethyl)-1H-pyrazol-5-yl]benzaldehyde in accordance with procedures F and D described hereinbefore.

$^1$H NMR: (300 MHz, D2O) δ ppm 7.63/7.46 (m, 4H), 6.81 (s, 1H), 4.21 (AB, 2H), 3.65 (s, 3H), 3.5/3.19 (2m, 2H), 3.26/3 (2m, 2H), 2.91 (m, 2H), 2.15/1.69 (2m, 2H), 1.87/1.4 (2m, 2H), 1.58 (m, 2H), 1.11 (m, 2H)

$^{19}$F NMR: (300 MHz, D2O) δ ppm −61.8

ESI/FIA/HR and MS/MS: [M+H]+=489.1869 (489.1878)

Elemental analysis: C=51.64 (51.64); H=6.03 (5.78); N=11.47 (11.47)

RP: −27.030 (589 nm, T=20° C., C=0.9)

EXAMPLE 233: (3S)-3-(4-AMINOBUTYL)-4-HYDROXY-4-OXO-1-[[2-(TRIFLUOROMETHYL)-PHENYL]METHYL]-1,4-AZAPHOSPHINANE-3-CARBOXYLIC ACID

Example 233 is obtained starting from intermediate 129 and 2-trifluoromethylbenzaldehyde in accordance with procedures F and D described hereinbefore.

$^1$H NMR: (300 MHz, D2O) δ ppm 7.88-7.6 (m, 4H), 4.51 (AB, 2H), 3.69/3.43 (2m, 2H), 3.48/3.25 (2m, 2H), 2.92 (m, 2H), 2.22/1.78 (2m, 2H), 1.93/1.49 (2m, 2H), 1.59 (m, 2H), 1.23/1.09 (2m, 2H)

$^{19}$F NMR: (300 MHz, D2O) δ ppm −58.3

ESI/FIA/HR and MS/MS: [M+H]+=409.1492 (409.1499)

Elemental analysis: C=49.52 (50.00); H=5.85 (5.92); N=7.00 (6.86)

RP: −38.120 (589 nm, T=20° C., C=1.0)

EXAMPLE 234: (3S)-3-(4-AMINOBUTYL)-1-[(4-FLUORO-2-PYRIMIDIN-5-YLPHENYL)METHYL]-4-HYDROXY-4-OXO-1,4-AZAPHOSPHINANE-3-CARBOXYLIC ACID

Example 234 is obtained starting from intermediate 129 and 4-fluoro-(2-pyrimidin-5-yl)benzaldehyde in accordance with procedures F and D described hereinbefore.

$^1$H NMR: (300 MHz, D2O) δ ppm 9.2 (s, 1H), 8.82 (s, 2H), 7.7 (dd, 1H), 7.35 (td, 1H), 7.2 (dd, 1H), 4.38/4.28 (2*d, 2H), 3.5/3.15 (2*m, 2H), 3.25/2.9 (2*m, 2H), 2.9 (t, 2H), 2.1/1.6 (2*m, 2H), 1.85/1.6 (2*m, 2H), 1.6/1.1 (2*m, 2H), 1.38/1.1 (2*m, 2H)

ESI/FIA/HR and MS/MS: [M+H]+=437.1740 (437.1753)

Elemental analysis: C=54.96 (55.04); H=4.82 (6.00); N=12.78 (12.84)

RP: −23.070 (589 nm, T=20° C., C=1.1)

EXAMPLE 235: (3S)-3-(4-AMINOBUTYL)-4-HYDROXY-1-[[2-(2-METHYLPYRAZOL-3-YL)PHENYL]METHYL]-4-OXO-1,4-AZAPHOSPHINANE-3-CARBOXYLIC ACID

Example 235 is obtained starting from intermediates 129 and 280 in accordance with procedures F and D described hereinbefore.

$^1$H NMR: (300 MHz, D2O) δ ppm 7.7-7.35 (m, 4H), 7.65 (d, 1H), 6.45 (d, 1H), 4.25/4.15 (dd, 2H), 3.6 (s, 3H), 3.5/3.2 (2m, 2H), 3.3/3 (dd, 2H), 2.9 (m, 2H), 2.15/1.7 (2m, 2H), 1.9/1.4 (2m, 2H), 1.6 (m, 2H), 1.3-1 (m, 2H)

ESI/FIA/HR and MS/MS: [M+H]+=421.1998 (421.2004)

Elemental analysis: C=57.19 (57.13); H=7.08 (6.95); N=13.43 (13.33)

RP: −29.970 (589 nm, T=19.5° C., C=1.0)

EXAMPLE 236: (3S)-3-(4-AMINOBUTYL)-1-[[4-FLUORO-2-(2-METHYLPYRAZOL-3-YL)PHENYL]-METHYL]-4-HYDROXY-4-OXO-1,4-AZAPHOSPHINANE-3-CARBOXYLIC ACID

Example 236 is obtained starting from intermediates 129 and 277 in accordance with procedures F and D described hereinbefore.

$^1$H NMR: (400 MHz, D2O) δ ppm 7.7 (dd, 1H), 7.65 (d, 1H), 7.39 (td, 1H), 7.24 (dd, 1H), 6.5 (d, 1H), 4.25/4.13 (AB, 2H), 3.61 (s, 3H), 3.48/3.18 (m, 2H), 3.29/3 (m, 2H), 2.94 (m, 2H), 2.17/1.7 (m, 2H), 1.9/1.41 (m, 2H), 1.6 (m, 2H), 1.2/1.1 (m, 2H)

ESI/FIA/HR and MS/MS: [M+H]+=439.1903 (439.1905)

Elemental analysis: C=54.74 (54.79); H=6.38 (6.44); N=12.57 (12.78)

RP: −26.790 (589 nm, T=21° C., C=1.0)

EXAMPLE 237: (3S)-3-(4-AMINOBUTYL)-4-HYDROXY-1-[(2-IMIDAZO[1,2-A]PYRIDIN-3-YLPHENYL)METHYL]-4-OXO-1,4-AZAPHOSPHINANE-3-CARBOXYLIC ACID

Example 237 is obtained starting from intermediates 129 and 227 in accordance with procedures F and D described hereinbefore.

$^1$H NMR: (300 MHz, D2O) δ ppm 7.98 (d, 1H), 7.68 (s, 1H), 7.65 (d, 1H), 7.65 (m, 2H), 7.52 (m, 1H), 7.45 (dd, 1H), 7.22 (m, 1H), 6.98 (t, 1H), 4.25 (m, 2H), 3.45/3.1 (2*m, 2H), 2.9 (m, 2H), 2.85 (m, 2H), 2.12/1.55 (2*m, 2H), 1.8/1.55 (2*m, 2H), 1.55/0.95 (2*m, 2H), 1.28/0.95 (2*m, 2H)
ESI/FIA/HR and MS/MS: [M+H]+=457.1993 (457.1999)
Elemental analysis: C=60.73 (60.52); H=6.00 (6.40); N=12.29 (12.27)
RP: −33.550 (589 nm, T=19° C., C=0.9)

EXAMPLE 238: (3S)-3-(4-AMINOBUTYL)-1-[[4-FLUORO-2-(3-HYDROXYPHENYL)PHENYL]-METHYL]-4-HYDROXY-4-OXO-1,4-AZAPHOSPHINANE-3-CARBOXYLIC ACID

Example 238 is obtained starting from intermediates 129 and 254 in accordance with procedures F and D described hereinbefore.
$^1$H NMR: (400 MHz, dmso-d6) δ ppm 7.6 (dd, 1H), 7.4 (m, 1H), 7.25 (m, 1H), 7.15 (d, 1H), 6.95 (dd, 1H), 6.9 (dd, 1H), 6.85 (s, 1H), 4.4 (d, 1H), 4.25 (d, 1H), 3.5-3.3 (m, 1H), 3.25-3 (m, 2H), 2.95 (m, 2H), 2.85 (dd, 1H), 2.1 (m, 1H), 1.85 (m, 1H), 1.65 (m, 1H), 1.6 (m, 2H), 1.35 (m, 1H), 1.2-1 (m, 2H)
ESI/FIA/HR and MS/MS: [M+H]+=451.1794 (451.1793)
Elemental analysis: C=58.81 (58.66); H=5.81 (6.27); N=6.19 (6.22)
RP: −19.520 (589 nm, T=21° C., C=1.0)

EXAMPLE 239: (3S)-3-(4-AMINOBUTYL)-1-[[4-FLUORO-2-(6-METHOXYPYRIDIN-3-YL)PHENYL]-METHYL]-4-HYDROXY-4-OXO-1,4-AZAPHOSPHINANE-3-CARBOXYLIC ACID

Example 239 is obtained starting from intermediate 129 and 4-fluoro-2-(6-methoxy-3-pyridinyl)benzaldehyde in accordance with procedures F and D described hereinbefore.
$^1$H NMR: (400 MHz, D2O) δ ppm 8.1 (d, 1H), 7.8 (dd, 1H), 7.65 (dd, 1H), 7.3 (td, 1H), 7.15 (dd, 1H), 7 (d, 1H), 4.4/4.3 (2 d, 2H), 3.9 (s, 3H), 3.45 (m, 1H), 3.2 (dd, 1H), 3.1 (m, 1H), 2.95 (m, 2H), 2.85 (dd, 1H), 2.1 (m, 1H), 1.85 (m, 1H), 1.65 (m, 1H), 1.6 (m, 2H), 1.35 (m, 1H), 1.1 (m, 2H)
ESI/FIA/HR and MS/MS: [M+H]+=466.1903 (466.1902)
Elemental analysis: C=57.18 (56.77); H=6.17 (6.28); N=9.05 (9.03)
RP: −11.850 (589 nm, T=20° C., C=0.9)

EXAMPLE 240: (3S)-3-(4-AMINOBUTYL)-4-HYDROXY-1-[[2-(6-HYDROXYPYRIDIN-3-YL)PHENYL]METHYL]-4-OXO-1,4-AZAPHOSPHINANE-3-CARBOXYLIC ACID

Example 240 is obtained starting from intermediate 129 and 2-(6-methoxy-3-pyridinyl)benzaldehyde in accordance with procedures F and D described hereinbefore.
$^1$H NMR: (400 MHz, D2O) δ ppm 7.7 (dd, 1H), 7.6 (d, 1H), 7.55-7.4 (2 m, 4H), 6.7 (d, 1H), 4.4 (2 d coal., 2H), 3.5 (m, 1H), 3.3 (dd, 1H), 3.2 (m, 1H), 3 (dd, 1H), 2.95 (m, 2H), 2.1 (m, 1H), 1.9 (m, 1H), 1.7 (m, 1H), 1.6 (m, 2H), 1.4 (m, 1H), 1.1 (m, 2H)
ESI/FIA/HR and MS/MS: [M+H]+=434.1840 (434.1839)
Elemental analysis: C=58.14 (58.19); H=6.38 (6.51); N=9.60 (9.69)
RP: −8.440 (589 nm, T=20° C., C=0.8)

EXAMPLE 241: (3S)-3-(4-AMINOBUTYL)-1-[[4-FLUORO-2-(6-HYDROXYPYRIDIN-3-YL)PHENYL]-METHYL]-4-HYDROXY-4-OXO-1,4-AZAPHOSPHINANE-3-CARBOXYLIC ACID

Example 241 is obtained starting from intermediate 129 and 4-fluoro-2-(6-methoxy-3-pyridinyl)benzaldehyde in accordance with procedures F and D described hereinbefore.
$^1$H NMR: (400 MHz, D2O) δ ppm 7.7 (dd, 1H), 7.6 (m, 2H), 7.3 (td, 1H), 7.2 (dd, 1H), 6.7 (d, 1H), 4.35 (2 d coal., 2H), 3.5 (m, 1H), 3.25 (m, 1H), 3.2 (m, 1H), 3 (dd, 1H), 2.95 (m, 2H), 2.1 (m, 1H), 1.9 (m, 1H), 1.7 (m, 1H), 1.6 (quint, 2H), 1.4 (m, 1H), 1.1 (m, 2H)
ESI/FIA/HR and MS/MS: [M+H]+=452.1746 (452.1745)
Elemental analysis: C=55.62 (55.87); H=5.85 (6.03); N=9.16 (9.31)
RP: −7.630 (589 nm, T=20° C., C=0.7)

EXAMPLE 242: (3S)-3-(4-AMINOBUTYL)-4-HYDROXY-1-[[4-HYDROXY-2-(6-METHOXY-PYRIDIN-3-YL)PHENYL]METHYL]-4-OXO-1,4-AZAPHOSPHINANE-3-CARBOXYLIC ACID

Example 242 is obtained starting from intermediates 129 and 230 in accordance with procedures F and D described hereinbefore.
$^1$H NMR: (400 MHz, D2O) δ ppm 7.95 (d, 1H), 7.6 (dd, 1H), 7.4 (d, 1H), 6.9 (m, 2H), 6.7 (d, 1H), 4.2-4.1 (2d, 2H), 3.8 (s, 3H), 3.3-2.95 (2m, 2H), 3.1-2.7 (2m, 2H), 2.85 (m, 2H), 2.0-1.5 (2m, 2H), 1.75-1.25 (2m, 2H), 1.5 (m, 2H), 1.0 (m, 2H)
Elemental analysis: C=56.79 (57.01); H=6.62 (6.52); N=8.99 (9.07)
RP: −27.320 (589 nm, T=20° C., C=0.8)

EXAMPLE 243: (3S)-3-(4-AMINOBUTYL)-4-HYDROXY-4-OXO-1-[(2-OXO-1,3-DIHYDROBENZ-IMIDAZOL-5-YL)METHYL]-1,4-AZAPHOSPHINANE-3-CARBOXYLIC ACID

Example 243 is obtained starting from intermediate 129 and 2-oxo-1,3-dihydrobenzothiazole-5-carbaldehyde in accordance with procedures F and D described hereinbefore.
$^1$H NMR: (400 MHz, D2O) δ ppm 7.25 (s, 1H), 7.2 (m, 2H), 4.45 (d, 1H), 4.25 (d, 1H), 3.8-3.65 (m, 1H), 3.55-3.4 (m, 1H), 3.35 (m, 1H), 3.1 (dd, 1H), 2.95 (m, 2H), 2.3-2.15 (m, 1H), 2-1.85 (m, 1H), 1.85-1.7 (m, 1H), 1.6 (m, 2H), 1.55-1.4 (m, 1H), 1.3-1 (m, 2H)
ESI/FIA/HR and MS/MS: [M+H]+=397.1635 (397.1635)

EXAMPLE 244: (3S)-3-(4-AMINOBUTYL)-1-[[4-FLUORO-2-(6-METHOXYPYRIDIN-2-YL)PHENYL]-METHYL]-4-HYDROXY-4-OXO-1,4-AZAPHOSPHINANE-3-CARBOXYLIC ACID

Example 244 is obtained starting from intermediates 129 and 231 in accordance with procedures F and D described hereinbefore.
$^1$H NMR: (300 MHz, D2O) δ ppm 8.2 (t, 1H), 7.8 (dd, 1H), 7.7 (dd, 1H), 7.55 (m, 2H), 7.2 (d, 1H), 4.7 (d, 1H), 4.5 (d, 1H), 4.2 (s (+m, 3H), 3.9 (m, 1H), 3.6 (m, 3H), 3.2 (t (+m, 2H), 2.6 (m, 1H), 2.05 (m, 2H), 1.8 (m, 2H), 1.7 (m, 1H), 1.4/1.3 (2m, 2H)
$^{19}$F NMR: (300 MHz, D2O) δ ppm −110.9
ESI/FIA/HR and MS/MS: [M+H]+=466.1901 (466.1902)
Elemental analysis: C=57.09 (56.77); H=6.16 (6.28); N=8.87 (9.03)
RP: −69.790 (589 nm, T=19° C., C=0.8)

EXAMPLE 245: (3S)-3-(4-AMINOBUTYL)-1-[[4-FLUORO-2-(1,3-THIAZOL-2-YL)PHENYL]METHYL]-4-HYDROXY-4-OXO-1,4-AZAPHOSPHINANE-3-CARBOXYLIC ACID

Example 245 is obtained starting from intermediates 129 and 232 in accordance with procedures F and D described hereinbefore.

¹H NMR: (300 MHz, D2O) δ ppm 8 (d, 1H), 7.7 (m, 2H), 7.7 (dd, 1H), 7.3 (td, 1H), 4.5 (d, 1H), 4.3 (d, 1H), 3.85 (m, 1H), 3.45 (m, 2H), 3.15 (dd, 1H), 2.9 (m, 2H), 2.3 (m, 1H), 1.85 (m, 2H), 1.55 (m, 3H), 1.2 (m, 1H), 1 (m, 1H)

¹⁹F NMR: (300 MHz, D2O) δ ppm −109

ESI/FIA/HR and MS/MS: [M+H]+=442.1358 (442.1360)

Elemental analysis: C=51.13 (51.69); H=5.30 (5.71); N=9.42 (9.52); S=7.25 (7.26)

RP: −99.540 (589 nm, T=18° C., C=0.8)

EXAMPLE 246: (3S)-3-(4-Aminobutyl)-4-hydroxy-1-[[4-hydroxy-2-(3-methylimidazol-4-yl)phenyl]methyl]-4-oxo-1,4-azaphosphinane-3-carboxylic acid, hydrobromide Example 246 is obtained starting from intermediates 129 and 276 in accordance with procedures F and D described hereinbefore.

¹H NMR: (300 MHz, D2O) δ ppm 8.85 (s, 1H), 7.65 (d, 1H), 7.6 (s, 1H), 7.2 (dd, 1H), 7 (d, 1H), 4.4 (m, 1H), 4.15 (m, 1H), 3.7 (m, 1H), 3.6 (s, 3H), 3.55-3.2 (2 m, 2H), 3.1 (m, 1H), 2.9 (m, 2H), 2.15 (m, 1H), 1.9 (m, 2H), 1.6 (m, 3H), 1.25 (2 m, 2H)

ESI/FIA/HR and MS/MS: [M+H]+=437.1947 (437.1948)

Elemental analysis: C=39.13 (40.15); H=5.22 (5.22); N=8.85 (9.37)

RP: −15.390 (589 nm, T=21° C., C=1.0)

EXAMPLE 247: (3S)-3-(4-AMINOBUTYL)-4-HYDROXY-1-[[4-HYDROXY-2-(2-METHYL-PYRAZOL-3-YL)PHENYL]METHYL]-4-OXO-1,4-AZAPHOSPHINANE-3-CARBOXYLIC ACID

Example 247 is obtained starting from intermediate 129 and 4-hydroxy-2-(2-methylpyrazol-3-yl)benzaldehyde in accordance with procedures F and D described hereinbefore.

¹H NMR: (400 MHz, D2O) δ ppm 7.63 (s, 1H), 7.52 (dd, 1H), 7.08 (d, 1H), 6.9 (s, 1H), 6.44 (d, 1H), 4.18/4.05 (2m, 2H), 3.61 (s, 3H), 3.45/3.15 (2m, 2H), 3.26/2.95 (2dd, 2H), 2.95 (m, 2H), 2.15/1.68 (2m, 2H), 1.9/1.4 (2m, 2H), 1.6 (m, 2H), 1.2/1.1 (2m, 2H)

ESI/FIA/HR and MS/MS: [M+H]+=437.1947 (437.1948)

Elemental analysis: C=55.22 (55.04); H=6.48 (6.70); N=12.72 (12.84)

RP: −44.210 (589 nm, T=20° C., C=1.0)

EXAMPLE 248: (3S)-3-(4-AMINOBUTYL)-1-[[2-(3,4-DIMETHOXYPHENYL)PHENYL]METHYL]-4-HYDROXY-4-OXO-1,4-AZAPHOSPHINANE-3-CARBOXYLIC ACID

Example 248 is obtained starting from intermediate 129 and 2-(3,4-dimethoxyphenyl)benzaldehyde in accordance with procedures F and D described hereinbefore.

¹H NMR: (300 MHz, D2O) δ ppm 7.6 (dd, 1H), 7.5 (m, 2H), 7.35 (dd, 1H), 7.1 (d, 1H), 7 (d, 1H), 6.9 (dd, 1H), 4.45/4.3 (2 d, 2H), 3.85 (2 s, 6H), 3.35/3.1 (2 m, 2H), 3.1/2.9 (m+dd, 2H), 2.95 (m, 2H), 2.1/1.65 (2 m, 2H), 1.85/1.35 (2 m, 2H), 1.6 (m, 2H), 1.05 (m, 2H)

ESI/FIA/HR and MS/MS: [M+H]+=477.2147 (477.2149)

Elemental analysis: C=60.13 (60.50); H=6.84 (6.98); N=5.68 (5.88)

RP: −21.710 (589 nm, T=18° C., C=1.0)

EXAMPLE 249: (3S)-3-(4-AMINOBUTYL)-1-[[2-(2,3-DIMETHYLIMIDAZOL-4-YL)-4-HYDROXY-PHENYL]METHYL]-4-HYDROXY-4-OXO-1,4-AZAPHOSPHINANE-3-CARBOXYLIC ACID

Example 249 is obtained starting from intermediates 129 and 275 in accordance with procedures F and D described hereinbefore.

¹H NMR: (400 MHz, D2O) δ ppm 7.55 (d, 1H), 7.45 (s, 1H), 7.15 (dd, 1H), 6.95 (s, 1H), 4.15 (sl, 2H), 3.65-3.5 (m, 1H), 3.45 (s, 3H), 3.35 (m, 1H), 3.2 (m, 1H), 2.95 (dd, 1H), 2.95 (t, 2H), 2.65 (s, 3H), 2.15 (m, 1H), 1.9 (m, 1H), 1.75 (m, 1H), 1.6 (m, 2H), 1.45 (m, 1H), 1.35-1.05 (2m, 2H)

ESI/FIA/HR and MS/MS: [M+H]+=451.2102 (451.2105)

Elemental analysis: C=46.98 (47.47); H=6.05 (6.07); N=10.40 (10.54)

RP: −37.730 (589 nm, T=20.5° C., C=1.0)

EXAMPLE 250: (3S)-3-(4-AMINOBUTYL)-1-[[2-(2,3-DIMETHYLIMIDAZOL-4-YL)PHENYL]-METHYL]-4-HYDROXY-4-OXO-1,4-AZAPHOSPHINANE-3-CARBOXYLIC ACID

Example 250 is obtained starting from intermediates 129 and 226 in accordance with procedures F and D described hereinbefore.

¹H NMR: (400 MHz, D2O) δ ppm 7.75-7.45 (m, 4H), 7.45 (s, 1H), 4.25 (m, 2H), 3.5/3.2 (2m, 2H), 3.4/3.1 (m, 2H), 3.4 (s, 3H), 2.9 (m, 2H), 2.65 (s, 3H), 2.1/1.7 (2m, 2H), 1.9/1.45 (2m, 2H), 1.6 (m, 2H), 1.25/1.1 (2m, 2H)

ESI/FIA/HR and MS/MS: [M+H]+=435.2179 (435.2161)

Elemental analysis: C=49.57 (50.37); H=5.92 (5.88); N=9.92 (10.21)

RP: −23.310 (589 nm, T=20° C., C=0.9)

EXAMPLE 251: (3S)-3-(4-AMINOBUTYL)-1-[[4-FLUORO-2-(4-FLUORO-3-HYDROXYPHENYL)-PHENYL]METHYL]-4-HYDROXY-4-OXO-1,4-AZAPHOSPHINANE-3-CARBOXYLIC ACID

Example 251 is obtained starting from intermediate 129 and 4-fluoro-2-(4-fluoro-3-hydroxyphenyl)benzaldehyde in accordance with procedures F and D described hereinbefore.

¹H NMR: (400 MHz, D2O) δ ppm 7.6 (d, 1H), 7.25 (2*m, 2H), 7.15 (d, 1H), 6.95 (d, 1H), 6.8 (m, 1H), 4.4 (d, 1H), 4.3 (d, 1H), 3.5-3.35 (m, 1H), 3.2-3.05 (m, 2H), 2.95 (m, 2H), 2.85 (dd, 1H), 2.1 (m, 1H), 1.85 (m, 1H), 1.65 (m, 1H), 1.6 (m, 2H), 1.35 (m, 1H), 1.2-1 (m, 2H)

ESI/FIA/HR and MS/MS: [M+H]+=469.1696 (469.1698)

Elemental analysis: C=56.82 (56.41); H=5.77 (5.81); N=6.02 (5.98)

RP: −12.950 (589 nm, T=21° C., C=1.0)

EXAMPLE 252: (3S)-3-(4-AMINOBUTYL)-4-HYDROXY-4-OXO-1-[(2-PYRIDIN-4-YLPHENYL)-METHYL]-1,4-AZAPHOSPHINANE-3-CARBOXYLIC ACID

Example 252 is obtained starting from intermediate 129 and 2-(4-pyridyl)benzaldehyde in accordance with procedures F and D described hereinbefore.

¹H NMR: (400 MHz, D2O) δ ppm 8.6 (d, 2H), 7.64 (m, 1H), 7.57 (m, 2H), 7.42 (d, 2H), 7.41 (m, 1H), 4.42/4.3 (dd, 2H), 3.44/3.09 (dd, 2H), 3.18/2.88 (dd, 2H), 2.93 (m, 2H), 2.09/1.64 (2*m, 2H), 1.85/1.35 (2*m, 2H), 1.59 (m, 2H), 1.08 (m, 2H)

ESI/FIA/HR and MS/MS: [M+H]+=418.1897 (418.1895)

Elemental analysis: C=61.00 (60.42); H=6.62 (6.76); N=10.20 (10.07)

RP: −17.980 (589 nm, T=28° C., C=0.9)

Procedure H: Synthesis of the Azaphosphepanes

Intermediate 180

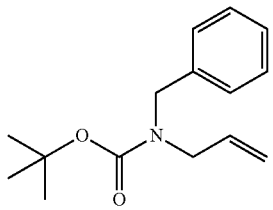 [SMILES: C=CCN(Cc1ccccc1)C(=O)OC(C)(C)C]

A solution of N-Boc allylamine (30 g, 190 mmol) in THF (170 mL) is added dropwise to a 60% NaH suspension (11.45 g, 285 mmol, 1.5 eq) in THF (100 mL) and under an argon atmosphere. The mixture is left in contact for 1 hour 30 minutes, and then benzyl bromide (34 mL, 285 mmol, 1.5 eq) in solution in THF (30 mL) is added. The reaction mixture is stirred at ambient temperature for 48 hours. The THF is evaporated off under reduced pressure and the evaporate is taken up in DCM (10 mL) cooled in an ice-water bath and then poured slowly onto H₂O (100 mL). The organic phase is separated off, and the aqueous phase is re-extracted with DCM (2×100 mL). The combined organic phases are washed with H₂O (2×50 mL), dried over MgSO₄ and then evaporated. The residue obtained is purified by flash chromatography on silica gel using as eluant a heptane/DCM gradient (from 50:50 to 0:100). Intermediate 180 is obtained in the form of a colourless oil (39.8 g, 160.92 mmol) with a yield of 85%.

¹H NMR: (400 MHz, DMSO-d6) δ ppm 7.65 (t, 2H), 7.22 (m, 3H), 5.75 (m, 1H), 5.1 (m, 2H), 4.33 (s, 2H), 3.75 (m, 2H), 1.39 (s, 9H)

Intermediate 181

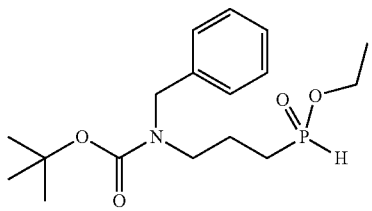 [SMILES: CCO[PH](=O)CCCN(Cc1ccccc1)C(=O)OC(C)(C)C]

Tetraethoxysilane (38.35 mL, 173 mmol, 2 eq) is added dropwise to a solution of hypophosphorous acid (11.42 g, 173 mmol, 2 eq) in acetonitrile (224 mL) at 0° C. and under an argon atmosphere. After returning to ambient temperature, there are added to the reaction mixture (degassed with argon) intermediate 180 (21.4 g, 86.5 mmol) in solution in MeCN (44.7 mL), Xantphos (0.55 g, 11 mmol) and then Pd₂dba₃ (0.396 g, 5 mmol). The mixture is heated at reflux for 16 hours. After concentration under reduced pressure, the residue obtained is purified by flash chromatography on silica gel using as eluant an AcOEt/EtOH gradient (from 95:5 to 90:10). Intermediate 181 is obtained in the form of a colourless oil (10.1 g, 29.58 mmol) with a yield of 34%.

¹H NMR: (400 MHz, DMSO-d6) δ ppm 7.32 (t, 2H), 7.22 (m, 3H), 6.95 (d, 1H), 4.38 (s, 2H), 3.99 (m, 2H), 3.19 (m, 2H), 1.65 (m, 4H), 1.4 (m, 9H), 1.21 (t, 3H)

³¹P NMR: (400 MHz, DMSO-d6) δ ppm 40.7

Intermediate 182

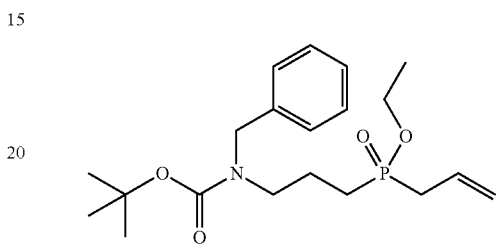

A solution of 1M LiHMDS in THF (29.6 mL, 29.6 mmol, 1 eq) is added to a solution of intermediate 181 (10.1 g, 29.6 mmol) in THF (100 mL) previously degassed with argon. After stirring for 30 minutes at −70° C., allyl bromide (2.56 mL, 29.6 mmol, 1 eq) is added. The reaction mixture is stirred for 2 hours at ambient temperature and then poured onto a saturated aqueous NH₄Cl solution. The mixture is extracted with DCM (3×100 mL), and the organic phase is washed with H₂O (2×100 mL) and dried over Na₂SO₄. After concentration under reduced pressure, the residue obtained is purified by flash chromatography on silica gel using as eluant an AcOEt/EtOH gradient (from 100%-90:10). The expected intermediate 182 is obtained in the form of a colourless oil (9.3 g, 24.3 mmol) with a yield of 82%.

¹H NMR: (400 MHz, DMSO-d6) δ ppm 7.4-7.2 (m, 5H), 5.2 (m, 1H), 5.18 (2dd, 2H), 4.4 (s, 2H), 3.91 (quad, 2H), 3.15 (m, 2H), 2.6 (dd, 2H), 1.6 (m, 4H), 1.4 (sl, 9H), 1.2 (t, 3H)

Intermediate 183

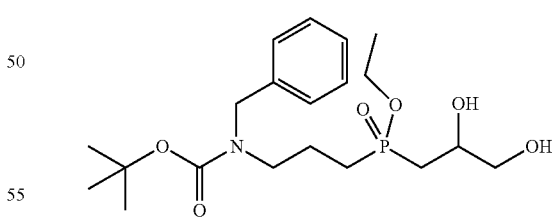

A 4% solution of OsO₄ in H₂O (4.64 mL, 0.73 mmol) at ambient temperature is added dropwise to a solution of intermediate 182 (9.3 g, 24.3 mmol) and 4-methylmorpholine N-oxide (3.14 g, 26.7 mmol, 1.1 eq) in 100 mL of an acetone/H₂O mixture (2:1). The reaction mixture is stirred at ambient temperature for 16 hours and then poured onto a 10% solution of sodium metabisulphite in H₂O (100 mL). The mixture is extracted with AcOEt (2×100 mL). The organic phases are combined and washed with H₂O (1×100 mL), dried over MgSO₄ and then concentrated in vacuo.

Intermediate 183 (9.8 g, 23.58 mmol) is obtained without further purification in the form of a dark-coloured oil with a yield of 97%.

$^1$H NMR: (400 MHz, DMSO-d6) δ ppm 7.35-7.2 (m, 5H), 4.8/4.78 (2d, 1H), 4.65 (2t, 1H), 4.36 (s, 2H), 3.9 (m, 2H), 3.75 (m, 1H), 3.35-3.2 (m, 2H), 3.15 (m, 2H), 1.9/1.7 (m, 2H), 1.63 (m, 4H), 1.4 (m, 9H), 1.17 (t, 3H)

$^{31}$P NMR: (400 MHz, DMSO-d6) δ ppm 58.6/57.7

Intermediate 184

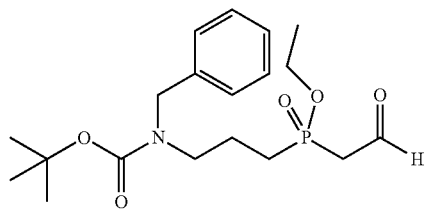 [SMILES: CCOP(=O)(CC=O)CCCN(Cc1ccccc1)C(=O)OC(C)(C)C]

Sodium periodate (20.16 g, 94.25 mmol, 4 eq) is added in portions to a solution of intermediate 183 (9.79 g, 23.5 mmol) in 320 mL of a THF/H$_2$O mixture (3:1) at ambient temperature. Stirring is maintained for 72 hours at ambient temperature. The reaction mixture is then extracted with AcOEt (2×150 mL), and the organic phases are combined and washed with H$_2$O (1×100 mL), dried over MgSO$_4$ and then concentrated in vacuo. Intermediate 184 (8.13 g, 21.2 mmol) is obtained without further purification in the form of an oil with a yield of 90%.

$^1$H NMR: (400 MHz, dmso-d6) δ ppm 9.6 (m, 1H), 7.35-7.2 (m, 5H), 4.38 (s, 2H), 4-3.75 (m, 2H), 3.25 (dd, 2H), 3.15 (m, 2H), 1.65 (m, 4H), 1.4 (m, 9H), 1.2 (m, 3H)

Intermediate 186

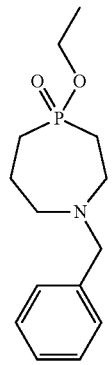 [SMILES: CCOP1(=O)CCCN(Cc2ccccc2)CC1]

A solution of intermediate 184 (8.13 g, 21.2 mmol) in 2N HCl (53 mL, 106 mmol, 5 eq) is stirred for 4 hours at ambient temperature. The reaction mixture is concentrated in vacuo to yield intermediate 185, which is used directly without being purified further. Intermediate 185 is dissolved in DCM (150 mL) and stirred for 1 hour with MgSO$_4$ (10 g). NaBH(OAc)$_3$ (6.75 g, 31.8 mmol, 1.5 eq) is then added in portions at 0° C., and the reaction mixture is stirred at ambient temperature for 16 hours. After filtering off the insoluble components, the organic phase is washed with a 10% saturated aqueous NaHCO$_3$ solution (2×100 mL) and then with H$_2$O (1×100 mL), and dried over MgSO$_4$. After concentration under reduced pressure, the residue obtained is purified by flash chromatography on silica gel using as eluant a DCM/EtOH gradient (98:2 to 94:6). The expected product is obtained in the form of a colourless oil (1.9 g, 7.1 mmol) with a yield of 33%.

$^1$H NMR: (400 MHz, DMSO-d6) δ ppm 7.3 (m, 5H), 3.9 (quadd, 2H), 3.7 (s, 2H), 2.7 (m, 4H), 2-1.6 (m, 6H), 1.2 (t, 3H)

$^{31}$P NMR: (400 MHz, DMSO-d6) δ ppm 62

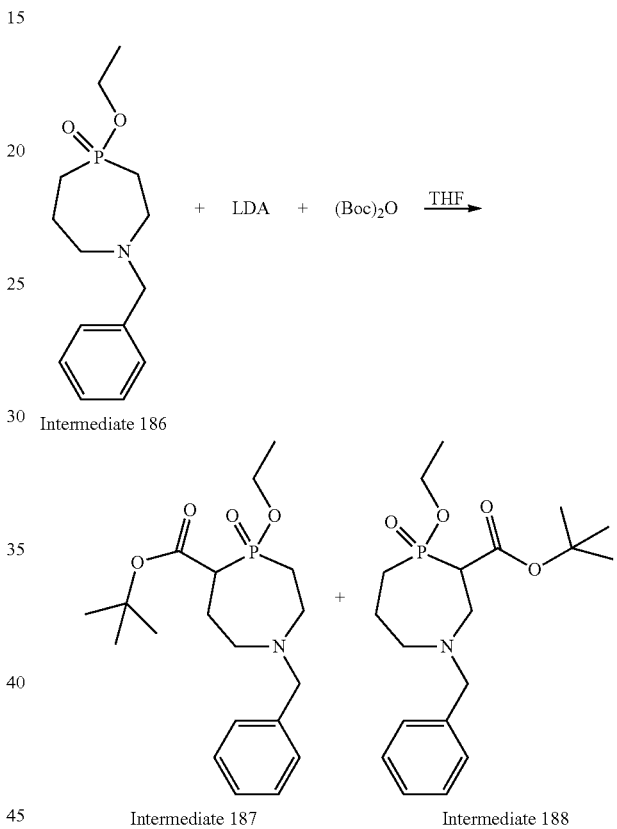

2N LDA in THF (5.33 mL, 10.6 mmol, 1.5 eq) is added dropwise to a solution of intermediate 186 (1.9 g, 7.1 mmol) in THF (18 mL) at −78° C. under an argon atmosphere. After 30 minutes, di-tert-butyl dicarbonate (2.17 g, 9.95 mmol, 1.4 eq) dissolved in THF (9 mL) is added. The reaction mixture is stirred for 1 hour 30 minutes, the temperature being maintained at −78° C. A further 1.5 eq of 2N LDA in THF (5.33 mL, 10.6 mmol) is added dropwise. After 2 hours, the reaction mixture is hydrolysed while cold with an aqueous NH$_4$Cl solution (10 mL) followed by AcOEt (10 mL). After returning to ambient temperature, the reaction mixture is extracted with AcOEt (2×100 mL). The organic phases are combined, washed with H$_2$O (100 mL), dried over MgSO$_4$ and then concentrated in vacuo. The residue obtained is purified by flash chromatography on silica gel using as eluant an AcOEt/THF gradient (from 100% to 70:30). The expected intermediates 187 and 188 are obtained in the form of an oily mixture (1.7 g, 4.62 mmol) with a yield of 63%.

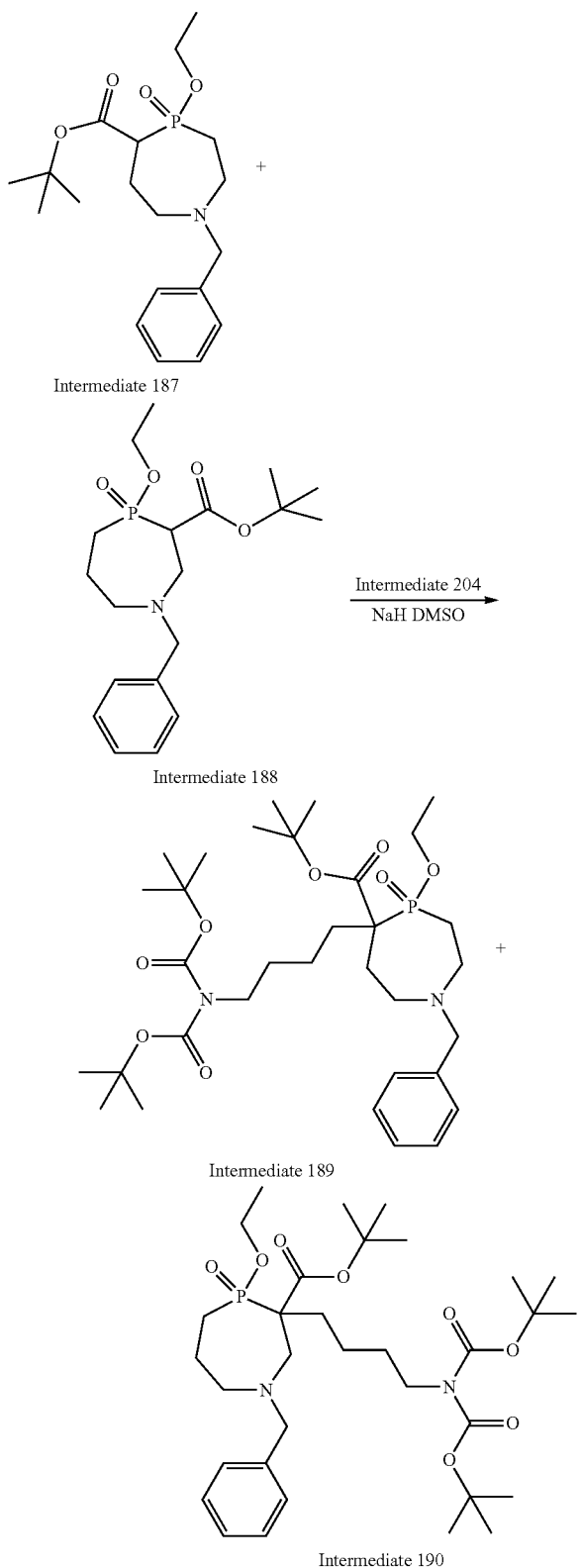

60% NaH (0.287 g, 7.18 mmol, 1.6 eq) is added, at 10° C. and in portions, to a solution of intermediate 204 (1.74 g, 4.94 mmol, 1.1 eq) in DMSO (10 mL) under argon. Intermediates 187 and 188 (1.65 g, 4.49 mmol) in solution in DMSO (5.9 mL) are then added to the suspension and the mixture is stirred for 6 hours at ambient temperature. The reaction mixture is then hydrolysed with an aqueous NH₄Cl solution (30 mL) and extracted with AcOEt (2×50 mL). The organic phase is washed with H₂O (2×50 mL), dried over MgSO₄ and concentrated in vacuo. The residue obtained is purified by flash chromatography on silica gel using as eluant a DCM/AcOEt gradient (90:10 to 50:50). Intermediate 189 (0.342 g, 0.54 mmol) and intermediate 190 (1 g, 1.6 mmol) are obtained in the form of a mixture of diastereoisomers with a yield of 36% and 12%, respectively.

EXAMPLE 253: 5-(4-AMINOBUTYL)-1-BENZYL-4-HYDROXY-4-OXO-1,4-AZAPHOSPHEPANE-5-CARBOXYLIC ACID

TMSBr (0.87 mL, 6.6 mmol, 12 eq) is added dropwise to a solution of intermediate 189 (0.342 g, 0.54 mmol) in DCM (4 mL) under argon and at ambient temperature. The mixture is stirred for 16 hours at ambient temperature and then concentrated in vacuo. The residue is taken up in MeOH (20 mL) and stirred for 20 minutes at ambient temperature, before being evaporated to dryness. The evaporate is dissolved in DCM (4 mL), and trifluoroacetic acid (0.81 mL, 10.9 mmol, 20 eq) is added. The reaction mixture is stirred for 10 hours at ambient temperature and then concentrated in vacuo. The residue obtained is purified by reverse-phase chromatography using as eluant an H₂O/MeCN gradient. Example 253 (0.11 g, 0.31 mmol) is obtained in the form of a white solid with a yield of 57%.

$^1$H NMR: (400 MHz, D2O) δ ppm 7.42 (s, 5H), 4.32 (AB, 2H), 3.5-3.2 (m, 4H), 2.9 (m, 2H), 2.1-1 (m, 10H)
$^{31}$P NMR: (400 MHz, D2O) δ ppm 40.25
ESI/FIA/HR and MS/MS: [M+H]+=355.1780 (355.1786)
Elemental analysis: C=57.16 (57.62); H=7.28 (7.68); N=7.83 (7.90)

EXAMPLE 254: 3-(4-AMINOBUTYL)-1-BENZYL-4-HYDROXY-4-OXO-1,4-AZAPHOSPHEPANE-3-CARBOXYLIC ACID

TMSBr (2.53 mL, 19.2 mmol, 12 eq) is added dropwise to a solution of intermediate 190 (1 g, 1.61 mmol) in solution in DCM (5 mL) under argon and at ambient temperature. The mixture is stirred for 16 hours at ambient temperature and then concentrated in vacuo. The residue is taken up in MeOH (20 mL) and stirred for 20 minutes at ambient temperature, before being evaporated to dryness. The evaporate is dissolved in DCM (4 ml), and trifluoroacetic acid (2.37 mL, 32 mmol, 20 eq) is added. The reaction mixture is stirred for 10 hours at ambient temperature and then concentrated in vacuo. The residue obtained is purified by reverse-phase chromatography using as eluant an H₂O/MeCN gradient. Example 254 (0.34 g, 0.96 mmol) is obtained in the form of a white solid with a yield of 60%.

$^1$H NMR: (400 MHz, D2O) δ ppm 7.5 (m, 5H), 4.35 (m, 2H), 3.75-3.1 (m, 4H), 2.95 (t, 2H), 2.15-1.4 (m, 4H), 2.1 (m, 2H), 1.6 (m, 2H), 1.35/1.2 (m)+(m, 1+1H)
ESI/FIA/HR and MS/MS: [M+H]+=355.1780 (355.1786)
Elemental analysis: C=57.16 (57.62); H=7.28 (7.68); N=7.83 (7.90)

EXAMPLE 255: 5-(5-AMINOPENTYL)-1-BENZYL-4-HYDROXY-4-OXO-1,4-AZAPHOSPHEPANE-5-CARBOXYLIC ACID

Example 255 is obtained in accordance with procedure H described hereinbefore, replacing intermediate 204 by intermediate 206.

¹H NMR: (500 MHz, D2O) δ ppm 7.54 (m, 5H), 4.41/4.34 (d)+(d, 1+1H), 3.7/3.63 (m)+(m, 1+1H), 3.51/3.22 (m)+(m, 1+1H), 2.99 (t, 2H), 2.16/1.58 (m)+(m, 1+1H), 2.14/1.51 (m)+(m, 1+1H), 2.11/1.82 (m)+(m, 1+1H), 1.67 (quint., 2H), 1.39 (quint., 2H), 1.35/1.18 (m)+(m, 1+1H)
¹³C NMR: (500 MHz, D2O) δ ppm 129.4, 61, 54.7, 51.8, 39.1, 32.3, 29.4, 26, 26, 25.8, 23.
³¹P NMR: (500 MHz, D2O) δ ppm 37
ESI/FIA/HR and MS/MS: [M+H]+=369.1955 (369.1943)
Elemental analysis: C=58.53 (58.68); H=7.80 (7.93); N=7.51 (7.60)

Intermediate 191: tert-Butyl 5-{4-[bis(tert-butoxycarbonyl)amino]butyl}-4-ethoxy-4-oxo-1-[(3-phenylphenyl)methyl]-1,4-azaphosphepane-5-carboxylate Intermediate 191 is obtained in accordance with procedure H described hereinbefore, replacing benzyl bromide by 3-phenylbenzyl bromide.
¹H NMR: (400/500 MHz, dmso-d6) δ ppm 7.65 (d, 2H), 7.63 (t, 1H), 7.59 (s, 1H), 7.53 (d, 1H), 7.46 (t, 2H), 7.41 (t, 1H), 7.31 (d, 1H), 4.06 (m, 2H), 3.69/3.63 (2*d, 2H), 3.44 (t, 2H), 2.83/2.71 (2*m, 2H), 2.8/2.67 (2*m, 2H), 2.21/1.6 (2*m, 2H), 2.12/1.88 (2*m, 2H), 1.9/1.67 (2*m, 2H), 1.42 (m, 2H), 1.41 (s, 18H), 1.39 (s, 9H), 1.22 (t, 3H), 1.22/0.99 (2*m, 2H)
¹³C NMR: (400/500 MHz, dmso-d6) δ ppm 129.1, 128.9, 127.9, 127.6, 127, 126.7, 125.4, 61.5, 60.3, 50.8, 48.2, 45.8, 31.2, 31.2, 29, 28.3, 28, 28, 21.6, 16.6

EXAMPLE 256: 5-(4-AMINOBUTYL)-4-HYDROXY-4-OXO-1-[(3-PHENYLPHENYL)METHYL]-1,4-AZAPHOSPHEPANE-5-CARBOXYLIC ACID

Example 256 is obtained starting from intermediate 191 in accordance with procedure D described hereinbefore.
¹H NMR: (400 MHz, D2O) δ ppm 7.8-7.4 (m, 9H), 4.45/4.35 (d, 2H), 3.7-3.2 (m, 4H), 2.95 (m, 2H), 2.2-1.75 (m, 4H), 1.6-1.2 (m, 6H)
³¹P NMR: (400 MHz, D2O) δ ppm 86
ESI/FIA/HR and MS/MS: [M+H]+=431.2092 (431.2094)
Elemental analysis: C=63.35 (64.17); H=6.85 (7.26); N=6.42 (6.51)

Intermediate 192: tert-Butyl 3-{4-[bis(tert-butoxycarbonyl)amino]butyl}-4-ethoxy-4-oxo-1-[(3-phenylphenyl)methyl]-1,4-azaphosphepane-3-carboxylate Intermediate 192 is obtained in accordance with procedure H described hereinbefore, replacing benzyl bromide by 3-phenylbenzyl bromide.
¹H NMR: (400 MHz, dmso-d6) δ ppm 7.7 (s, 1H), 7.66 (d, 2H), 7.5 (t, 1H), 7.42 (t, 2H), 7.35 (m, 2H), 7.32 (t, 1H), 4.06 (m, 2H), 4.01/3.8 (2*d, 2H), 3.45 (t, 2H), 3.32/2.76 (dd, 2H), 2.62-2.45 (m, 2H), 2-1.3 (m, 8H), 1.4/1.1 (2*m, 2H), 1.4 (s, 27H), 1.25 (t, 3H)

EXAMPLE 257: 3-(4-AMINOBUTYL)-4-HYDROXY-4-OXO-1-[(3-PHENYLPHENYL)METHYL]-1,4-AZAPHOSPHEPANE-3-CARBOXYLIC ACID

Example 257 is obtained starting from intermediate 192 in accordance with method D described hereinbefore.
¹H NMR: (400 MHz, D2O) δ ppm 7.8-7.4 (m, 9H), 4.45/4.35 (d, 2H), 3.6-3.25 (m, 4H), 2.8 (m, 2H), 2.1-1.9 (m, 4H), 1.75-1.1 (m, 6H)
³¹P NMR: (400 MHz, D2O) δ ppm 86
ESI/FIA/HR and MS/MS: [M+H]+=431.2095 (431.2094)
Elemental analysis: C=63.89 (64.17); H=6.92 (7.26); N=6.50 (6.51)

Intermediate 193: tert-Butyl 3-{4-bis(tert-butoxycarbonyl)amino]butyl}-4-ethoxy-4-oxo-1-[(4-phenylphenyl)methyl]-1,4-azaphosphepane-3-carboxylate Intermediate 193 is obtained in accordance with procedure H described hereinbefore, replacing benzyl bromide by 4-phenylbenzyl bromide.
¹H NMR: (400 MHz, dmso-d6) δ ppm 7.7-7.55 (2d, 4H), 7.5 (m, 2H), 7.45 (d, 2H), 7.35 (m, 1H), 4.1 (m, 2H), 3.95 (d, 1H), 3.8 (d, 1H), 3.45 (t, 2H), 3.3 (m, 1H), 2.8 (m, 1H), 2.55 (m, 1H), 2-1.35 (m, 9H), 1.4 (3s, 27H), 1.25 (t, 3H), 1.25 (m, 1H), 1.1 (m, 1H)

EXAMPLE 258: 3-(4-AMINOBUTYL)-4-HYDROXY-4-OXO-1-[(4-PHENYLPHENYL)METHYL]-1,4-AZAPHOSPHEPANE-3-CARBOXYLIC ACID

Example 258 is obtained starting from intermediate 193 in accordance with procedure D described hereinbefore.
¹H NMR: (400 MHz, D2O) δ ppm 7.7 (2d, 4H), 7.5 (t+d, 4H), 7.4 (td, 1H), 4.35 (2d, 2H), 3.5-3.2 (m, 4H), 2.85 (m, 2H), 2.15-1 (m, 10H)
ESI/FIA/HR and MS/MS: ESI-HR+/−: [M+H]+=431.2093 (431.2094)
Elemental analysis: C=63.92 (64.17); H=7.15 (7.26); N=6.47 (6.51)

Intermediate 62: tert-Butyl 5-{4-[bis(tert-butoxycarbonyl)amino]butyl}-4-ethoxy-4-oxo-1-[(4-phenylphenyl)methyl]-1,4-azaphosphepane-5-carboxylate Intermediate 62 is obtained in accordance with procedure H described hereinbefore, replacing benzyl bromide by 4-phenylbenzyl bromide.

EXAMPLE 259: 5-(4-AMINOBUTYL)-4-HYDROXY-4-OXO-1-[(4-PHENYLPHENYL)METHYL]-1,4-AZAPHOSPHEPANE-5-CARBOXYLIC ACID

Example 259 is obtained starting from intermediate 62 in accordance with procedure D described hereinbefore.
¹H NMR: (400 MHz, D2O) δ ppm 7.75 (d, 2H), 7.7 (d, 2H), 7.6 (d, 2H), 7.5 (m, 2H), 7.45 (m, 1H), 4.45/4.35 (2d, 2H), 3.75-3.1 (m, 4H), 2.95 (t, 2H), 2.2-1.85 (m, 3H), 1.8 (m, 1H), 1.7-1.05 (m, 6H)
ESI/FIA/HR and MS/MS: EI-HR: [M+H]+=431.2093 (431.2094)
Elemental analysis: C=64.46 (64.17); H=7.17 (7.26); N=6.46 (6.51)

Intermediate 194: tert-Butyl 3-{4-[bis(tert-butoxycarbonyl)amino]butyl}-4-ethoxy-4-oxo-1-[(2-phenylphenyl)methyl]-1,4-azaphosphepane-3-carboxylate Intermediate 194 is obtained in accordance with procedure H described hereinbefore, replacing benzyl bromide by 2-phenylbenzyl bromide.

¹H NMR: (400 MHz, dmso-d6) δ ppm 7.88 (d, 1H), 7.48-7.2 (m, 5H), 7.35 (m, 2H), 7.15 (d, 1H), 4.05 (m, 2H), 3.9/3.7 (2*d, 2H), 3.42 (t, 2H), 3.2/2.65 (dd, 2H), 2.33 (m, 2H), 2-1.5 (m, 6H), 1.42 (s, 18H), 1.4 (m, 2H), 1.4 (s, 9H), 1.25 (t, 3H), 1.15/1 (2*m, 2H)

EXAMPLE 260: 3-(4-AMINOBUTYL)-4-HY-DROXY-4-OXO-1-[(2-PHENYLPHENYL)METHYL]-1,4-AZAPHOSPHEPANE-3-CARBOXYLIC ACID

Example 260 is obtained starting from intermediate 194 in accordance with procedure D described hereinbefore.
¹H NMR: (400 MHz, D2O) δ ppm 7.7-7.3 (m, 9H), 4.45 (d, 1H), 4.4 (d, 1H), 3.25-3 (m, 4H), 2.95 (q, 2H), 1.95-1.5 (m, 5H), 1.65 (m, 2H), 1.35 (m, 1H), 1.3-1.05 (m, 2H)
ESI/FIA/HR and MS/MS: [M+H]+=431.2094 (431.2094)
Elemental analysis: C=63.81 (64.17); H=7.03 (7.26); N=6.45 (6.51)

Intermediate 67: tert-Butyl 5-{4-[bis(tert-butoxycarbonyl)amino]butyl}-4-ethoxy-4-oxo-1-[(2-phenylphenyl)methyl]-1,4-azaphosphepane-5-carboxylate Intermediate 67 is obtained in accordance with procedure H described hereinbefore, replacing benzyl bromide by 2-phenylbenzyl bromide.

EXAMPLE 261: 5-(4-AMINOBUTYL)-4-HY-DROXY-4-OXO-1-[(2-PHENYLPHENYL)METHYL]-1,4-AZAPHOSPHEPANE-5-CARBOXYLIC ACID

Example 261 is obtained starting from intermediate 67 in accordance with procedure D described hereinbefore.
¹H NMR: (300/500 MHz, D2O) δ ppm 7.63/7.61 (m, 1H), 7.54-7.45 (m, 4H), 7.44 (m, 1H), 7.38 (m, 1H), 7.33/7.31 (m, 2H), 4.38 (m, 2H), 3.48-2.77 (m, 4H), 2.94 (m, 2H), 2.05/1.42 (m, 2H), 2.03/1.43 (m, 2H), 2.01/1.66 (m, 2H), 1.6 (m, 2H), 1.33/1.14 (m, 2H)
¹³C NMR: (300/500 MHz, D2O) δ ppm 178.5, 143.3, 130.4, 129.4, 129.3, 129.2, 128.7, 127.7, 57.8, 55.1/51.6, 38.8, 31.7, 28.9, 26.3, 25.9, 20.5
³¹P NMR: (300/500 MHz, D2O) δ ppm 36.5
ESI/FIA/HR and MS/MS: [M+H]+=431.2095 (431.2094)
Elemental analysis: C=63.81 (64.17); H=7.14 (7.26); N=6.45 (6.51)

Preparation of Example 262

Intermediate 195

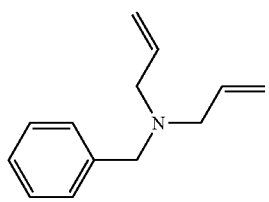

Allyl alcohol (15.27 mL, 224 mmol, 8 eq), triethylborane (6.4 mL, 6.39 mmol, 0.23 eq) and tributylphosphorus (1.17 mL, 5.6 mmol, 0.2 eq) are added in succession to a solution, degassed with argon for 30 minutes, of benzylamine (3 g, 28 mmol) and palladium acetate (0.31 g, 1.4 mmol) in THF (64 mL). The reaction mixture is degassed for 15 minutes with argon and heated at 70° C. for 20 hours. The mixture is concentrated under reduced pressure. The residue obtained is purified by flash chromatography on silica gel using a DCM/AcOEt gradient (from 100% to 95:5) as eluant. Intermediate 195 (3.45 g, 18.4 mmol) is obtained in the form of an oil with a yield of 66%.

¹H NMR: (400 MHz, CDCl₃) δ ppm 7.3 (m, 5H), 5.9 (m, 2H), 5.15 (m, 4H), 3.6 (s, 2H), 3.1 (s, 4H)

Intermediate 196

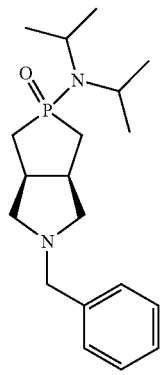 [SMILES: CC(C)N(C(C)C)P1(=O)C[C@H]2CN(Cc3ccccc3)C[C@H]2C1]

A solution of diisopropylamino-phosphorus dichloride (4.96 g, 24.6 mmol, 2 eq) in DCM (41.5 mL) is added to a suspension of aluminium chloride (3.27 g, 24.6 mmol, 2 eq) in DCM (41.5 mL) at −20° C. and under an argon atmosphere. The mixture is stirred for 1 hour at ambient temperature and then cooled to −20° C., and intermediate 195 (2.3 g, 12.3 mmol) in solution in 10 mL of DCM is then added. The reaction mixture is stirred for 16 hours at ambient temperature and then heated for 1 hour at reflux. A solution (25 mL, 1:1) of EDTA (0.2M in H₂O) and NaHCO₃ (10% in H₂O) is then added 0° C., and the mixture is stirred for 16 hours at ambient temperature. The reaction mixture is then added to 100 mL of DCM cooled by an ice bath and rendered basic with a saturated Na₂CO₃ solution. The organic phase is separated off and washed with H₂O (2×50 mL), dried over MgSO₄ and concentrated in vacuo. The residue obtained is purified by flash chromatography on a silica column using as eluant an AcOEt/THF gradient (from 100% to 95:5). Intermediate 196 (2.3 g, 6.8 mmol) is obtained in the form of an oil with a yield of 54%.

¹H NMR: (400 MHz, dmso-d6) δ ppm 7.3 (m, 5H), 3.52 (2s, 2H), 3.33 (m, 2H), 2.78/2.6 (m, 2H), 2.62 (m, 2H), 2.3 (m, 2H), 1.99/1.72 (m, 2H), 1.4 (m, 2H), 1.17 (2d, 12H)
³¹P NMR: (400 MHz, DMSO-d6) δ ppm 69.2/66.9

Intermediate 197

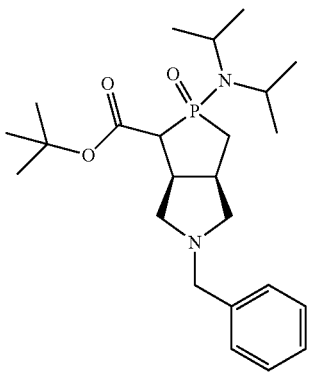 [SMILES: CC(C)N(C(C)C)P1(=O)C[C@H]2CN(Cc3ccccc3)C[C@H]2C1C(=O)OC(C)(C)C]

A solution of 2N LDA in THF (4.81 mL, 9.6 mmol, 1.4 eq) is added to a solution of intermediate 196 (2.3 g, 6.87 mmol) in THF (16.5 mL) at −70° C. and under an argon atmosphere. After stirring for 15 minutes at −70° C., a solution of (Boc)₂O (2.1 g, 9.6 mmol, 1.4 eq) in THF (5 mL) is added dropwise, and stirring is maintained for 90 minutes at −70° C. A further 1.4 eq of 2N LDA in THF (4.81 mL, 9.6 mmol, 1.4 eq) is then added. When the addition is complete, the reaction mixture is maintained at −70° C. for 90 minutes. A saturated NH₄Cl solution (30 mL) as well as AcOEt (60 mL) are then added, and the reaction mixture is slowly returned to ambient temperature. The mixture is extracted with AcOEt (2×100 mL). The organic phases are combined, dried and then concentrated under reduced pressure. The product obtained is purified by flash chromatography on silica gel using as eluant an AcOEt/THF gradient (50:50 to 20:80). Intermediate 197 (0.808 g, 1.86 mmol), a mixture of diastereoisomers, is obtained in the form of a yellow oil with a yield of 27%.

$^1$H NMR: (400 MHz, dmso-d6) δ ppm 7.25 (m, 5H), 3.55 (m, 2H), 3.25 (m, 2H), 2.91 (m, 1H), 2.72 (m, 2H), 2.6/2.3 (m, 4H), 2.15/1.65 (m, 2H), 1.39 (s, 9H), 1.15 (m, 12H)

$^{31}$P NMR: (400 MHz, DMSO-d6) δ ppm 68.58

Intermediate 198: tert-Butyl (3aR*, 4S*, 6aS*)-2-benzyl-4-{4-[bis(tert-butoxy-carbonyl)amino]butyl}-5-[di(propan-2-yl)amino]-5-oxo-octahydrophospholo[3,4-c]pyrrole-4-carboxylate A solution of intermediate 204 (0.71 g, 2 mmol, 1.1 eq) in DMSO (1.5 mL) is added under argon to a 60% suspension of NaH (0.12 g, 2 mmol, 1.1 eq) in DMSO (6 mL). Intermediate 197 (0.8 g, 1.84 mmol) in solution in DMSO (2 mL) is then added and the mixture is stirred for 15 hours at ambient temperature. The reaction mixture is then hydrolysed at 0° C. with an aqueous NH₄Cl solution (10 mL) and extracted with DCM (50 mL). The organic phase is washed with H₂O (2×10 mL), dried over MgSO₄ and concentrated in vacuo. The residue obtained is purified by flash chromatography on silica gel using as eluant an AcOEt/THF gradient (from 100% to 80:20). Intermediate 198 (0.232 g, 0.33 mmol), a mixture of diastereoisomers, is obtained in the form of an oil with a yield of 18%.

$^1$H NMR: (400 MHz, dmso-d6) δ ppm 7.3 (m, 4H), 7.22 (m, 1H), 3.58/3.43 (d)+(d, 1+1H), 3.42 (m, 2H), 3.29 (m, 1H), 3.1/2.09 (m)+(m, 1+1H), 2.87 (m, 1H), 2.82/2.59 (m)+(m, 1+1H), 2.81 (m, 1H), 2.05/1.46 (m)+(m, 1+1H), 1.92/1.65 (m)+(m, 1+1H), 1.45 (m, 2H), 1.42 (2*(s, 27H), 1.26/1.09 (m)+(m, 1+1H), 1.17 (d, 12H)

$^{13}$C NMR: (400 MHz, DMSO-d6) δ ppm 128.1, 126.6, 60.8, 59.1, 55.7, 45.5, 45.4, 44.1, 34.3, 29.1, 27.7, 27.3, 26.6, 22.9, 22.3

EXAMPLE 262: (3AR*,4S*,6AS*)-4-(4-AMINOBUTYL)-2-BENZYL-5-HYDROXY-5-OXO-OCTAHYDROPHOSPHOLO[3,4-C]PYRROLE-4-CARBOXYLIC ACID, TRIFLUOROACETATE

Intermediate 198 (0.232 g, 0.328 mmol) and 6N hydrochloric acid (5 mL, 30 mmol) are heated at reflux for 7 hours. The reaction mixture is concentrated under reduced pressure and then lyophilised. The residue is purified by reverse-phase chromatography on RP18 silica gel using as eluant an H₂O/MeCN/TFA gradient. Example 262 (0.040 g, 0.109 mmol) is obtained in the form of a TFA salt after lyophilisation with a yield of 33%.

$^1$H NMR: (500 MHz, D₂O+NaOD) δ ppm 7.4-7.25 (m, 5H), 3.59 (m, 2H), 3.18/2.07 (m)+(m, 1+1H), 2.9 (m, 1H), 2.84/2.37 (m)+(m, 1+1H), 2.7 (m, 1H), 2.48 (m, 2H), 1.85/1.31 (m)+(m, 1+1H), 1.78/1.22 (m)+(m, 1+1H), 1.31 (m, 2H), 1.24/1.07 (m)+(m, 1+1H)

$^{13}$C NMR: (500 MHz, D₂O+NaOD) δ ppm 127-129, 60.9, 59.2, 55.5, 44.1, 40.1, 33.5, 32.2, 29.3, 28, 23

ESI/FIA/HR and MS/MS: [M+H]+=367.1789 (367.1786)

Preparation of Example 263

Intermediate 199

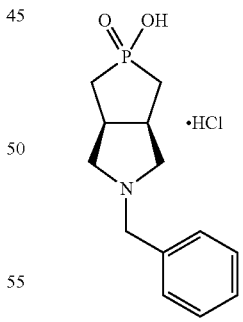

Intermediate 196 (6.15 g, 18.4 mmol) and 6N hydrochloric acid (12.2 mL, 73.2 mmol) are heated at reflux for 6 hours. The reaction mixture is concerted in vacuo, taken up in ethanol (50 mL) and concentrated under reduced pressure. Intermediate 199 (7.57 g, 26.3 mmol) is used without being purified further.

$^1$H NMR: (400 MHz, dmso-d6) δ ppm 11.2 (sl, 1H), 7.6 (m, 2H), 7.4 (m, 3H), 4.3 (d, 2H), 2.95; 2.8 (m, 2*1H H), 3.6; 3.3 (m, 2H), 3.2; 2.95 (m, 2H), 1.85; 1.5 (m, 4H)

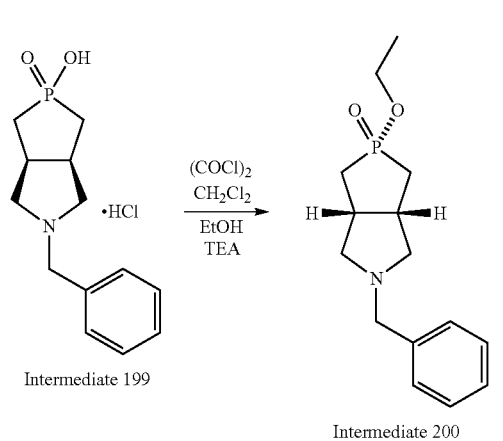

Intermediate 199

Intermediate 200

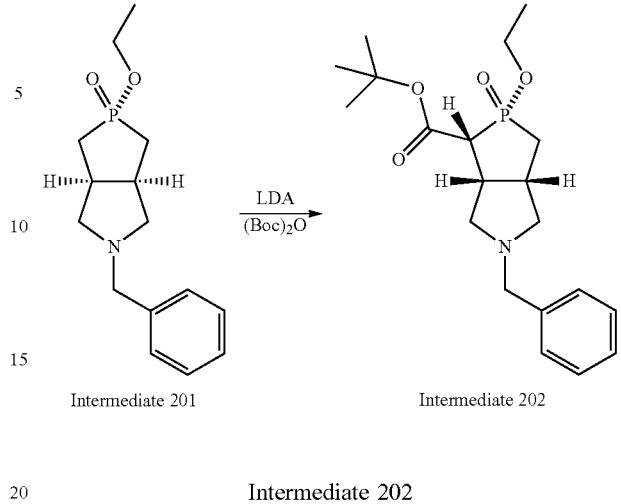

Intermediate 201

Intermediate 202

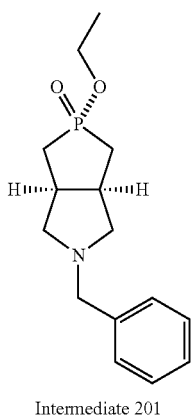

Intermediate 201

Intermediates 200 and 201

An oxalyl chloride solution (3.16 mL, 36.8 mmol, 2 eq) is added dropwise to a solution of intermediate 199 (5.29 g, 18.4 mmol) in solution in DCM (170 mL) at 0° C. and under an argon atmosphere. The reaction mixture is stirred for 4 hours at ambient temperature, evaporated in vacuo and then dried under reduced pressure. The residue is taken up in anhydrous DCM (150 mL), and DMAP (0.0225 g, 0.18 mmol) is then added. The mixture is cooled to −70° C. TEA (3.1 mL, 22 mmol, 1.2 eq) and EtOH (1.3 mL, 22 mmol, 1.2 eq) are added in succession. The mixture is stirred for 2 hours at ambient temperature, poured onto an aqueous $NH_4Cl$ solution and then rendered basic with an aqueous $NaHCO_3$ solution. The solution is extracted with DCM (150 mL). The organic phase is washed with $H_2O$ (2×50 mL), dried over $Na_2SO_4$ and then concentrated in vacuo. The product obtained is purified by flash chromatography on silica gel using a DCM/EtOH gradient (from 95:5 to 85:15) as eluant. Intermediates 200 (0.291 g, 1.04 mmol) and 201 (2.95 g, 10.56 mmol) are obtained with a yield of 5% and 57%, respectively.

Intermediate 202

A 2M LDA solution in THF (14.7 mmol, 7.39 mL, 1.4 eq) is added to a solution of intermediate 201 (2.95 g, 10.5 mmol) in THF (31 mL) at −70° C. and under argon. After 15 minutes at −70° C., a solution of $Boc_2O$ (4.16 g, 14.7 mmol, 1.4 eq) in 10 mL of THF is then added dropwise. Stirring is maintained for 90 minutes, and 1.4 eq of 2M LDA in THF (14.7 mmol, 7.39 mL) are then added dropwise. When the addition is complete, the reaction mixture is maintained at −70° C. for 90 minutes. A saturated $NH_4Cl$ solution (30 mL) as well as AcOEt (60 mL) are added, and the reaction mixture is brought slowly to ambient temperature again. The product is then extracted with AcOEt (2×150 mL). The organic phases are combined, washed with a saturated NaCl solution (2×150 mL), dried over $MgSO_4$ and concentrated under reduced pressure. The residue obtained is purified by flash chromatography on silica gel using an AcOEt/THF gradient (from 100% to 70:30) as eluant. Intermediate 202 (2.52 g, 6.64 mmol) is obtained in the form of a yellowish oil with a yield of 63%.

Intermediate 203: tert-Butyl (3aR*,4R*,6aS*)-2-benzyl-4-{4-[bis(tert-butoxycarbonyl)-amino]butyl}-5-ethoxy-5-oxo-octahydrophospholo[3,4-c]pyrrole-4-carboxylate DMSO (5 mL) and 60% NaH (0.425 g, 10.6 mol, 1.6 eq) are introduced in succession, under an argon atmosphere, into a 250 mL three-necked flask. The flask is maintained at ambient temperature by means of a water bath. A solution of intermediate 204 (2.57 g, 7.3 mol, 1.1 eq) in DMSO (7.2 mL) is then added dropwise over a period of 5 minutes. A solution of intermediate 202 (2.52 g, 6.64 mmol) in DMSO (7.2 mL) is then added dropwise, the temperature being maintained below 20° C. After 7 hours, the reaction mixture is cooled by means of an ice-water bath and hydrolysed by addition of 5 mL of a saturated $NH_4Cl$ solution. The mixture is then extracted with DCM (3×50 mL). The organic phases are then combined, washed with a saturated NaCl solution (2×50 mL) and dried over $MgSO_4$, before being concentrated under reduced pressure. The residue so obtained is purified by chromatography on silica gel using an AcOEt/THF mixture (from 100% to 80:20) as eluant. Intermediate 203 (1.86 g, 2.86 mmol) is obtained with a yield of 43%.

$^1$H NMR: (500 MHz, $CDCl_3$) δ ppm 7.29 (m, 4H), 7.23 (m, 1H), 4.15 (m, 2H), 3.66/3.58 (d)+(d, 1+1H), 3.58 (m, 2H), 3.06/2.49 (m)+(m, 1+1H), 2.99/2.23 (m)+(m, 1+1H), 2.73 (m, 1H), 2.69 (m, 1H), 2.07/1.63 (m)+(m, 1+1H), 2.02/1.78 (m)+(m, 1+1H), 1.65-1.5 (m, 2H), 1.45/1.19 (s)+ (s, 18+9H), 1.4 (m, 2H), 1.31 (t, 3H)

$^{13}$C NMR: (500 MHz, CDCl$_3$) δ ppm 128.1, 126.6, 61.2, 60.4, 59.4, 56.7, 45.8, 45.1, 33.8, 32.9, 29.2, 27.9, 26.9, 22.1, 16.5

$^{31}$P NMR: (500 MHz, CDCl$_3$) δ ppm 74.9

EXAMPLE 263: (3AR*,4R*,6AS*)-4-(4-AMIN-OBUTYL)-2-BENZYL-5-HYDROXY-5-OXO-OC-TAHYDROPHOSPHOLO[3,4-C]PYRROLE-4-CARBOXYLIC ACID

Intermediate 203 (1.85 g, 2.84 mmol) and trimethylsilane bromide (4.5 mL, 34.11 mmol, 12 eq) in solution in DCM (20 mL) are stirred overnight at ambient temperature and then concentrated in vacuo. The residue is taken up in MeOH (20 mL), stirred for 20 minutes and then concentrated in vacuo. The product is taken up in DCM (20 mL), and TFA (4.22 mL, 56.8 mmol, 20 eq) is added. The mixture is stirred overnight at ambient temperature. The reaction mixture is then concentrated under reduced pressure and purified by reverse-phase chromatography using an H$_2$O/ CH$_3$CN gradient as eluant. Example 263 (0.29 g, 0.79 mmol) is obtained in the form of a lyophilisate with a yield of 28%.

$^1$H NMR: (500 MHz, D$_2$O+NaOD) δ ppm 7.4-7.25 (m, 5H), 3.57 (m, 2H), 3.08/2.38 (m, 1+1H), 3.04/2.17 (m)+(m, 1+1H), 2.52 (t, 2H), 2.45 (m, 1H), 2.42 (m, 1H), 1.73/1.45 (m)+(m, 1+1H), 1.67 (m, 2H), 1.35 (m, 2H), 1.28 (m, 2H)

$^{13}$C NMR: (500 MHz, D$_2$O+NaOD) δ ppm 127-129, 60.5, 59.1, 57.4, 46.1, 40, 33.9, 33.2, 32.4, 28.3, 22.9

C=58.27 (59.01); H=7.24 (7.43); N=7.58 (7.65)

ESI/FIA/HR and MS/MS: [M+H]$^+$=367.1775 (367.1786)

Pharmacological Study

EXAMPLE 264: INHIBITION OF TAFIA (HIPPURYL-ARG TEST)

Human TAFI (4 nM) is incubated with human thrombin (10 nM) and human thrombomodulin (5 nM) in the presence of calcium (10 mM). After incubation for 20 minutes, the activation reaction is stopped by addition of PPACK (1 μM final), an irreversible thrombin inhibitor.

The reactions take place in Hepes buffer (25 mM Hepes, 137 mM NaCl, 3.5 mM KCl)+0.1% bovine albumin, pH 7.4 at 28° C. and with stirring.

The test compound is added to the solution of TAFIa (2 nM) and incubated for 45 minutes in the presence of hippuryl-arginine (5 mM). The reaction is stopped by addition of hydrochloric acid (1M) neutralised subsequently with sodium hydroxide (1M), and then the mixture is buffered with disodium hydroxyphosphate (1M pH 7.4). The reaction product—hippuric acid—is revealed by addition of cyanuryl chloride (6%). The reaction mixture is stirred (vortex) and then centrifuged. The supernatant is transferred to a 96-well microplate, and the absorbance is measured using a spectrophotometer at 405 nm (Spectramax plus, Molecular Devices).

The OD value of a well containing the reagents without TAFI is subtracted from all the OD values measured. The percentage inhibition of TAFIa at a given concentration of the test compound is determined by means of the following formula:

% inhibition=100−[(OD compound×100)/OD carrier]

The compounds are evaluated at 10 nM and 20 nM under the experimental conditions described above and the results are expressed as the percentage inhibition relative to a control containing the carrier in the absence of compound.

| Example | % inhibition at 10 nM | % inhibition at 20 nM |
| --- | --- | --- |
| 48 | 45 (+/−6) | 54 (+/−9) |
| 49 | 60 (+/−3) | 73 (+/−3) |
| 50 | 53 (+/−5) | 66 (+/−6) |
| 104 | 37 (+/−13) | 68 (+/−3) |
| 105 | 44 (+/−10) | 66 (+/−10) |
| 108 | 25 (+/−1) | 29 (+/−6) |
| 109 | 58 (+/−10) | 71 (+/−9) |
| 113 | 68 (+/−14) | 90 (+/−9) |
| 114 | 42 (+/−11) | 51 (+/−1) |
| 164 | 66 (+/−18) | 87 (+/−10) |
| 165 | 76 (+/−8) | 91 (+/−4) |
| 166 | 66 (+/−11) | 93 (+/−14) |
| 167 | 61 (+/−3) | 67 (+/−1) |
| 174 | 43 (+/−12) | 51 (+/−2) |
| 175 | 55 (+/−2) | 77 (+/−1) |
| 179 | 74 | 83 (+/−3) |
| 180 | 54 (+/−8) | 73 (+/−9) |
| 182 | 81 (+/−1) | 95 (+/−7) |
| 183 | 73 (+/−8) | 88 (+/−14) |
| 184 | 67 (+/−6) | 95 (+/−1) |
| 185 | 69 (+/−1) | 85 (+/−0) |
| 187 | 74 (+/−14) | 97 (+/−2) |
| 188 | 64 (+/−1) | 86 (+/−14) |
| 189 | 71 (+/−8) | 78 (+/−7) |
| 190 | 88 (+/−12) | 95 (+/−6) |
| 191 | 66 (+/−4) | 83 (+/−4) |
| 192 | 77 (+/−11) | 91 (+/−6) |
| 194 | 64 (+/−2) | 80 (+/−0) |
| 195 | 74 (+/−4) | 87 (+/−3) |
| 196 | 77 (+/−1) | 91 (+/−1) |
| 197 | 60 (+/−1) | 78 (+/−1) |
| 198 | 72 (+/−6) | 91 (+/−5) |
| 199 | 54 (+/−6) | 73 (+/−2) |
| 200 | 28 (+/−11) | 46 (+/−8) |
| 201 | 69 (+/−5) | 84 (+/−3) |
| 202 | 74 (+/−3) | 87 (+/−2) |
| 203 | 75 (+/−4) | 89 (+/−1) |
| 204 | 70 (+/−7) | 86 (+/−2) |
| 206 | 67 (+/−7) | 80 (+/−5) |
| 207 | 71 (+/−13) | 85 (+/−10) |
| 208 | 35 (+/−2) | 46 (+/−7) |
| 209 | 76 (+/−4) | 87 (+/−2) |
| 210 | 71 | 79 (+/−9) |
| 211 | 85 (+/−2) | 95 (+/−0) |
| 212 | 62 (+/−6) | 86 (+/−2) |
| 213 | 83 (+/−4) | 92 (+/−1) |
| 214 | 79 (+/−4) | 91 (+/−1) |
| 215 | 82 (+/−4) | 91 (+/−2) |
| 216 | 71 (+/−4) | 85 (+/−4) |
| 217 | 66 (+/−10) | 83 (+/−5) |
| 218 | 67 (+/−6) | 83 (+/−6) |
| 219 | 92 (+/−9) | 98 (+/−3) |
| 220 | 83 (+/−3) | 97 (+/−1) |
| 221 | 75 (+/−2) | 88 (+/−3) |
| 222 | 73 (+/−5) | 85 (+/−4) |
| 223 | 71 (+/−2) | 83 (+/−4) |
| 224 | 86 (+/−3) | 93 (+/−2) |
| 225 | 76 (+/−2) | 85 (+/−3) |
| 226 | 71 (+/−3) | 88 (+/−3) |
| 227 | 84 (+/−7) | 91 (+/−13) |
| 228 | 63 (+/−4) | 82 (+/−1) |
| 229 | 81 | 89 |
| 232 | 80 (+/−10) | 89 (+/−19) |
| 234 | 68 (+/−8) | 79 (+/−1) |
| 235 | 60 (+/−3) | 77 (+/−5) |
| 236 | 81 (+/−4) | 91 (+/−6) |
| 237 | 77 (+/−5) | 84 (+/−4) |
| 238 | 70 (+/−7) | 87 (+/−0) |
| 239 | 85 (+/−3) | 96 (+/−4) |
| 240 | 66 (+/−1) | 80 (+/−5) |
| 241 | 77 (+/−11) | 91 (+/−9) |
| 242 | 75 (+/−2) | 88 (+/−1) |

157
-continued

| Example | % inhibition at 10 nM | % inhibition at 20 nM |
|---|---|---|
| 244 | 49 (+/−1) | 68 (+/−6) |
| 245 | 38 (+/−2) | 52 (+/−5) |
| 246 | 72 (+/−4) | 86 (+/−1) |
| 247 | 85 (+/−16) | 89 (+/−11) |
| 248 | 87 (+/−14) | 95 (+/−6) |
| 249 | 88 (+/−6) | 94 (+/−4) |
| 250 | 88 (+/−1) | 97 (+/−1) |
| 251 | 70 (+/−14) | 90 (+/−11) |
| 252 | 76 (+/−7) | 90 (+/−2) |

EXAMPLE 265: PHARMACEUTICAL COMPOSITION—TABLET

Formulation for the preparation of 1000 tablets each containing 10 mg:

| | |
|---|---|
| Compound of one of Examples 1 to 263 | 10 g |
| Hydroxypropylcellulose | 2 g |
| Wheat starch | 10 g |
| Lactose | 100 g |
| Magnesium stearate | 3 g |
| Talc | 3 g |

EXAMPLE 266: PHARMACEUTICAL COMPOSITION—TABLET IN ASSOCIATION WITH WARFARIN

Formulation for the preparation of 1000 tablets each containing 10 mg:

| | |
|---|---|
| Compound of one of Examples 1 to 263 | 10 g |
| Warfarin | 2 g |
| Hydroxypropylcellulose | 2 g |
| Wheat starch | 10 g |
| Lactose | 100 g |
| Magnesium stearate | 3 g |
| Talc | 3 g |

EXAMPLE 267: PHARMACEUTICAL COMPOSITION—TABLET IN ASSOCIATION WITH ASPIRIN

Formulation for the preparation of 1000 tablets each containing 10 mg:

| | |
|---|---|
| Compound of one of Examples 1 to 263 | 10 g |
| Aspirin | 100 g |
| Hydroxypropylcellulose | 2 g |
| Wheat starch | 10 g |
| Lactose | 100 g |
| Magnesium stearate | 3 g |
| Talc | 3 g |

EXAMPLE 268: INJECTABLE SOLUTION

Formulation for the preparation of 10 ml of solution:

| | |
|---|---|
| Compound of one of Examples 1 to 263 | 200 mg |
| Injectable preparation of 0.9% NaCl | 10 ml |

The invention claimed is:

1. A compound of formula (I):

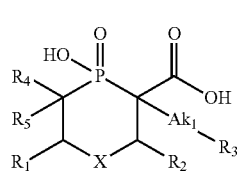

(I)

wherein:
$Ak_1$ represents a $C_1$-$C_6$-alkyl chain;
X represents —$(CH_2)_m$—, —CH(R)—, —N(R)—, —$CH_2$—N(R)—, —N(R)—$CH_2$— or —$CH_2$—N(R)—$CH_2$—;
m represents 0 or an integer from 1 to 4;
R represents a hydrogen atom, $C_1$-$C_6$-alkyl, -$Ak_2$-$Ar_1$, -$Ak_2$-$Ar_1$-$Ar_2$, -$Ak_2$-$Ar_1$-O—$Ar_2$, -$Ak_2$-cycloalkyl or -$Ak_2$-OH;
$Ak_2$ represents a linear or branched $C_1$-$C_6$-alkyl chain;
$Ar_1$ and $Ar_2$, which may be identical or different, each represent an aryl or heteroaryl group;
$R_1$ and $R_2$ each represent a hydrogen atom when X represents —$(CH_2)_m$—, —CH(R)—, —N(R)—, —$CH_2$—N(R)— or —N(R)—$CH_2$—,
or together form a bond when X represents —$CH_2$—N(R)—$CH_2$—;
$R_3$ represents $NH_2$, Cy-$NH_2$, Cy-$Ak_3$-$NH_2$ or piperidin-4-yl;
Cy represents cycloalkyl, aryl or heteroaryl;
$Ak_3$ represents a $C_1$-$C_3$-alkyl chain;
$R_4$ and $R_5$, which may be identical or different, each represent a hydrogen atom or a fluorine atom;
its optical isomers, and addition salts thereof with a pharmaceutically acceptable acid.

2. The compound according to claim 1, wherein $R_1$, $R_2$, $R_4$ and $R_5$ each represent a hydrogen atom; $R_3$ represents $NH_2$; X represents —N(R)—, —$CH_2$—N(R)—, —N(R)—$CH_2$— or —$CH_2$—N(R)—$CH_2$—; and R represents a group selected from -$Ak_2$-$Ar_1$, -$Ak_2$-$Ar_1$-$Ar_2$ and -$Ak_2$-$Ar_1$-O—$Ar_2$.

3. The compound according to claim 1, which is a compound of formula (Ia):

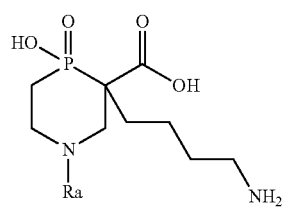

(Ia)

wherein Ra represents —$CH_2$-$Ar_1$ or —$CH_2$-$Ar_1$-$Ar_2$, wherein $Ar_1$ and $Ar_2$, which may be identical or different, each represent an aryl or heteroaryl group.

4. The compound according to claim 1, which is selected from the group consisting of (3S)-3-(4-aminobutyl)-1-[[2-(3,4-dimethoxyphenyl)-4-fluorophenyl]methyl]-4-hydroxy-4-oxo-1,4-azaphosphinane-3-carboxylic acid, and its optical isomers, and addition salts thereof with a pharmaceutically acceptable acid.

5. The compound according to claim 1, which is selected from the group consisting of (3S)-3-(4-aminobutyl)-1-[[4-fluoro-2-(4-methylphenyl)phenyl]methyl]-4-hydroxy-4-oxo-1,4-azaphosphinane-3-carboxylic acid, and its optical isomers, and addition salts thereof with a pharmaceutically acceptable acid.

6. The compound according to claim 1, which is selected from the group consisting of (3S)-3-(4-aminobutyl)-1-[[4-fluoro-2-(4-methoxyphenyl)phenyl]methyl]-4-hydroxy-4-oxo-1,4-azaphosphinane-3-carboxylic acid, and its optical isomers, and addition salts thereof with a pharmaceutically acceptable acid.

7. The compound according to claim 1, which is selected from the group consisting of (3S)-3-(4-aminobutyl)-1-[[4-fluoro-2-(4-fluorophenyl)phenyl]methyl]-4-hydroxy-4-oxo-1,4-azaphosphinane-3-carboxylic acid, and its optical isomers, and addition salts thereof with a pharmaceutically acceptable acid.

8. The compound according to claim 1, which is selected from the group consisting of (3S)-3-(4-aminobutyl)-4-hydroxy-1-[(4-hydroxy-2-phenylphenyl)methyl]-4-oxo-1,4-azaphosphinane-3-carboxylic acid, and its optical isomers, and addition salts thereof with a pharmaceutically acceptable acid.

9. The compound according to claim 1, which is selected from the group consisting of (3S)-3-(4-aminobutyl)-4-hydroxy-1-[2-(6-methoxypyridin-3-yl)benzyl]-4-oxo-1,4-azaphosphinane-3-carboxylic acid, and its optical isomers, and addition salts thereof with a pharmaceutically acceptable acid.

10. The compound according to claim 7, which is selected from the group consisting of (3S)-3-(4-aminobutyl)-1-[[2-(4-chlorophenyl)-4-fluorophenyl]methyl]-4-hydroxy-4-oxo-1,4-azaphosphinane-3-carboxylic acid, and its optical isomers, and addition salts thereof with a pharmaceutically acceptable acid.

11. The compound according to claim 1, which is selected from the group consisting of (3S)-3-(4-aminobutyl)-1-[4-fluoro-2-(1-methyl-1H-imidazol-5-yl)benzyl]-4-hydroxy-4-oxo-1,4-azaphosphinane-3-carboxylic acid, and its optical isomers, and addition salts thereof with a pharmaceutically acceptable acid.

12. The compound according to claim 1, which is selected from the group consisting of (3S)-3-(4-aminobutyl)-1-[2-(1,2-dimethyl-1H-imidazol-5-yl)-4-fluorobenzyl]-4-hydroxy-4-oxo-1,4-azaphosphinane-3-carboxylic acid, and its optical isomers, and addition salts thereof with a pharmaceutically acceptable acid.

13. The compound according to claim 1, which is selected from the group consisting of (3S)-3-(4-aminobutyl)-4-hydroxy-1-[[4-hydroxy-2-(4-methylphenyl)phenyl]methyl]-4-oxo-1,4-azaphosphinane-3-carboxylic acid, and its optical isomers, and addition salts thereof with a pharmaceutically acceptable acid.

14. The compound according to claim 1, which is selected from the group consisting of (3S)-3-(4-aminobutyl)-4-hydroxy-1-[4-hydroxy-2-(imidazo[1,2-a]pyridin-3-yl)benzyl]-4-oxo-14-azaphosphinane-3-carboxylic acid, and its optical isomers, and addition salts thereof with a pharmaceutically acceptable acid.

15. A pharmaceutical composition comprising the compound according to claim 1, in combination with one or more inert, non-toxic, pharmaceutically acceptable excipients or carriers.

16. The pharmaceutical composition according to claim 15, which further comprises a fibrinolytic, an anticoagulant or an anti-platelet agent.

17. A method for the treatment, prevention or secondary prevention of cerebrovascular accidents, myocardial infarction, angina pectoris, arteritis of the lower limbs, thromboses, including venous thromboses, pulmonary embolism, aortic aneurysms or vascular dementia, in a subject in need thereof, comprising administration of an effective amount of the compound of formula (I) according to claim 1, alone or in combination with one or more inert, non-toxic, pharmaceutically acceptable excipients or carriers.

18. The method according to claim 17, wherein the compound of formula (I) is administered in combination with a fibrinolytic, an anticoagulant or an anti-platelet agent.

19. The method according to claim 18, wherein the fibrinolytic is an injectable fibrinolytic selected from the group consisting of alteplase and tenecteplase.

* * * * *

UNITED STATES PATENT AND TRADEMARK OFFICE
CERTIFICATE OF CORRECTION

PATENT NO. : 10,138,260 B2  
APPLICATION NO. : 15/548533  
DATED : November 27, 2018  
INVENTOR(S) : Philippe Gloanec et al.

It is certified that error appears in the above-identified patent and that said Letters Patent is hereby corrected as shown below:

On the Title Page

Item (56) Under OTHER PUBLICATIONS, Line 7: "Korezyn" should read -- Korczyn --.

In the Claims

Column 159, Line 31: "claim 7" should read -- claim 1 --.

Column 160, Line 16: "-14-" should read -- -1,4- --.

Signed and Sealed this  
Eighth Day of January, 2019

Andrei Iancu  
*Director of the United States Patent and Trademark Office*